(12) United States Patent
Stevenson et al.

(10) Patent No.: US 11,406,817 B2
(45) Date of Patent: Aug. 9, 2022

(54) LOW EQUIVALENT SERIES RESISTANCE RF FILTER CIRCUIT BOARD FOR AN ACTIVE IMPLANTABLE MEDICAL DEVICE

(71) Applicant: Greatbatch Ltd., Clarence, NY (US)

(72) Inventors: Robert A. Stevenson, Canyon County, CA (US); Christine A. Frysz, Orchard Park, NY (US); Thomas Marzano, East Amherst, NY (US); Keith W. Seitz, Clarence Center, NY (US)

(73) Assignee: Greatbatch Ltd., Clarence, NY (US)

( * ) Notice: Subject to any disclaimer, the term of this patent is extended or adjusted under 35 U.S.C. 154(b) by 177 days.

(21) Appl. No.: 16/880,392

(22) Filed: May 21, 2020

(65) Prior Publication Data

US 2020/0276440 A1    Sep. 3, 2020

Related U.S. Application Data

(63) Continuation-in-part of application No. 16/827,171, filed on Mar. 23, 2020, now Pat. No. 11,071,858,
(Continued)

(51) Int. Cl.
*A61N 1/08* (2006.01)
*H01G 4/005* (2006.01)
*H01G 4/30* (2006.01)
*H01G 4/35* (2006.01)
*H01G 4/236* (2006.01)
(Continued)

(52) U.S. Cl.
CPC ............. *A61N 1/08* (2013.01); *A61N 1/3754* (2013.01); *A61N 1/3758* (2013.01); *H01G 4/005* (2013.01); *H01G 4/236* (2013.01); *H01G 4/30* (2013.01); *H01G 4/35* (2013.01); *A61N 1/086* (2017.08); *A61N 1/375* (2013.01); *A61N 1/3718* (2013.01); *H01G 4/12* (2013.01); *H03H 1/0007* (2013.01)

(58) Field of Classification Search
CPC ...... A61N 1/08; A61N 1/3754; A61N 1/3758; A61N 1/086; A61N 1/3718; A61N 1/375; H01G 4/005; H01G 4/236; H01G 4/30; H01G 4/35; H01G 4/12; H03H 1/0007
USPC .......................................................... 607/36
See application file for complete search history.

(56) References Cited

U.S. PATENT DOCUMENTS

2009/0243756 A1* 10/2009 Stevenson ............ A61N 1/3754
                                                                  333/172
2012/0016444 A1*  1/2012 Koester ................ A61N 1/3754
                                                                  607/57

* cited by examiner

*Primary Examiner* — Erin M Piateski
(74) *Attorney, Agent, or Firm* — Michael F. Scalise

(57) ABSTRACT

A filtered feedthrough assembly includes a ferrule configured to be installed in an AIMD housing. An insulator is disposed within a ferrule opening. A conductive pathway is disposed within a passageway through the insulator. A filter capacitor is disposed on a device side having active and ground electrode plates disposed within a capacitor dielectric k greater than 0 and less than 1,000. A capacitor active metallization is electrically connected to the active electrode plates. A ground capacitor metallization is electrically connected to the ground electrode plates. The filter capacitor is the first filter capacitor electrically connected to the conductive pathway coming from a body fluid side into the device side. An active electrical connection electrically connects the conductive pathway to the capacitor active metallization. A ground electrical connection electrically connects the ground capacitor metallization to the ferrule. The filter capacitor is a flat-through or an X2Y attenuator filter capacitor.

21 Claims, 91 Drawing Sheets

Related U.S. Application Data which is a continuation of application No. 16/121,716, filed on Sep. 5, 2018, now Pat. No. 10,596,369, which is a continuation-in-part of application No. 15/943,998, filed on Apr. 3, 2018, now Pat. No. 10,350,421, application No. 16/880,392, which is a continuation-in-part of application No. 15/797,278, filed on Oct. 30, 2017, now Pat. No. 10,272,253, which is a continuation-in-part of application No. 15/704,657, filed on Sep. 14, 2017, now Pat. No. 10,092,749, application No. 16/880,392, which is a continuation-in-part of application No. 15/603,521, filed on May 24, 2017, now Pat. No. 10,272,252, application No. 16/880,392, which is a continuation-in-part of application No. 15/250,210, filed on Aug. 29, 2016, now Pat. No. 9,931,514, which is a continuation-in-part of application No. 15/163,241, filed on May 24, 2016, now Pat. No. 9,764,129, which is a continuation-in-part of application No. 14/826,229, filed on Aug. 14, 2015, now Pat. No. 9,427,596, which is a continuation-in-part of application No. 14/688,302, filed on Apr. 16, 2015, now Pat. No. 9,757,558, which is a continuation-in-part of application No. 14/202,653, filed on Mar. 10, 2014, now Pat. No. 9,108,066, which is a continuation-in-part of application No. 13/873,832, filed on Apr. 30, 2013, now Pat. No. 8,868,189, application No. 16/880,392, which is a continuation-in-part of application No. 13/408,020, filed on Feb. 29, 2012, now abandoned, application No. 16/880,392, which is a continuation-in-part of application No. 16/589,752, filed on Oct. 1, 2019, which is a continuation of application No. 16/004,569, filed on Jun. 11, 2018, now Pat. No. 11,198,014.

(60) Provisional application No. 62/646,552, filed on Mar. 22, 2018, provisional application No. 62/552,363, filed on Aug. 30, 2017, provisional application No. 62/461,872, filed on Feb. 22, 2017, provisional application No. 62/450,187, filed on Jan. 25, 2017, provisional application No. 62/443,011, filed on Jan. 6, 2017, provisional application No. 62/422,064, filed on Nov. 15, 2016, provisional application No. 62/420,164, filed on Nov. 10, 2016, provisional application No. 61/841,419, filed on Jun. 30, 2013, provisional application No. 61/448,069, filed on Mar. 1, 2011, provisional application No. 61/448,069, filed on Mar. 1, 2011, provisional application No. 62/979,600, filed on Feb. 21, 2020.

(51) Int. Cl.
*A61N 1/375* (2006.01)
*H01G 4/12* (2006.01)
*H03H 1/00* (2006.01)
*A61N 1/37* (2006.01)

BODY
FLUID
SIDE

BODY
FLUID
SIDE

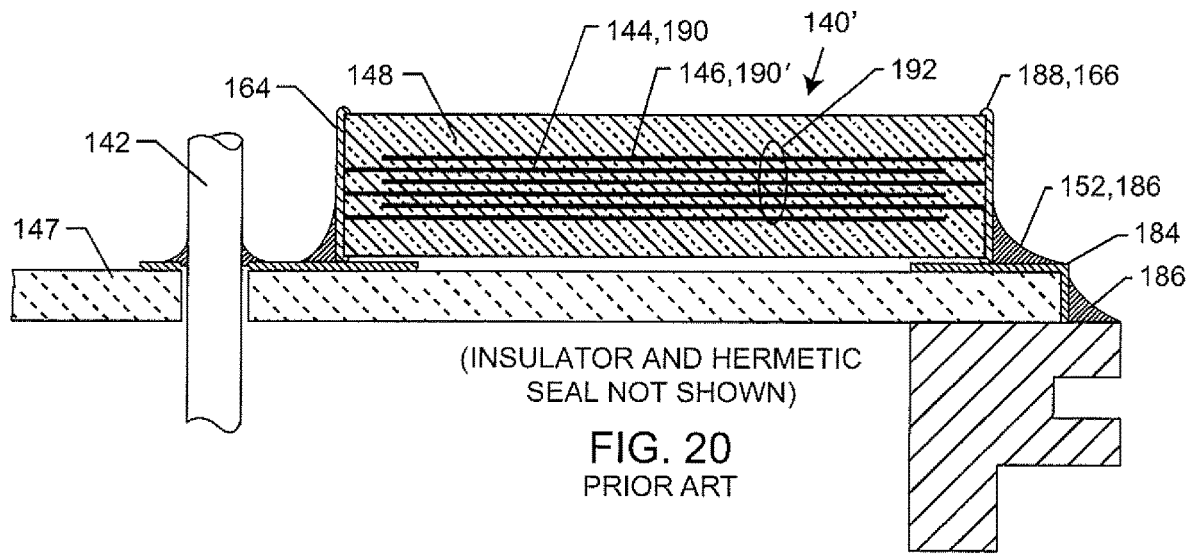
(INSULATOR AND HERMETIC SEAL NOT SHOWN)
FIG. 20
PRIOR ART
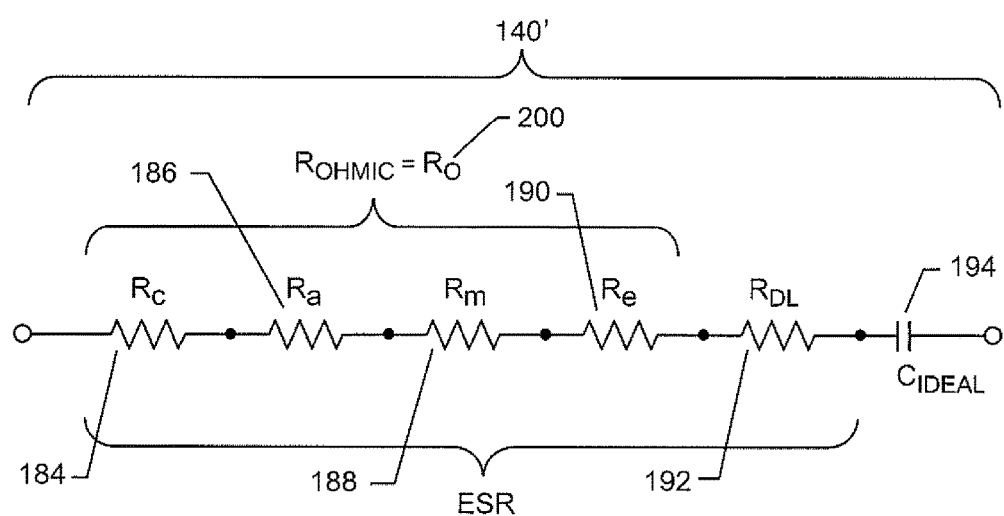
FIG. 21
FIG. 22
$$C = \frac{kA\,(n-1)}{d}$$
Where
A = Active Area
C = Capacitance
$k$ = Dielectric Constant
n = Number of Electrode Plates
d = Dielectric Thickness $$X_c = -j\left(\frac{1}{\omega C}\right)$$

$$z = \sqrt{X_c^2 + (ESR)^2}$$

$$DF = \frac{i^2\, ESR}{i^2\, |X_c|} = (\omega C)\cdot(ESR) = 1/Q$$

$$\tan\delta = \frac{ESR}{|X_c|} = DF.$$

C = Capacitance
$R_{DL}$ = R dielectric
$R_o$ = R ohmic loss
IR = Insulation Resistance
ESL = Equivalent Series Inductance
ESR = Equivalent Series Resistance Example of Losses in a 2000 P.F. X7R Capacitor DF is a percentage of Xc ≈ dielectric loss tangent Example: 2% DF Dielectric; 2000 picofarad FT    (2.5% MAX Per EIA RS-198C)

| Frequency | Xc (Ω) | DF (Ω) | R (Ω) | ESR = DF+R (Ω) |
|---|---|---|---|---|
| 1 kHz | 79,599.54 | 1591.55 | 0.432 | 1591.98 |
| 1 MHz | 79.58 | 1.59 | 0.432 | 2.02 |
| 10 MHz | 7.96 | 0.159 | 0.432 | 0.59 |
| 100 MHz | 0.796 | 0.016 | 0.432 | 0.45 |
| 500 MHz | 0.159 | 0.003 | 0.432 | 0.44 |

FIG. 29

Example of Losses in a 2000 P.F. COG (NPO) Capacitor

DF is a percentage of Xc

Example: 0.15% DF Dielectric; 2000 picofarad FT

| Frequency | Xc (Ω) | DF (Ω) | R (Ω) | ESR = DF+R (Ω) |
|---|---|---|---|---|
| 1 kHz | 79,577.54 | 119.40 | 0.2 | 119.6 |
| 1 MHz | 79.58 | 0.12 | 0.2 | 0.32 |
| 10 MHz | 7.96 | 0.012 | 0.2 | 0.212 |
| 100 MHz | 0.796 | 0.001 | 0.2 | 0.201 |
| 500 MHz | 0.159 | 0.0 | 0.2 | 0.200 |

FIG. 30

$$R_{et} = \frac{1}{\frac{1}{R_{e_1}} + \frac{1}{R_{e_2}} + \cdots \frac{1}{R_{e_n}}}$$

(TOP VIEW OF DEVICE SIDE)

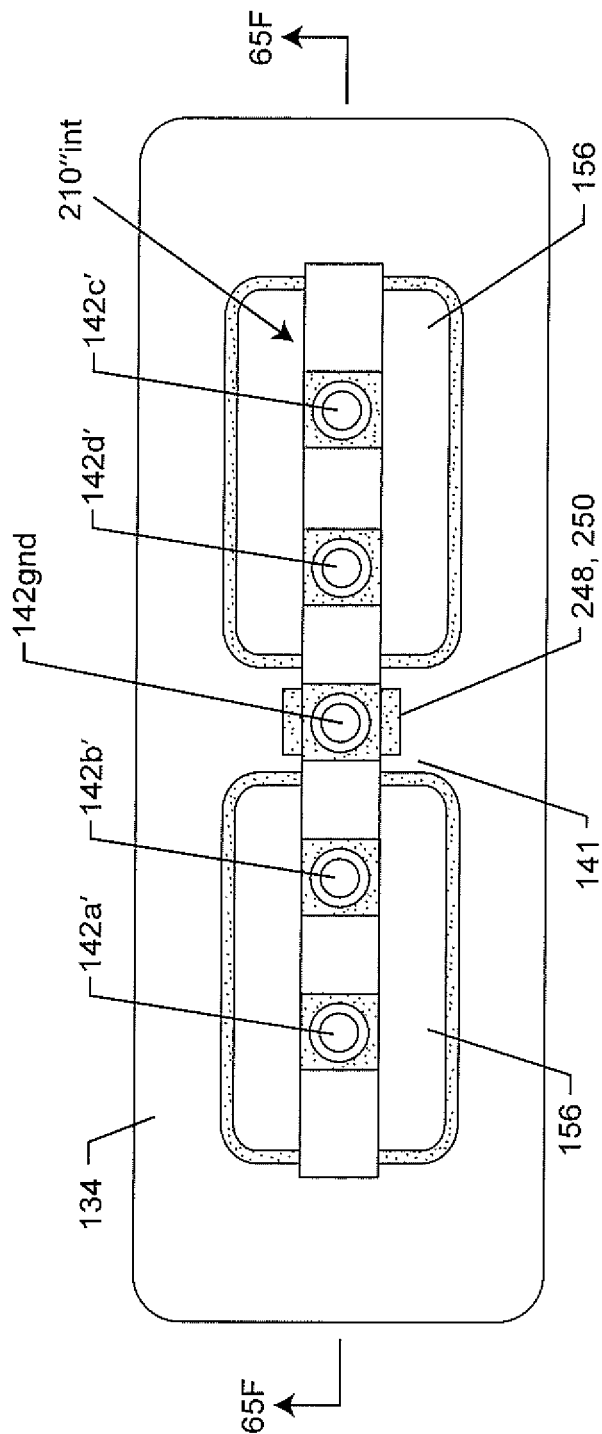

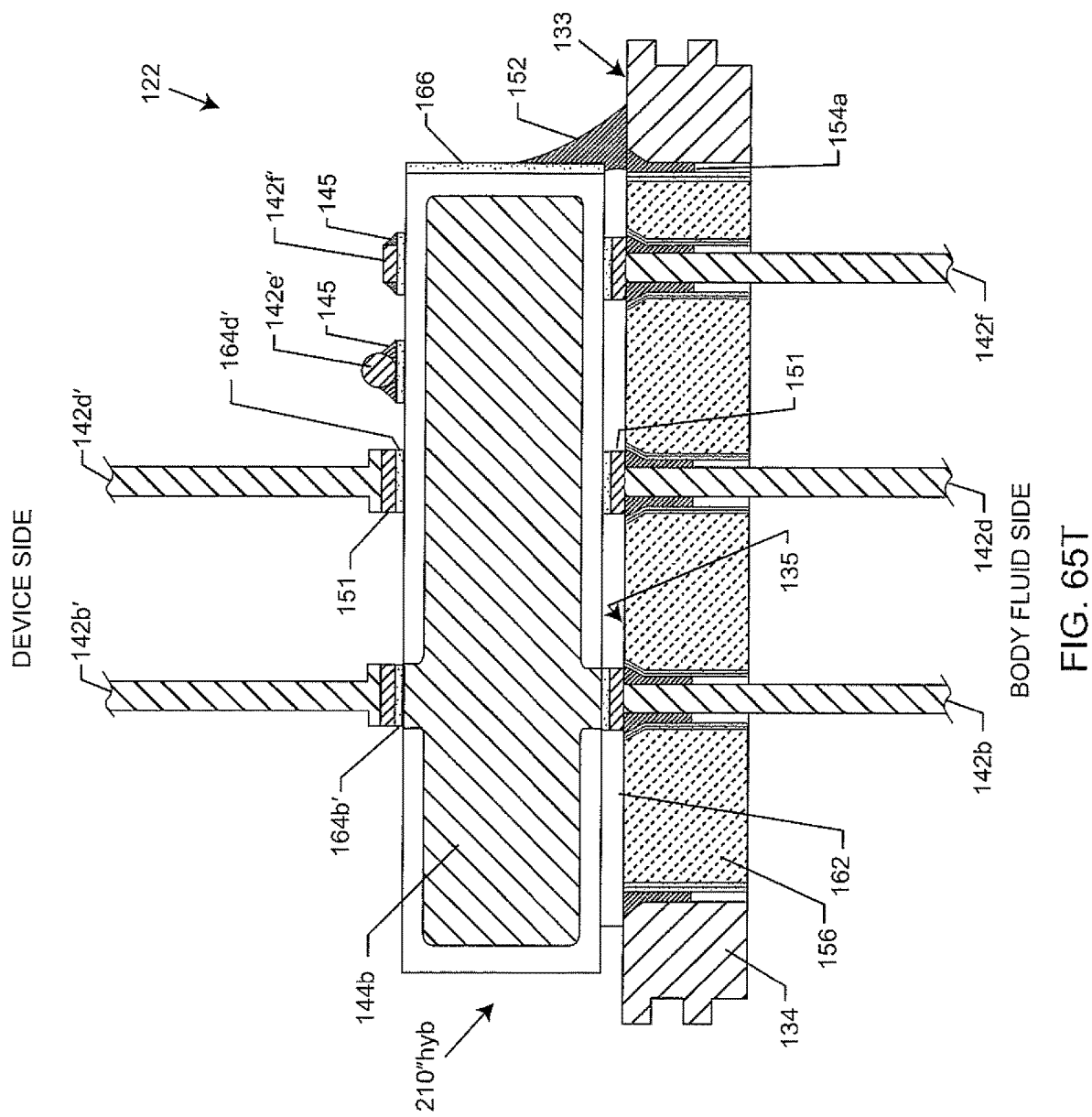

(TOP VIEW OF DEVICE SIDE)

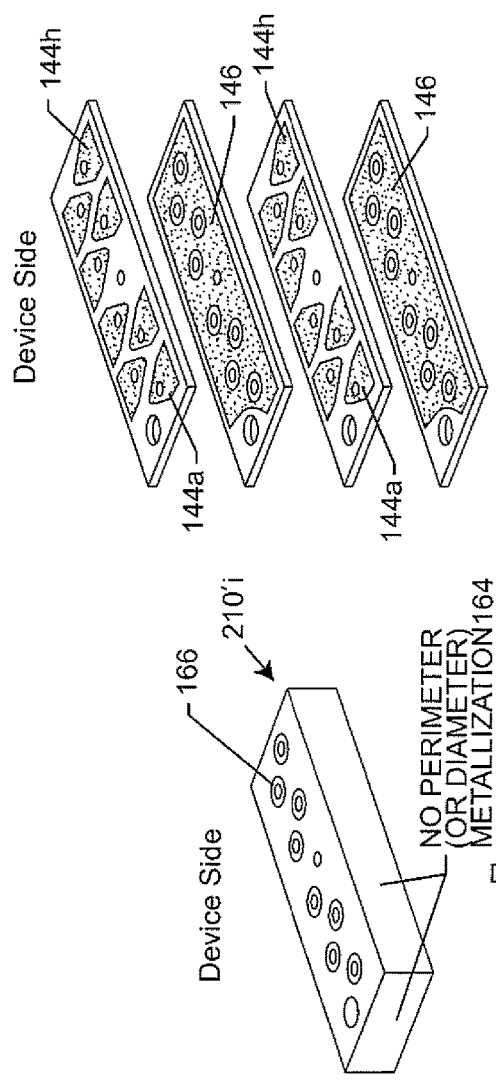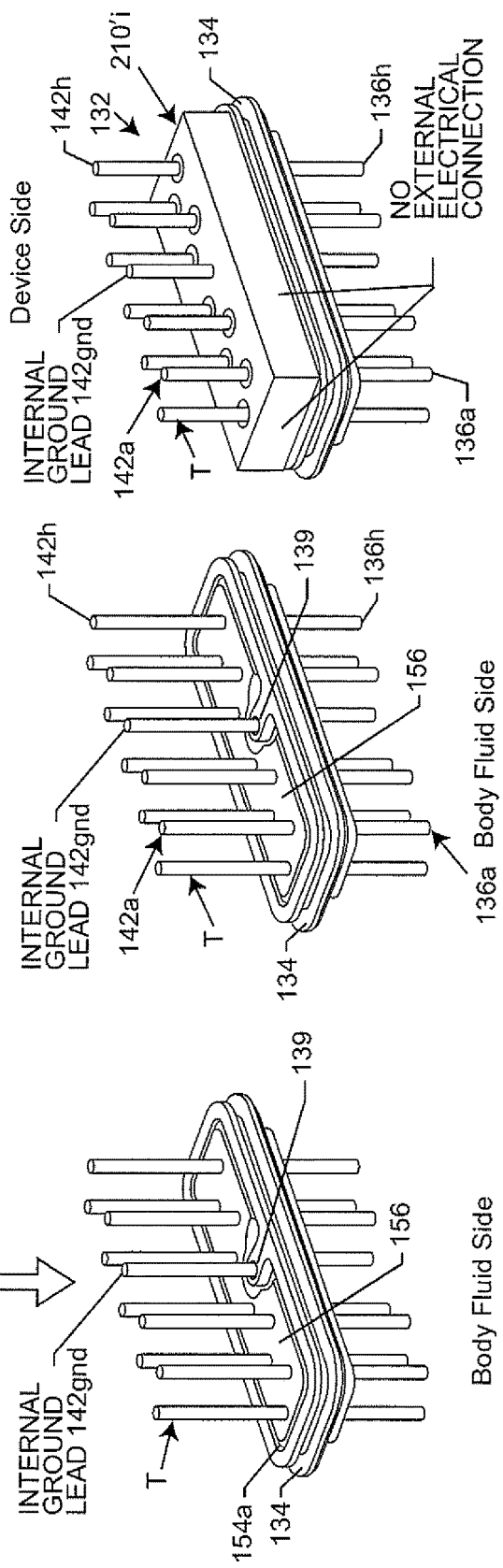
FIG. 74A PRIOR ART
FIG. 74B PRIOR ART
FIG. 74C PRIOR ART (BEFORE PRESSING)

(AFTER PRESSING)

US 11,406,817 B2

LOW EQUIVALENT SERIES RESISTANCE RF FILTER CIRCUIT BOARD FOR AN ACTIVE IMPLANTABLE MEDICAL DEVICE

CROSS-REFERENCE TO RELATED APPLICATIONS

The present application is a continuation-in-part of U.S. application Ser. No. 16/827,171, filed on Mar. 23, 2020, now U.S. Pat. No. 11,071,858, which is a continuation of U.S. application Ser. No. 16/121,716, filed on Sep. 5, 2018, now U.S. Pat. No. 10,596,369, which is a continuation-in-part to U.S. application Ser. No. 15/943,998, filed on Apr. 3, 2018, now U.S. Pat. No. 10,350,421, which claims priority from U.S. App. Ser. No. 62/646,552, filed on Mar. 22, 2018.

The present application is also a continuation-in-part of U.S. application Ser. No. 15/797,278, filed on Oct. 30, 2017, now U.S. Pat. No. 10,272,253, which is a continuation-in-part of U.S. application Ser. No. 15/704,657, filed on Sep. 14, 2017, now U.S. Pat. No. 10,092,749, which claims priority from U.S. App. Ser. No. 62/552,363, filed on Aug. 30, 2017.

The present application is also a continuation-in-part of U.S. application Ser. No. 15/603,521, filed on May 24, 2017, now U.S. Pat. No. 10,272,252, which claims priority from U.S. App. Ser. Nos. 62/461,872, filed on Feb. 22, 2017; 62/450,187, filed on Jan. 25, 2017; 62/443,011, filed on Jan. 6, 2017; 62/422,064, filed on Nov. 15, 2016; and 62/420,164, filed on Nov. 10, 2016.

The present application is also a continuation-in-part of U.S. application Ser. No. 15/250,210, filed on Aug. 29, 2016, now U.S. Pat. No. 9,931,514, which is a continuation of U.S. application Ser. No. 15/163,241, filed on May 24, 2016, now U.S. Pat. No. 9,764,129, which is a continuation-in-part to U.S. application Ser. No. 14/826,229, filed on Aug. 14, 2015, now U.S. Pat. No. 9,427,596, which is a continuation of U.S. application Ser. No. 14/688,302, filed on Apr. 16, 2015, now U.S. Pat. No. 9,757,558, which is a continuation-in-part to U.S. application Ser. No. 14/202,653, filed on Mar. 10, 2014, now U.S. Pat. No. 9,014,808, which is a continuation of U.S. application Ser. No. 14/808,849, filed on Nov. 25, 2013, now U.S. Pat. No. 8,855,768, which claims priority from U.S. App. Ser. No. 61/841,419, filed on Jun. 30, 2013.

The present application is also a continuation-in-part of U.S. application Ser. No. 13/408,020, filed on Feb. 29, 2012, abandoned, which claims priority from U.S. App. Ser. No. 61/448,069, filed on Mar. 1, 2011.

The present application is also a continuation-in-part of U.S. application Ser. No. 16/589,752, filed on Oct. 1, 2019, which is a continuation of Ser. No. 16/004,569, filed on Jun. 11, 2018, now U.S. Pat. No. 11,198,014.

The present application also claims priority to U.S. App. Ser. No. 62/979,600 filed on Feb. 21, 2020.

The contents of all the above applications are fully incorporated herein by these references.

FIELD OF THE INVENTION

This invention generally relates to the problem of RF energy induced into implanted leads during medical diagnostic procedures such as magnetic resonant imaging (MRI), and provides methods and apparatus for redirecting RF energy to locations other than the distal tip electrode-to-tissue interface. More specifically, the present invention utilizes either an MLCC chip capacitor, a flat-through filter capacitor or an X2Y attenuator having a dielectric k greater than 0 and less than 1,000 to provide electromagnetic interference (EMI) protection to sensitive active implantable medical device (AIMD) electronics.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one proceeds to the websites of the major cardiac pacemaker manufacturers in the United States, which include St. Jude Medical, Medtronic and Boston Scientific (formerly Guidant), one will see that the use of MRI is generally contra-indicated for patients with implanted pacemakers and cardioverter defibrillators. See also recent press announcements of the Medtronic Revo MRI pacemaker which was recently approved by the U.S. FDA. With certain technical limitations as to scan type and location, this is the first pacemaker designed for MRI scanning. See also:
(1) "Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel;
(5) "Advanced Engineering Electromagnetics", C. A. Balanis, Wiley, 1989; (6) Systems and Methods for Magnetic-Resonance-Guided Interventional Procedures, U.S. Pat. No. 7,844,319, Susil and Halperin et al., filed Apr. 15, 2002;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Pat. No. 7,844,534, Susil et al., issued Nov. 30, 2010.
The contents of the foregoing are all incorporated herein by these references.

However, an extensive review of the literature indicates that, despite being contra-indicated, MRI is indeed often used to image patients with pacemaker, neurostimulator and other active implantable medical devices (AIMDs). As such, the safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF-pulse field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that can be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the International Society for Magnetic Resonance in Medicine (ISMRM), which was held on 5-6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This includes certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the RF-pulse field which is generated by a body coil or a head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of about 21 MHz to about 500 MHz depending upon the static magnetic field strength. The frequency of the RF pulse for hydrogen scans varies by the Lamour equation with the field strength of the main static field where: RF-PULSE FREQUENCY in MHz=(42.56) (STATIC FIELD STRENGTH IN TESLA). There are also phosphorous and other types of scanners wherein the Lamour equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 2-5 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas wherein voltages (EMFs) are induced along their length. These antennas are not very efficient due to the damping effects of body tissue; however, this can often be offset by extremely high-power fields (such as MRI pulse fields) and/or body resonances. At very high frequencies (such as cellular telephone frequencies), EMI signals are induced only into the first area of the leadwire system (for example, at the header block of a cardiac pacemaker). This has to do with the wavelength of the signals involved wherein the signals couple efficiently into the system.

Magnetic field coupling into an implanted lead system is based on loop areas. For example, in a cardiac pacemaker unipolar lead, there is a loop formed by the lead as it comes from the cardiac pacemaker housing to its distal tip electrode, for example, located in the right ventricle. The return path is through body fluid and tissue generally straight from the tip electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields are induced through enclosed loop areas. However, the RF-pulse fields generated by the body coil are primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power [Specific Absorption Rate (SAR) Level] and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that can occur. Also, distal tip design is very important as it can heat up due to MRI RF induced energy.

The cause of heating in an MRI environment is twofold: (a) RF field coupling to the lead can occur which induces significant local heating; and (b) currents induced between the distal tip and tissue during MRI RF pulse transmission sequences can cause local Ohms Law (resistive) heating in tissue next to the distal tip electrode of the implanted lead.

The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred includes an increase in pacing threshold, venous ablation, larynx or esophageal ablation, myocardial perforation and lead penetration, or even arrhythmias caused by scar tissue. Such long-term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications. For example, spinal cord stimulators or deep brain stimulators can include at least ten pad electrodes to make contact with nerve tissue. A good example of this also occurs in a cochlear implant. In a typical cochlear implant there are sixteen pad electrodes placed up into the cochlea. Several of these pad electrodes make contact with auditory nerves.

Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker lead length and implant trajectory can significantly affect how much heat is generated. A paper entitled, HEATING AROUND INTRAVASCULAR GUIDEWIRES BY RESONATING RF WAVES by Konings, et al., journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The content of this paper is fully incorporated herein by this reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different, and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating of said tissue to the point of tissue ablation or even tissue perforation, which can be life threatening for cardiac patients. For neurostimulator patients, such as deep brain stimulator patients, thermal injury can cause coma, permanent disability or can even be life-threatening. Similar issues exist for spinal cord stimulator patients, cochlear implant patients and the like.

Interestingly, the inventors performed an experiment in an MRI scanner with a human body gel-filled phantom. In the phantom, placed in an anatomic position, was an operating pacemaker and a lead. This was during evaluation of the efficacy of bandstop filters at or near the distal tip electrode for preventing the distal tip electrode from overheating. Bandstop filters for this purpose are more thoroughly described in U.S. Pat. No. 7,363,090, the content of which is fully incorporated herein by this reference. During the experiments, there was a control lead that had no bandstop filter. During a particularly RF intense scanning sequence, Luxtron probes measured a distal helix tip electrode temperature rise of 30° C. Of course, the 30° C. temperature rise in a patient would be very alarming as it can lead to pacing capture threshold changes or even complete loss capture due to scar tissue formation. An identical lead with the bandstop filter in place only had a temperature rise of 3° C. This was a remarkable validation of the efficacy of bandstop filters for implantable electrodes. However, something very interesting happened when we disconnected the pacemaker. We disconnected the pacemaker and put a silicone lead cap over the proximal end of the lead. Again, we put the gel phantom back inside the MR scanner and this time we measured an 11° C. temperature rise on the lead with the bandstop filter. This was proof positive that the housing of the AIMD acts as part of the system. The prior art feedthrough capacitor created a fairly low impedance at the input to the pacemaker and thereby drew RF energy out of the lead and diverted it to the housing of the pacemaker. It has recently been discovered that the impedance, and in particular, the ESR of these capacitors, is very important so that maximal energy can be pulled from the lead and diverted to the pacemaker housing while at the same time, not unduly overheating the feedthrough capacitor.

Accordingly, there is a need for novel low ESR diverting capacitors and circuits which are frequency selective and are constructed of passive components for implantable leads and/or leadwires. Further, there is a need for very low ESR diverter element capacitor(s) which are designed to decouple a maximum amount of induced RF energy from an implanted lead to an AIMD housing while at the same time not overheat. The present invention fulfills these needs and provides other related advantages.

SUMMARY OF THE INVENTION

An exemplary embodiment of the present invention is a filtered feedthrough assembly attachable to an opening of a housing of an active implantable medical device. The filtered feedthrough assembly comprises: a hermetic feedthrough comprising: (I) a metallic and electrically conductive ferrule configured to be installed in the opening of the housing of the active implantable medical device, the ferrule separating a body fluid side opposite a device side, and the ferrule comprising a ferrule opening extending from the body fluid side to the device side; (ii) an insulator disposed at least partially within the ferrule opening; (iii) a first hermetic seal disposed between the insulator and the ferrule opening hermetically sealing the insulator to the ferrule; (iv) at least one passageway disposed through the insulator extending from the body fluid side to the device side; (v) a conductive pathway disposed within the at least one passageway, the conductive pathway hermetically sealed to the at least one passageway. At least one filter capacitor is disposed on the device side, comprising: (i) at least one active electrode plate and at least one ground electrode plate disposed within a capacitor dielectric body in spaced and interleaved relation with each other; (ii) a capacitor active metallization attached to the capacitor dielectric body and electrically connected to the at least one active electrode plate; (iii) a ground capacitor metallization attached to the capacitor dielectric body and electrically connected to the at least one ground electrode plate; (iv) wherein the at least one filter capacitor is the first filter capacitor electrically connected to the conductive pathway coming from the body fluid side into the device side; (v) wherein the capacitor dielectric body (148) has a dielectric constant k that is greater than 0 and less than 1,000. An active electrical connection electrically connects the conductive pathway to the capacitor active metallization, and a ground electrical connection electrically connects the ground capacitor metallization to the ferrule. Further embodiments of the invention are now discussed herein.

As best shown in FIGS. 63-64C and 65A-65R, the at least one filter capacitor may be a flat-through filter capacitor.

Furthermore, the flat-through filter capacitor may be disposed at least partially over the insulator in a tombstone mounting position, wherein the at least one active electrode plate and the at least one ground electrode plate are disposed perpendicular in relation to an outside surface of the ferrule on the device side, best shown in FIGS. 65A-65R.

The ground capacitor metallization may be disposed at an edge of the flat-through filter capacitor as shown in FIG. 65A. The ground electrical connection may comprise a conductive wire gold brazed or welded to the ferrule. The ground electrical connection may comprise a conductive material electrically connecting the ground capacitor metallization to the conductive wire gold brazed or welded to the ferrule. The ground electrical connection may comprise a gold pocket-pad disposed within a pocket formed in the outside surface of the ferrule. The ground electrical connection may comprise a conductive material electrically connecting the ground capacitor metallization to the gold pocket-pad. The ground electrical connection may comprise a conductive material electrically connecting the ground capacitor metallization to a gold braze forming the first hermetic seal. The ground electrical connection may comprise a metallization layer disposed on the outside surface of the ferrule which is overlaid by an electrically conductive adhesive. The ground electrical connection may comprise a conductive material electrically connecting the ground capacitor metallization to the electrically conductive adhesive.

The ground capacitor metallization may be disposed in a middle of the flat-through filter capacitor as best shown in FIG. 65E. The ground electrical connection may comprise a conductive wire gold brazed or welded to a peninsula or a bridge extending into the ferrule opening of the ferrule. The ground electrical connection may comprise a conductive material electrically connecting the ground capacitor metallization to the conductive wire gold brazed or welded to the ferrule. The ground electrical connection may comprise a gold pocket-pad disposed within a pocket formed in the outside surface of a peninsula or a bridge extending into the ferrule opening of the ferrule. The ground electrical connection may comprise a conductive material electrically connecting the ground capacitor metallization to the gold pocket-pad.

As best shown in FIG. 65I, the ground capacitor metallization may comprise a first ground capacitor metallization disposed at an edge of the flat-through filter capacitor and a second ground capacitor metallization disposed in a middle of the flat-through capacitor, wherein the second ground metallization is electrically connected to the ferrule at a peninsula or a bridge extending into the ferrule opening of the ferrule.

The flat-through filter capacitor may be disposed on a circuit board, the circuit board comprising at least one ground plate disposed in or on the circuit board, and wherein the at least one ground plate is electrically connected to the ground capacitor metallization and to the ferrule.

The at least one filter capacitor may be an X2Y attenuator filter capacitor.

As best shown in FIGS. 70C and 70D, the at least one filter capacitor may be disposed at least partially over the insulator in a tombstone mounting position, wherein the at least one active electrode plate and the at least one ground electrode plate are disposed perpendicular in relation to an outside surface of the ferrule on the device side. The ground electrical connection may comprise a conductive material electrically connecting the ground capacitor metallization to a gold braze forming the first hermetic seal.

The X2Y attenuator filter capacitor may be disposed on a circuit board, the circuit board comprising at least one ground plate disposed in or on the circuit board, and wherein the at least one ground plate is electrically connected to the ground capacitor metallization and to the ferrule.

The first hermetic seal may comprise a first gold braze. The conductive pathway may comprise a leadwire, the leadwire hermetically sealing the at least one passageway by a second gold braze.

The conductive pathway may comprise a platinum fill co-fired with the insulator or the conductive pathway may comprise a ceramic reinforced metal composite co-fired with the insulator.

As best shown in FIGS. 70C and 70D, another embodiment of the present invention is a filtered feedthrough assembly attachable to an opening of a housing of an active implantable medical device, the filtered feedthrough assembly comprising: a) a hermetic feedthrough, comprising: (i) a metallic and electrically conductive ferrule configured to be installed in the opening of the housing of the active implantable medical device, the ferrule separating a body fluid side opposite a device side, and the ferrule comprising a ferrule opening extending from the body fluid side to the device side; (ii) an insulator disposed at least partially within the ferrule opening; (iii) a first hermetic seal disposed between the insulator and the ferrule opening hermetically sealing the insulator to the ferrule; (iv) a first and a second passageway disposed through the insulator extending from the body fluid side to the device side; (v) a first and a second conductive pathway disposed respectively within the first and the second passageway, the conductive pathways hermetically sealed to their respective passageways; b) an X2Y attenuator filter capacitor disposed on the device side, comprising: (i) at least a first and a second active electrode plate and at least one ground electrode plate (146) disposed within a capacitor dielectric body in spaced and interleaved relation with each other; (ii) a first and a second capacitor active metallization attached to the capacitor dielectric body and electrically connected respectively to the first and the second active electrode plates; (iii) a ground capacitor metallization attached to the capacitor dielectric body and electrically connected to the at least one ground electrode plate; (iv) wherein the X2Y attenuator filter capacitor is the first filter capacitor electrically connected to the conductive pathways coming from the body fluid side into the device side; (v) wherein the X2Y attenuator filter capacitor is disposed at least partially over the insulator in a tombstone mounting position, wherein the at least the first and the second active electrode plate and the at least one ground electrode plate are disposed perpendicular in relation to an outside surface of the ferrule on the device side; c) a first active electrical connection electrically connecting the first conductive pathway to the first capacitor active metallization; d) a second active electrical connection electrically connecting the second conductive pathway to the second capacitor active metallization; and e) a ground electrical connection electrically connecting the ground capacitor metallization to the ferrule.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 20 illustrates a cross-sectional view of an MLCC chip capacitor mounted to separate circuit traces;

FIG. 21 is a schematic representation explaining the elements that are components of the FIG. 20 capacitor's equivalent series resistance (ESR);

FIG. 22 is an equation that relates the capacitance with the capacitor's active area, dielectric constant, number of electrode plates and dielectric thickness;

FIG. 29 illustrates the reactance and real losses of a 2,000-picofarad X7R feedthrough capacitor;

FIG. 30 illustrates the reactance and real losses of a 2,000-picofarad C0G (NP0) capacitor;

FIG. 65Ja is an enlarged partial cross-sectional view generally taken from section 65Ja-65Ja from FIG. 65J now showing a new embodiment of a grounding structure;

FIG. 65Jb is an enlarged partial cross-sectional view generally taken from section 65Jb-65Jb from FIG. 65J now showing a new embodiment of a grounding structure;

FIG. 65Jc is an enlarged partial cross-sectional view generally taken from section 65Jc-65Jc from FIG. 65J now showing a new embodiment of a grounding structure;

FIG. 65Jd is an enlarged partial cross-sectional view generally taken from section 65Jd-65Jd from FIG. 65J now showing a new embodiment of a grounding structure;

FIG. 73 is a cross-sectional view taken along lines 73-73 of FIG. 72B;

FIG. 74A is a perspective view of an internally grounded feedthrough capacitor of the present invention before it is installed onto the ferrule;

FIG. 74B is a view similar to FIG. 74A now showing the electrode plate stack up;

FIG. 74C is a view similar to FIGS. 74A and 74B now showing the internally grounded feedthrough capacitor installed;

FIG. 75 is a top view illustrating how a rectangular capacitor can overhang the ferrule;

FIG. 76 is a cross-sectional side view taken along lines 76-76 from FIG. 75;

FIG. 77 is a cross-sectional side view of another embodiment of the present invention utilizing a cermet disposed within a via hole in the insulator along with an internally grounded capacitor utilizing the gold pocket-pad for the oxide-resistant connection to the ferrule;

FIG. 78 is a cross-sectional view very similar to FIG. 77 now showing the use of an anisotropic film for making electrical connection on the device side;

FIG. 79 is a cross-sectional side view illustrating a variety of filled vias utilizing co-fired fills that can be used with the present invention;

FIG. 80 is a top view of another embodiment of a filtered feedthrough of the present invention;

FIG. 81 is a sectional top view taken along lines 81-81 of FIG. 82;

FIG. 82 is a cross-sectional side view taken along lines 82-82 of FIG. 80;

Figure 80:
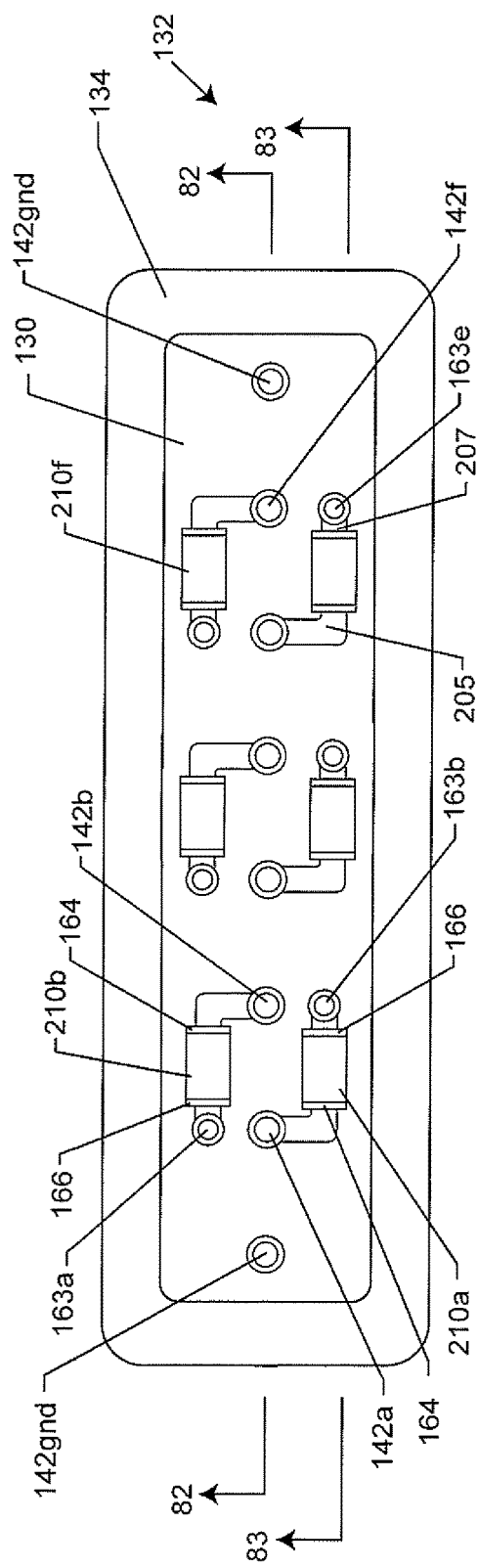
Figure 83:
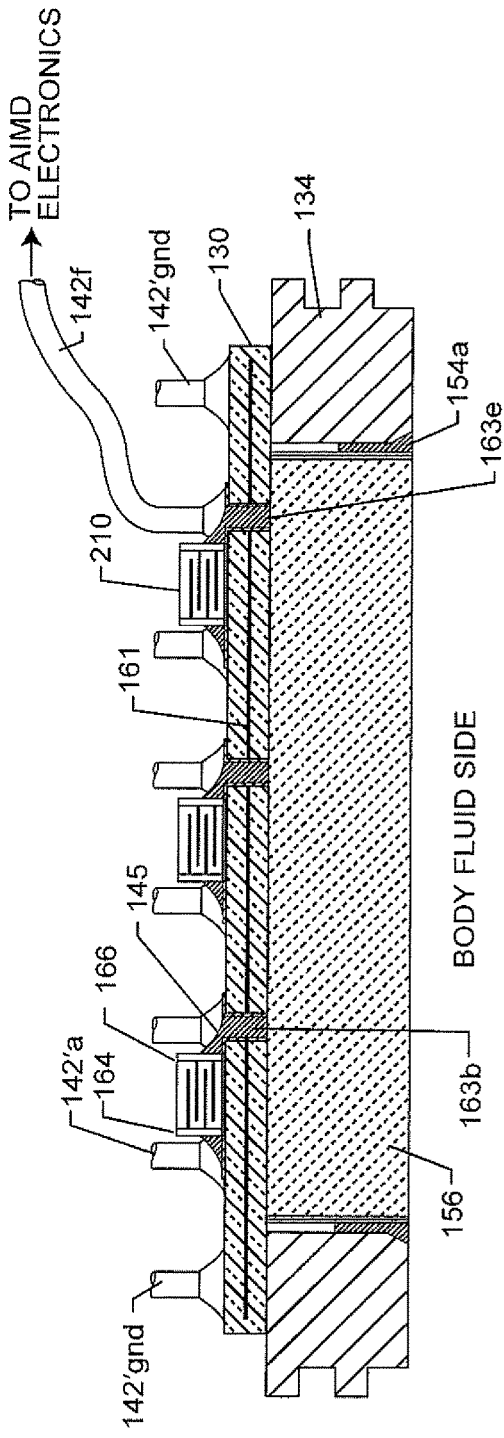
Figure 84:
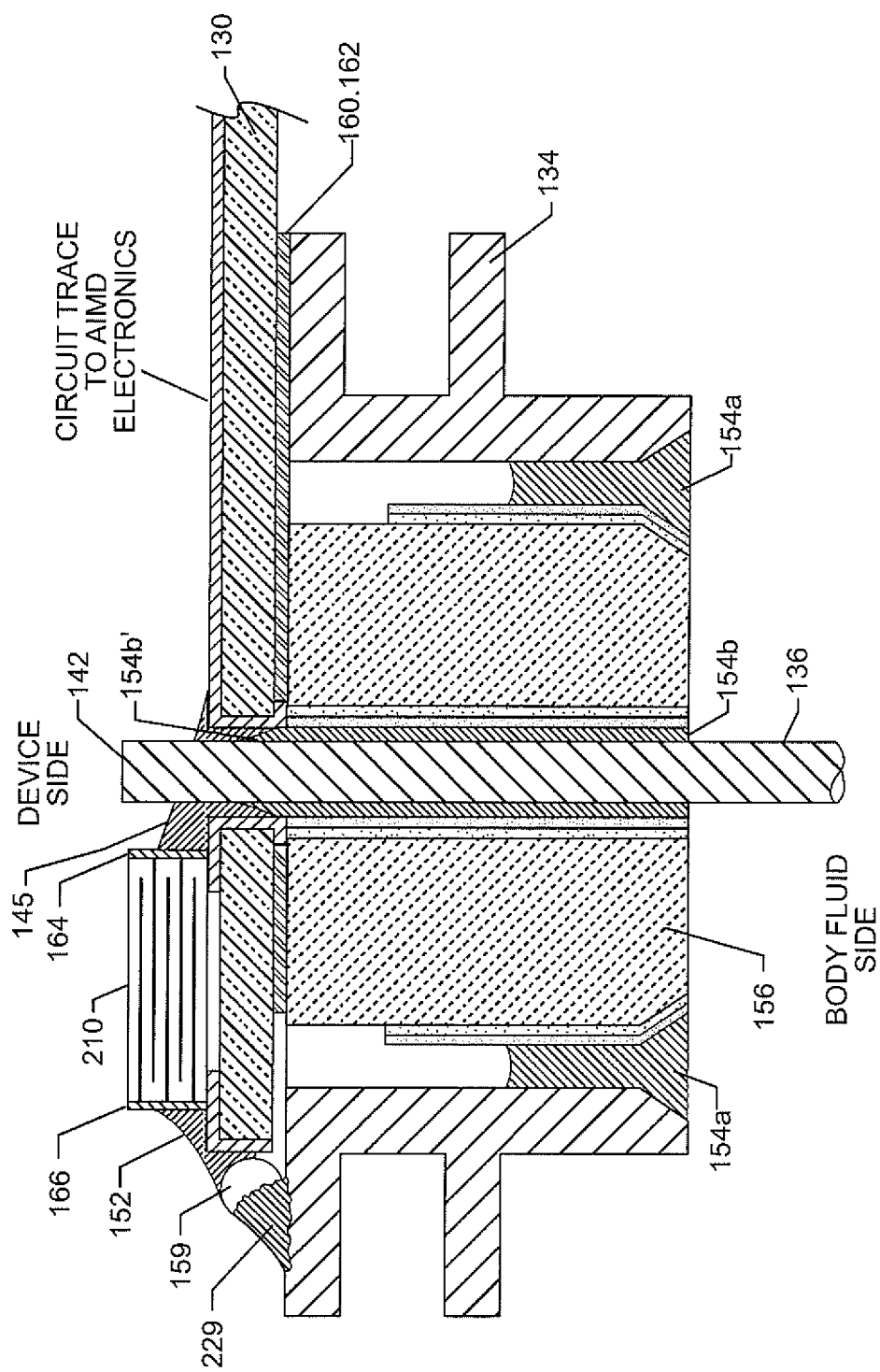
Figure 85:
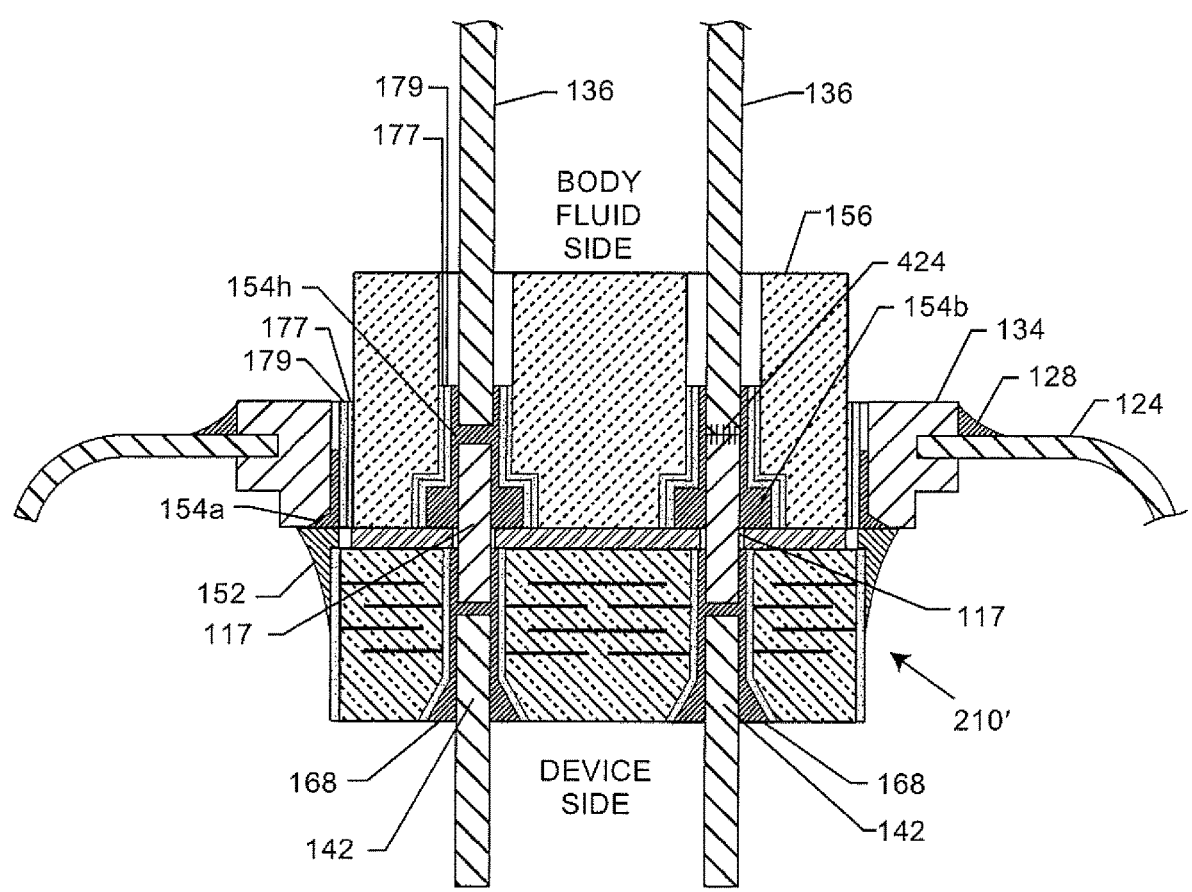
Figure 86:
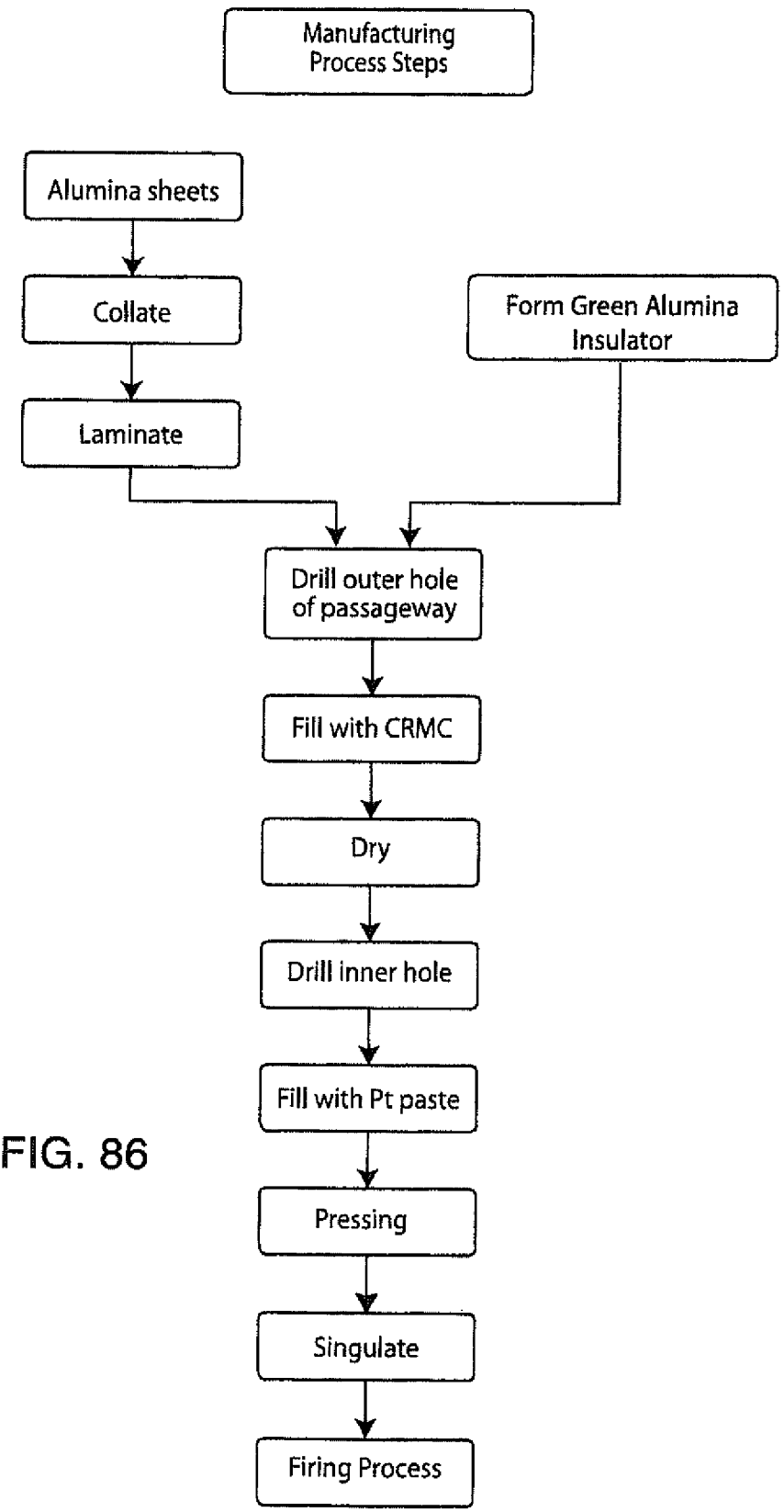
Figure 87:
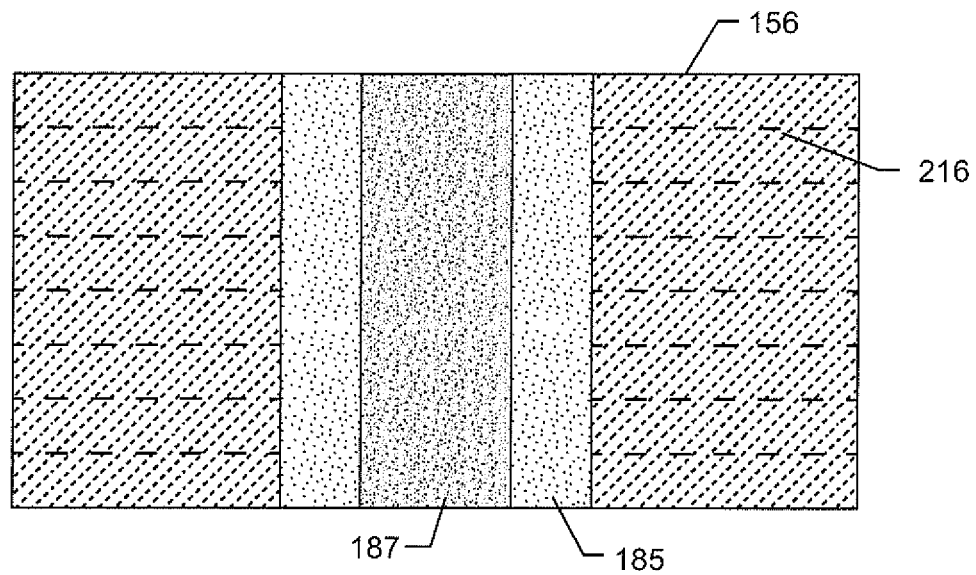
Figure 88:
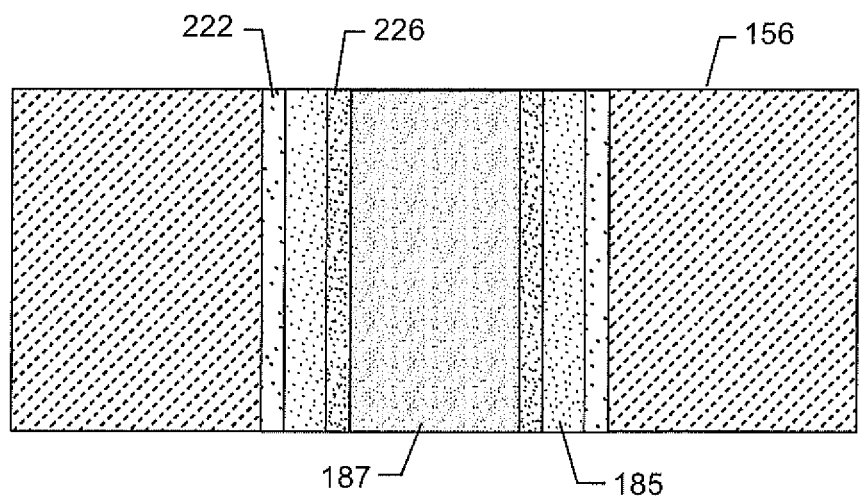

FIG. 83 is a cross-sectional side view taken along lines 83-83 of FIG. 80;

FIG. 84 is a cross-sectional side view illustrating the use of a metal addition for an oxide resistant attachment;

FIG. 85 is cross-sectional side view of another embodiment of the present invention utilizing a two-part pin extending through the insulator;

FIG. 86 is a flow chart including a novel pressing step for a co-fired insulator assembly having a conductive composite sintered paste via for achieving improved hermeticity and durability;

FIG. 87 is a cross-sectional view of the insulator assembly in the green state of FIG. 87 before pressing; and FIG. 88 is a cross-sectional view of the structure of FIG. 88 after the pressing step resulting in a mixing zone between the different structures.

DETAILED DESCRIPTION OF THE PREFERRED EMBODIMENTS

Figure 1:
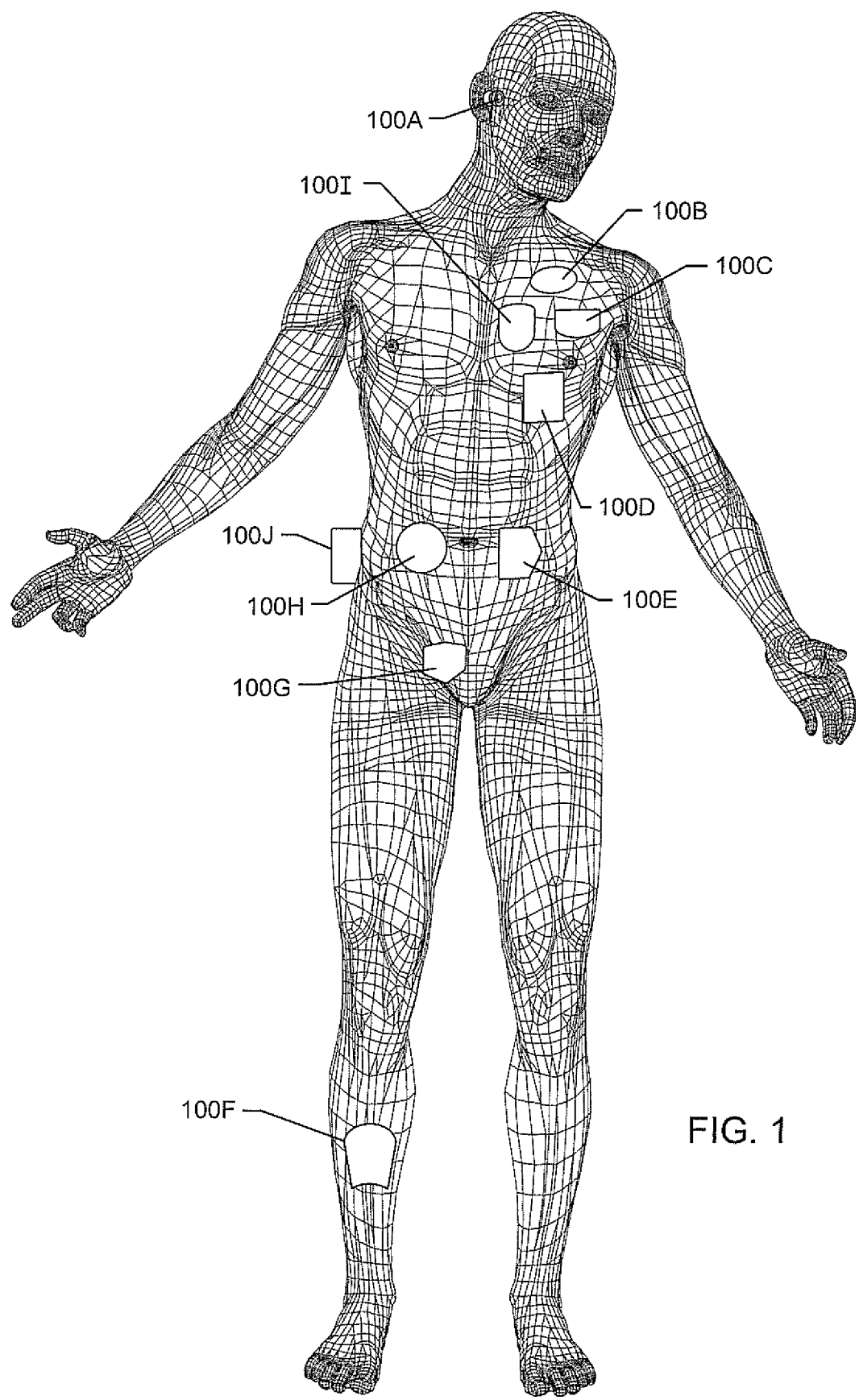
FIG. 1 is a wire-formed diagram of a generic human body showing a number of exemplary implanted medical devices.

FIG. 1 illustrates various types of active implantable medical devices (AIMD) referred to generally by the reference numeral 100 that are currently in use. FIG. 1 is a wire formed diagram of a generic human body showing a number of exemplary implanted medical devices. Numerical designation 100A is a family of implantable hearing devices which can include the group of cochlear implants, piezoelectric sound bridge transducers and the like. Numerical designation 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing, for example, the onset of a seizure and also providing electrical stimulation to brain tissue to prevent a seizure from actually happening. Numerical designation 100C shows a cardiac pacemaker which is well-known in the art. Numerical designation 100D includes the family of left ventricular assist devices (LVAD's), and artificial hearts, including the artificial heart known as the Abiocor. Numerical designation 100E includes an entire family of drug pumps which can be used for dispensing of insulin, chemotherapy drugs, pain medications and the like. Drug pumps are evolving from passive devices to ones that have sensors and closed loop systems. For example, insulin pumps provide real time monitoring of blood sugar levels and can dispense insulin in accordance with the insulin levels sensed. Such active pump devices tend to be more sensitive to EMI than passive pumps that have no sense circuitry or externally implanted leadwires. 100F includes a variety of implantable bone growth stimulators for rapid healing of fractures. Numerical designation 100G includes urinary incontinence devices. Numerical designation 100H includes the family of pain relief spinal cord stimulators and anti-tremor stimulators. Numerical designation 100H includes an entire family of other types of neurostimulators used to block pain. Numerical designation 100I includes a family of implantable cardioverter defibrillator (ICD) devices and also includes the family of congestive heart failure devices (CHF), also known in the art as cardio resynchronization therapy devices or CRT devices. Numerical designation 100J illustrates an externally worn pack. Exemplary externally worn packs include external insulin pumps, external drug pumps, external neurostimulators and even ventricular assist devices.

Referring to U.S. Pat. No. 7,844,319, the content of which is fully incorporated herein by this reference, paragraphs 79 through 82 describe metallic structures, particularly leads, that when placed in MRI scanners, can pick up high electrical fields, which results in local tissue heating. Such local heating tends to be most concentrated at the ends of the electrical structure (either at the proximal or distal lead ends), which is a safety issue. Such heating safety issues can be addressed using the disclosed systems and methods of the present invention. A significant concern is that the distal electrodes, which are in contact with body tissue, can cause local tissue burns, and may even permanently damage tissue at the burn site.

As defined herein, an active implantable medical device (AIMD) includes any device or system that is designed to be totally or partially introduced or implanted within a human body for diagnostic or therapeutic purposes and includes at least one electronic circuitry. AIMDs may have primary or secondary (rechargeable) batteries as their energy sources. AIMDs may also harvest energy from the body either through mechanical motion, body motion, thermal energy, chemical or biochemical battery cell type effects or externally induced ultrasonic energy. An AIMD may also contain a resonant circuit whereby it captures energy from external pulsing electromagnetic field. An example of this is what is known in the industry as the Bion®. In general, AIMDs are connected to either a leadwire or are directly connected to electrodes without a leadwire wherein, these electrodes are contactable to biological cells. AIMD electrodes may be used for therapy delivery, sensing of biological signals or both. AIMDs may also be integrated with fiber optic cables and receive their power or signals optically wherein there is an optical converter which may convert the optical signals to either digital signals or to power.

A subclass of AIMDs is known as cardiac implantable electronic devices (CIEDs). CIEDs include all types of pacemakers, implantable cardioverter defibrillators, implantable loop recorders, subcutaneous ICDs and the like. Another subclass of AIMDs includes all types of neurostimulators, including, but not limited to spinal cord stimulators, deep brain stimulators, urinary incontinence stimulators and the like. An AIMD may include an external component, such as an RF transmitter, an RF telemetry device or even a worn wrist watch, which sends signals to an implanted device and its associated electrodes. In other words, the AIMD, as defined herein can have externally worn components in addition to implanted components.

In general, an AIMD usually has a housing, which is generally conductive and forms an electromagnetic shield (Faraday cage) thereby protecting one or more internal electronic circuits from undesirable electromagnetic interference (EMI). As used herein, the body fluid side of an AIMD is defined as the exterior or the outside of the AIMD housing. Any components residing on the outside of an AIMD housing are on the body fluid side of the AIMD (e.g., header block, therapy delivery leads). The device side of the AMID, also known as an inboard side, is defined as the interior of or the inside the AIMD housing. Any components or electronic circuits residing within an AIMD housing are on the device side of the AIMD (e.g., AIMD active electronic circuit board, the battery and/or capacitor).

It is understood by those skilled in the art that the use of the term body fluid side and device side can be applied to the filter feedthrough assembly before it is installed into the housing of the AIMD. It is known and shown throughout this specification that the filter capacitor is generally installed on the device side of the feedthrough, however, can alternatively be installed on the body fluid side of the feedthrough.

As used herein, the terms insulator substrate and insulator body are synonymous and can be used interchangeably. Furthermore, the terms dielectric, dielectric substrate and dielectric body are synonymous and can be used interchangeably.

As used herein, the word "adjacent" means either adjoining a structure, attached to an adjacent structure, or near an adjacent structure. For example, FIG. 78 describes a capacitor 140 that is mounted adjacent to the ferrule 134 or the insulator 156. Mounted adjacent to the ferrule, in this context, can mean mounted right on the ferrule, mounted right on the insulator or spaced by an air gap or spaced by some sort of an adhesive washer or the like. In this context, adjacent has a broad meaning, simply meaning that the capacitor has to be near or on one of the ferrule or the insulator. Throughout the specification, the word "adjacent" means next to, adjoining, contiguous, on, neighboring, approximate or even slightly spaced away from (such as lying near).

As used herein, the conductive composite paste fill takes on the shape of the insulator passageway within which it is disposed. Post sintering, the paste fill becomes a conductive composite sintered paste fill which forms a solid conductive structure. The conductive composite sintered paste fill conformally forms a hermetic seal within the insulator passageway, thereby separating the body fluid side of the hermetic seal from the device side of the hermetic seal. To one skilled in the art, it is understood that the conductive composite paste fill before sintering does not have a defined shape, but rather is a thick, soft, moist paste filling an insulator passageway. After sintering, the paste takes on a defined shape conformal with that of the insulator passageway.

As used herein, the lead means an implanted lead, including its conductors and electrodes, the electrodes being contactable with body tissue. In general, for an AIMD, the term lead means the lead that is outside of the AIMD housing and is implanted or directed into body tissues. The term leadwire as used herein refers to the wiring or circuit traces that are generally inside of the active implantable medical device (AIMD) and are not exposed directly to body fluids.

Figure 2:
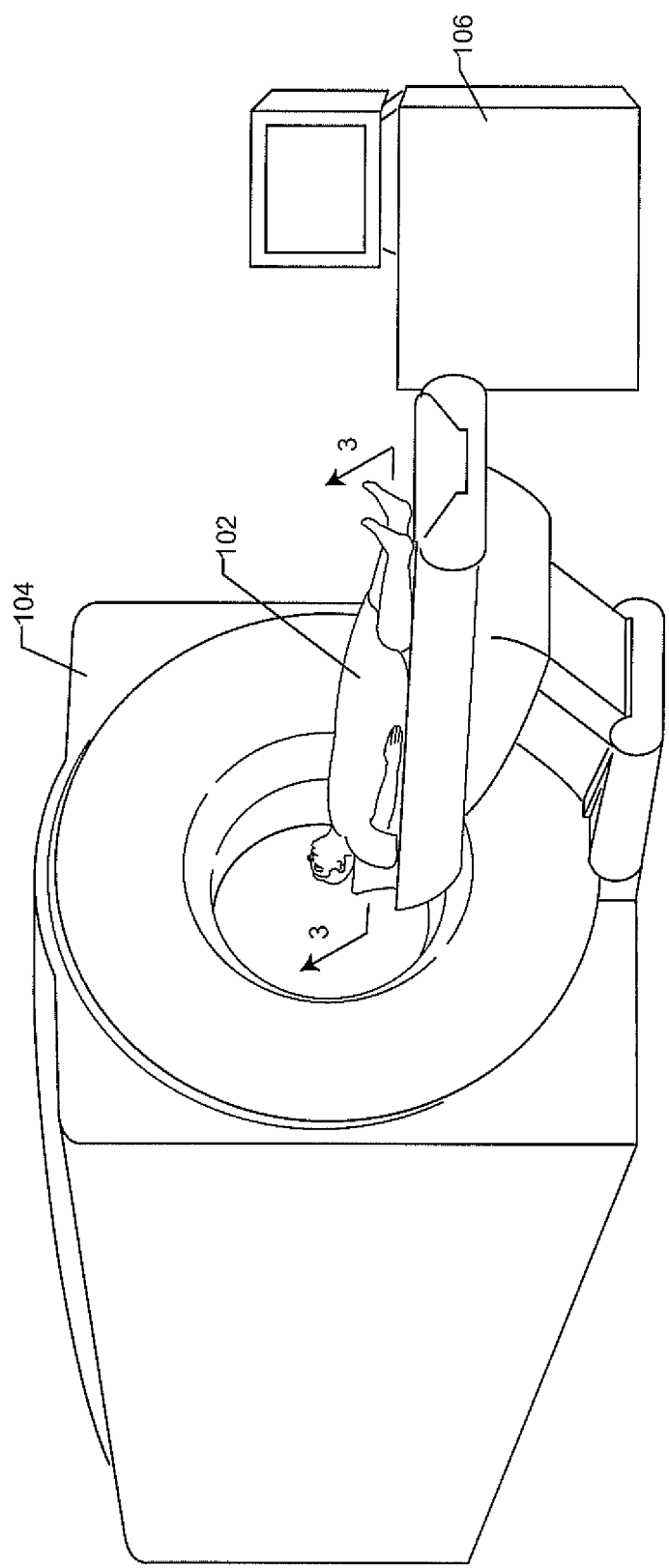
FIG. 2 is a pictorial view of an AIMD patient who is about to be placed into an MRI scanner.

FIG. 2 illustrates an AIMD patient 102 about to be conveyored into an MRI scanner 104. Imaging processing equipment is shown as 106.

Figure 3:
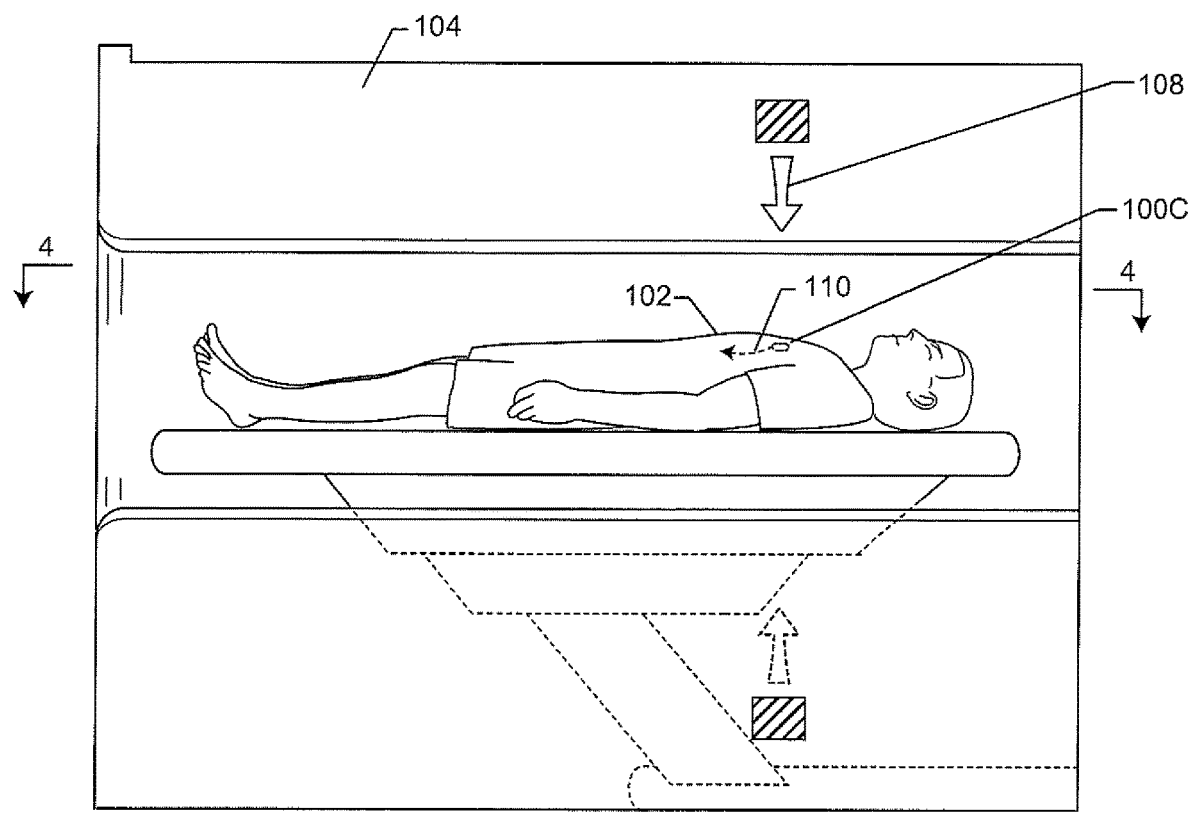
FIG. 3 shows a side view of the patient within the scanner showing an intense RF field impinging on the implanted medical device and its associated lead.

FIG. 3 is a side view showing the AIMD patient 102 within the bore of an MRI scanner 104. An intense RF-pulse field 108 is generated by the scanner's bird cage coil. As can be seen, this RF field is impinging on both the implanted cardiac pacemaker 100C and its associated leads 110.

Figure 4:
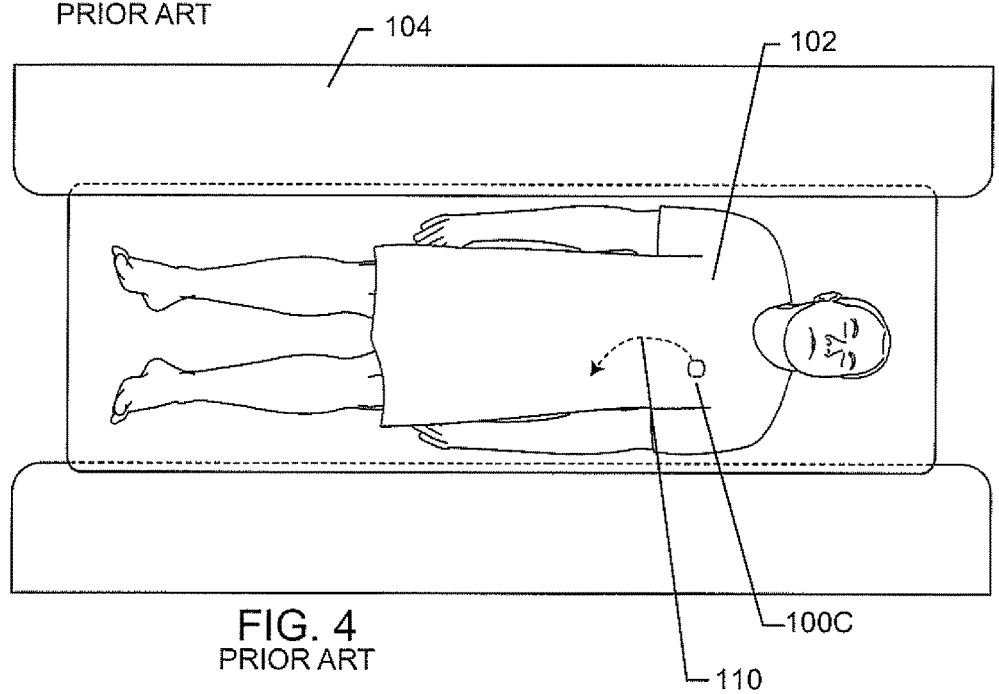
FIG. 4 is a top view of the patient in the MRI scanner showing one location of the AIMD and its associated lead.

FIG. 4 is a top view of the AIMD patient 102 inside the bore of the MRI scanner 104. As can be seen, the implanted cardiac pacemaker 100C is in a left pectoral pocket with the leads 110 routed transvenously into the interior chambers of the human heart.

Figure 5:
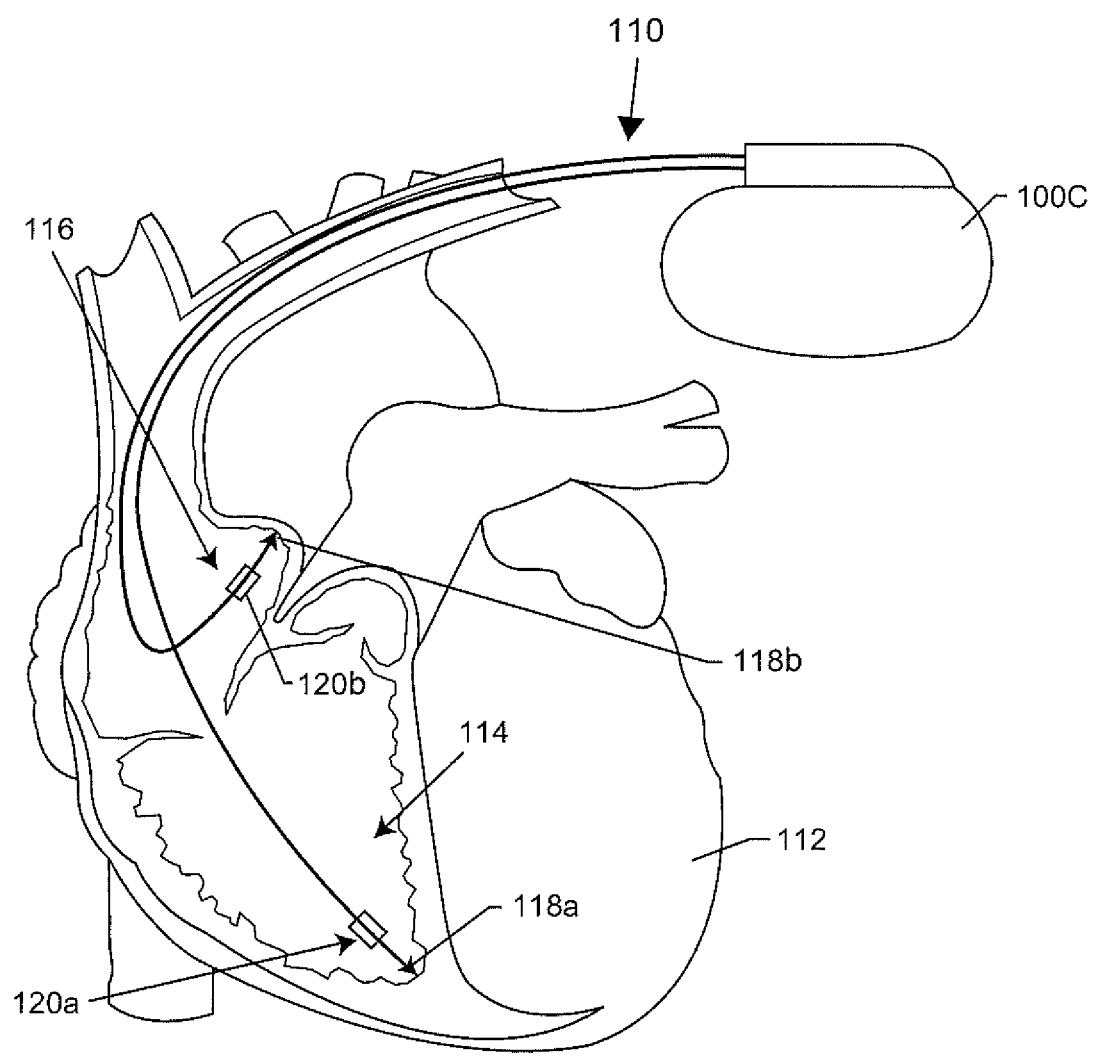
FIG. 5 is a line drawing of a human heart with cardiac pacemaker dual chamber bipolar leads shown in the right ventricle and the right atrium.

FIG. 5 is a line drawing of a human heart 112 and an implantable cardiac pacemaker 100C having dual chamber bipolar leads 110 shown in the right ventricle 114 and the right atrium 116.

Referring once again to FIG. 5, as previously mentioned, it is very important that the leads 110 of the implantable cardiac pacemaker 112 do not overheat during MRI procedures particularly at or near the distal tip electrodes 118a, 118b and ring electrodes 120a, 120b. If either or both the distal tip electrodes 118a, 118b and ring electrodes 120a, 120b become overgrown by body tissue, excessive overheating can cause scarring, burning or necrosis of the heart tissue. This can result in loss of capture (loss of pacing pulses) which can be life-threatening for a pacemaker dependent patient.

Figure 6:
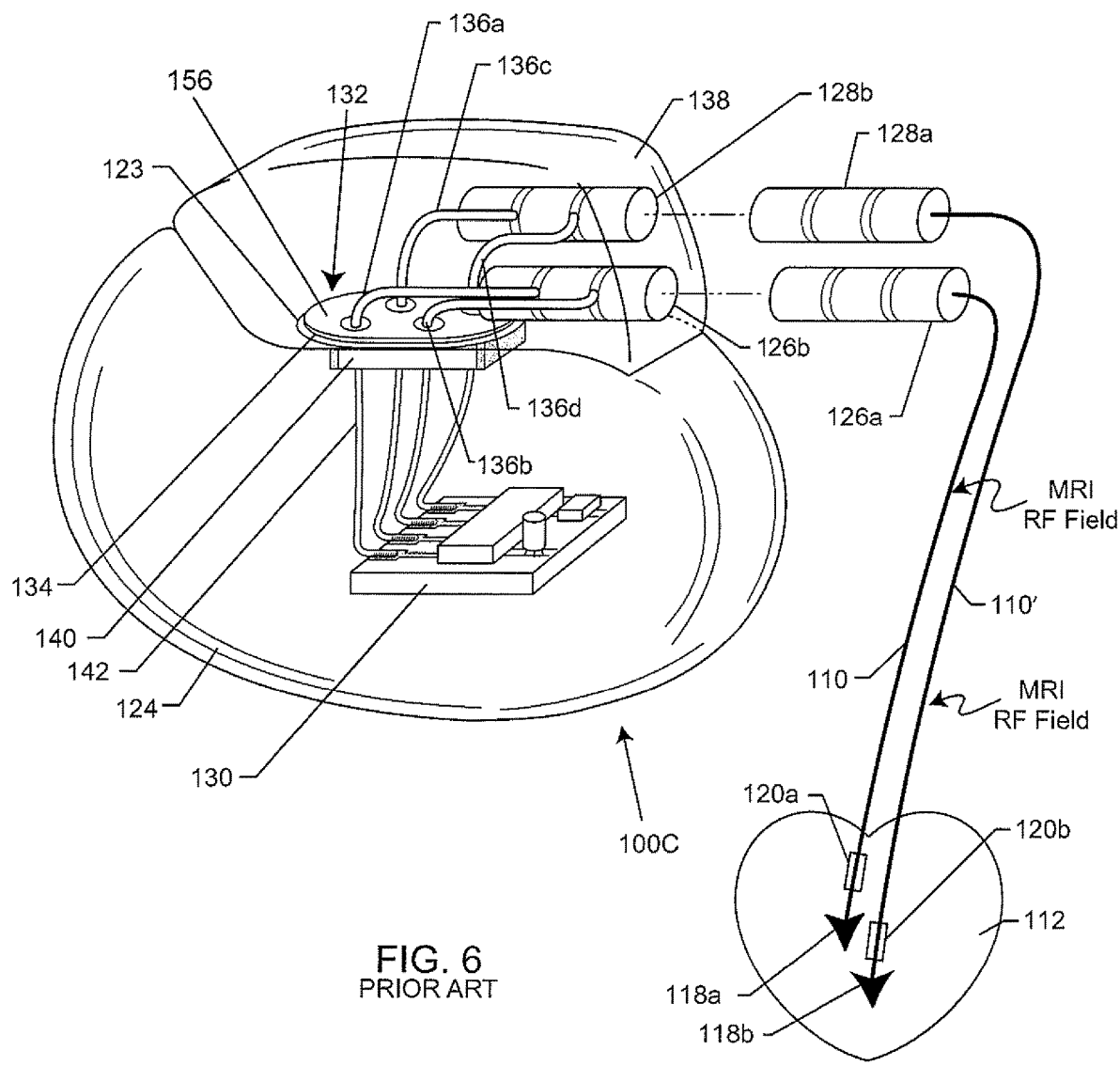
FIG. 6 illustrates a dual chamber cardiac pacemaker with its associated leads and electrodes implanted into a human heart.

FIG. 6 is similar to FIG. 2 taken from U.S. Pat. No. 10,350,421, the content of which is fully incorporated herein by this reference. FIG. 6 illustrates a dual chamber implantable cardiac pacemaker 100C with its bipolar leads 110, 110'. The distal tip electrodes 118a and 118b and distal ring electrodes 120a and 120b of the bipolar leads 110, 110' are shown routed to a human heart. During an MRI scan, the leads 110, 110' are exposed to a powerful RF-pulse field which induces electromagnetic energy on the leads. As the leads 110, 110' are electrically connected to such electronic circuitry through the ISO Standard IS-1 or DF-1 connectors 126a, 126b, 128a, 128b of the header block 138, the electromagnetic energy induced in the leads 110, 110' can undesirably couple to sensitive electronic circuitry inside of the hermetically sealed pacemaker housing 124, thereby potentially causing dangerous AIMD malfunction. The header block 138 electrically connects leads 110, 110' to the AIMD circuit board 130 by way of the leadwires 136a through 136d of the hermetic feedthrough 132. The hermetic feedthrough 132 is shown with a metal ferrule 134, which is generally laser welded into the AIMD housing 124 of the cardiac pacemaker 100C. Leadwires 136a through 136d extend through the insulator hermetically sealed to the ferrule 134 of the hermetic feedthrough 132.

Referring once again to FIG. 6, illustrated is a hermetic feedthrough 132, which is typically laser welded into an opening 123 of the titanium housing 124 of the implantable cardiac pacemaker 100C, thereby hermetically sealing the pulse generator of the implantable cardiac pacemaker 100C. The hermetic seal of the pulse generator of the implantable cardiac pacemaker 100C keeps body fluids from getting into the inside of the pacemaker housing 124. The hermetic feedthrough 132 typically comprises an electrically conductive ferrule 134 comprising a ferrule opening 131 (not labelled) extending to a ferrule body fluid side opposite a ferrule device side and an insulator 156 residing in the ferrule opening wherein a gold braze hermetically seals the insulator to the ferrule.

Figure 7:
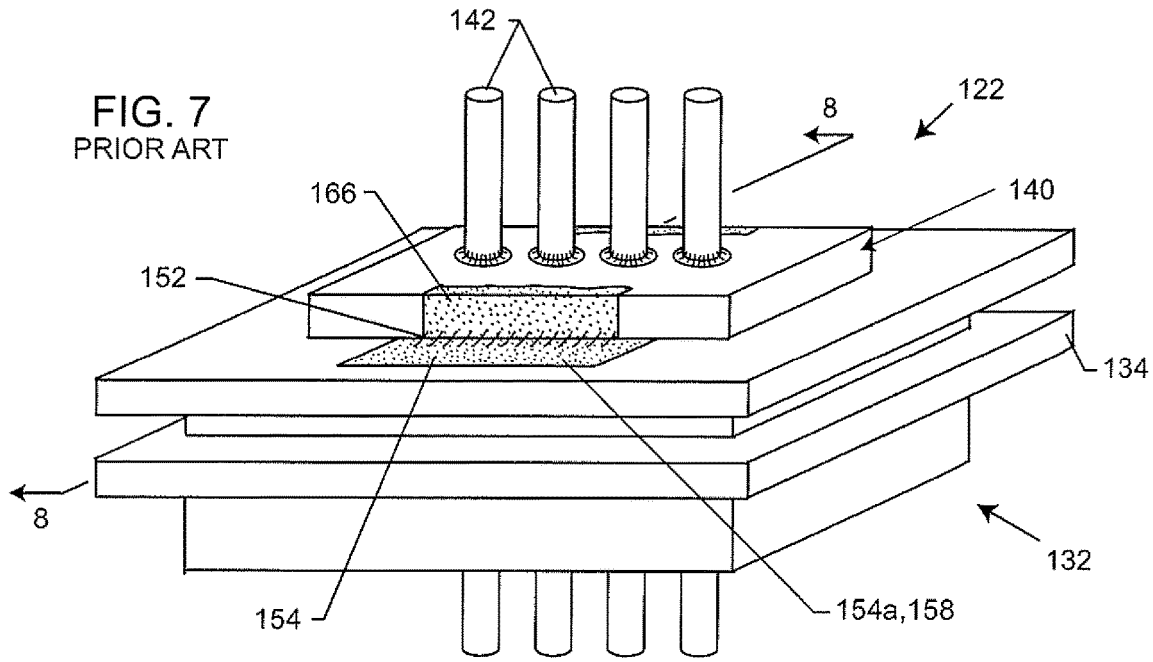
FIG. 7 is an isometric view illustrating the rectangular feedthrough capacitor mounted to a hermetic terminal.
Figure 8:
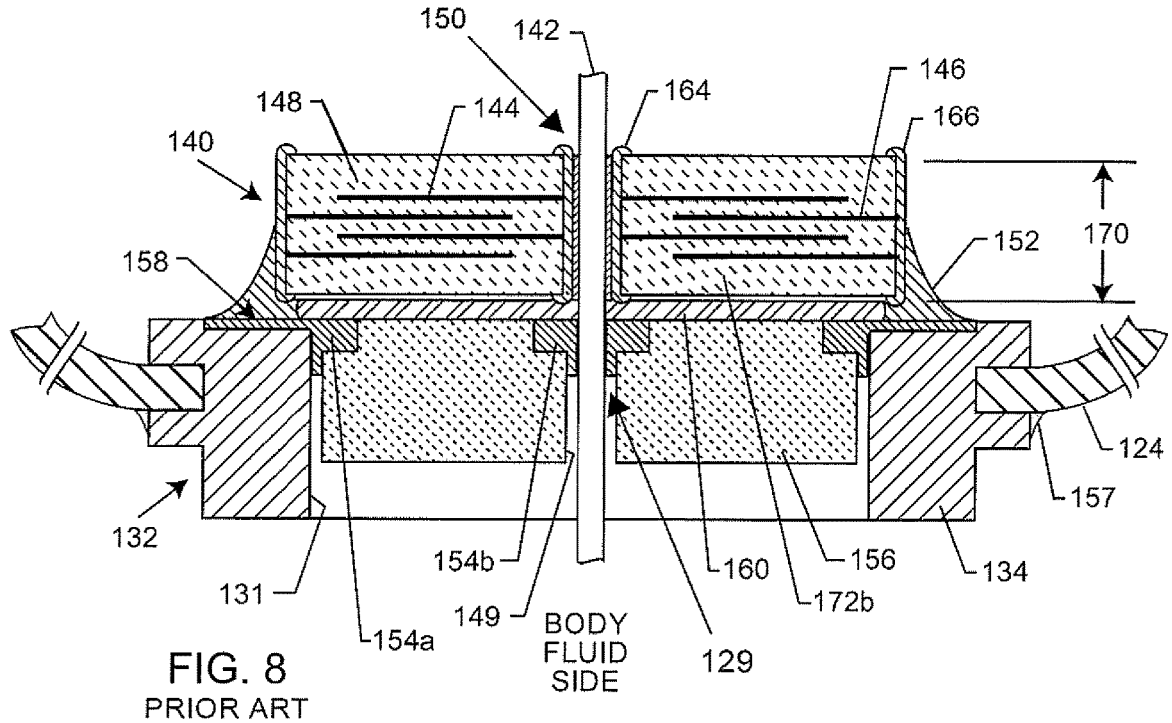
FIG. 8 is an enlarged cross-sectional view taken generally along the line 8-8 of FIG. 7.

FIG. 6 illustrates feedthrough conductive pathways 129 (not labelled) comprising leadwires 136a through 136d passing through an insulator passageway 149 (not labelled) in non-conductive relation with the ferrule 134 of the hermetic feedthrough 132, the leadwires 136a through 136d extending to a body fluid side and a device side of the implantable cardiac pacemaker 100C. The hermetic feedthrough 132 of the implantable cardiac pacemaker 100C may comprise a glass, a glass-ceramic, or a ceramic insulator 156. The hermetic feedthrough further comprises a leak rate no greater than $1 \times 10^{-7}$ std cc He/sec. As illustrated in FIG. 6, the hermetic feedthrough 132 comprises a feedthrough filter capacitor 140, which is mounted adjacent to one of the ferrule 134, the insulator 156 or both the ferrule and the insulator of the hermetic feedthrough 132. An embodiment of an exemplary hermetic feedthrough 132 comprises an alumina insulator 156 gold brazed to a titanium ferrule 134, the insulator comprising at least one insulator passageway 149 disposed through the insulator 156. The at least one insulator passageway 149 extends to a body fluid side and to a device side of the insulator 156. The at least one insulator passageway 149 comprises a feedthrough conductive pathway 129 disposed therewithin, the feedthrough conductive pathway 129 being hermetically sealed to the at least one insulator passageway. The feedthrough conductive pathway 129 comprises an electrical conductor. The electrical conductor of the hermetic feedthrough 132 is selected from the group consisting of a leadwire, a lead wire, a terminal pin, a pin, a two-part pin, a lead conductor, a sintered conductive via, a sintered paste-filled via, a co-sintered via, a co-sintered paste-filled via, a co-sintered via with one or more metallic inserts, or combinations thereof. FIGS. 7 and 8 provide another exemplary hermetic feedthrough embodiment in accordance with the teachings of FIG. 6.

FIGS. 7 and 8 illustrate an exemplary rectangular quad polar (planar array) feedthrough filter capacitor 140 mounted to the hermetic feedthrough 132 of a cardiac pacemaker in accordance with U.S. Pat. No. 5,333,095 to Stevenson et al., the content of which is fully incorporated herein by this reference. It is understood that a feedthrough filter capacitor 140 may be mounted adjacent to one of the ferrule 134, the insulator 156, or both the ferrule and the insulator of the hermetic feedthrough 132. Once a filter capacitor is placed on the hermetic feedthrough 132, then the assembly is considered a filtered feedthrough 122.

Figure 11:
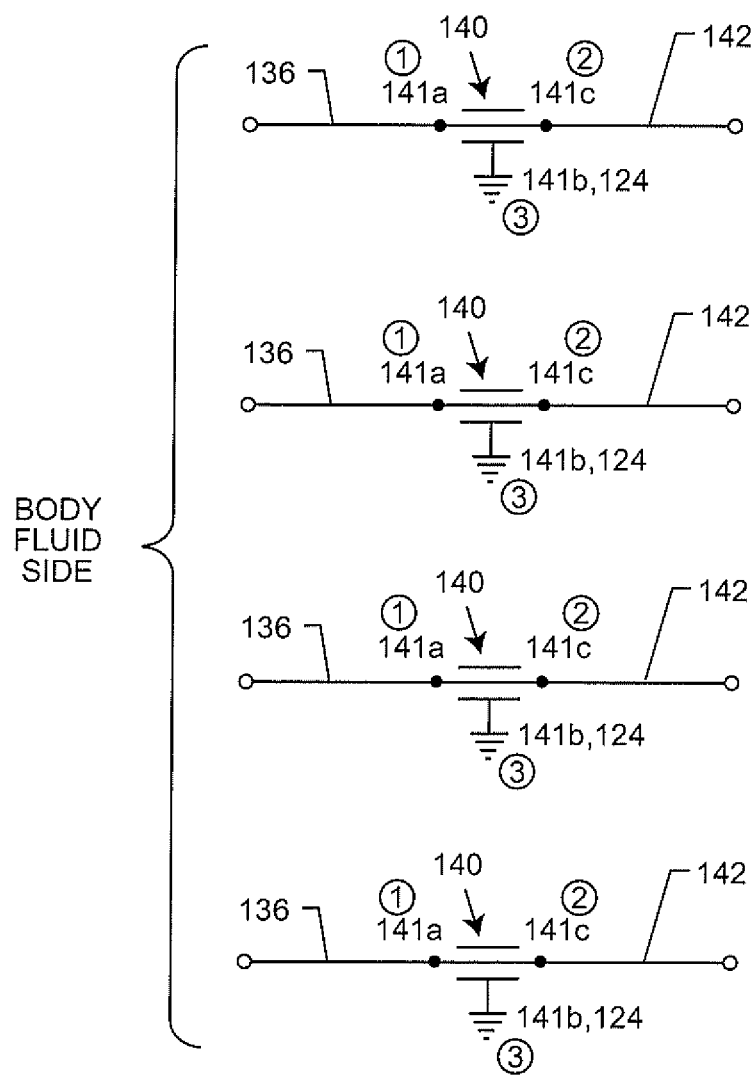
FIG. 11 is an electrical schematic diagram of the quad polar feedthrough capacitor of FIGS. 7-10.

As illustrated in FIGS. 7 and 8, in a typical broadband or lowpass EMI filter construction, a ceramic feedthrough filter capacitor 140 is electrically connected to a hermetic feedthrough 132 to suppress and decouple undesired interference or noise transmission along one or more terminal pins 142. The feedthrough filter capacitor 140 comprises active electrode plates 144 and ground electrode plates 146, which are embedded in spaced relation within a dielectric body 148. The feedthrough filter capacitor 140 is typically formed as either a ceramic monolithic or a ceramic multi-layered structure. The active electrode plates 144 are electrically connected to an inner diameter cylindrical surface to an active capacitor metallization 164 of the feedthrough filter capacitor 140 and to the active terminal pins 142 so that the desired electrical signal or signals may pass along an active conductive path (FIG. 11 illustrates the electrical schematic diagram). The ground electrode plates 146 are electrically coupled to a ground capacitor metallization 166 at a sidewall of the dielectric body 148, the ground capacitor metallization in this embodiment being an outer edge metallization of the feedthrough filter capacitor 140. The ground capacitor metallization 166 is shown electrically connected to a gold pocket-pad 158 of a rectangular electrically conductive ferrule 134 using an electrically conductive material 152. The gold pocket-pad 158 embodiment of FIG. 8 is a part of the gold braze 154a hermetically sealing the insulator 156 of the hermetic feedthrough 132 to the ferrule 134. It is noted that the structure of the gold pocket-pad 158 may be a separate pocket structure from the gold braze hermetically sealing the insulator to the ferrule or may be a gold pocket-pad area that is a structural extension of the gold braze hermetically sealing the insulator to the ferrule as shown in FIG. 8. As used herein, a gold pocket-pad that is separate from the gold braze hermetically sealing the insulator to the ferrule and a gold pocket-pad area that is a structural extension of the gold braze hermetically sealing the insulator to the ferrule each provide oxide-resistant electrical attachment to a feedthrough filter capacitor 140. In the prior art, without regard to high frequency capacitor ESR, the number and dielectric thickness spacing of the active electrode plates 144 and the ground electrode plates 146 will vary in accordance with the capacitance value and the voltage rating of the feedthrough filter capacitor 140.

In operation, the coaxial feedthrough filter capacitor 140 permits passage of relatively low frequency electrical signals along the terminal pins 142, while also shielding and decoupling/attenuating undesired interference signals of typically high frequency to the conductive housing 124. Feedthrough filter capacitors 140 of this general type are available in unipolar (one), bipolar (two), tripolar (three), quad polar (four), pentapolar (five), hexpolar (6), "n" polar and can be designed to accommodate various terminal pin design configurations and/or terminal pin design layouts. Such feedthrough filter capacitors 140 can further be of various shapes, for example, round, oval, rectangular, discoidal and even custom configurations. Such feedthrough filter capacitors 140 are commonly employed in active implantable medical devices (AIMD) such as implantable cardiac pacemakers, defibrillators, neurostimuators and the like, wherein the AIMD housing 124 of these AIMDs is constructed from a biocompatible metal such as, but not limited to, titanium or a titanium alloy. As a result, the filter capacitor and hermetic feedthrough prevent entrance of interference signals to the interior of the pacemaker housing 124, wherein such interference signals can otherwise adversely affect the desired cardiac pacing, defibrillation or neurostimulation function.

As illustrated in FIG. 7, the electrically conductive material 152 (for example, an electrically conductive polyimide, an electrically conductive adhesive, an electrically conductive epoxy, an electrically conductive thermal-setting polymer or a solder) connects the ground capacitor metallization 166 and the gold pocket-pad area 158. The gold pocket-pad area 158 forms a metallurgical bond with the titanium of the ferrule 134 of the hermetic feedthrough 132 and precludes any possibility of an unstable oxide forming. Gold is a noble metal that does not readily oxidize and remains very stable even at elevated temperatures. The novel gold braze structure and construction methodology illustrated in FIG. 7 guarantee that the ohmic losses of the feedthrough filter capacitor 140 will remain very small at all frequencies. By connecting the ground electrode plates 146 of the feedthrough filter capacitor 140 to a low resistivity oxide-resistant material such as the gold pocket-pad area 158, one is guaranteed that this electrical connection will not substantially contribute to the overall ESR of the feedthrough filter capacitor 140. Keeping the ESR of the feedthrough filter capacitor 140 as low as possible is very important for diverting a high amount of RF current such as is induced in the AIMD lead system during MRI scanning. One is referred to U.S. Pat. No. 6,765,779 to Stevenson et al. for additional information on electrically connecting to oxide-resistant materials, the content of which is fully incorporated herein by this reference.

FIG. 8 is a cross-section of feedthrough filter capacitor 140 and the hermetic feedthrough 132 of FIG. 7. One can see that the gold braze 154*a* that forms the hermetic seal between the alumina insulator 156 and the titanium ferrule 134 is desirably on the feedthrough capacitor side. This makes it easy to manufacture the gold pocket-pad area 158 for convenient attachment by the electrically conductive material 152. In other words, designing the gold pocket-pad area 158 on the same side as the gold braze 154*a* hermetically sealing the insulator 156 to the ferrule 134 permits the gold pocket-pad 158 to be co-formed at the same time as the gold braze 154*a* is formed in one manufacturing operation in a gold braze vacuum furnace regardless of whether the gold pocket-pad area is structurally a part of the gold braze hermetic seal or a separate gold pocket-pad spaced apart from the gold braze hermetic seal. FIG. 8 also illustrates an insulative material 160 (which can be an insulating washer) disposed between the feedthrough filter capacitor 140 and the underlying hermetic feedthrough 132. As illustrated, the insulator 156 is at least partially disposed within a ferrule opening 131. Also shown is an insulator passageway 149 formed in the insulator 156 allowing a terminal pin 142 or a leadwire 136 (such as illustrated in FIG. 6) to be hermetically sealed by gold braze 152*b*. The terminal pin 142 of FIG. 8 extends to the body fluid and device sides of the hermetic feedthrough 132. The device side portion of the terminal pin 142 further extends through a capacitor conductive pathway 150 of a feedthrough filter capacitor 140.

Figure 9:
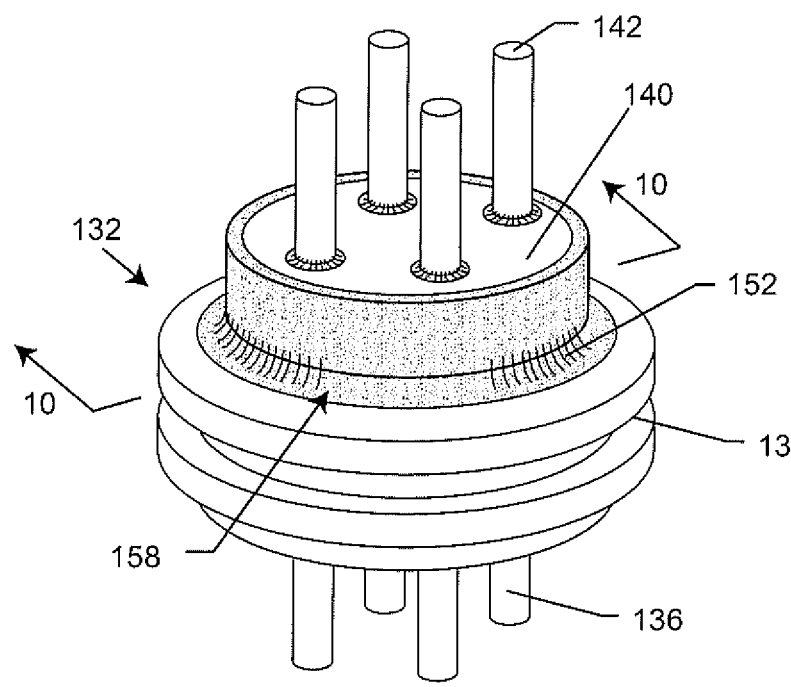
FIG. 9 is an isometric view of a round hermetic terminal showing a quad polar RF diverter feedthrough capacitor.

FIG. 9 is a quad polar feedthrough filter capacitor 140 mounted to a hermetic feedthrough 132 similar to that described in FIG. 7 except that, in this case, the filter capacitor structure is round or discoidal. It is understood that a filtered feedthrough may comprise any filter capacitor shape instead of a round or discoidal filter capacitor, such as oval, rectangular, square and custom designed filter capacitor shapes.

Figure 10:
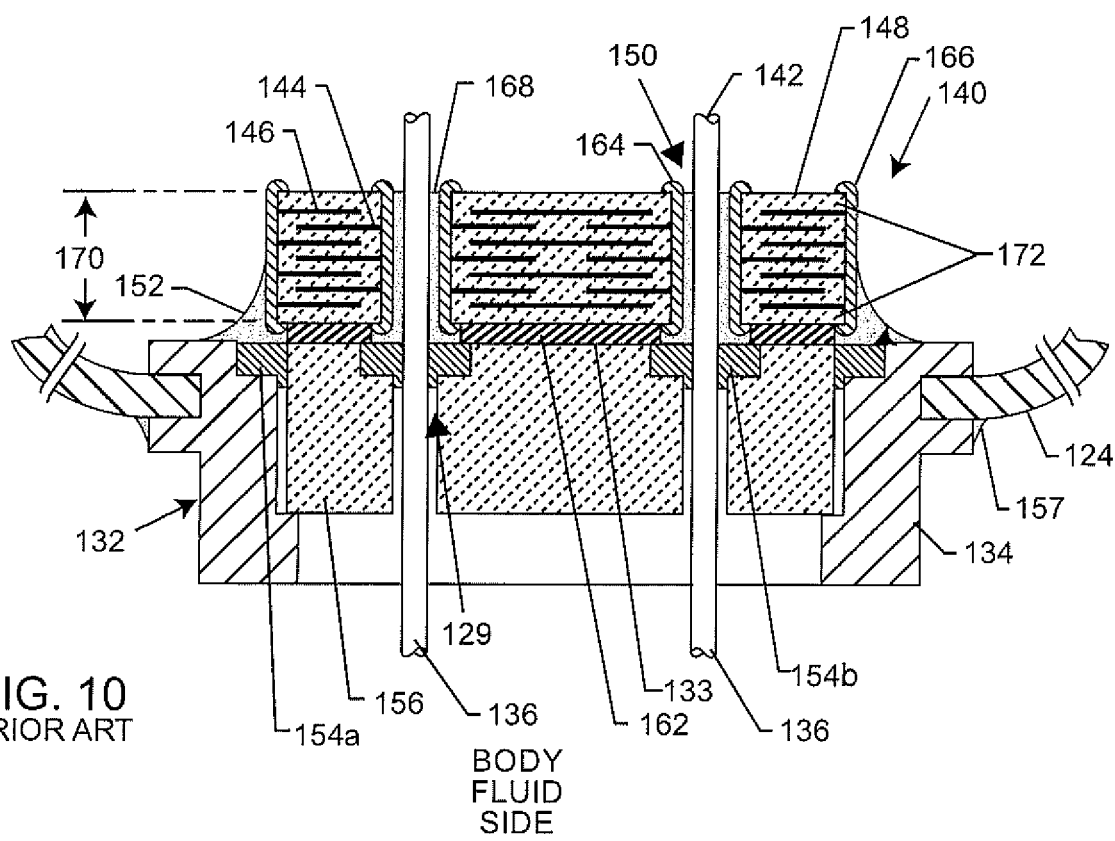
FIG. 10 is an enlarged cross-sectional view taken generally along the line 10-10 from FIG. 9.

FIG. 10 is a cross-sectional view taken generally from section 10-10 of FIG. 9. There are four feedthrough terminal pins 142 each residing in a feedthrough conductive pathway 129, which extend through the feedthrough filter capacitor 140. The feedthrough filter capacitor comprises ground electrode plates 146 and active electrode plates 144.

As shown in FIG. 10, there are only three active electrode plates 144 and four ground electrode plates 146. This low electrode plate count results in a feedthrough filter capacitor 140 that has a relatively high ESR at high frequencies. In an experiment conducted by the inventors, a typical EIA X7R 400-picofarad capacitor with only four electrode plates had an ESR at 64 MHz of 4.8 Ohms. Re-design of the same geometry (size) capacitor with an EIA NP0 dielectric for a 400-picofarad capacitor with over 20 electrode plates resulted in an ESR at 64 MHz of approximately 300 milliohms (0.3 Ohms). This sixteen to one reduction at 64 MHz is a dramatic illustration of the importance of designing the AIMD MRI diverter feedthrough filter capacitor 140 for low ESR. For example, for an X7R capacitor, the impedance is the square root of the sum of the capacitor's reactance squared plus the ESR squared. A 400-pF capacitor has a reactance of 2.49 ohms at 64 MHz. This results in a capacitor impedance Z which is equal to −j2.49+4.8 or approximately 5.41 Ohms. Assuming an MRI induced RF voltage at the AIMD input at 64 MHz of 10 Volts, the RF current diverted through the X7R capacitor is 10 Volts divided by 5.41 Ohms which is 1.85 Amps. The power dissipation due to the X7R capacitor's ESR ($I^2R$) is $(1.85)^2(4.8)=16.43$ Watts. This amount of power dissipation is excessive for such a small component and will cause a temperature rise of over 20° C. On the other hand, a 400-pF NP0 capacitor's impedance is equal to −j2.49+0.3 or Z=2.51 Ohms. This lower impedance will result in a much better filter (higher attenuation) and will drop the RF voltage from 10 Volts to approximately 3.71 Volts. This voltage drop is caused by the lead's characteristic impedance and the fact that more current has been drawn through this impedance. This causes a voltage drop in the lead's characteristic impedance as measured at the input to the AIMD. The RF current through the NP0 capacitor is then 3.71 Volts divided by Z of 2.51 Ohms which is 1.48 Amps. The power dissipation ($I^2R$) is $(1.48\text{ Amps})^2(0.3\text{ Ohm})$ which equals 0.66 Watts which will result in a much smaller temperature rise. Accordingly, the low ESR diverter feedthrough filter capacitor design (FIG. 32 labelled 210 and FIG. 34 labelled 210') of the present invention offers the following advantages: (1) a much lower impedance at 64 MHz and therefore a more effective EMI filter; (2) higher attenuation, therefore acts to reduce the MRI induced RF voltage at the input to the AIMD; and (3) as will be shown, the diverter feedthrough filter capacitor 210, 210' can be designed to conduct or convect heat away for dissipation over a larger surface area.

The above examples of ESR and impedance are just illustrative examples of many thousands of possibilities. For active implantable medical devices, in general, capacitance values range anywhere from 300-pF to 15,000-pF. Each design has a different physical geometry, size and number of internal electrode plates. In other words, there are many other examples that have different values of ESR. The general principles illustrated above, however, do apply across the board for all such capacitor design variations. Low k dielectrics will always mean a higher number of electrode plates and therefore a lower ESR. That means that the low ESR designs will have much less heating of the capacitor itself in an MRI environment.

The feedthrough filter capacitor 140 is bonded with an insulating washer 162 (which comprises an insulative material) to the hermetic feedthrough 132. An electrically conductive material 152, such as an electrically conductive polyimide, an electrically conductive adhesive, an electrically conductive epoxy, an electrically conductive thermal-setting polymer or a solder, attaches the outside diameter ground capacitor metallization 166 of the feedthrough filter capacitor 140 and the gold braze 154a. The necessity to make an oxide-resistant (that is, an essentially oxide-free) attachment between the feedthrough filter capacitor 140 and the ferrule 134 is described in U.S. Pat. No. 6,765,779, the content of which is fully incorporated herein by this reference. The insulator 156 of FIG. 10, such as an alumina ceramic, is hermetically sealed to the ferrule 134 by means of a gold braze 154a. It is understood that the insulator 156 may alternatively comprise a glass or a glass-ceramic, which may form either a hermetic compression seal or a hermetic matched seal. As glass-based seals are generally fusion seals, instead of a hermetic gold braze 154a, an oxide-resistant pocket-pad or a gold pocket-pad area 158 such as disclosed by FIG. 8 is used to make an oxide-resistant attachment to the feedthrough filter capacitor 140. The four terminal pins 142 of FIG. 10 are hermetically sealed to the insulator 156 via gold braze 154b (as there are four terminal pins 142, there are four gold brazes 154b), each brazed terminal pin forming a feedthrough conductive pathway 129. The four terminal pins 142 are attached to the active electrode plates 144 of the feedthrough filter capacitor 140 using an electrically conductive material 168, such as an electrically conductive polyimide, an electrically conductive adhesive, an electrically conductive epoxy, an electrically conductive thermal-setting polymer or a solder. The electrically conductive material 168 electrically connects the active capacitor metallization 164, which is electrically connected to the active electrode plates 144 of the feedthrough filter capacitor, thereby forming four capacitor conductive pathways 150, each conductive pathway comprising one of the four terminal pins 142 of the hermetic feedthrough 132.

Referring once again to FIG. 8, one can see that there are only two active electrode plates 144 and two ground electrode plates 146. A low electrode plate count is typically the case for prior art feedthrough filter (diverter) capacitors 140 used in AIMD applications such as cardiac pacemakers, ICDs and the like, so that a capacitance value is generally kept low, as a high capacitance value loads down the output of an AIMD. For example, too high of a capacitance value distorts pacemaker therapeutic pulses and also rob energy from the active implantable medical system. An even more extreme example is in the case of an implantable cardioverter defibrillator, where a filter capacitance value is too high such that the high voltage monophasic or biphasic shock wave form is seriously degraded. In the experience of the inventors, the capacitance value for an AIMD diverter feedthrough filter capacitor 140 is in a relatively narrow range from 10 picofarads to 20,000-picofarads. In most cases, the capacitance value is between 350 picofarads and 10,000-picofarads. Having a capacitance value between these ranges effectively attenuates most emitters from which AIMDs can be affected. This includes microwave ovens, cellular telephones and the like, which typically operate in the GHz frequency range. The thickness 170 of the feedthrough filter capacitor 140, however, cannot be below a certain minimum or the barium titanate based ceramic capacitor dielectric body 148 becomes too fragile. The entire hermetic feedthrough 132 and the feedthrough filter capacitor 140 must be able to withstand thermal cycles and shocks including installation of the filtered feedthrough into the AIMD housing 124 by a laser weld 157. Accordingly, it is very unusual to see the thickness 170 of a diverter feedthrough filter capacitor 140 less than 20/1000 of an inch (0.020 inches or 20 mils). Notwithstanding, when one looks at a cross-section of a typical prior art feedthrough filter capacitor 140 for human implant, one sees that there are very few electrode plates 144, 146 relative to the overall thickness 170 of said feedthrough filter capacitor. In fact, there are usually a number of blank dielectric cover sheets/layers 172 (blank meaning that there are no electrode plates on the dielectric cover sheets/layers) added on the top and/or bottom of the feedthrough filter capacitor 140 consisting of ceramic material which is co-fired to add mechanical strength. There is a serious downside, however, to having very few electrode plates 144, 145, and that is that the high frequency equivalent series resistance (ESR) of the capacitor increases. For example, prior art AIMD diverter feedthrough filter capacitors 140 having significant dielectric and/or ohmic resistance at high frequencies simply does not matter. This is because the power induced from a typical emitter, such as a cellular telephone or microwave oven results in a trivial amount of RF current flowing through the diverter feedthrough filter capacitor 140. Even in the most extreme examples, only a few milliwatts of heat is generated within the capacitor structure itself. For high power RF current handling applications, however, for example, MRI conditional AIMDs that require diverting of the MRI induced RF energy, the capacitor dielectric loss and high frequency ESR become critical and must be kept as low as possible. Accordingly, it is a feature of the present invention to have a relatively high number of electrode plates 144, 146 (generally greater than 10 active and 10 ground). It is noted, however, that a high number of electrode plates in a feedthrough filter capacitor comprising a high k barium titanate based ceramic dielectric with a dielectric constant of around 2,500 as typically used in the prior art, results in a very high (too high) capacitance value. The present application resolves this issue through the use of a relatively low dielectric constant material, such as EIA Standard NP0 material. NP0 material has a much lower k (generally, in the area of 60 to 90). A low k dielectric material is defined herein as having a k greater than 0 but less than 1,000, referred herein as k<1,000. In some embodiments, a low k dielectric material has a k greater than 0 but less than 200, k<200. In some embodiments, a low k dielectric material has a k greater than 0 but less than 100, k<100. Accordingly, in order to achieve a desired capacitance value (in the range of 350 picofarads to 10,000 picofarads or the range of 10 picofarads to 20,000 picofarads as previously disclosed), a much greater number of electrode plates is required. The higher number of electrode plates creates more parallel paths for RF current flow and greatly reduces the ESR of the feedthrough capacitor. One is referred to the equation illustrated in FIG. 22 to understand the relationship between capacitance and the number of electrode plates and other factors.

FIG. 11 is a schematic diagram of the quad polar feedthrough capacitor 140 of FIGS. 7-10. Feedthrough capacitors are three-terminal devices labelled in FIG. 11 as 141a (terminal 1), 141b (terminal 3), and 141c (terminal 2).

Figure 12:
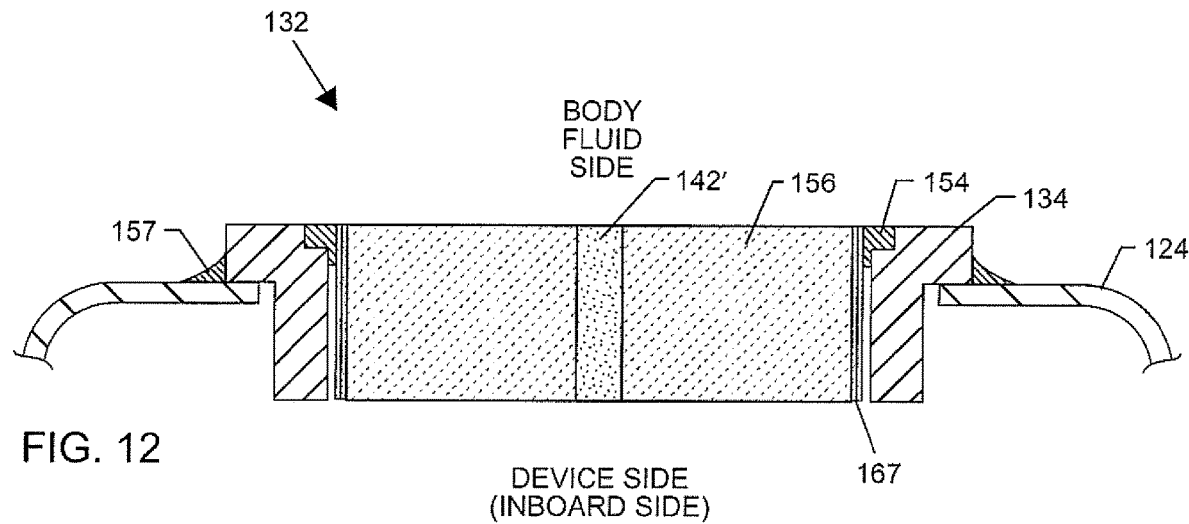
FIG. 12 is a cross-sectional view of an embodiment of a hermetic terminal subassembly installed in a housing of an AIMD.
Figure 17:
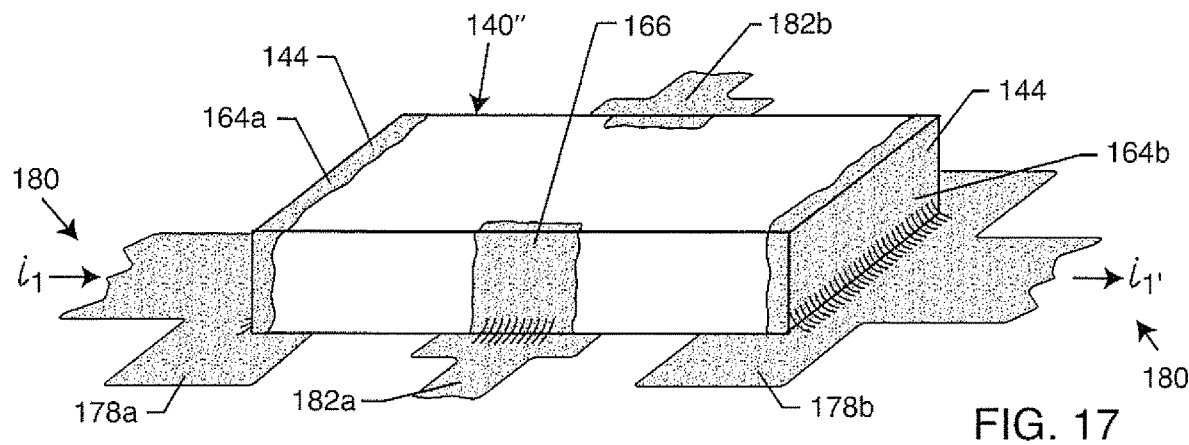
FIG. 17 is an isometric view of a flat-through three-terminal capacitor.

FIG. 12 is a cross-sectional view of an embodiment of a novel hermetic feedthrough installed in a housing of an AIMD taken from FIG. 17 of U.S. Pat. No. 8,653,384, the content of which is fully incorporated herein by this reference. The outer surface of the insulator 156 (which may be a ceramic insulator, for example, an alumina insulator) of the hermetic feedthrough 132 has an insulator external metallization 167 disposed at least partially on the outer surface of the insulator. The insulator external metallization 167 may comprise two metallization layers, an adhesion metallization layer and a wetting metallization layer, wherein the adhesion metallization layer may be disposed at least partially on the outside surface of the insulator 156, and wherein the wetting metallization layer may be disposed on the adhesion metallization layer so that during brazing a braze 154 (such as a gold braze) melts and hermetically bonds to the insulator 156 and the ferrule 134 of the hermetic feedthrough 132. The braze 154 contacting the insulator external metallization 167 of the insulator 156 and the electrically conductive ferrule 134 thereby forms the hermetic seal between the insulator and the ferrule. It is understood that, while two metallization layers are illustrated, the insulator external metallization 167 may only comprise one metallization layer or may comprise more than two metallization layers. The ferrule 134 may be installed into the AIMD housing 124 by forming a laser weld 157, however, other joining processes such as brazing, micro welding, micro TIG welding, ultrasonic welding, resistance welding, friction welding, butt welding, arc welding, gas welding, projection welding, flash welding, upset welding, solid state welding, diffusion welding, induction welding, percussion welding, electron beam welding, multi-stage brazing, or reactive brazing may be used. In this embodiment, instead of a feedthrough leadwire 136 or terminal pin 142, this embodiment comprises a sintered paste-filled via 142'. It is a novel feature of this embodiment that this sintered paste-filled via 142' be of essentially pure platinum that is co-fired with the essentially high purity alumina ceramic substrate 156. As will be shown later, a ceramic reinforced metal composite (CRMC) may alternatively be used instead of a high purity platinum to form the sintered paste-filled via. Such sintered paste-filled vias offer customizable feedthrough conductive pathways design options while providing ease of manufacturing and cost-effective feedthrough design alternatives.

In general, hermetically sealed AIMDs have a body fluid side and a device side. As used herein, the device side (inboard side) is located inside the conductive housing 124 of the AIMD, and the body fluid side is located outside the conductive housing 124 of the AIMD. After laser welding a hermetic feedthrough 132 to the conductive housing 124 of the AIMD, the feedthrough conductive pathways 129 (not labelled in FIG. 12), which comprise an electrical conductor, pass through the conductive pathway 129 to a body fluid side and to a device side. As previously disclosed, an electrical conductor of a hermetic feedthrough 132 may be selected from the group consisting of a leadwire, a lead wire, a terminal pin, a pin, a two-part pin, a lead conductor, a sintered conductive via, a sintered paste-filled via, a co-sintered via, a co-sintered paste-filled via, a co-sintered via with one or more metallic inserts, or combinations thereof. Thus, the feedthrough conductive pathway 129 through the insulator 156 of the hermetic feedthrough 132 between the body fluid side and the device side can be made from a leadwire 136, a terminal pin 142 or, as shown in FIG. 12, a conductive sintered paste-filled via 142'. The conductive pathway 129 between the body fluid side and the device side can also be a combination of conductive inserts co-sintered within conductive pastes of the sintered past-filled via 142'. Accordingly, the distal end of the feedthrough conductive pathways 129 on the body fluid side are external of the AIMD housing 124 (hence is exposed to body fluid) and the opposite distal end of the feedthrough conductive pathways 129 on the inboard side or device side is located inside of the AIMD housing (hence is connectable to the AIMD electronic circuits residing internal to the AIMD housing).

Figure 13:
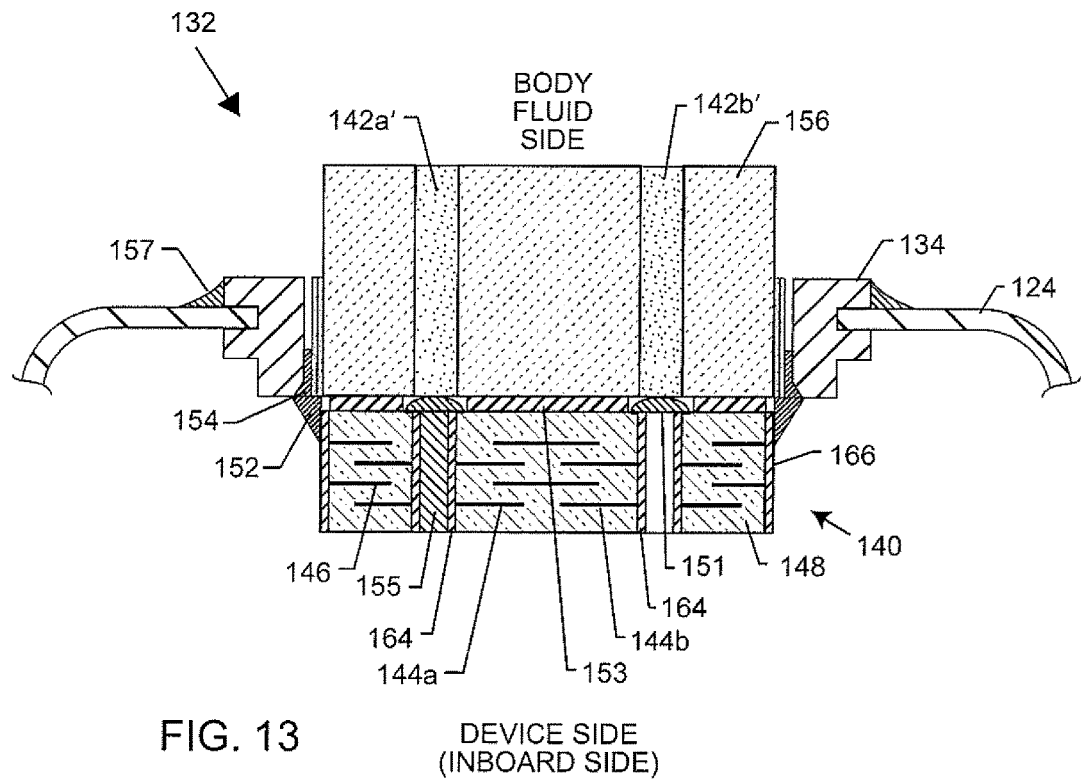
FIG. 13 is a cross-sectional view of another embodiment of a hermetic terminal subassembly now showing a capacitor with a filled and a bore-coated via.

FIG. 13 is a cross-sectional view of another embodiment taken from FIG. 22 of U.S. Pat. No. 8,653,384, showing a hermetic feedthrough 132 and an attached filter 140 having a coated (metallized) bore filled with electrically conductive material and a coated (metallized) bore without any fill in the bore. One is directed to U.S. Pat. No. 8,179,658, the content of which is fully incorporated herein by this reference, which illustrates a capacitor bore and a solid feedthrough leadwire in the capacitor bore. In this embodiment, the capacitor bore has no metallization, and the solid feedthrough leadwire is directly connected to the capacitor active electrode plates by only the electrically conductive material filling the un-metallized capacitor bore. Referring to the embodiment of FIG. 13, the feedthrough filter capacitor 140 is mounted directly to one or more of the co-sintered platinum filled vias of the insulator of the hermetic feedthrough as shown in the exemplary co-sintered filled vias 142a', 142b' of FIG. 13. In this embodiment, an adhesively backed insulator washer 153 is used to affix the feedthrough filter capacitor 140 onto the surface of the alumina substrate 156.

There are two different methods of electrical attachment to the feedthrough filter capacitor illustrated in FIG. 13. In the left-hand capacitor bore, there is a solid fill of, for example, a solder, a braze or a thermal-setting conductive material 155. Such a solid fill capacitor bore may also be used for connection in the embodiments of the '658 patent, which have no capacitor bore metallization. A simplified electrical attachment is shown on the right-hand capacitor bore, wherein a solder bump or ball grid array (BGA) 151 is first dispensed at the metallized but un-filled capacitor bore and then the filter capacitor is aligned and placed over co-sintered paste-filled vias of the hermetic feedthrough as shown. Then, a temperature is applied to reflow the solder into place. The solder makes electrical contact with the co-sintered paste-filled filled via 142a', 142b' and also with the active capacitor metallizations (terminations) 164 of the metallized un-filled capacitor bore.

In accordance with good EMC principles, the feedthrough filter capacitor 140 is disposed immediately at the point of EMI ingress into the inside of the device housing 124. In this way, high frequency EMI can be decoupled and diverted to the device housing 124 without adversely affecting AIMD sensitive electronic circuits. Feedthrough filter capacitor active electrode plates 144*a* and 144*b* are both each connected to the active capacitor metallization 164 of their respective capacitor bores. The capacitor ground electrode plates 146 make contact with the ground capacitor metallization 166. An electrically conductive material 152 provides electrical connection to the ground capacitor metallization 166 and to the gold braze 154 of the ferrule 134, which makes a low impedance and low resistance essentially oxide-free electrical connection, required for superior high frequency performance.

Figure 14:
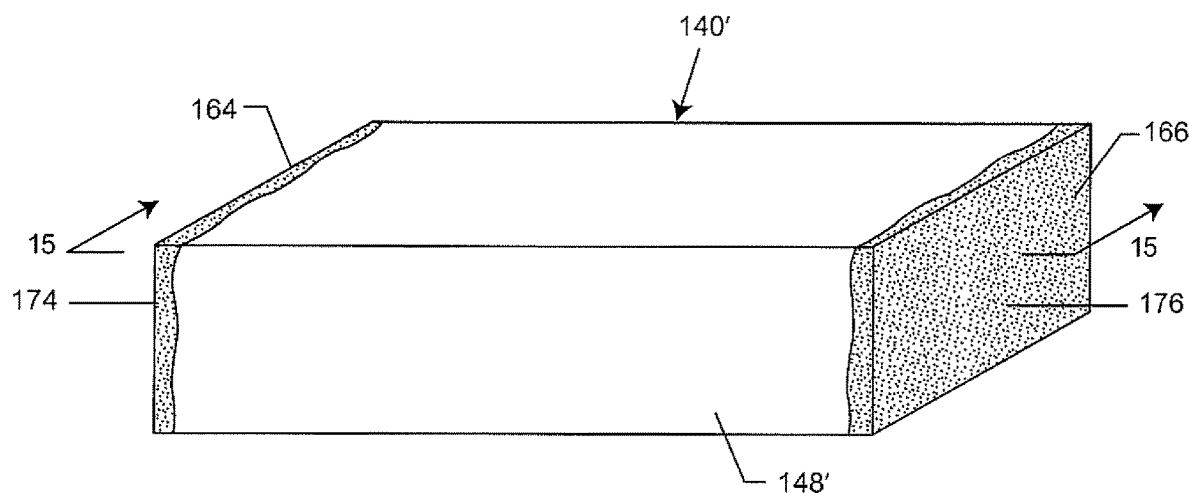
FIG. 14 is an isometric view of a monolithic multi-layer ceramic capacitor (MLCC) chip capacitor.

FIG. 14 is a prior art multi-layer ceramic capacitor (MLCC) 140'. MLCC chip capacitors are made by the hundreds of millions per day to service consumer electronics and other markets. Virtually all computers, cell phones and other types of electronic devices have many MLCC chip capacitors. One can see that the MLCC chip capacitor 140' has a body generally consisting of a high dielectric constant ceramic body 148' such as barium titanate. The MLCC chip capacitor 140' also has a pair of solderable terminations (the active capacitor metallization 164 and the ground capacitor metallization 166) at either end. These solderable active and ground terminations, that is the active capacitor metallization 164 and the ground capacitor metallization 166, provide a convenient way to make an electrical connection to the internal electrode plates 144, 146 of the MLCC chip capacitor 140'. The filter capacitors of FIG. 14 can also comprise other shapes and types of filter capacitor technologies, including rectangular, cylindrical, round, tantalum, aluminum electrolytic, stacked film or any other such capacitor shapes and technologies. It is understood by those skilled in the art that the MLCC chip capacitor 140' can be flipped such that the corresponding capacitor metallizations 164 and 166 are reversed, as it is only when the MLCC chip capacitor 140' is installed that one can identify which metallization is the active capacitor metallization 164 and which metallization is the ground capacitor metallization 166.

Figure 15:
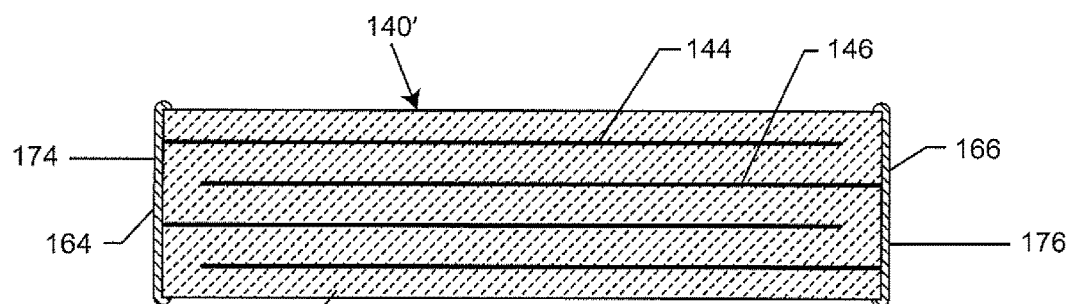
FIG. 15 is a cross-sectional view of the monolithic ceramic capacitor, taken along the line 15-15 of FIG. 14.

FIG. 15 is a cross-sectional view taken from section 15-15 of FIG. 14. The MLCC 140' includes left-hand side electrode plates 144 and right-hand side electrode plates 146. One can see that the left-hand side electrode plates 146 are electrically connected to an external capacitor metallization 164. The right-hand side electrode plates 146 are shown connected to the external capacitor metallization 166. Prior art MLCC 140' and equivalent chip capacitors are also known as two-terminal capacitors. That is, there are only two ways electrical energy can connect to the body of the capacitor. In FIGS. 14 and 15, the first terminal 174 is on the left-hand side and the second terminal 176 is on the right-hand side of the capacitor. As defined herein, MLCC chip capacitors are two-terminal devices. In contrast, feedthrough filter capacitors are three-terminal devices, which have very low self-inductance and make excellent high frequency EMI filters.

Figure 16:
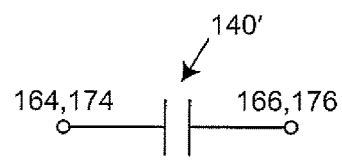
FIG. 16 is an electrical schematic diagram of an ideal MLCC chip capacitor as illustrated in FIGS. 14 and 15.

FIG. 16 is the schematic diagram of the MLCC 140' illustrated in FIGS. 14 and 15.

FIG. 17 illustrates another type of prior art three-terminal filter capacitor known as a flat-through capacitor 140". The flat-through capacitor 140" is connected to circuit traces 178*a*, 178*b* at active capacitor metallizations 164*a*, 164*b* at each end of the flat-through capacitor forming an active circuit path. A circuit current 180 passes all the way through the capacitor 140" along the active circuit path as illustrated. The capacitor 140" is also connected to ground circuit traces 182*a*, 182*b* at ground capacitor metallizations 166 forming a ground circuit path. The overlap of the active electrode plates and the ground electrode plates creates the capacitance of the flat-through capacitor 140".

Figure 18:
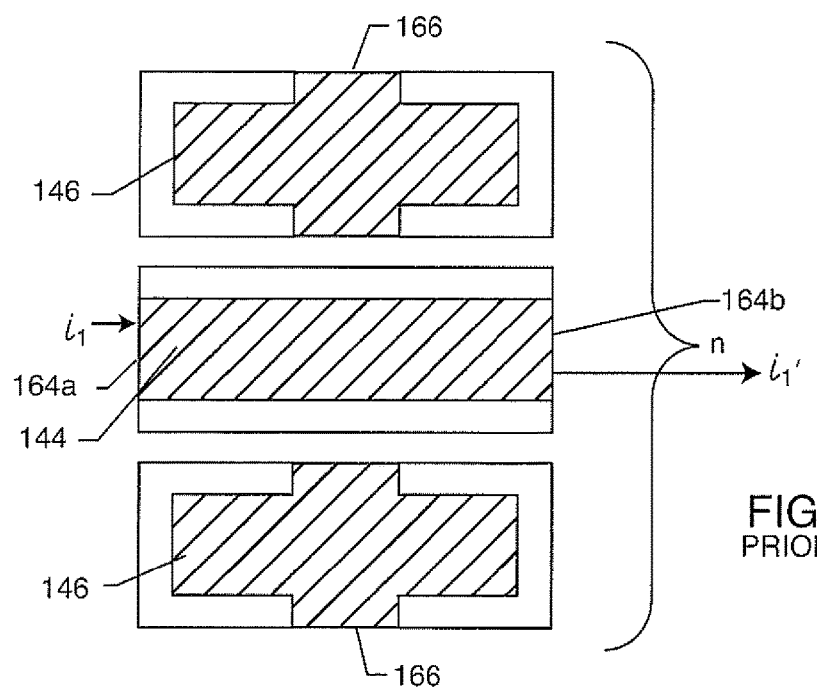
FIG. 18 illustrates the internal electrode plates of the flat-through capacitor of FIG. 17.

FIG. 18 illustrates the internal electrode plates of the flat-through capacitor 140" of FIG. 17. Ground electrode plates 146 are connected to ground capacitor metallizations 166. The through active electrode plates 144 are connected to active capacitor metallizations 164*a*, 164*b*. The electrode plate embodiment of the flat-through capacitor 140" of FIG. 17 comprises a through or active electrode plate 144 sandwiched between two ground electrode plates 146. As previously disclosed, the through or active electrode plate 144 is connected at both ends of the flat-through capacitor by the active capacitor metallizations 162*a*, 162*b*, which are terminals 1 and 2 respectively of the flat-through capacitor 140". When the flat-through capacitor is mounted between the circuit traces 178*a*, 178*b* as shown in FIG. 17, the active circuit path is made. Referring to the active electrode plate of FIG. 18, one can see the current $i_1$ enters at 164*a* (terminal 1). If the current is a high frequency EMI current, it is attenuated along the length of the flat-through capacitor by the capacitance of the flat-through capacitor and emerges as a much smaller amplitude EMI signal at 164*b* (terminal 2) as current $i_{1'}$.

Figure 18A:
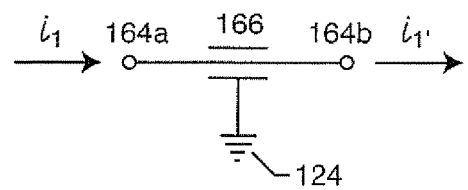
FIG. 18A is the electrical schematic of FIGS. 17 and 18.

FIG. 18A is the schematic of the three-terminal flat-through capacitor of FIG. 17. One can see that the flat-through capacitor is a true three-terminal device consisting of terminals 164*a* (terminal 1), 164*b* (terminal 2) and ground 166 (terminal 3). The circuit current 180 passes through the active electrode plate 144 from the first terminal 164*a* to the second terminal 164*b*. The ground terminal which is the third terminal, is the AIMD housing 124. As shown, the circuit current $i_1$-$i_{1'}$ passes all the way through the flat-through capacitor, as illustrated.

Figure 19:
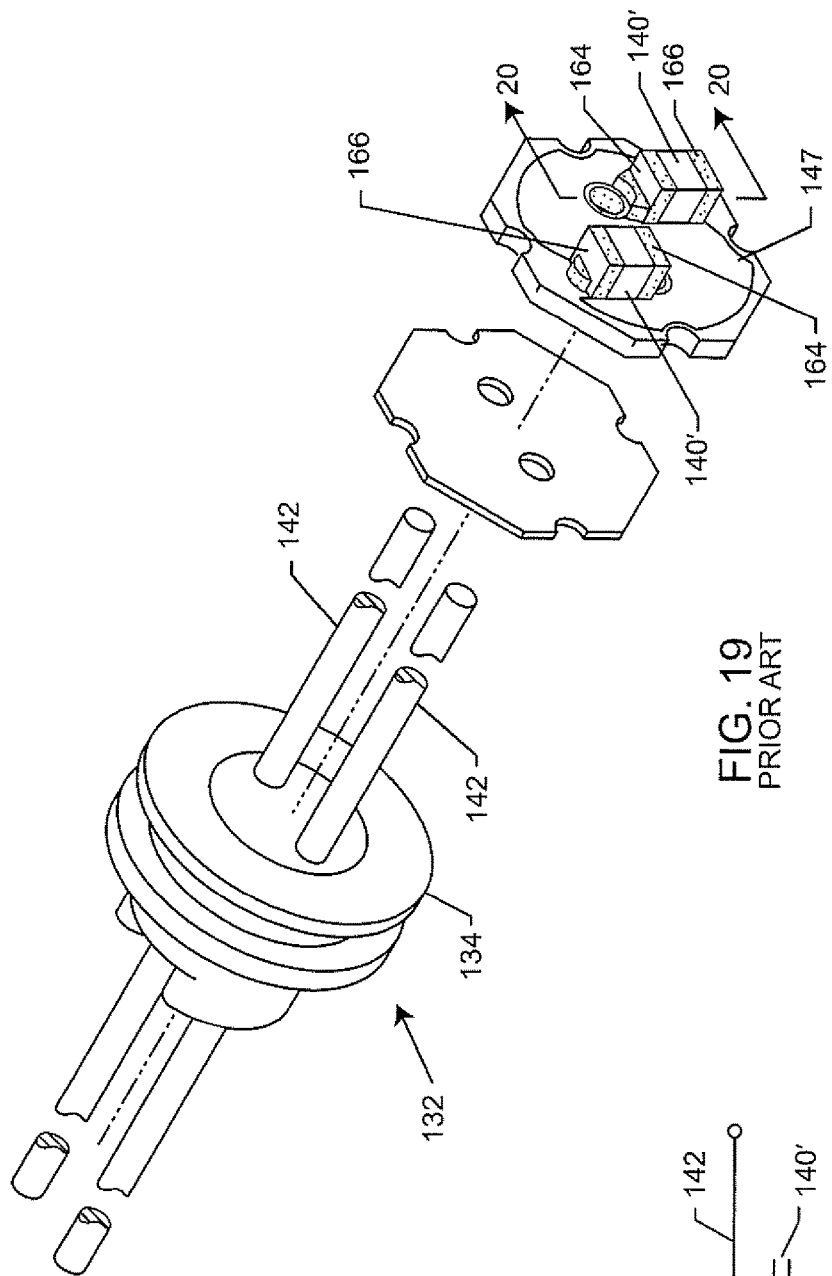
FIG. 19 is an isometric exploded view of a multi-lead hermetic feedthrough with substrate mounted MLCC chip capacitors showing use of a substrate between the feedthrough and the filter support assembly.

FIG. 19 illustrates a method of attaching MLCCs 140' directly to the hermetic feedthrough 132. In accordance with the present invention, the MLCCs 140' are relatively low dielectric constant (low k), like NP0, such that they have a high number of electrode plates thereby minimizing capacitor ESR. This makes MLCC chip capacitors very effective in diverting high levels of RF current at an MRI RF-pulse frequency. One is referred to U.S. Pat. Nos. 5,896,267 and 5,650,759, both to Hittman et al., which more thoroughly describe the use of MLCC chip capacitors as feedthrough filter capacitors attached at or near the hermetic feedthrough of an active implantable medical device. The contents of these two patents are fully incorporated herein by these references.

Figure 19A:
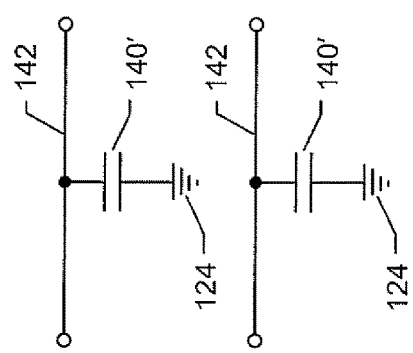
FIG. 19A is the electrical schematic of FIG. 19.

FIG. 19A is the schematic diagram of the bipolar MLCC chip capacitors 140' of FIG. 19. As shown, these are two-terminal capacitors with terminal 1 connected to the terminal pin 142 and terminal 2 connected to ground, which is also the AIMD housing 124.

FIG. 20 is a cross-section of a typical MLCC chip capacitor 140', such as those of FIGS. 14 and 19. It is noted, as previously disclosed, that the ESR of the capacitors of FIGS. 14 and 19 is high due to a low number of electrode plates 144, 146. The design principles illustrated in this cross-section are equally applicable to any type of feed-through filter capacitor 140, including the filter capacitors described in FIGS. 7 and 9 of the present application. In general, the equivalent series resistance (ESR) of a filter capacitor depends upon a number of very important variables. A filter capacitor's ESR is the sum of the connection resistance ($R_c$) 184, the resistance of attachment material ($R_a$) 186, the resistance of capacitor metallization (used to attach to internal electrode plates) ($R_m$) 188, the electrode resistance ($R_e$) 190 and 190' of the electrode plates 144 and 146 and also the resistance of the dielectric loss tangent ($R_{DL}$) 192. There is also another type of resistance (not shown) which occurs at very high frequency, known as skin effect ($R_s$). Skin effect is understood by those skilled in the art as the tendency of a high-frequency current to flow near the surface of a conductor as opposed to the interior of a conductor resulting in an increase of resistance in the conductor with increasing frequency. Hence skin effect is a situation in which the bulk of the current flow is on the skin (near the surface) of the electrode plates and the circuit connections instead of uniformly distributed throughout the full body of the conductor. This also has the effect of increasing a capacitor's ESR. In general, for typical MRI RF-pulse frequencies, skin effect can be ignored (as skin effect is mostly a greater than 500 MHz phenomenon).

FIG. 21 is the schematic diagram of the MLCC chip capacitor 140' of FIG. 20 showing that the capacitor's ESR is the sum of the connection resistance ($R_c$) 184, the connection material resistance ($R_a$) 186, the capacitor metallization resistance ($R_m$) 188, the electrode resistance ($R_e$) 190 and the capacitor's dielectric loss resistance ($R_{DL}$) 192. The capacitor's dielectric loss resistance ($R_{DL}$) 192 is frequency variable, which will be explained in further detail. For a well-designed and properly installed filter capacitor, many of these resistances are so small that they can be ignored. For example, referring once again to the MLCC chip capacitor 140' of FIG. 20, if the capacitor metallizations 164, 166 are well designed and are properly attached to the filter capacitor, then the capacitor metallizations will have a trivially small resistance ($R_m$) 188. In a similar fashion, if the electrical attachment material 152 is a solder or a proper thermal-setting conductive adhesive, the attachment material resistance ($R_a$) 186 will also be a trivial amount. If the system is attached to gold or another similar oxide-resistant material, then the connection resistance ($R_c$) 184 will also be trivially small. Referring once again to MLCC chip capacitor 140' of FIG. 21, the total ohmic loss $R_o$ 200, therefore, consists almost entirely of the total electrode plate resistance ($R_e)_{total}$ 190 190'. This is why it is so important in the present invention to maximize the number of electrode plates of a low k filter capacitor. A low k filter capacitor is defined herein as comprising a low k dielectric material having a k<1,000. In some embodiments, a low k capacitor comprises a dielectric material having a k<200. At high frequency, the ohmic loss of the low k filter capacitor is almost entirely due to the resistive loss of the active and ground electrode plates ($R_e)_{total}$ 190, 190'.

FIG. 22 provides the equation relating capacitance C to the dielectric constant k, the active area A, which is the overlap area of the active electrode plate and the ground electrode plate of a capacitor, the number of electrode plates n and the dielectric thickness d of the filter capacitor. Since the dielectric constant k is directly related to the capacitance C, one can see how dramatically the capacitance of a capacitor rises when the dielectric constant k is 2,500 as opposed, for example, to a dielectric constant k below 200 such as an EIA Class I dielectric. Assuming a constant capacitor dielectric thickness d for a particular filter capacitor voltage rating, the only way to increase the capacitance of a filter capacitor comprising a dielectric having a k below 200 so that the original capacitance value of the filter capacitor comprising the dielectric having a k of 2,500 is achieved requires greatly increasing the number of electrode plates in this capacitor comprising the dielectric having k less than 200. In the prior art, using a dielectric having a k less than 200 in a feedthrough filter capacitor is counterintuitive. However, in the present invention, a capacitor having a dielectric with a k less than 200 is exactly what we want to do. A high number of electrode plates drives down the high frequency ohmic losses of the filter capacitor and thereby greatly increases the efficiency of the filter capacitor comprising such low k dielectrics so that RF energy can effectively be pulled out of an implanted lead during MRI scans. In addition, the high number of electrode plates of such a filter capacitor has a very low equivalent series resistance at the MRI RF-pulse frequency, thereby significantly reducing the amount of heat produced in, for example, a low k diverter feedthrough filter capacitor 140 or a low k diverter MLCC chip capacitor 140'.

Figures 23, 24:
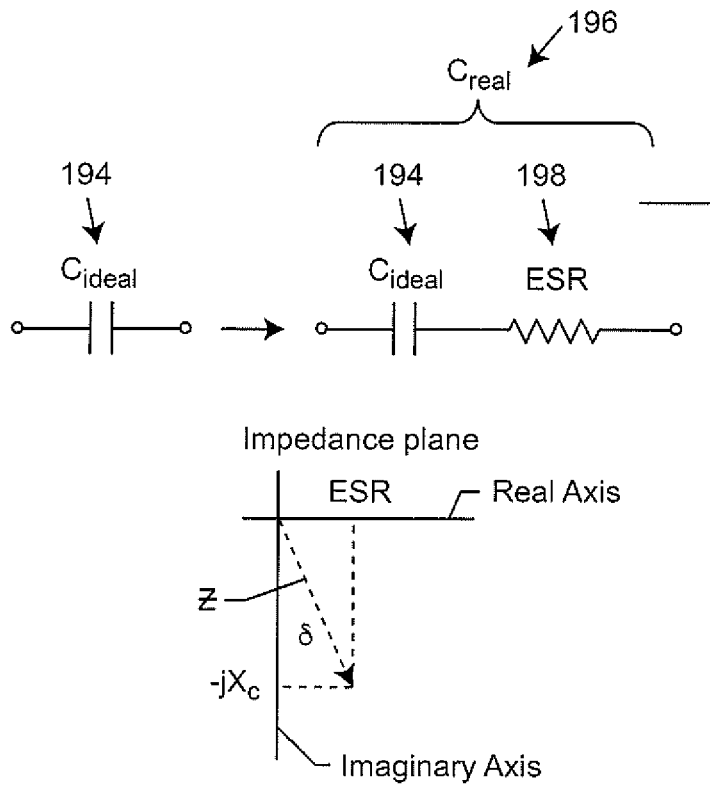
FIG. 23 shows the difference between an ideal capacitor and a real capacitor, including dielectric loss tangent and dissipation factor.
FIG. 24 gives the formulas for capacitive reactance, dissipation factor, equivalent series resistance (ESR) and dielectric loss tangent.

FIG. 23 illustrates the schematics of an ideal capacitor 194 and also a real (non-ideal) capacitor 196 which consists of an ideal capacitor 194 in series with its ESR 198. For the purpose of the present discussion, a capacitor's series inductance or insulation resistance (a parallel resistance) can both be ignored. This is because the inductance of feedthrough filter capacitors is quite low at MRI RF-pulse frequencies. Further, the filter capacitor's insulation resistance is generally in the megohms or gigohms range, which is so high, it can also be ignored as a parallel path. Also shown in FIG. 23 is a graph of the impedance plane showing the capacitor ESR in the real axis and the capacitive reactance $-jX_C$ shown on the imaginary axis. The capacitor's loss tangent $\delta$ is also illustrated.

In FIG. 24, equations are given for capacitive reactance $X_C$, impedance Z, dissipation factor DF and loss tangent of $\delta$, which is also defined as the dissipation factor DF. Historically, dissipation factor has been expressed as a percent, such as 2.5% maximum. This means that the allowable dissipation factor is 2.5% of a capacitor's capacitance reactance at a particular frequency. Usually, due to dielectric losses, this number is dominated at low frequencies by the capacitor's dielectric loss. The capacitor's dielectric loss is generally related to its dielectric constant and the frequency of the driving energy. For example, if the frequency of an applied sinusoid is relatively low (say 60 Hz), then the crystal lattice of the capacitor has plenty of time to deflect back and forth under the electrical stress and, in so doing, produces a significant amount of heat, which is a type of real or resistive loss. At 1 kHz, the capacitor dielectric structure (or dipoles, if one uses that theory) vibrates at a higher frequency. As one goes higher and higher in frequency, say to 10 MHz, then for the low k Class I dielectrics of the present invention, there is very little movement in the crystal lattice and, accordingly, very little heat generated due to dielectric loss. It will be further illustrated how dielectric loss varies with frequency. In the past, particularly as described by testing specifications such as MIL-STD-202 and MIL-STD-220 among others, dissipation factor is measured either at 1 kHz, or in some cases, at 1 MHz. Unfortunately, this data is misleading at MRI RF-pulse frequencies, which generally are 21.28 MHz (0.5 T), 64 MHz (1.5 T), 128 MHz (3 T) or higher. For most dielectrics, the high frequency ohmic loss, due to the capacitor's electrode plates, is so low that it is masked by the capacitor's dielectric loss when measured at low frequencies such as 1 kHz or 1 MHz. This will be explained in subsequent figures.

Figure 25:
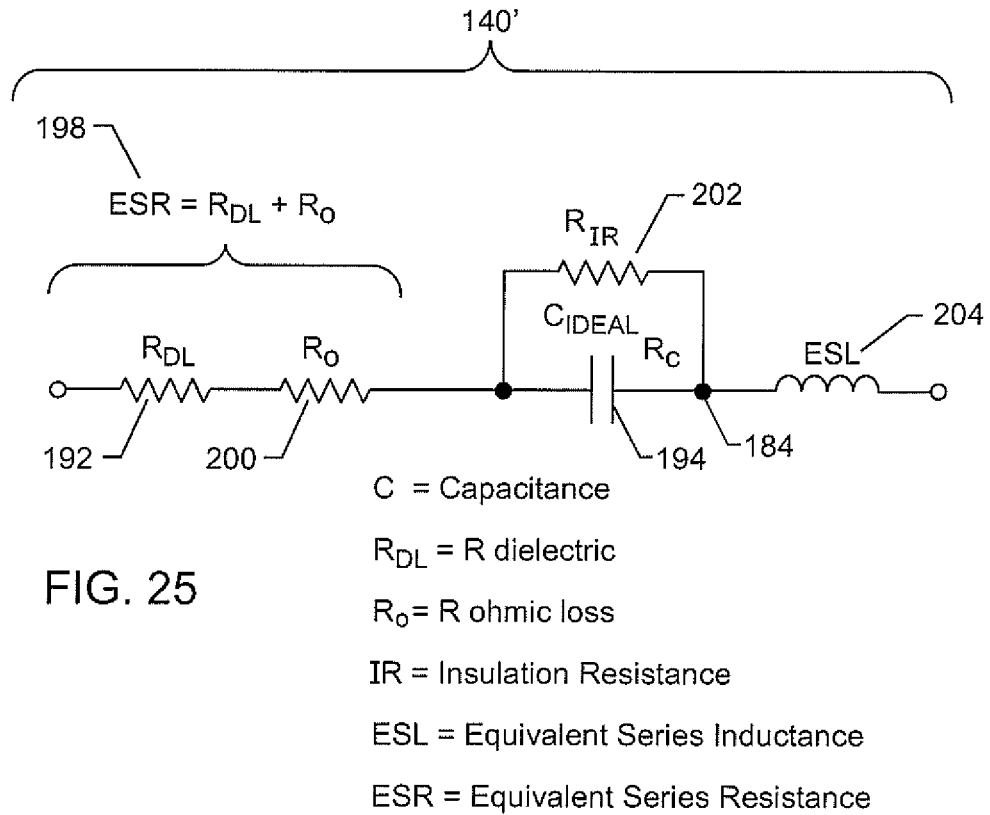
FIG. 25 is an equivalent circuit model for a real capacitor.

FIG. 25 is a more complete schematic for an MLCC chip capacitor 140', which has been simplified from FIG. 21. ($R_o$)

represents total ohmic loss 200 which is the sum of the ohmic losses by connection resistance (Re) 184, the attachment material resistance ($R_a$) 186, the metallization resistance ($R_m$) 188, and the electrode resistance ($R_e$) 190. Assuming that the connection resistance ($R_c$) 184 is very low, such as in an attachment to gold, and that the attachment material resistance ($R_a$) 186 has a very low resistivity, such as a thermal-setting conductive adhesive or a solder, and assuming that the capacitor metallization materials have very little ohmic resistance to the electrode plates, then one can assume that the bulk of the total ohmic loss ($R_o$) 200 of the MLCC chip capacitor 140' is equal to the entire electrode stack of said MLCC chip capacitor, meaning that the total ohmic loss (Ro) 200 is essentially equal to the electrode resistance $(R_e)_{total}$ 190 of the MLCC chip capacitor 140'. As previously disclosed, the resistance of the electrode stack of the capacitor depends on the length, the width and the thickness of the electrode plates and also, importantly, on the number of electrode plates that are in parallel. Therefore, reducing the dielectric loss and maximizing the number of electrode plates are key features of the filter capacitor embodiments of the present invention.

Figure 26:
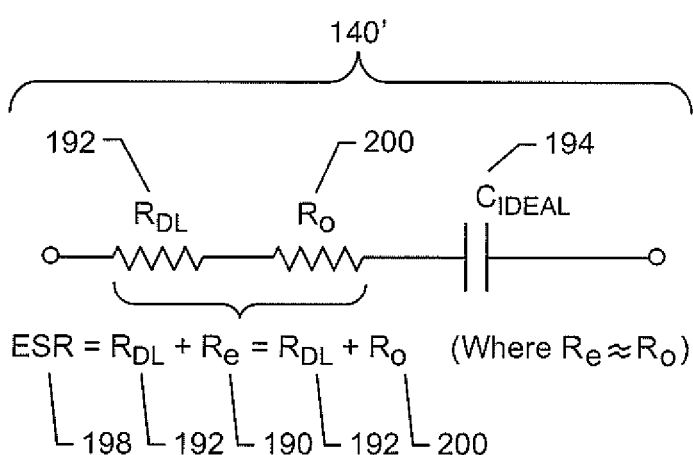
FIG. 26 is a schematic illustrating a simplified model for capacitor ESR.

FIG. 26 is a simplified schematic diagram of FIG. 25 showing that the ESR 198 of the MLCC chip capacitor 140' is the sum of the dielectric loss tangent resistance (RDL) 192 plus the total electrode resistance $(R_e)_{total}$ 190 of the parallel electrode stack of said MLCC chip capacitor. Referring once again to FIG. 25, one can see that there is a resistor in parallel with the ideal capacitor C 194. This resistor comprises an insulation resistance ($R_{IR}$) 202, which is the insulation resistance of the MLCC chip capacitor 140'. In a high-quality capacitor, this insulation resistance value tends to be in the hundreds of megohms or higher and does not significantly contribute to the capacitor ESR, therefore, for the purpose herein, can be ignored as part of the filter capacitor equivalent circuit model. The ($R_{IR}$) also has negligible effect on capacitor high frequency performance. For three-terminal or physically small MLCC chip capacitors, the equivalent series inductance (ESL) 204 shown in FIG. 25 can also be ignored because inductive reactance is very low at low frequencies and filter capacitor inductance can be considered negligible at high frequencies. Accordingly, the ESR 198 of the AIMD diverter MLCC chip capacitor 140' of FIG. 26 is the sum of the dielectric loss tangent resistance ($R_{DL}$) 192, the total ohmic loss ($R_o$) 200 and any losses due to skin effect ($R_s$), which is not labelled in FIG. 26. Specifically, regarding skin effect, at low frequencies, skin effect is negligible, and for physically small MLCC chip capacitors and feedthrough filter capacitors, skin effect does not really play a role until one gets to very high frequencies, for example, above 200 MHz. It is noted, therefore, that for the MRI RF frequencies 21.28 MHz (0.5 T), 64 MHz (1.5 T), and 128 MHz (3 T), skin effect (Rs) is negligible and may be ignored, which is why FIG. 26 does not label ($R_s$). Hence, assuming that the filter capacitor has good metallization, essentially oxide-free connection to the ferrule and good electrical attachment materials, then the total ohmic loss ($R_o$) 200 is completely dominated by the electrode resistance ($R_e$) 190. Thus, for the purpose of the present invention, at MRI RF frequencies the ESR 198 of the filter capacitor is generally equal to the dielectric loss tangent resistance ($R_{DL}$) 192 plus the electrode resistance ($R_e$) 190. Both of these parameters, ($R_{DL}$) and ($R_e$), must be carefully controlled for the high-power RF diverter MLCC chip capacitor 140' of the present invention.

In summary, it has been shown that dielectric loss is a frequency variable and that, for at least the MRI RF-pulse frequencies 21.28 MHz (0.5 T), 64 MHz (1.5 T), and 128 MHz (3 T), the dielectric loss for a low k EIA Class I ceramic filter capacitor drops to a very low value (essentially zero) such that the ESR 198 of a diverter low k filter capacitor is primarily determined by the total resistance of its electrode plates.

Figure 27:
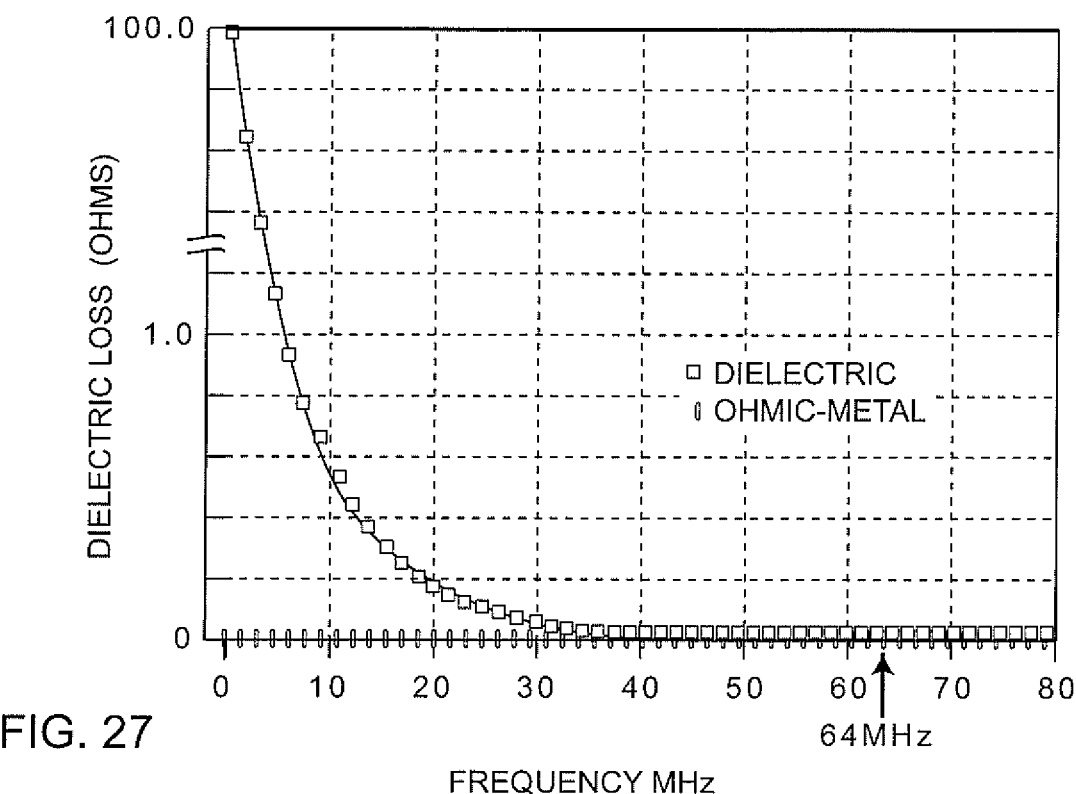
FIG. 27 is a graph illustrating capacitor dielectric loss versus frequency.

FIG. 27 is a more detailed illustration of the dielectric loss in ohms of a relatively low k ceramic filter capacitor. One can see, at low frequencies, the dielectric loss in ohms can be over 100 ohms or even much greater. However, as one increases in frequency, one can see that the dielectric loss drops and is nearly zero at 64 MHz (the RF-pulse frequency of a 1.5 T MRI scanner).

Figure 28:
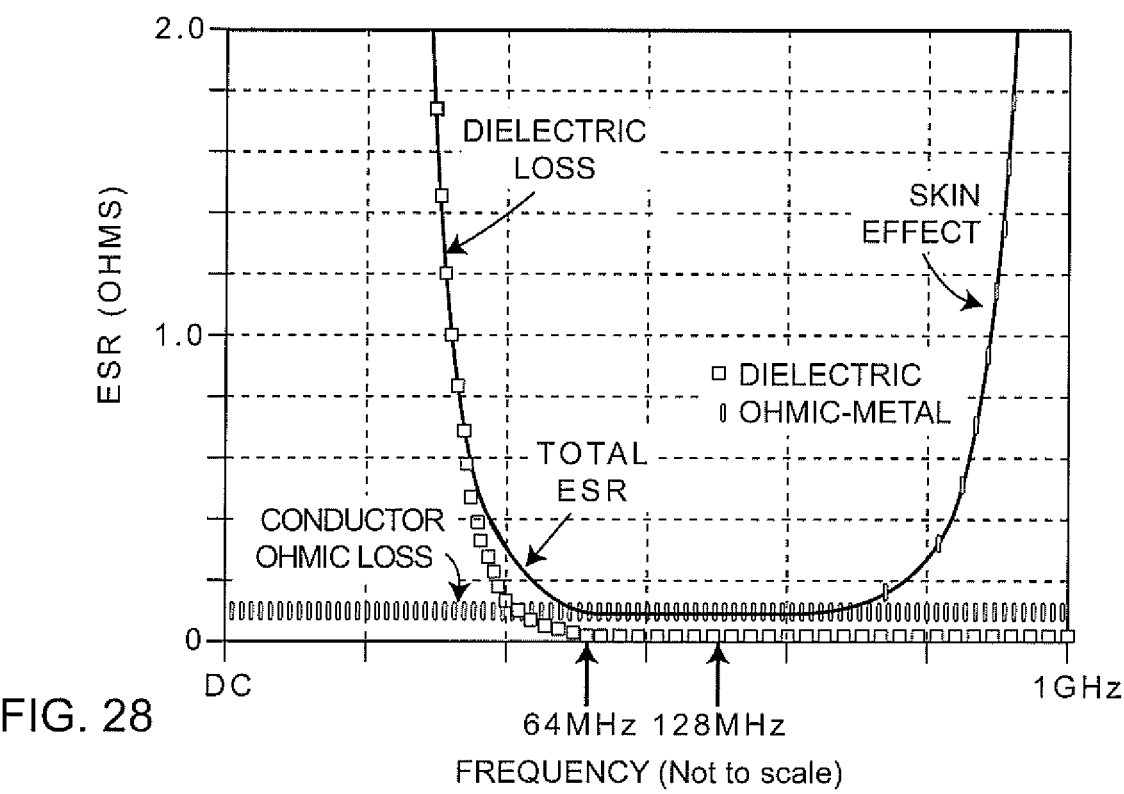
FIG. 28 is a graph illustrating normalized curves which show the capacitor equivalent series resistance (ESR) on the y axis, versus frequency on the x axis.

FIG. 28 shows a U-shaped composite curve. The composite curve is the summation of filter capacitor ohmic loss, which includes the total resistance of capacitor electrodes, capacitor metallization, electrical attachment materials, and electrical connection. As one can see, and ignoring skin effect, the conductor ohmic loss for the filter capacitor is relatively constant from low frequency all the way to very high frequencies. For an EIA Class I dielectric, the filter capacitor dielectric loss (marked with small squares) is a very high value at low frequency, and then drops to near zero at MRI RF frequencies such as 64 MHz and 128 MHz. Skin effect is also shown, which is an ohmic loss for two-terminal type filter capacitors. The total ESR is the solid line, which is the summation of the capacitor dielectric loss, the capacitor conductor ohmic loss and skin effect. The present invention is directed to make sure the center of this total ESR U-shaped curve includes the range of MRI RF-pulse frequencies at the near zero value.

FIG. 29 is a table showing an example of losses (which are measured losses) for a prior art 2,000-picofarad X7R (2,500 k) feedthrough filter capacitor. One can see that at the 1 kHz frequency, the X7R capacitor dissipation factor DF loss is about 1591.55 ohms and the ohmic loss is 0.432 ohms. When the dissipation factor DF loss is added to the ohmic loss, the X7R capacitor equivalent series resistance (ESR) is about 1591.98 ohms. Even at 1 MHz frequency, the X7R capacitor measures a dissipation factor DF loss of about 1.59 ohms, which, when added to the ohmic loss of 0.432 ohms, yields an ESR of about 2.024 ohms. It becomes apparent that at both the 1 kHz and 1 MHz frequencies the X7R capacitor dissipation factor DF losses dominate the ohmic losses. As a result, the ohmic loss is essentially hidden or indistinguishable due to such a significantly higher DF loss at these frequencies. It is not until a frequency of at least 10 MHz that the DF loss no longer dominates the capacitor ESR measurement and the ohmic loss of the X7R filter capacitor becomes discernable. This is very important in understanding a filter capacitor's real losses. As shown by FIG. 29, at a testing frequency greater than 10 MHz, the X7R filter capacitor has an ESR ranging from about 0.59 to about 0.44 ohms, which is still significant. Referring once again to the curve of FIG. 28, an ESR ranging from about 0.59 to about 0.44 ohms at frequencies from 10 MHz to 500 MHz substantially raises the center of the U-shaped curve away from the near zero ESR value desirable for effectively diverting RF energy induced in AIMD leads at MRI RF-pulse frequencies. Hence, as one can see, despite the specifications of MIL-STD-202 and MIL-STD-220 among others, measuring an AIMD filter capacitor's losses at 1 kHz and 1 MHz is not a useful way to analyze a filter capacitor's actual losses at MRI RF-pulse frequencies. In summary, to properly assess filter capacitor losses at MRI RF-pulse frequencies, one needs to analyze loss measurements in the range of 10 MHz to 500 MHz because at frequencies above 10 MHz the dissipation factor drops and the ohmic losses of the capacitor become visible making it easier to distinguish between acceptable and unacceptable capacitor high frequency performance.

FIG. 30 dramatically illustrates the difference in capacitor performance when one uses an EIA Class I dielectric, such as C0G (NP0), which has a dielectric constant of less than 200. Because of this low dielectric constant, a high number of electrode plates of the capacitor is necessary to achieve the filtering performance required for AIMDs. The high number of electrode plates has the effect of greatly reducing the capacitor's ohmic losses. In addition, EIA Class I dielectrics have a lower dissipation factor, particularly at high frequency. Comparing 100 MHz frequency measurements of the X7R capacitor of FIG. 29 and the C0G (NP0) capacitor of FIG. 30, one can see that the ESR of the C0G (NP0) capacitor is about 0.201 ohms vs. an ESR of about 0.45 of the X7R capacitor. The ESR of the C0G (NP0) capacitor is reduced by more than 50% the ESR of the X7R capacitor, which, for AIMD applications, is considered a significant ESR reduction. By also increasing the number of electrode plates (see capacitors 210, 210' in FIGS. 32, 34-36), the ESR of the C0G (NP0) capacitor may be further reduced to below 0.1 ohms. Thus, the dielectric material C0G (NP0) and the increased number of electrode plates of the AIMD diverter feedthrough filter capacitor of the present application substantially lowers capacitor ESR and will significantly reduce heat generation in said AIMD diverter feedthrough filter capacitor (for example, the feedthrough filter capacitor 210, 210' or even 210" and 210''' of the present application).

Further regarding the present invention, the inventors have contemplated using a dielectric material having dielectric constant k<1,000 for filter capacitors. The inventors have developed a mid k dielectric filter capacitor for making filter capacitors for use in AIMDs (for example, the feedthrough filter capacitor 210, 210', 210" and 210''' of the present application). The mid k dielectric filter capacitor is on the order of 500, comprising a dielectric constant of approximately 500 to as much as 700. The inventors used various dopants and firing conditions, such that, the new mid k dielectric provides an ohmic loss ($R_o$) of less than 100 milliohms at frequencies from 10 MHz to 100 MHz. In some embodiments, the inventors have achieved resistance losses on the order of 50 milliohms. Since the dielectric loss at the 10 MHz to 100 MHz frequency range is nearly zero, this means that the total ESR of the new mid k capacitors essentially only reflect the ohmic loss (Ro), thus are the order of 50 milliohms to as much as 100 milliohms at MRI RF-pulse frequencies. As, for example, a 1.5 Tesla MR scanner has an RF-pulse frequency of 64 MHz, it is very important to have low resistances in order to minimize capacitor heating as the AIMD diverter capacitor diverts the RF-pulse frequency during an MRI scan. This is accomplished by the capacitors of the present application having a dielectric material of a dielectric constant k<1,000.

Figure 31:
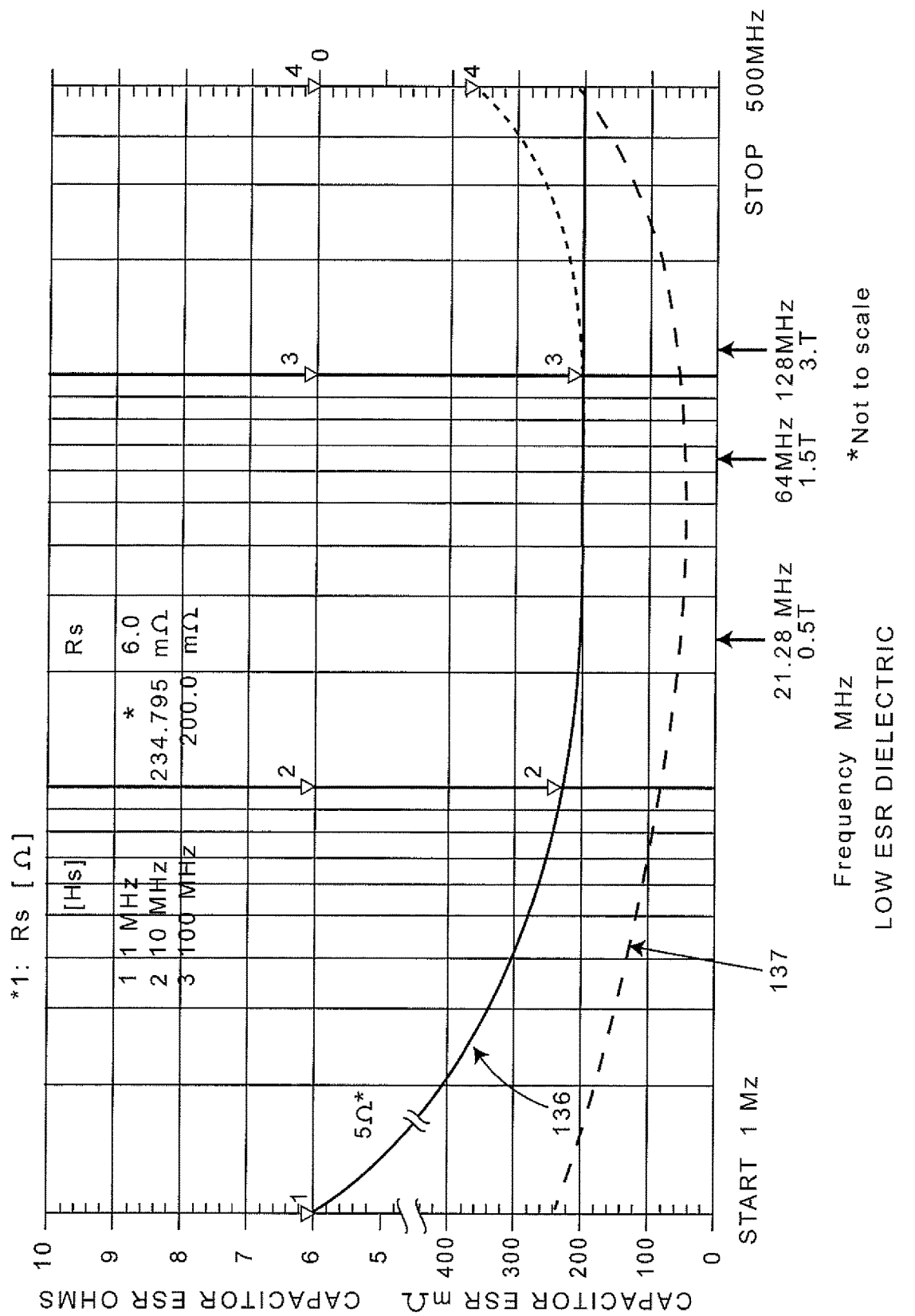
FIG. 31 is a graph illustrating capacitor equivalent series resistance versus frequency as illustrated in a sweep from an Agilent E4991A materials analyzer.

FIG. 31 is an equivalent series resistance (ESR) versus frequency graph from a frequency sweep done on a low k feedthrough filter capacitor 210 of the present application using an Agilent E4991A materials analyzer. At a start frequency of 1 MHz (curve 136), one can see that the ESR of the low k feedthrough filter capacitor 210 is on the order of 6 ohms, which is considered very high. However, by the time one reaches about 21.28 MHz (the frequency of a 0.5 T MRI scanner), the ESR of the low k feedthrough filter capacitor comprising an EIA Class I dielectric begins to flatten out. As dielectric loss at about the 10 MHz to 100 MHz frequency range is nearly zero, the only loss reflected by curve 136 is the ohmic loss of the low k feedthrough filter capacitor 210, which at 100 MHz is only 200 milliohms. It is noted that the ESR of said capacitor is also 200 milliohms at the RF-pulse frequencies for a 1.5 Tesla scanner (64 MHz) and a 3 Tesla scanner (128 MHz).

Since the 1960s, as previously mentioned, it has been a common practice in the capacitor industry to measure capacitance and dissipation factor at 1 kHz. The dissipation factor is usually defined as a percentage, for example, 2.5% maximum. What this means is that the dielectric loss resistance can be no more than 2.5% of the capacitive reactance at a certain frequency (which characteristically has been 1 kHz). As an example, if the capacitive reactance for a particular capacitor is 80,000 ohms at 1 kHz with a 2% dissipation factor this equates to 1,600 ohms of resistance at the 1 kHz frequency. Referring once again to FIG. 28, it is noted that the dielectric loss essentially goes to about zero at high frequency. For typical low k dielectric constant EIA Class 1 ceramic capacitors, frequencies above 10-20 MHz is sufficiently high so that the dielectric loss is no longer a dominating factor in the capacitor ESR measurement. Hence, as the ESR of a capacitor varies with the capacitance value, the number of electrode plates, and the length and width of the electrode plates, a wide range of "normal" ESR readings can be obtained for many types of capacitors by using the teachings of the present application (see the filter feedthrough capacitors 210, 210', 210" and 2101. For example, one particular capacitor may have a normal ESR reading of 0.05 ohms while another capacitor design may have a normal ESR as much as 10 ohms.

Referring once again to FIG. 31, one can see curve 137, which represents the inventors new mid k dielectric (k on the order of 500 to 700). As can be seen, the new mid k dielectric, in general, yields filter capacitors that have a total equivalent series resistance of less than 100 milliohms between 10 MHz and 100 MHz frequencies. There are even certain design configurations with a sufficient number of electrode plates where the capacitor's ESR is between 10 and 50 milliohms in the 10 MHz to 100 MHz frequency range.

Figures 32, 33:
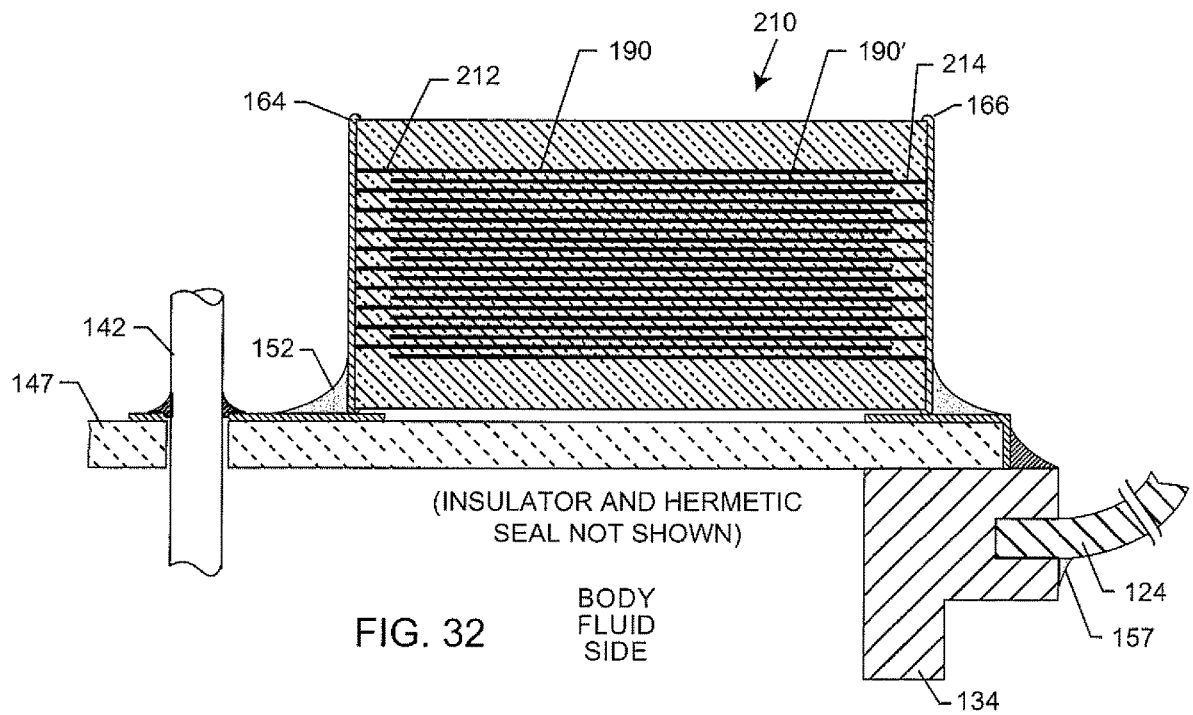
FIG. 32 is a cross-sectional view of a low k MLCC chip capacitor with an increased number of electrode plates to minimize ESR.
FIG. 33 is an equation showing that the total high frequency electrode resistive losses drop in accordance with the parallel plate formula for capacitor electrode plates.
Figure 34:
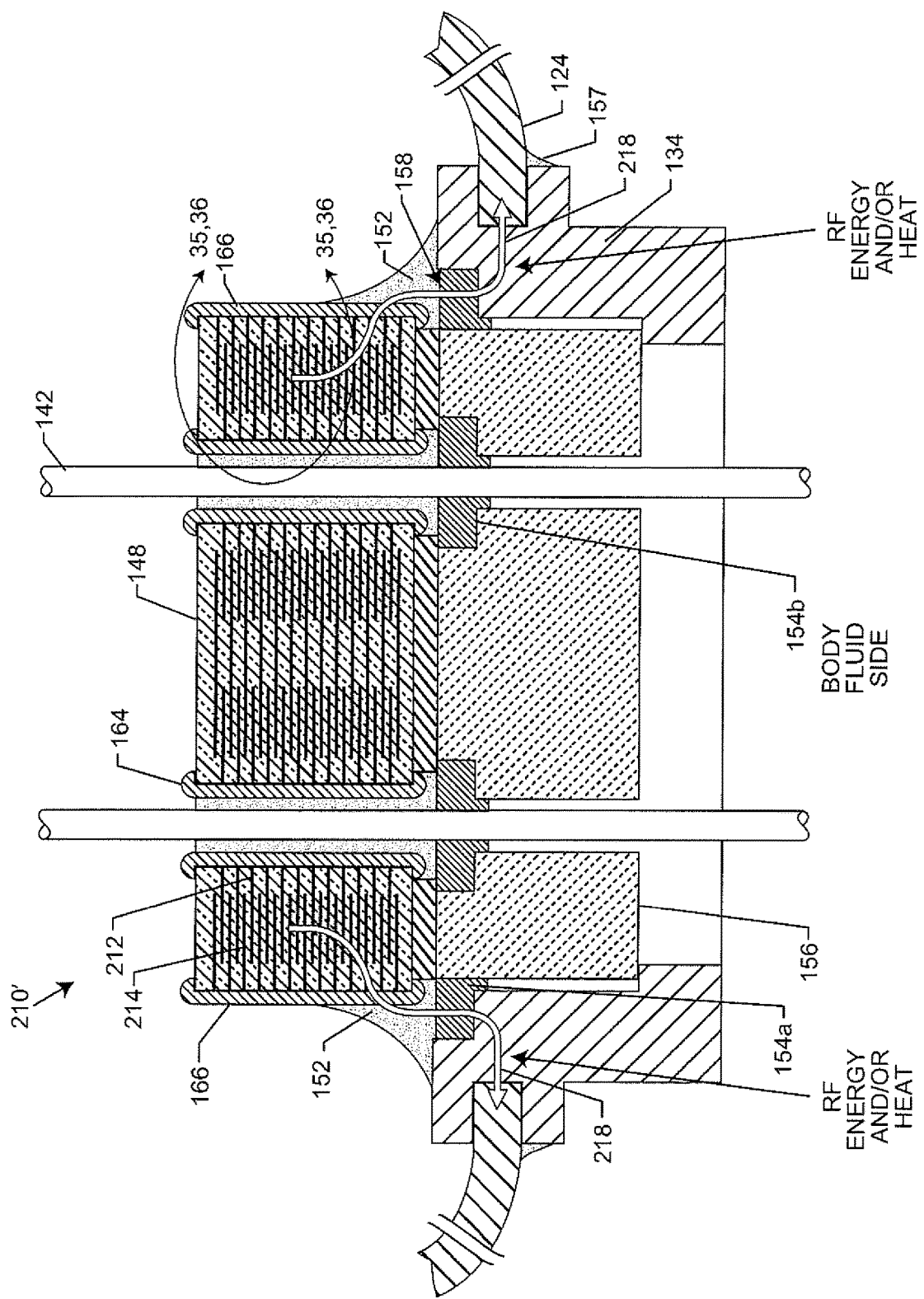
FIG. 34 is a cross-sectional view of a quad polar feedthrough capacitor similar to FIGS. 9 and 10 except that it is low ESR and designed for maximal heat flow.

Regarding number of electrode plates, maximization of the number of electrode plates in order to reduce the electrode resistance ($R_e$) of an MLCC chip capacitor becomes paramount (shown in the low k MLCC chip capacitor 210 of FIG. 32 and feedthrough filter capacitor 210' in FIG. 34). In general, in order to increase the number of electrode plates, the effective capacitance area (ECA) can be minimized and the dielectric constant k lowered so that one ends up with a relatively high number of electrode plates. One might ask, why doesn't one simply make the electrode plates much thicker in order to decrease their resistance? It is true that making the electrode plates very thick reduces their resistance, however, there is an undesirable consequence. The capacitor is longer monolithic and is simply like a sandwich or somewhat like a deck of cards that is ready to come apart at the first thermal shock or piezoelectric effect. It is a basic tenet of ceramic engineering that electrodes be thin enough, and contain enough ceramic powder such that when sintered, the ceramic capacitor structure becomes truly monolithic. This leaves the designer with only a few effective ways to control the capacitor's ESR. For a given geometry, which is usually dictated by the AIMD design, there are very few degrees of freedom in the length, width and geometry of capacitor electrode plates. Accordingly, in the present invention, maximizing the number of electrode plates becomes a key design factor. This goes hand in hand with the dielectric constant k of the capacitor. In other words, reducing the dielectric constant of a capacitor dielectric means that the number of capacitor electrode plates must increase to achieve the same capacitance value as a capacitor using a dielectric material having a high dielectric constant. The increase in the number of electrode plates naturally reduces the ESR of the capacitor and increases the ability of the capacitor to handle high levels of RF current. Another reason to keep the ESR of the diverter filter capacitor 210, 210' extremely low is so the filter capacitor does not overheat while diverting high levels of RF currents to the housing 124 of the AIMD 100, the AIMD housing being an energy dissipating surface (EDS). In the present application, feedthrough filter capacitors and MLCC chip capacitors can act as high-power RF energy diverters. Energy diverters using an energy dissipation surface (such as a ferrule 134 or an AIMD housing 124) are more thoroughly described in U.S. Pat. Nos. 8,219,208 and 7,751,903, the contents of which are fully incorporated herein by these references. In a diverter filter capacitor, the RF currents are literally conducted through the electrode plates 212, 214 of the filter capacitor 210, 210' and hence through the electrode plate resistance (Re) 190. Electrode plate resistance ($R_e$) 190 is the sum total of the resistance of all of the electrode plates 212, 214 acting in parallel. If the electrode plate resistance (Re) 190 is high, then there is a tremendous amount of $I^2R$ power loss that occurs and the filter capacitor 210, 210' rapidly gets very hot and perhaps destroys itself and/or the surrounding electrical connections or materials. Another reason to keep the ESR 198 of the filter capacitor 210, 210' relatively low is so that the ESR represents a very low impedance Z at the MRI RF-pulse frequency. This will increase ability of the filter capacitor 210, 210' to draw energy from the implanted lead 110 and divert the energy to the energy dissipating surface of the AIMD housing 124. If the filter capacitor represented too high of an impedance, which reduces the current, but also means that more energy is undesirably left in the implanted lead 110. Lowering the impedance Z of the diverter filter capacitor 210, 210' also means that it is a better EMI filter by offering increased attenuation at the MRI RF-pulse frequency.

Even so, it is most important to keep the overall resistance 190 of the electrode plates extremely low (in other words, extremely low ESR) so that overheating of the primary filter capacitor 210 itself is prevented. It has been demonstrated that overheating of the filter capacitor causes the adjacent AIMD housing 124 to also overheat. This is highly undesirable in a human incision pocket. Typically, the AIMD is placed under the skin, under the fat or even under a muscle. There are various FDA and CEM42 Standards that limit the amount of heat introduced to various types of body tissue. In general, the amount of heating is limited to 4° C. (that can vary with body tissue). For example, for a deep brain stimulator, a subdural implanted AIMD must have a much lower temperature rise due to the extreme thermal sensitivity of brain matter. This is in contrast to a pectoral pocket created for cardiac pacemaker or ICD, which represents less thermally sensitive tissues and fats. In any event, it is a major feature of the embodiments herein to prevent the overheating of the primary filter capacitor in order to minimize or eliminate heating of the AIMD housing 124.

In general, the filter capacitor 210, 210' of the present invention may have at least 10 electrode plates. The filter capacitor comprises a dielectric material having a k up to 1,000. It is contemplated that the filter capacitor 210, 210' may comprise an intermediate dielectric constant (mid k) of say 400, 500 or even 600. A mid k dielectric material makes it possible to design a capacitor with less than 10 electrode plates, for example, 5 electrode plates (depending upon their length and width) and still have a low enough ESR in accordance with the present invention (meaning, 5 active electrode plates with 5 ground electrode plates). Alternatively, the number of electrode plates can be as high as 20, 40 or even 100 or more; nonetheless, the critical parameter is that the equivalent series resistance (ESR) of the filter capacitor never exceeds 2 ohms at the MRI RF-pulse frequency. In some embodiments, the ESR can be <0.5 ohm. In some embodiments, the ESR is 0.1 ohm.

FIG. 32 illustrates a cross-section of a multi-layer ceramic capacitor MLCC chip capacitor 210 of the present invention, which is similar to the prior art MLCC chip capacitor 140' illustrated in FIGS. 14, 19 and 20, except that the number of electrode plates in the MLCC chip capacitor of FIG. 32 is substantially increased to minimize ESR. As previously disclosed, the number of electrode plates is a key factor for reducing capacitor ESR. Both the active electrode plates 212 and the ground electrode plates 214 are substantially increased in order to reduce the ESR 198 of the MLCC chip capacitor 210 to less than 2 ohms at the MRI RF-pulse frequency. In an embodiment, the ESR 198 of the MLCC chip capacitor 210 is less than 1 ohm. In addition to the increased number of electrode plates, the MLCC chip capacitor 210 comprises a low k dielectric material (k<1,000) so that the capacitance value is not too high. In an embodiment, the dielectric material is an EIA Class I capacitor such as NP0.

Referring once again to FIG. 32, one can see that the active electrode plates 212 (on the left-hand side) and the ground electrode plates 214 (on the right-hand side) are stacked in an interleaved relation. An electrical attachment material 152 connects the active capacitor metallization 164 to the terminal pin 142 on the left-hand side and the ground capacitor metallization 166 to the ferrule 134 of a hermetic feedthrough 132 on the right-hand side. In general, the electrical connection material 152 is highly electrically conductive, but not necessarily highly thermally-conductive. In summary, the MLCC chip capacitor 210 of FIG. 32 is based on an EIA Class I dielectric, which means its dielectric constant is relatively low and its temperature coefficient, in accordance with standard ANSI/EIA-198-1, published Oct. 29, 2002, Table 2, namely, a permissible capacitance change from 25° C. (ppm/° C.) for Class I ceramic dielectrics. Thus, the maximum allowable capacitance change varies from +400 to −7112 parts per million per degree centigrade. As previously mentioned, an embodiment comprises the C0G dielectric, which is also commonly referred to as NP0.

FIG. 33 is an equation showing the effect of the parallel plate resistances. FIG. 33 gives the equation for the total resistance of the electrode plates ($R_{et}$) of the MLCC chip capacitor being the summation of all parallel electrode plates 212, 214 ("n" electrode plates) of the MLCC chip capacitor.

FIG. 34 is very similar to the cross-section of the quad polar feedthrough filter capacitor previously described in FIGS. 9-10, except that the number of electrode plates 212, 214 have been increased in accordance with the present invention such that the FIG. 34 quad polar diverter feedthrough filter capacitor 210' has a high frequency ESR 198 less than 2 ohms. Referring once again to FIG. 34, one can see that the outside diameter ground capacitor metallization 166 is attached to a gold pocket-pad area 158 of ferrule 134 using a conductive material 152. All of these connections, when properly done, have negligible resistance. Accordingly, the ESR 198 of the feedthrough filter capacitor 210' at high frequency comprises the electrode resistance ($R_e$) 190 of the ground electrode plates 214 and the electrode resistance ($R_e$) 190' of the active electrode plates 212 all acting in parallel. As previously stated, for EIA Class I dielectrics, the dielectric loss tangent resistance 192 of the feedthrough filter capacitor 210' can be ignored at MRI RF-pulse frequencies since said dielectric loss tangent resistance becomes negligible at RF-pulse frequencies. Also, for a feedthrough filter capacitor geometry, skin effect ($R_s$) is also negligible. Referring once again to FIGS. 7-8, one can see a rectangular quad polar capacitor that is similarly attached to a gold pocket-pad area 158.

Figure 35:
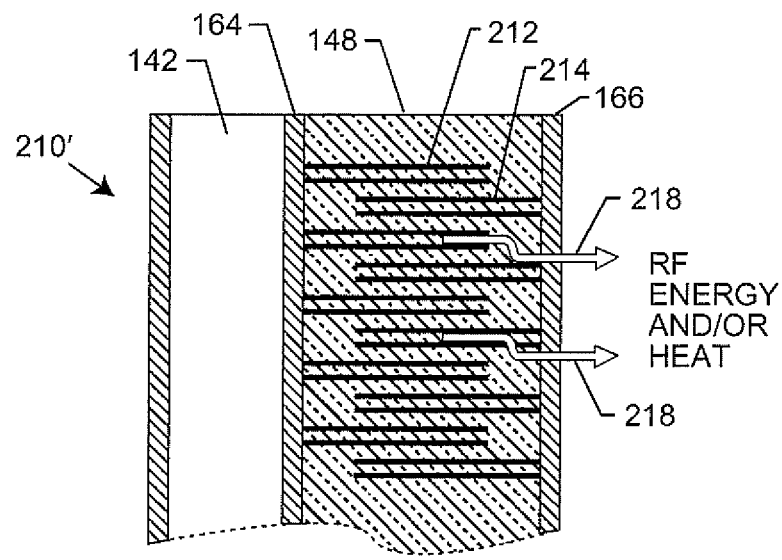
FIG. 35 is a partial cross-section taken from section 35-35 from FIG. 34 illustrating dual electrode plates to minimize capacitor ESR and maximize heat flow out of the capacitor.

FIG. 35 is taken from section 35-35 of FIG. 34 and illustrates a doubling (dual electrode plates) of the active electrode plates 212 and the ground electrode plates 214 of the feedthrough filter capacitor 210'. Doubling the electrode plates 212, 214 is very effective since both electrode plates are still exposed to the internal electric fields of the feedthrough filter capacitor; therefore, both the active and the ground electrode plates, each having doubled plates, will more effectively support electrode plate displacement current flow (RF currents). Dual electrode plate capacitor designs greatly increase the number of electrode plates of a capacitor, which, as shown by the equation of FIG. 33, significantly reduces the overall total electrode plate resistance ($R_{et}$). Dual electrodes are disclosed in U.S. Pat. No. 5,978,204 to Stevenson et al., the content of which is fully incorporated herein by this reference. In the '204 patent, the dual electrodes were utilized to facilitate high pulse currents, for example, in an implantable defibrillator application. Dual electrodes as applied to the present application are very useful in driving down electrode resistance ($R_e$), thereby driving down the high frequency ESR 198 of the feedthrough filter capacitor 210' while also enhancing conduction of RF energy and/or heat 218 out of the feedthrough filter capacitor 210' during exposure to high power MRI RF-pulse environments.

Figure 36:
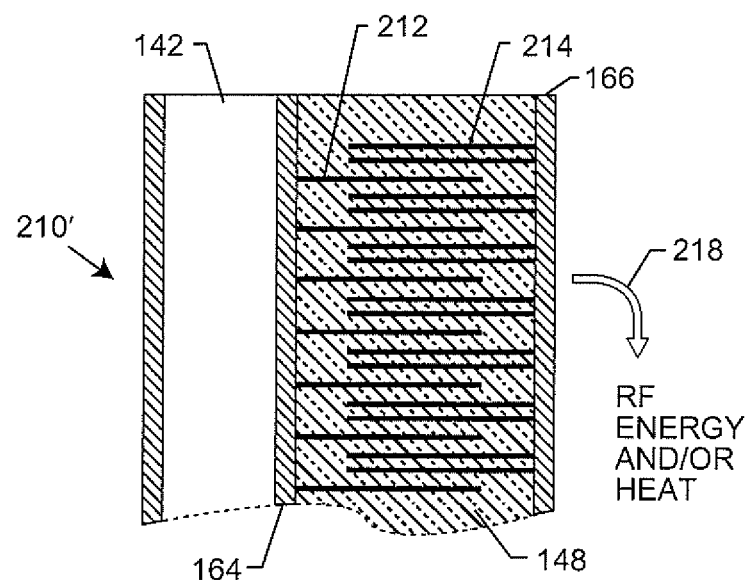
FIG. 36 is similar to FIG. 35 except that just the ground electrode plates have been doubled.

FIG. 36 is very similar to FIG. 35, except in this case only the ground electrode plates 214 have been doubled. Increasing the number of ground plates 214 is particularly efficient in the removal of RF energy and/or heat. As shown, the ground plates 214 are utilized to conduct heat away from the diverter feedthrough filter capacitor 210', directing the heat through the ferrule 134 of the hermetic feedthrough 132 to the housing 124 of the AIMD 100, the housing 124 having a relatively large surface area for heat dissipation. The relatively large surface area of the housing 124 of the AIMD 100 means that a great deal of RF energy and/or heat 218 can be dissipated without concentrating such energy in a small location, which can lead to a very high temperature rise and possibly cause damage to surrounding body tissue.

Figure 37:
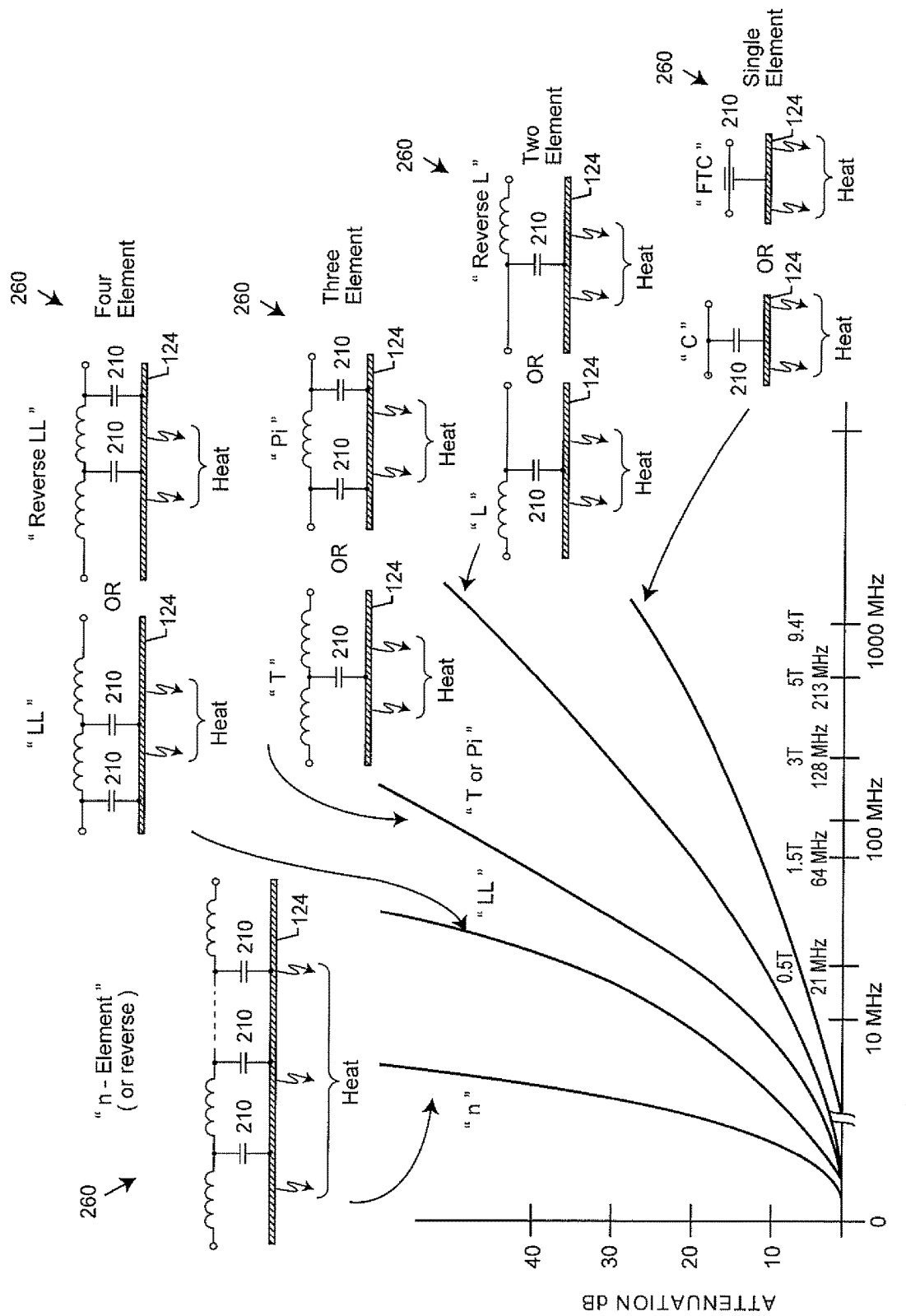
FIG. 37 illustrates a family of lowpass filters indicating the present invention can be anything from a simple diverter capacitor 140 to an n-element lowpass filter.

FIG. 37 illustrates a family of lowpass filters 260 that all incorporate diverter capacitors of the present invention. As can be seen, these lowpass filters 260 incorporate a variety of capacitor designs ranging from a simple MLCC chip capacitor "C" to a three-terminal "feedthrough capacitor-FTC". These diverter capacitors (generally labelled 210 for simplicity) can be combined in various ways with inductors to form "L", "reverse L", "T", "Pi" ($\pi$), "LL", "reverse LL" or "n" element lowpass filters. In other words, as illustrated in FIG. 37, any of the high-power RF handling diverter capacitors of the present application can be combined with any of the lowpass filter circuits of an AIMD for the purpose of protecting the AIMD electronics from EMI, while at the same time pulling MRI induced RF energy or heat from an implanted lead.

Figure 38:
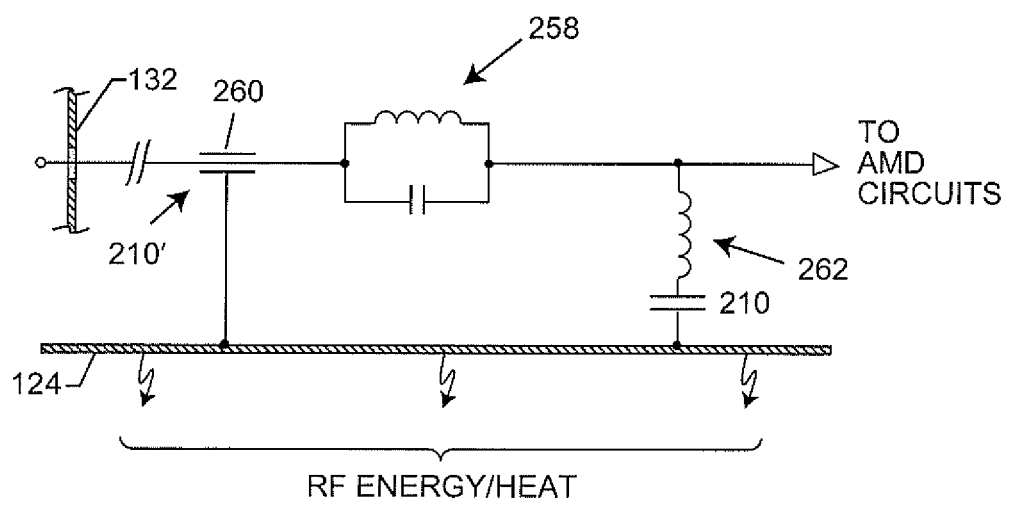
FIG. 38 illustrates a feedthrough diverter capacitor, a bandstop filter and an L-C trap.

FIG. 38 is similar to FIG. 83 of U.S. Pat. No. 9,014,808, the content of which is fully incorporated herein by this reference. The electrical schematic of FIG. 38 represents the simplest form of the lowpass filters of FIG. 37. Represented is a lead in connection with an AIMD hermetic feedthrough 132, which is in connection with a lowpass filter 260, which can comprise any diverter capacitor of FIG. 37. FIG. 38 illustrates the general lowpass filter 260 being an exemplary feedthrough filter capacitor 210' which is connected in series with a bandstop filter 258, which is, in turn, connected with an L-C trap filter 262 disposed between the circuit trace or leadwire and the AIMD housing 124.

Figure 39:
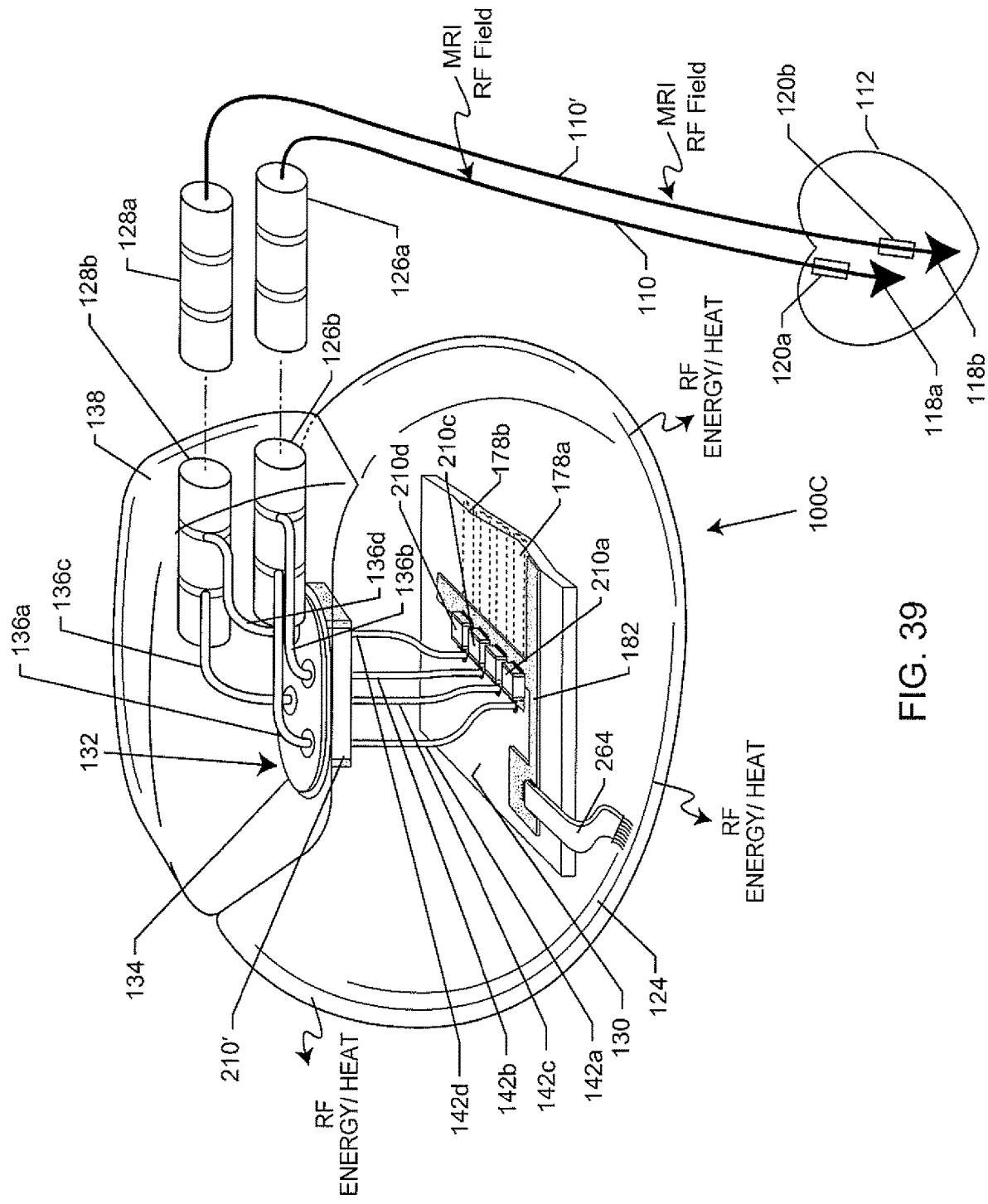
FIG. 39 illustrates a cardiac pacemaker with a diverter feedthrough capacitor and also a circuit board mounted chip capacitor filter which forms a composite filter and also spreads out heat generation.

FIG. 39 shows a dual chamber bipolar cardiac pacemaker 100C with leads implanted into the right atrium and right ventricle of the heart 112. As shown, header block 138 comprises industry standard IS-1 connectors 126a, 128a, 126b, 128b. MRI energy is shown being induced on the implanted leads 110 and 110'. As this energy enters the pacemaker housing 124, it encounters diverter capacitor 210'. The diverter capacitor 210' is designed to dissipate high RF energy or heat in accordance with the present invention. Accordingly, diverter capacitor 210' has a low dielectric loss at high frequency and also very low high frequency ESR. In this case, there is a secondary row of MLCC chip capacitors 210a through 210d that are mounted on the AIMD circuit board 130 at a location distant from the primary diverter capacitor 210'. In this case, the primary diverter capacitor 210' can have a lower capacitance value with the rest of the capacitance comprising either circuit board mounted capacitors 210a through 210d or other similar electrical components. As illustrated, the AIMD circuit board 130 comprises a ground circuit trace 182 that is connected through a low impedance RF conductor, which in FIG. 39 is an RF grounding strap 264, that conducts the RF energy or heat to the AIMD housing 124. This low impedance RF grounding strap 264 is important to conducting MRI RF currents efficiently to the housing 124 of the AIMD 100C. In order to spread out heat, multiple low impedance RF conductors can be used (not shown) of various shapes and configurations, and in any shape and configuration combination. A major advantage of the embodiment shown in FIG. 39 is that by spreading out the filtering function, RF energy/heat or MRI RF energy induced heat is dissipated or spread out over much larger areas. This avoids hot spots on the AIMD housing 124. Referring once again to FIG. 39, it is appreciated that if the capacitance value of the primary filter capacitor 210' (which can be a feedthrough capacitor, an MLCC chip capacitor, an X2Y attenuator, a flat-through capacitor or combinations thereof) is sufficiently large, then the MLCC chip capacitors 210 shown on the circuit board 130 are not necessary. Alternatively, if the circuit board 130 was placed immediately adjacent to the ferrule 134, then it is possible to eliminate the feedthrough capacitor 210' and instead have an MLCC chip capacitor, an X2Y attenuator, a flat-through capacitor or combinations thereof each associated with one of the quad polar leads to act as high frequency RF energy diverters. In summary, referring back to FIG. 39, it is appreciated that one can have a primary filter capacitor 210' that is backed up by one or more onboard chip capacitors 210 or only a feedthrough capacitor 210 or only one or more board-mounted chip capacitors, for example, MLCC chip capacitors 210a through 210d.

Figure 39A:
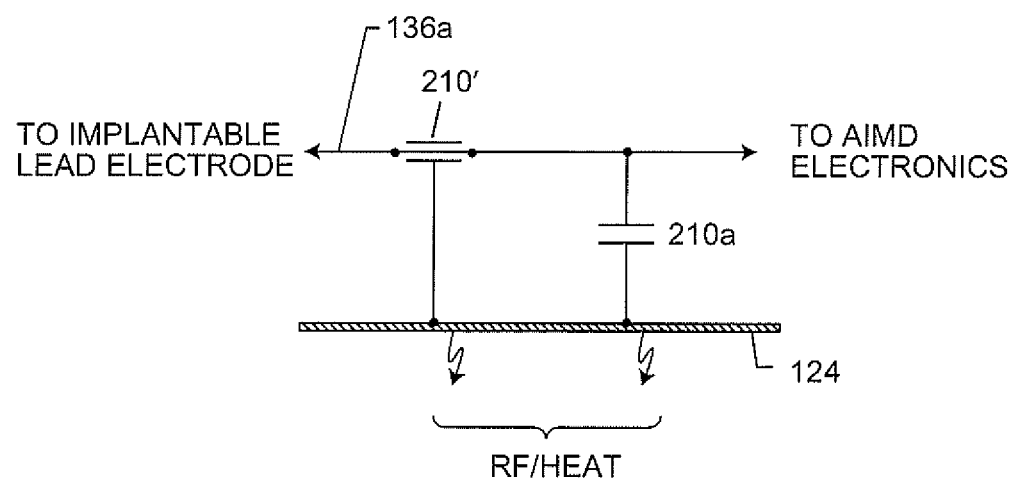
FIG. 39A illustrates the electrical schematic of FIG. 39.

FIG. 39A is the electrical schematic of one of the leadwire circuits 136a of the cardiac pacemaker 100C of FIG. 39. The first low ESR feedthrough filter capacitor 210' is shown in parallel with a two-terminal capacitor 210a. It is appreciated that all four of the quad polar leads 136a through 136d have the same electrical schematic parallel representation.

Referring once again to FIG. 39, it is noted that at least two of the leadwires 136a through 136d extend through the hermetic feedthrough 132 in non-conductive relationship with the ferrule 134 and then extending through respective bores of the feedthrough filter capacitor 210'. These leadwires 136a through 136d then extend to the device side, which is inside the AIMD housing 124, and each are electrically connected to either a via hole or circuit trace land of the AIMD circuit board 130. Each via hole or circuit trace land on circuit board 130 are electrically connected to a capacitor metallization of one of the MLCCs 210a through 210d by leadwires 142a through 142d. For the purposes of this invention, we will refer to the internal electrode plates of the MLCC chip capacitors 210 as having ground electrode plates and active electrode plates. The ground electrode plates are connected to the MLCC chip capacitor's end termination and are therefore electrically connected to the ground circuit trace 182. The capacitor's active electrode plates are electrically connected to at least two leadwires of the leadwires 142a through 142d. It is appreciated by those skilled in the art that circuit board 130 can be an alumina ceramic board, a single layer board, a multi-layer board, fiberglass or FR4 or any number of materials of which circuit boards are made. It will also be appreciated that a connection from the active side of the capacitors 210 can be accomplished by a flex cable (not shown). In such an embodiment, the flex cable replaces the leadwires 142a through 142d on the device side (the inside or inboard side) of the AIMD housing and the flex cable connects to shortened leadwires adjacent the feedthrough filter capacitor 210'. The use of a flex cable greatly simplifies and facilitates the assembly of the AIMD internal circuits. It should also be noted that the ground circuit traces 182 and the embedded circuit traces 178 of circuit board 130 (and other circuit traces not shown) can be made from a variety of materials. Since these are inside the hermetically sealed and biocompatible AIMD housing 124, the circuit traces need not be biocompatible themselves. In fact, they can be made of copper, silver, platinum or any other highly conductive material. In an alternative embodiment (FIG. 39B), the chip capacitors 210a through 210d of the circuit board 130 of FIG. 39 can instead be mounted directly to the flex cable 171 of FIG. 39B.

Figure 39B:
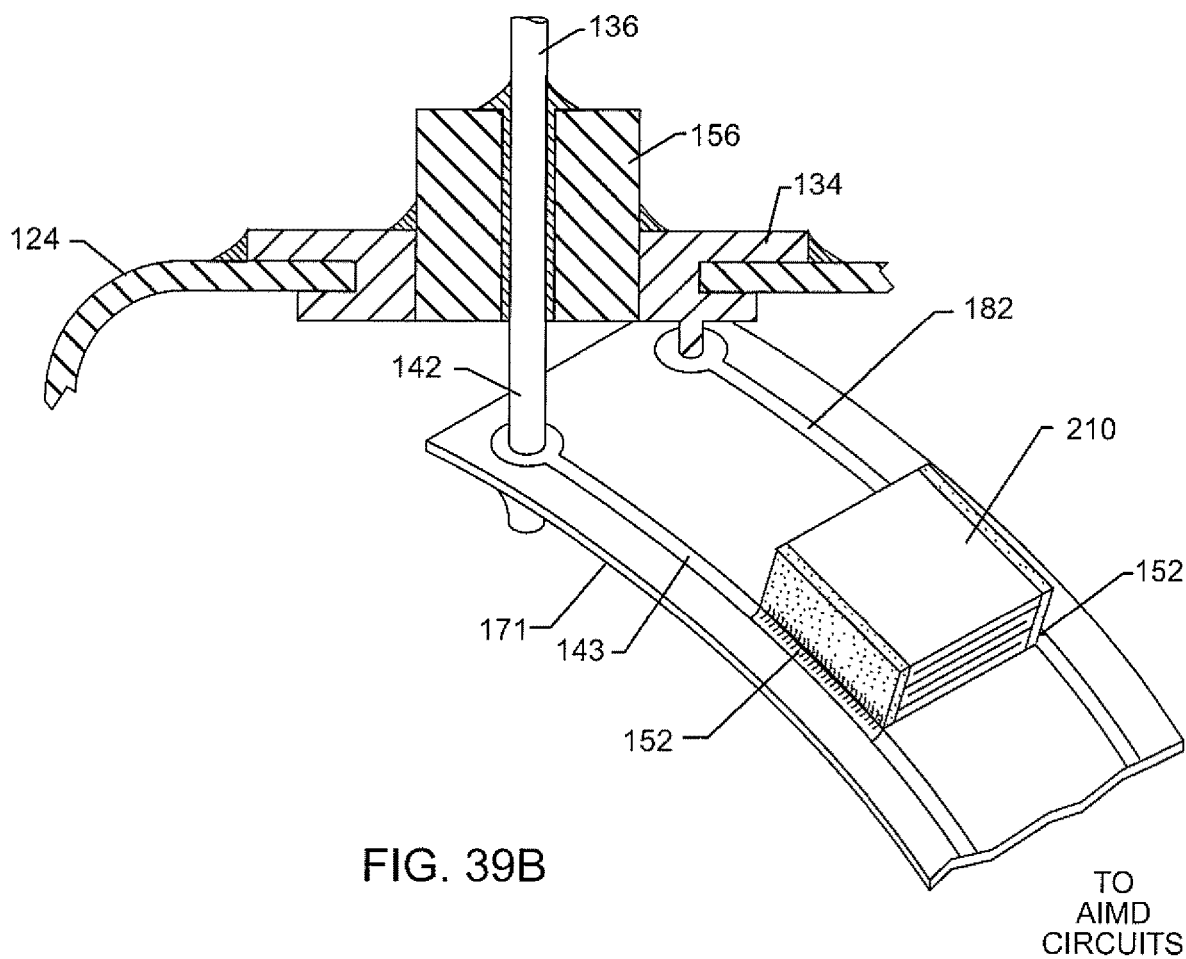
FIG. 39B is a perspective view showing the capacitor mounted to a flexible connection.

FIG. 39B illustrates a unipolar hermetic feedthrough consisting of a ferrule 134, an alumina insulator 156 and a leadwire 136, wherein, the leadwire is labelled 136 on the body fluid side and the same leadwire is labelled 142 on the device side (or inboard side). Shown is a flex cable 171, wherein a first circuit trace (an active circuit trace 143) is connected to the hermetic device side terminal pin 142 of the feedthrough. There is also a second circuit trace (a ground circuit trace 182) which is connected to the ferrule 134, which is the ground connection (the potential of the ferrule 134 is the ground potential). Importantly, the ferrule 134 is welded to the AIMD housing 124. The MLCC chip capacitor 210, which has a k<1,000 in accordance with the present invention, is shown electrically connected between the ground circuit trace 182 and the active circuit trace 143 using an electrically conductive material 152. Electrical connection material 152 can be a solder, a thermal-setting conductive adhesive, a thermal setting conductive epoxy, a thermal setting conductive polymer or similar such conductive material.

Referring once again to FIG. 39, one can see that the MLCC chip capacitors 210a through 210d are a considerable distance from the point of leadwire ingress of the device side terminal pins 142a through 142d of the hermetic feedthrough 132. The embodiment shown in FIG. 39B positions the MLCC chip capacitor 210 closer to the point of leadwire ingress of the device side terminal pin 142 in comparison with the positioning of MLCC chip capacitors 210a through 210d to the ingress of the device side terminal pins 142a through 142d of FIG. 39. The ingress of the device side terminal pin 142 is also the point of ingress of undesirable EMI signals that may be picked up on an implanted lead. Having the MLCC chip capacitors as close as possible to the ingress of the device side terminal pin 142 of the hermetic feedthrough 132 is desirable since at this ingress point the inductance or inductive loop inside the device is reduced. This helps to prevent the so-called "genie-in-the-bottle" effect wherein, once EMI is inside the AIMD housing, it can cross-couple, re-radiate or couple through antenna action to sensitive electronic AIMD circuits thereby causing disruption in device therapy delivery. At MRI RF-pulse frequencies this is not a particular concern since, for a 1.5 T scanner, the RF-pulse frequency is 64 MHz. The wavelength of a 64 MHz signal is so long that it really does not effectively re-radiate once inside an AIMD housing. However, if the MRI filter MLCC chip capacitor 210 is also to be used as a broadband lowpass filter, for example, where it must filter out very high frequency signals above 1 GHz, such as those signals from cellular telephones, then it is desirable to have the MLCC chip capacitor 210 as close as possible to the point of leadwire ingress. Using an MLCC chip capacitor for both diverting MRI RF-pulse frequencies and also as a broadband lowpass filter means that one desirably places the MLCC chip capacitor as close as possible to the point of leadwire ingress. This is specifically shown in FIG. 19 with MLCC chip capacitors 140', which of course, can be MLCC chip capacitors 210 in accordance with the present invention. One is also referred to FIG. 54, which places the MLCC chip capacitors 210a and 210b directly at the point of leadwire ingress into an AIMD housing, where the MLCC chip capacitors 210a and 210b are each connected to a terminal pin (142a and 142b respectively) and to the gold braze 152' of the ferrule 134, thereby providing the lowest impedance connection possible. Mounting MLCC chip capacitors directly at the point of leadwire ingress is further taught by U.S. Pat. Nos. 5,650,759 and 5,896,267, the contents of which are fully incorporated herein by these references.

Figure 39C:
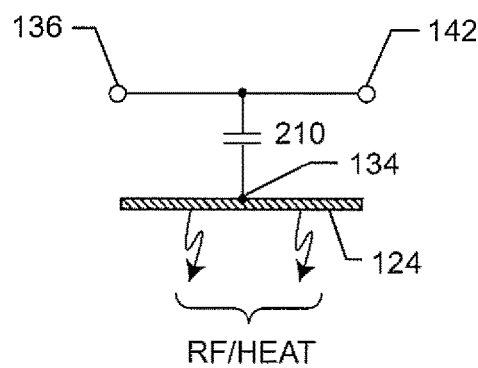
FIG. 39C illustrates the electrical schematic of FIG. 39B.

FIG. 39C illustrates the electrical schematic of FIG. 39B.

Figure 40:
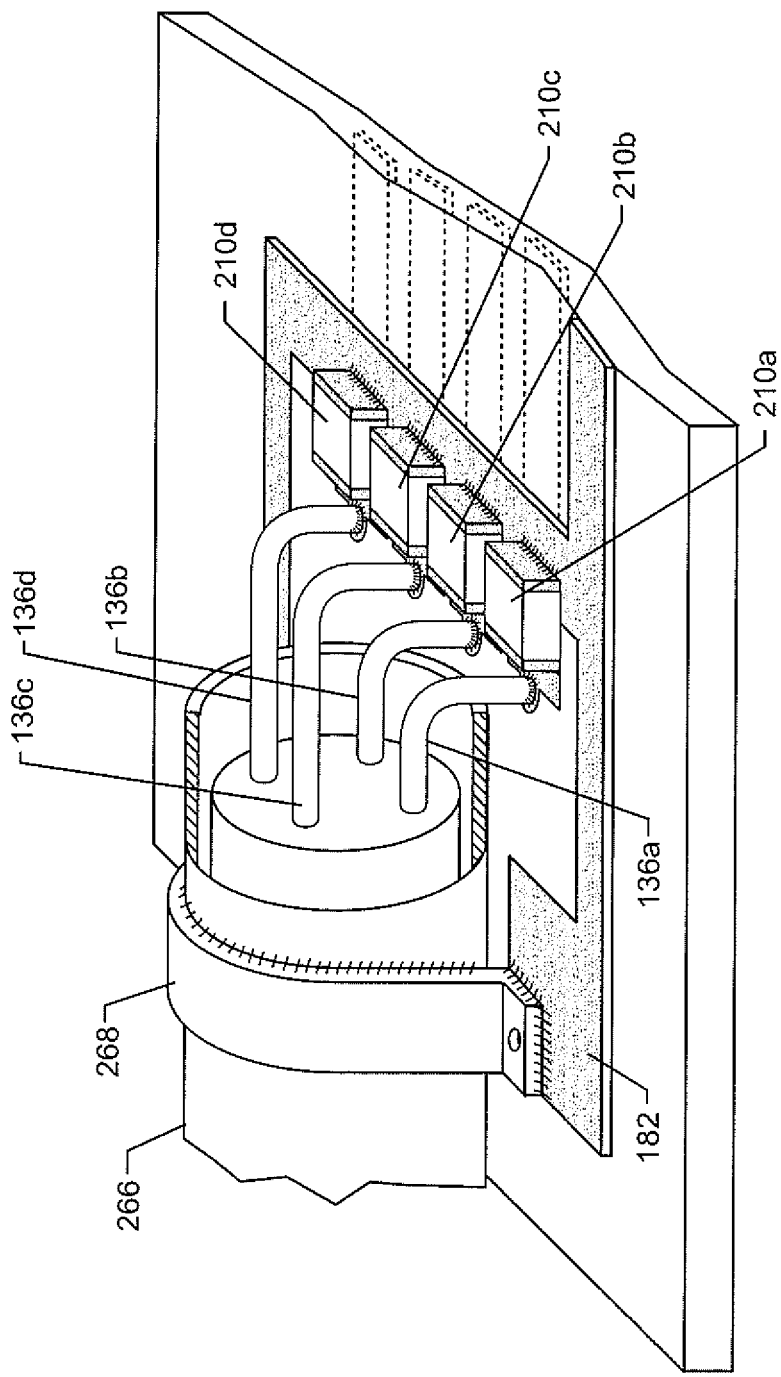
FIG. 40 is a fragmented perspective view of an EMI shield conduit mounted to a circuit board having multiple MLCC chip capacitors.

FIG. 40 illustrates an alternative embodiment to FIG. 39. Similar to FIG. 39, an AIMD circuit board and MLCC chip capacitors 210a through 210d are shown; however, in the embodiment of FIG. 40, the ground circuit trace 182 does not require an RF conductor such as the RF grounding strap 264 to the AIMD housing. Instead, a shielded conduit assembly 266 is attached to the ferrule of the hermetic terminal (not shown). This shielded conduit 266 is grounded with a strap 268 which is connected to the ground circuit trace 182. This type of EMI shielded conduit assembly is more thoroughly described in U.S. Pat. No. 8,095,224 to Truex et al., the content of which is fully incorporated herein by this reference.

Figure 41:
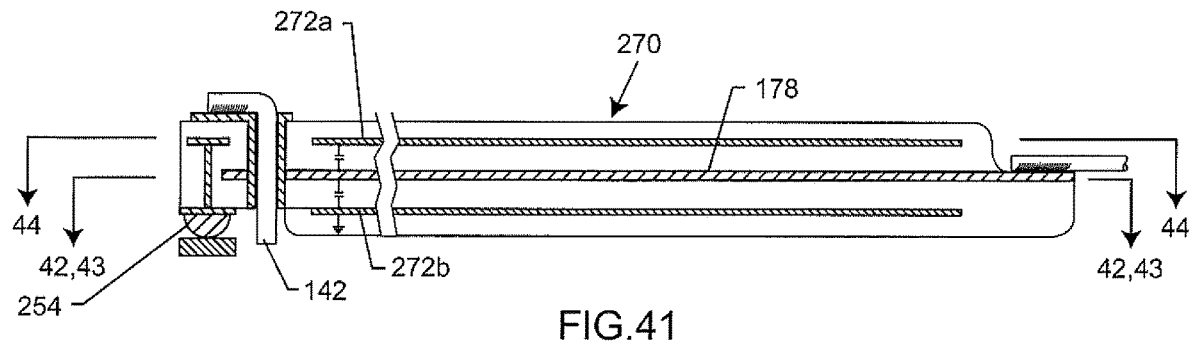
FIG. 41 is a cross-sectional view of a flex cable embodying the present invention.

FIG. 41 shows a cross-sectional view of a flexible circuit board 270, which can also be a flex cable. The flexible circuit board 270 is attached on the left-hand side using a ball grid array (BGA) type attachment 151. BGA attachment 151 is further connected to a terminal pin 142 that passes through a hermetic feedthrough 132 (not shown) of an AIMD. These types of flexible circuit boards, circuit traces or substrates are also described in the incorporated U.S. Pat. No. 8,095,224 to Truex et al.

Figure 42:
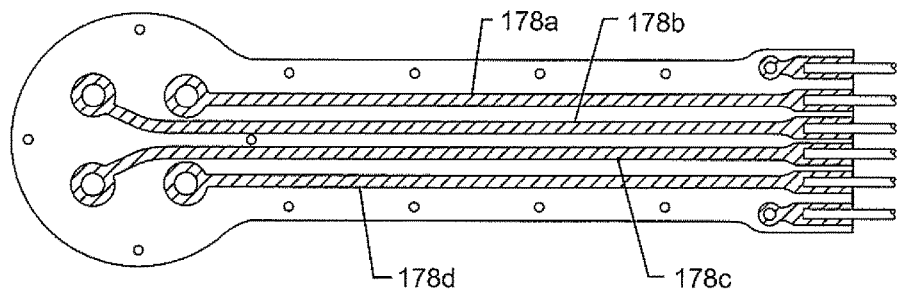
FIG. 42 is a sectional view taken along line 42-42 of FIG. 41.

FIG. 42 shows a sectional view generally taken from section 42-42 of FIG. 41 and shows the conductive circuit traces 178a through 178d.

Figure 43:
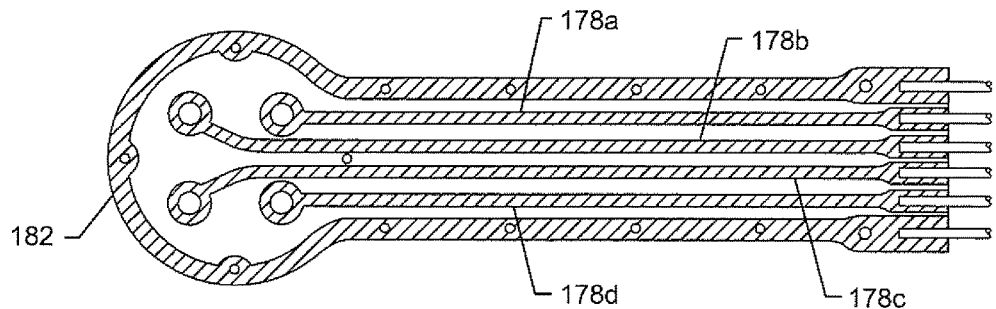
FIG. 43 is a sectional view taken along the line 43-43 of FIG. 41, illustrating an alternative to the internal circuit traces disclosed with respect to FIG. 42.

FIG. 43 illustrates a sectional view generally taken from section 43-43 of FIG. 41 and shows an optional embodiment wherein a ground circuit trace 182 is a ground circuit shield, the ground circuit trace surrounding the four circuit traces 178a through 178d.

Figure 44:
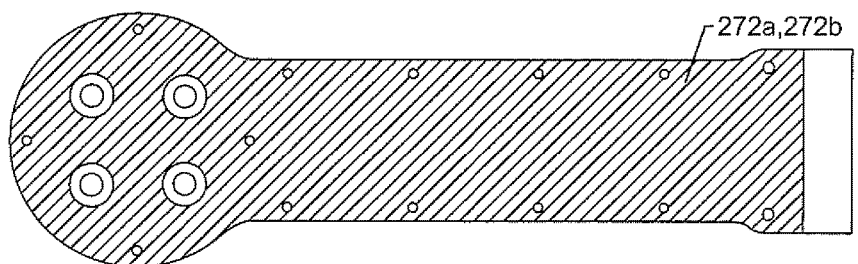
FIG. 44 is a sectional view taken along line 44-44 of FIG. 41, illustrating one of a pair of coaxially surrounding shields disposed about the circuit trace.

FIG. 44 is a sectional view taken generally from section 44-44 of FIG. 41 and illustrates shield layers 272a, 272b. These shield layers 272a, 272b are designed to surround each of the circuit trace layers 178 as previously described in FIG. 42 or 43. These shields 272a, 272b are not absolutely required, but greatly assist in preventing re-radiation of electromagnetic interference inside of the AIMD housing 124. This re-radiation of EMI can be very dangerous as it can couple to sensitive AIMD circuits and disrupt the proper functioning of the AIMD.

Figure 45:
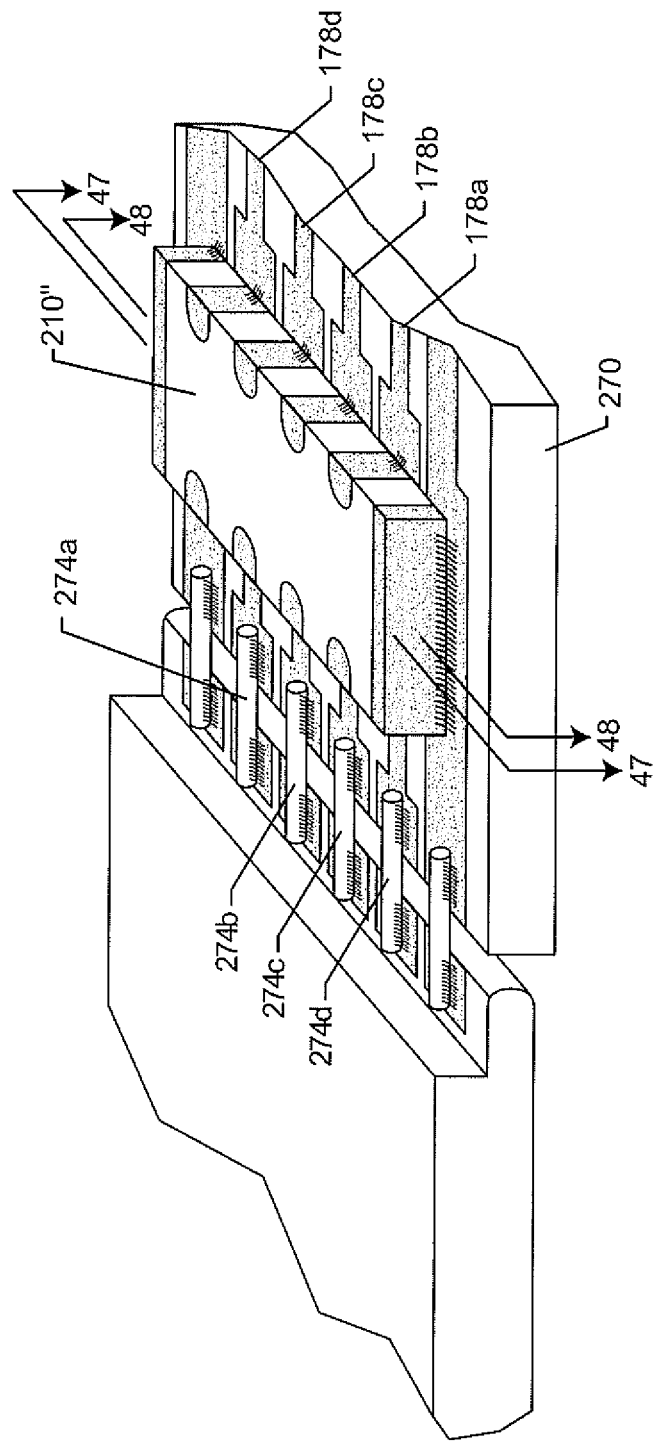
FIG. 45 is an isometric view of the flex cable of FIG. 41 connected to a circuit board or substrate having a flat-through capacitor.

FIG. 45 illustrates an embodiment in which the circuit traces 178a through 178d of FIGS. 41 through 44 are connected to a circuit board 270 or a circuit board substrate. Electrical attachments 274 are made to active circuit traces and in turn to a multi-element diverter flat-through capacitor 210". This three-terminal flat-through capacitor 210" is very similar to flat-through capacitor 140" previously described in FIGS. 17 and 18 except that the flat-through capacitor of FIG. 45 has four capacitors embedded in a single structure. Flat-through capacitor 210" may replace the individual MLCC chip capacitors 210a through 210d of FIGS. 39 and 40.

Figure 46:
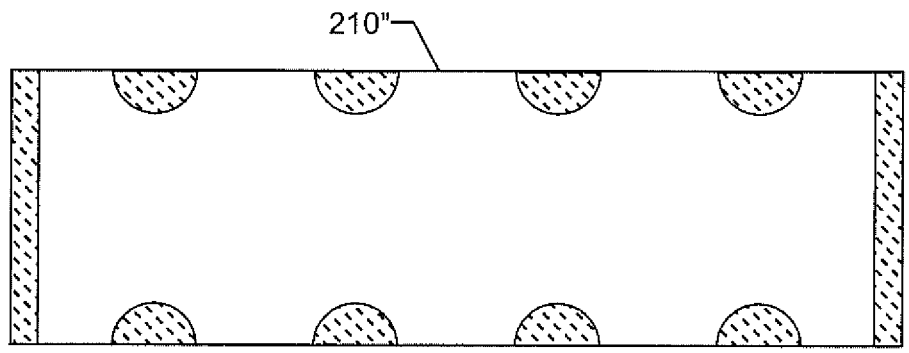
FIG. 46 is the top view of the flat-through capacitor from FIG. 45.

FIG. 46 shows a top view of the diverter flat-through capacitor 210" of FIG. 45.

Figure 47:
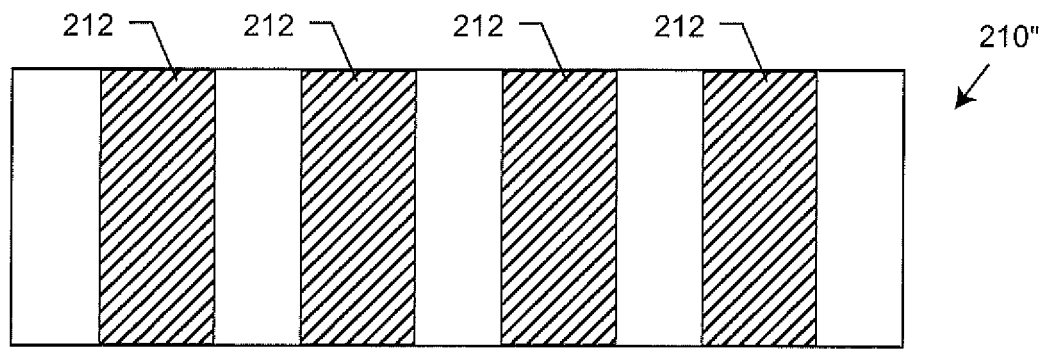
FIG. 47 illustrates the active electrode plates of the flat-through capacitor of FIGS. 45 and 46.

FIG. 47 is a sectional view taken generally from section 47-47 of FIG. 45 and shows the active electrode plates 212 of the flat-through capacitor 210" of FIG. 45.

Figure 48:
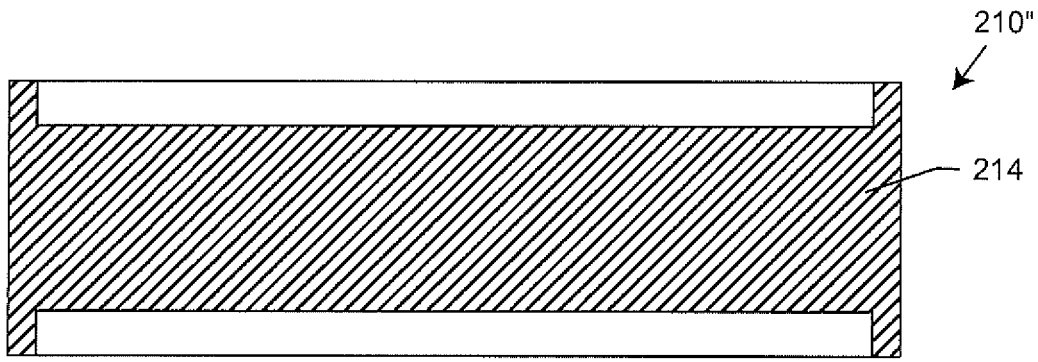
FIG. 48 illustrates the ground electrode plate of the flat-through capacitor of FIGS. 45 and 46.

FIG. 48 is a sectional view taken generally from section 48-48 of FIG. 45 and shows the ground electrode plate 214 of the flat-through capacitor 210" of FIG. 45.

Accordingly, regarding the foregoing, it is appreciated that the present application addresses the problems created when an MRI radio frequency (RF) pulse field couples to an implanted lead in such a way that electromagnetic forces (EMFs), voltages and current are induced in said implanted lead. The amount of RF energy that is induced is related to a number of complex factors, but in general, is dependent upon the local electric field that is tangent to the implanted lead and the integral electric field strength along the implanted lead. In certain situations, these EMFs can cause currents to flow into the distal electrodes of the implanted lead or at the point at which the electrode interfaces with body tissue. It has been documented that, when RF current becomes excessive, overheating of the implanted lead or its associated electrodes in contact with body tissue can occur. Consequently, overheating of the body tissue interfacing with the implanted lead electrodes can also occur, and subsequently potentially cause substantial body tissue damage. There have been cases of damage to cardiac tissue due to overheated electrodes, wherein the damage caused resulted in loss of capture of cardiac pacemaking pulses. Furthermore, with respect to neurostimulators, neurological tissue damage severe enough to result in brain damage or multiple limb amputations have also been documented.

The present invention relates generally to methods and apparatus for redirecting RF energy to locations other than the distal tip electrode-to-tissue interface. In addition, the present invention provides electromagnetic interference (EMI) protection to sensitive active implantable medical device (AIMD) electronics. The redirection of this RF energy is generally achieved by the use of frequency selective devices, such as inductors, capacitors and filtered networks. As described in U.S. Pat. No. 7,689,288, to Stevenson et al., the content of which is fully incorporated herein by this reference, filtered energy dissipation networks can range from a single capacitor, such as a feedthrough capacitor, to more complex filters that may include L-C traps and/or L-C bandstop filters co-operating in various ways with C, L, Pi ($\pi$), T or n-element lowpass filters. In general, this is accomplished through frequency selective lowpass filters or series resonant L-C trap filters, wherein the RF energy can be redirected to another surface or is converted to heat. In all of the above described frequency selective networks, it is the capacitor(s) (co-operating with other circuit elements) which diverts RF energy from an implantable lead to the conductive housing 124 of an AIMD. The relatively large surface area of the AIMD housing 124 acts as an energy dissipating surface (EDS) wherein a significant amount of the MRI energy can be harmlessly dissipated without significant temperature rise. However, the lowpass filter, also known as diverter capacitor elements, must be designed to handle a very high amount of RF current and power. Accordingly, the capacitor's internal resistive or real losses known as equivalent series resistance (ESR) must be kept quite low. The present application is directed to various embodiments of MRI diverter capacitor designs that minimize the diverter capacitor's equivalent series resistance (ESR). In addition, the capacitor is also designed to direct heat to relatively large surface area heat dissipation surfaces, thereby creating an efficient heat removal system. These high RF power/low ESR diverter capacitors are an important feature of the filter network of the present invention for diverting induced RF energy from an implanted lead to an energy dissipating surface, particularly a conductive housing 124 of an AIMD.

While these implantable lead systems are generally associated with AIMDs, such as cardiac pacemakers, cardioverter defibrillators, neurostimulators and the like, the present invention can also be incorporated into external devices, such as external pacemakers, externally worn neurostimulators (such as pain control spinal cord stimulators), catheters, probes, temporary external devices, temporarily implanted active devices and the like. It will be shown that for a given geometry constraint, a preferred means of reducing the diverter capacitor's ESR is to select the most ideal dielectric type so that its dielectric loss tangent (dielectric losses) is insignificant at the MRI RF-pulse frequency (ies). Of particular importance in the present invention is selection of a capacitor dielectric with the proper dielectric constant (k) value. The preferred capacitor dielectric will have a k of a sufficiently low value to thereby increase the number of active and ground electrode plates in the capacitor. This design feature dramatically reduces the ohmic losses in the capacitor at high frequency. Therefore, to accomplish a relatively high electrode plate count, a low k capacitor dielectric is used. A non-limiting example of one such dielectric material is an EIA standard, Class I dielectric material, C0G, which is also known as NP0 (negative-positive-zero)/(refer to EIA Standard ANSI/EIA-198-1-F-2002). Some low k capacitors may have a dielectric material having a k<1,000. Alternatively, some low k capacitors may have a dielectric material having a mid k value, such as 400 to 700. Additionally, some low k capacitors may have a dielectric material having a k<200. Some low k capacitors may also have a dielectric material having a k<100.

In general, at first glance, using an EIA Class I dielectric is counterintuitive. For example, consider a typical X7R MLCC chip capacitor dielectric, with a dielectric constant of around 2,500. With such a high efficiency dielectric material, which has a relatively high dielectric constant, it is possible to build, for example, a 1,000 picofarad filter capacitor with two to four electrode plates. Now consider using an EIA Class 1 C0G dielectric, wherein the dielectric constant is less than 100. A typical capacitor comprising the C0G dielectric material generally requires greater than 20 or even 40 electrode plates to achieve the same capacitance value as the X7R capacitor. The benefit of incorporating a C0G dielectric material within the capacitor design is generally a reduction of the capacitor's ESR at MRI RF-pulse frequencies. If designed properly, for example, designing the capacitor with an appropriate number of electrode plates, the RF energy heat that is produced when positioned within an MRI scanner can be significantly reduced such that the heat resulting from RF energy does not pose harm to biological tissue.

Hence, as disclosed above, one purpose of the low ESR diverter capacitor is to draw MRI induced RF energy out of the implanted lead and redirect said RF energy to the AIMD housing. Such low ESR capacitors have the effect of reducing the RF energy that reaches the distal tip electrode or its interface with body tissue. By redirecting said RF energy to locations at a point distant from the distal electrodes, ideally the AIMD housing, this minimizes or eliminates hazards associated with overheating of said distal electrodes during diagnostic procedures, such as MRI. Another purpose of these low ESR diverter capacitors and related lowpass filter circuits is to provide electromagnetic interference (EMI) filtering in order to protect sensitive AIMD electronic circuits from malfunctioning in the presence of MRI RF noise.

For maximum RF energy transfer out of the lead, frequency selective diverter circuits are needed to decouple, and transfer energy induced onto implanted leads from the MRI RF-pulse field to an energy dissipating surface. Importantly, while decoupling and transferring such energy, it is extremely important that the diverter circuits do not themselves overheat thereby creating hot spots on the AIMD housing, which can damage biological tissue, such as, in a pacemaker pectoral pocket. Recent experiments by the inventors resulted in temperature rises from 4° C. to 10° C. on a pacemaker housing directly over the location of the feedthrough capacitor during a 4 watt/kilogram MRI scan. In general, prior art MLCC chip capacitors are really not indicated for high power RF applications. The reason for this is that the impedance (capacitive reactance) drops so low that extremely high RF currents end up flowing through the MLCC chip capacitor's electrode plates. During a 4 watt/kilogram MRI scan where 16 to 20 volts may be induced at the AIMD input, the diverter MLCC chip capacitor may be handling anywhere from 0.5 amp to 4 amps of RF current. If the ESR of the MLCC chip capacitor, for example, is 0.5 ohm and the MLCC chip capacitor is diverting 2 amps, then the $I^2R$ loss is on the order of 2 wafts. Two watts of dissipation on this small MLCC chip capacitor component causes the MLCC chip capacitor to overheat significantly. The present invention resolves these issues and provides other related advantages.

In summary, the RF diverting circuits, in general, conduct MRI induced RF energy from the lead or its associated leadwires to an EDS such as the housing 124 of the AIMD. The design of the diverter circuit is very important. First of all, the diverter circuit should appear as a very low impedance at MRI RF frequencies such that a maximum amount of RF energy is diverted from the implantable lead to the EDS. In addition, it is also desirable that the diverter capacitor element be designed such that it does not overheat.

The mounting location of the diverter capacitor within an AIMD is also typically constrained by proper EMI design practices. Generally, EMI filters are designed such that undesirable RF energy is diverted at the point of leadwire ingress to the AIMD housing, instead of letting the EMI inside the AIMD housing and then trying to filter said EMI further downstream in the AIMD circuit path, for example, filtering at an internal circuit board instead of at leadwire ingress. In an embodiment, at least one of the low ESR diverter MLCC chip capacitors of the present application is mounted directly to the multi-pin hermetic feedthrough of the AIMD. This is an ideal location both to divert RF energy before it can enter the AIMD housing and this is also optimal for heat conduction and dissipation. Even with low ESR, the diverter MLCC chip capacitor will still be dissipating a significant amount of energy. This means, even with low ESR, the diverter MLCC chip capacitor is creating heat which must be conducted or convected away so that a hot spot does not occur on the AIMD housing at or near the filter capacitor. Therefore, by diverting both the RF energy and heat to the relatively large surface area of the housing of the AIMD, the MRI RF energy can be dissipated with only a small temperature rise, which does not adversely affect body tissue.

It is noted that the general principle of placing a primary filter capacitor (energy diverter) at the point of leadwire ingress in the AIMD housing is generally the preferred EMI design practice. For relatively low frequencies, such as an MRI RF-pulse frequency of 64 MHz, it is perfectly acceptable, however, to place the primary diverter filter capacitor on a circuit board remote from the hermetic feedthrough otherwise known as the point of leadwire ingress.

Figure 49:
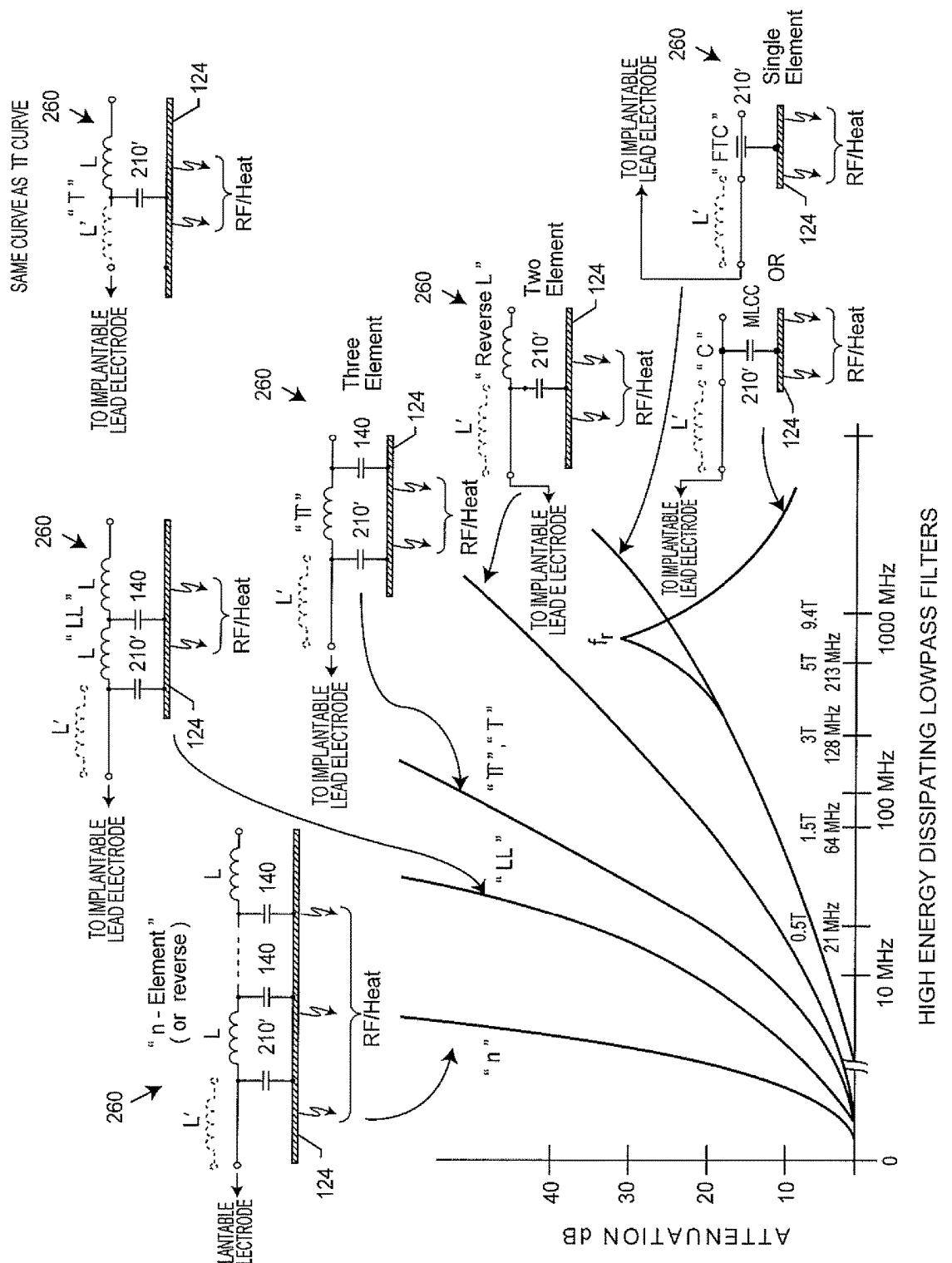
FIG. 49 illustrates a family of lowpass filters, which is very similar to the family of lowpass filters described in FIG. 37.

FIG. 49 illustrates a family of lowpass filters, which is very similar to the family of lowpass filters described in FIG. 37. The lowpass filters of FIG. 49 are also known as EMI filters, meaning that they allow low frequencies to pass, but provide a substantial amount of attenuation at higher frequencies. As previously disclosed, the lowpass filters 260 of FIG. 37 incorporate a variety of capacitor designs ranging from a simple MLCC chip capacitor "C" to a three-terminal "feedthrough filter capacitor-FTC". These diverter capacitors can be combined in various ways with inductors to form "L", "reverse L", "T", "Pi" (t), "LL", "reverse LL" or "n" element lowpass filters. As can be seen in FIG. 49, there is a capacitor element 210' in every one of the circuits that is directed towards the implantable lead electrode (body fluid side). The conduction path is from the electrode of the implantable lead, which is in contact with biological tissue, along the conductor of said implantable lead through the hermetic feedthrough of the AIMD along the feedthrough terminal pin directly to the capacitor 210'. In accordance with the present invention, the capacitor 210' is a high RF power, low ESR handling capacitor so that the capacitor 210' and the AIMD will not overheat in an MRI environment. One will also note that the n-element filter has been revised so that there is no longer an inductor directed toward the implantable lead electrode. The version of the LL filter, with the inductor directed to the implantable lead electrode has also been eliminated. In addition, the version of the two-element or L filter, with the inductor toward the implantable lead electrode has also been eliminated. These elements are eliminated because, in the present invention, it is very important that the primary high-power RF handling capacitor have a direct connection from its active electrode plates through the hermetic feedthrough to the one or more electrodes of the implantable lead.

Referring once again to FIG. 49, for the n-element, LL and Pi (π) filters, one can see that there are two capacitors 210' and 140 separated by an inductor. In the present invention, it is critical that capacitor 210' have an ESR<0.5 ohm at the MRI RF-pulse frequency and be made with a dielectric material having a dielectric constant k<1,000. This is so that it the capacitor 210' can have a high electrode plate count and a very low equivalent series resistance at MRI pulse frequencies. The capacitor element 140 can be constructed of a low ESR construction the same as capacitor 210' or capacitor element 140 can alternatively be constructed as prior art filter capacitors are typically constructed and that is with conventional ceramic dielectrics having a k>1,000. Another way of looking at this is that the first capacitor directed toward the implanted electrode is the work horse and is going to do the bulk of the diverting of RF energy from the lead, diverting it to the AIMD housing where the energy and or heat can be dissipated over a large surface area.

As a point of reference, the first EMI filter ever designed for an active implantable medical device was in the mid-1970s for the Xytron Medtronic pacemaker. These were unipolar feedthrough capacitor EMI filters that had a k>1,200. The principle designer on this filter design project was Robert Stevenson, one of the co-inventors herein. The next EMI filter to be designed for cardiac pacemaker was in 1979 for a St. Jude pacemaker. Robert Stevenson worked with St. Jude Vice President Buehl Truex to design in this filter, which generally had a k>2,200. The inventors herein have spent their entire careers designing EMI filters for a variety of applications, including AIMD applications. This is significant in that there has never been a case where the primary passive EMI lowpass filter (the work horse filter) had a k<1,200. In addition, the inventors have either been asked to bid, have been aware of, or have cross-sectioned and analyzed explants of other manufacturer's EMI filters and have found the same thing to be true and that is, prior art EMI filters have consistently been built around a dielectric structure that has a k of at least 1,200. For the last 30 years, almost all primary EMI filters (the work horse filter) have been designed with a k of greater than 1,200. There are several reasons why the industry has always designed EMI filters having a k of about 1,200 (and generally above 2,00 to 2,200). The first important reason is that active implantable medical devices must be very small in size and very low in weight. Another consideration is cost. By using a high k dielectric, one needs fewer electrode plates and can build the capacitor much thinner and in a much smaller overall volume or footprint. This is ideal for all AIMDs, again, where size and weight are critical. Until the MRI application came along, on which this patent focuses, it was never contemplated to do what is completely counterintuitive and that is to use a low k capacitor for AIMD filtering.

The parent application claims primary passive diverter capacitors (work horse capacitors) having k<200. There is also a general reason for this and that is that the major material suppliers in the ceramic dielectric industries, such as Ferro, typically offer dielectrics either above 1,200 k or below 200 k. As previously disclosed, the dielectrics below 200 k are known as Class 1 dielectrics. These Class 1 dielectrics find broad application in military and space applications, however, have never been used for the primary EMI lowpass filter capacitor for an AIMD until now. There is a vast desert in terms of material supply in the dielectrics industry in that there are almost no suppliers of dielectric materials having k between 200 k and 1,000 k. There are a couple of specialty ceramic powder manufacturers, one of which is Dimat, Inc. Dimat offers a range of specialty dielectrics, including an N2200, which has a dielectric constant of 250; an N3300, which has a dielectric constant of 400; an N4700, which has a dielectric constant of 600; and, an N5250, which has a dielectric constant of 700. There is also another company called MRA Materials, which offers a dielectric with a k of 485 and also a dielectric with a k of 600. Nevertheless, none of the specialty or niche dielectrics companies have ever used or suggested use of such low k dielectric materials for a primary lowpass EMI filter for an AIMD. The present application teaches and claims that the primary EMI filter capacitor, which is directly connected through wiring to an implantable lead conductor with distal electrodes, comprises a k<1,000. There is a practical reason for this. In some cases, the capacitance value can be considerably high, such as 1,800-pF. Building this capacitor out of a common commercially available dielectric, such as NP0 (having a k of 90) results in a capacitor that has so many electrode plates that it is often too thick to fit into a cardiac pacemaker. Accordingly, the inventors developed a mid k (intermediate) dielectric (between 200 k and 1,000 k), which presents an ideal tradeoff between volumetric efficiency, a lower k, a higher number of electrode plates and, correspondingly, an ESR of less than 0.5 ohm that will meet all of the design criteria, including small in size, low in weight and low in cost while effectively filtering.

In the embodiments herein, it is possible to split the primary capacitance, the primary capacitance comprising a primary diverter lowpass filter capacitor, which is the work horse capacitor of the AIMD, by breaking up said primary capacitance into two areas. Referring to FIG. 37, shown is a primary capacitance broken up using two different capacitors, for example but not limited to, a feedthrough filter capacitor (FTC) 210' and a board mounted capacitor MLCC chip capacitor 210. In a preferred functional primary capacitance design, the exemplary first capacitor 210' has a dielectric constant of less than 1,000 and even preferably less than 200. For example, for a needed overall functional primary capacitance value of 1,800-pF, the high-energy, low ESR first capacitor 210' can be 800-pF and the second board mounted capacitor 210 can be 1,000-pF. It is noted that the exemplary second board mounted capacitor 210 can be conventional technology with a dielectric constant above 1,000. Hence, the first capacitor 210' and the second board capacitor 210 add up in parallel to provide 1,800-pF, which is the functional primary capacitance design goal. The advantage of functionally designing primary capacitance in this way is that the first capacitor (FTC) 210' is thinner, thereby facilitating packaging of both the first capacitor and the AIMD circuit board. The capacitance values of 800-pF and 1,000-pF are chosen at random and are not necessarily representative of any particular functional primary capacitance design. In other words, the first capacitor 210' can have a capacitance of 200-pF and the board capacitor 210 can have a capacitance of 1,600-pF. Accordingly, a functional primary capacitance design comprises a first capacitor and one or more additional capacitors, the first capacitor comprising a first capacitance value and a dielectric material having k<1,000, and the one or more additional capacitors each comprising an additional capacitance value such that the sum of the first capacitance value and the additional capacitance values achieve a desired overall functional primary capacitance value. Furthermore, the capacitance value of the first capacitor and the capacitance value of the one or more additional capacitors may comprise any capacitance value in any value combination to achieve the desired overall functional primary capacitance value.

In summary, a primary filter capacitor (that is, a work horse filter capacitor) having a dielectric constant of less than 1,000 has never been built for use in AIMDs having a direct connection to the conductor of an implantable lead, the implantable lead having an electrode in contact with body tissues. As this application teaches, one of the reasons for this is that designing a capacitor with a dielectric constant of less than 1,000 is completely counterintuitive for incorporation into AIMDs, as such capacitors require high number of electrode plates typically making such low k capacitors too big for AIMDs. Moreover, it is only with the advent of MRI conditional AIMD systems and implantable leads and the recent discovery that a primary filter capacitor itself can substantially overheat during MRI scanning, causing the housing 124 of an AIMD implanted in a pectoral pocket to excessively overheat such that the patient can actually feel a burning discomfort in the pectoral area of the chest, that primary filter capacitors with a k<1,000 have become an attractive filtering design solution. While dielectric constant capacitors (k<1,000) require a high number of electrode plates for the ESR of the capacitor to be sufficiently low such that when the capacitor diverts RF energy (up to 6 amps) at MRI RF frequencies, the capacitor itself will not overheat, the present application teaches embodiments having sufficient number of electrode plates to reduce the electrode resistance of the capacitor in combination with a dielectric material having a dielectric constant k<1,000 such that the primary filter capacitor (the working horse capacitor) alone or in combination with one or more additional capacitors enables low ESR. As the ESR of a capacitor at high frequency is primarily an ohmic loss, and assuming all other electrical connections are solid, the ESR essentially comprises only the resistance of the electrode plates. Increasing the number of electrode plates significantly reduces ESR of low k capacitors. Dielectric constant selection of the dielectric material of the capacitor in combination with the number of electrode plates provides for overall functional primary capacitance value.

In the embodiments herein, the goal is to drop ESR substantially so that insignificant heat is produced by the filter capacitor itself and undue undesirable AIMD implant pocket heating does not occur. The FDA and the industry generally limit implant pocket heating to about 4° C. It has been demonstrated through experiments by the inventors that the combination of overheating of prior art primary lowpass filter capacitors with a k greater than 1,200 can by themselves result in the AIMD housing and the corresponding human pocket overheating significantly above 4° C. The embodiments disclosed herein resolves such heating problems among other related advantages.

Referring once again to FIG. 37, noted is a variation between the circuit diagrams of the "LL" and "reverse LL" as compared to the "L" and "reverse L". Referring to the LL filter, one can see that there is a capacitor 210 to the left of the inductor on the left-hand side circuit diagram. For the reverse LL, there is an inductor to the left of a capacitor 210 on the right-hand side circuit diagram. Referring to the L filter, one can see that the inductor is to the left of the capacitor 210 on the left-hand side circuit diagram (instead of the capacitor 210 being to the left of the inductor as shown by the LL circuit diagram). Similarly, for the reverse L filter, the capacitor 210 is to the left of the inductor on the right-hand side circuit diagram (instead of the inductor being to the left of the capacitor 210 as shown by the reverse LL circuit diagram). FIG. 37 illustrates that there is really no industry standard on what constitutes a reverse L or a reverse LL filter. In fact, when manufactured, as such filters can be installed by the user in either direction. As such, FIG. 49 illustrates a reverse L filter and a reverse LL filter both ways to emphasize that there really is no industry standard between the terms LL and reverse LL or L and reverse L. Hence, the reference in the claims to the LL, the reverse LL, the L and the reverse L filters refer to the specific electrical schematic shown in FIGS. 37 and 49 as well as in other detailed schematic diagrams herein.

Referring once again to FIG. 49, one will see that for a single element capacitor, said single element capacitor can be a two-terminal device "C" such as an MLCC chip capacitor or a three-terminal device "FTC" such as a feedthrough filter capacitor. It is understood by those skilled in the art that any of the capacitors 210' shown in FIG. 49, can be two-terminal capacitors "C" or three-terminal capacitors "FTC", wherein the two-terminal capacitors may comprise one of an MLCC chip capacitor, an X2Y attenuator, or combinations thereof; and wherein the three-terminal capacitor may comprise one of a feedthrough filter capacitor, an X2Y attenuator, a flat-through capacitor or combinations thereof. It is noted that X2Y attenuators comprise both two-terminal and three-terminal design configurations.

Referring once again to FIG. 49, one can see that the attenuation versus frequency insertion loss curve for the three-terminal single element feedthrough filter capacitor "FTC" does not have a significant resonant dip at high frequencies. However, when one refers to the insertion loss curve for a single element two-terminal MLCC chip capacitor "C", one can see that the single element two-terminal MLCC chip capacitor has a significant resonant dip at high frequencies shown as self-resonant frequencies fr. Such self-resonant frequencies fr of the MLCC chip capacitor is due to significant equivalent series inductance 204 as shown in the MLCC chip capacitor equivalent circuit diagram of FIG. 25. When a capacitor has equivalent series inductance, there is always going to be some frequency at which the capacitive reactance is equal and opposite to the inductive reactance. This is known as the self-resonant frequency of the capacitor. Observable in FIG. 49 is an insertion loss peak at the capacitor's self-resonant frequency fr. The two-terminal single element MLCC chip capacitor insertion loss versus frequency curve goes to infinity if it were not for the MLCC chip capacitor's equivalent series resistance. In other words, the MLCC chip capacitor has infinite attenuation in dB if not for the capacitor's equivalent series resistance (ESR). The problem of a decreasing insertion loss of the MLCC chip capacitor occurs at frequencies above its self-resonant frequency $f_r$. At higher frequencies above a self-resonant frequency, the inductive reactance becomes increasingly dominant, which undesirably reduces the filter attenuation in dB. Well mounted feedthrough filter capacitors tend to have essentially zero equivalent series inductance 204 as shown in FIG. 25 and therefore have a more ideal filter attenuation versus frequency insertion loss curve.

Figure 49A:
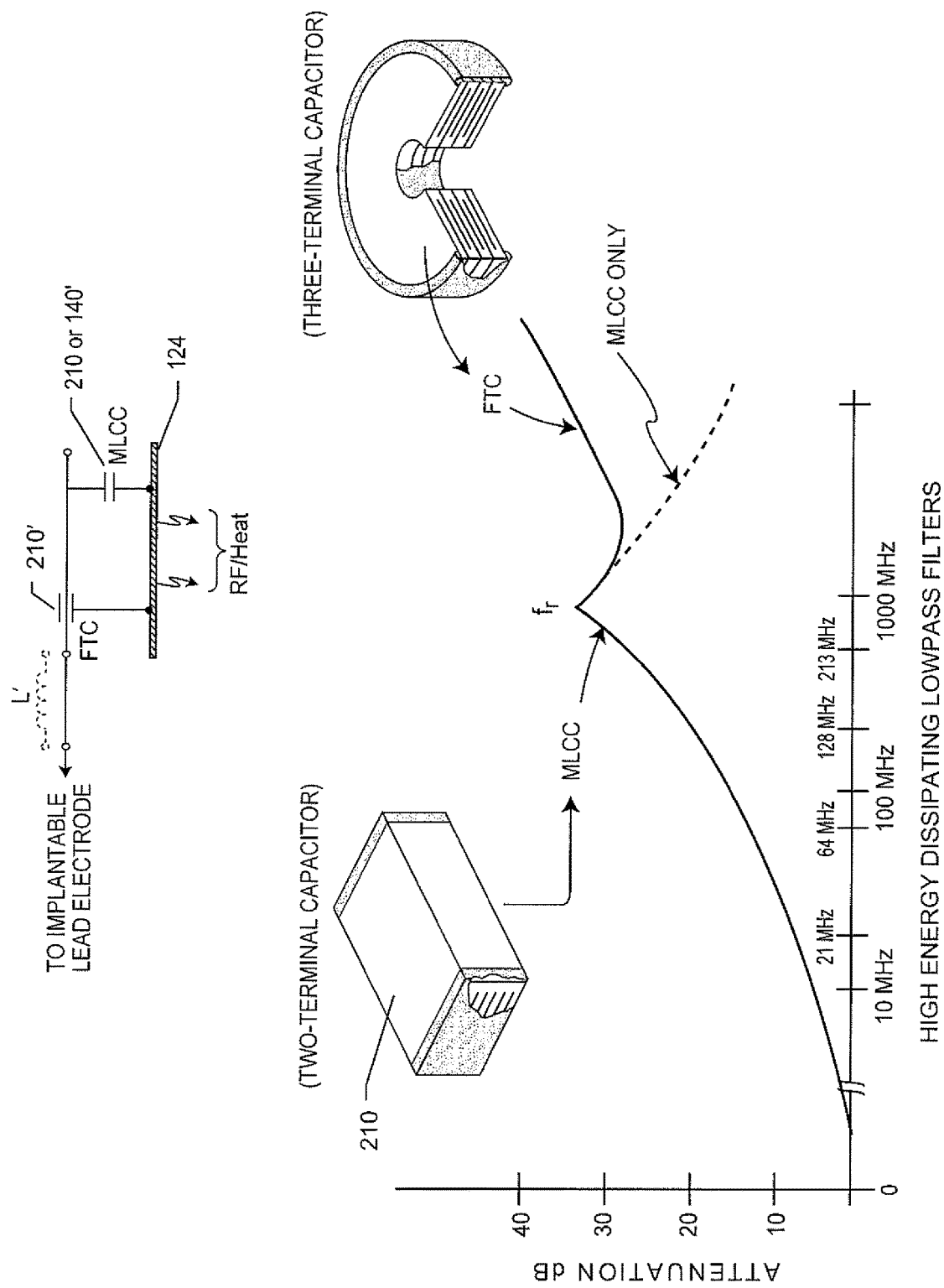
FIG. 49A is similar to FIG. 49 now showing the attenuation curve for a feedthrough capacitor with chip capacitor.

FIG. 49A reads on FIG. 39 and FIG. 39A. In FIG. 39, disclosed is that one can split up the functional primary filter capacitance of an AIMD into, for example, a feedthrough filter capacitor FTC 210' and a board-mounted capacitor MLCC chip capacitor 210a. Referring to FIG. 49A, the schematic diagram illustrates an exemplary embodiment of an FTC 210' in accordance with the present invention having a k<1,000 and extremely low ESR properties (an ESR of <2 ohms at the MRI RF-pulse frequency) in parallel with a board-mounted capacitor MLCC chip capacitor 210 (or 140'). The MLCC chip capacitor 210 (or 140'), can also have a k<1,000 (embodiment 210) in accordance with the present invention, or can have a k<200 (embodiment 210), or can be a prior art MLCC chip capacitor having a k>1,000 (embodiment 140'). Also shown in FIG. 49A is the composite insertion loss curve of the FTC 210' in parallel with the MLCC chip capacitor 210 (or 140'). The dashed line (labelled MLCC ONLY) represents the effect on attenuation as a function of frequency if the filter comprised only an MLCC chip capacitor. One can see that the attenuation of a filter having only an MLCC chip capacitor reaches a maximum and then degrades at higher frequencies. With the low k feedthrough filter capacitor FTC 210', which as previously disclosed has zero series inductance at high frequencies, one can see that the attenuation picks up (lifts up) the degradation and insertion loss that occurs from the MLCC chip capacitor only (in other words, improves attenuation at the high frequencies); hence, splitting up the functional primary filter capacitance of the filter between the FTC 210' and the MLCC chip capacitor 210 (or 140') yields an overall combined broadband lowpass filter attenuation performance which is preferred for AIMD EMI and MRI filters, as such filters provide electromagnetic interference (EMI) protection to sensitive active AIMD electronics and also handle RF energy or heat induced in an AIMD lead from an external RF field at a selected MRI frequency or a range of MRI frequencies.

Referring back again to FIG. 49, one can see that each one of the lowpass filter circuits has a phantom inductor L' drawn with dashed lines. The phantom inductor L' is included in order to acknowledge that all conductors have some amount of series inductance and that the amount of inductance is in series between the primary work horse capacitor (in the example FTC 210') and the distal lead conductor electrode. The embodiments of the present application targets such series inductances so that said series inductance L' is kept as low as possible (as close to zero as practical). If series inductance is too large, then a large inductive reactance occurs at MRI RF-pulse frequencies, thereby reducing the amount of energy that can be pulled from the lead. In other words, it is desirable that the first thing connected to the implantable lead electrode along the path of the implantable lead is the work horse capacitor (such as the exemplary FTC 210') so that said work horse capacitor can draw maximal energy out of the implanted lead. It is also critical that the work horse capacitor be very low in ESR, so that said work horse capacitor does not overheat while drawing literally amps of MRI induced energy out of the implanted lead. Many implantable leads themselves are made of spiraled or of coiled construction and some of these are insulated, while others are not insulated. The uninsulated lead conductors tend to short together, particularly when going through tortuous paths, such as bends in a venous system. Therefore, the parasitic conductance of the uninsulated leads will vary significantly due to design and lead trajectory differences. As such, the phantom inductors L' of FIG. 49 are meant to acknowledge that, pending AIMD system and lead design, some parasitic inductance can be associated with the direct connection of the primary work horse capacitor (for example, FTC 210') and a distal electrode. In summary, it is particularly important that the parasitic inductance be minimized from the point of leadwire ingress into the AIMD housing, that is, from the point where the leadwire passes through the conductive pathway of the insulator of the hermetic feedthrough. It is also very important that there be insignificant or very little parasitic inductance between the work horse capacitor and that point of leadwire ingress into the device side of the AIMD, namely inside of the AIMD housing.

Figure 50:
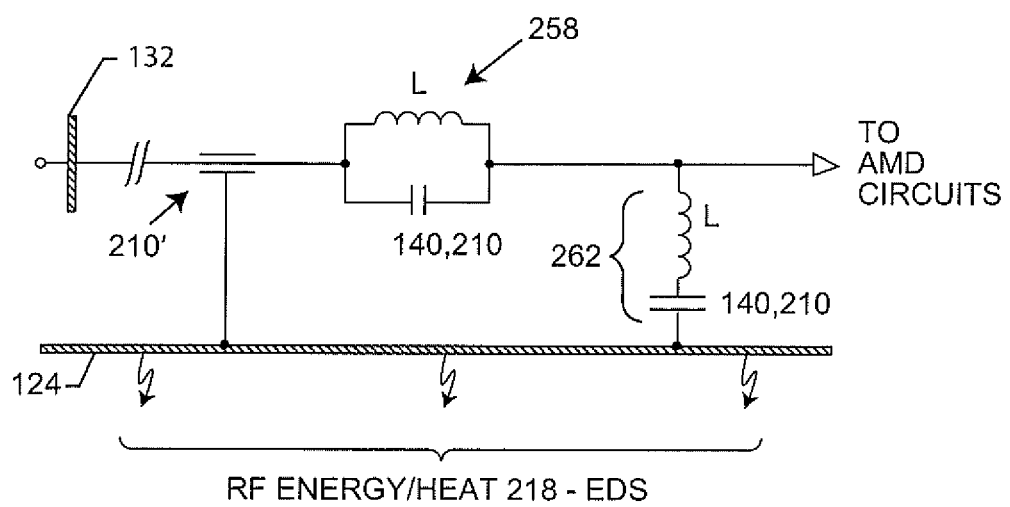
FIG. 50 illustrates that the high energy dissipating low ESR capacitor can be used in combination with other circuits.

FIG. 50 illustrates that a high energy dissipating low ESR capacitor 210' can be used in combination with other circuits, such as bandstop filter 258 and/or an L-C trap filter 262, the bandstop and the L-C trap filters each consisting of a capacitor 140 or 210 and an inductor L. Again, the capacitor of the bandstop filter 258 and the capacitor of the L-C trap can be conventional prior art filter capacitors or can be low k capacitors. Regardless, capacitor 2101 is the work horse capacitor and must comprise very low in ESR in accordance with the present invention, in other words, must be a low k capacitor.

Figure 51:
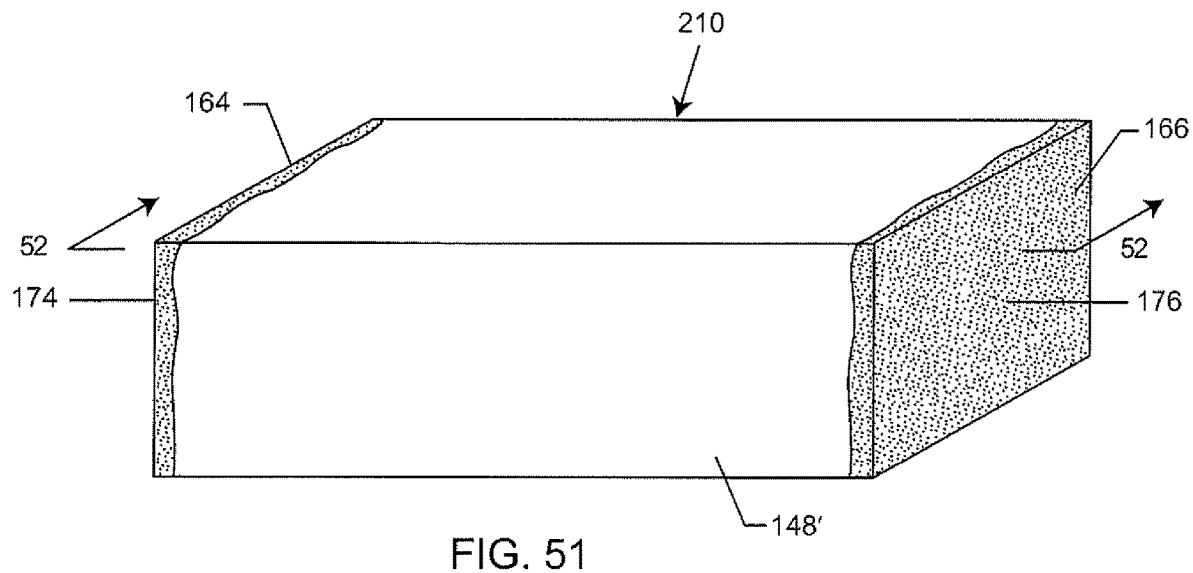
FIG. 51 shows an isometric view of an MLCC chip capacitor that is similar in its exterior appearance to the prior art MLCC chip capacitor previously described in FIGS. 14 and 15.
Figure 52:
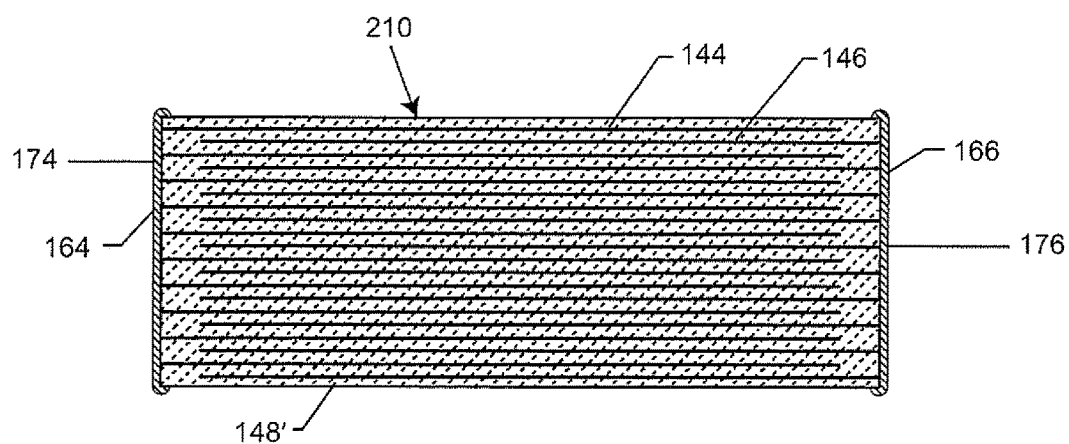
FIG. 52 is a cross-sectional view taken along lines 52-52 of FIG. 51.

FIG. 51 and FIG. 52 illustrate an MLCC chip capacitor 210 that is similar in its exterior appearance to the prior art MLCC chip capacitor 140' previously described in FIGS. 14 and 15. In accordance with the present invention, the MLCC chip capacitor 210 of FIGS. 51 and 52 comprises a dielectric material having a k<1,000 and an ESR of <0.5 ohm at the MRI RF-pulse frequency(ies). Also, in accordance with the present invention, The MLCC chip capacitor 210 comprises a relatively high number of active electrode plates 144 and ground electrode plates 146 compared to the prior art MLCC chip capacitor 140' of FIGS. 14 and 15.

Figure 53:
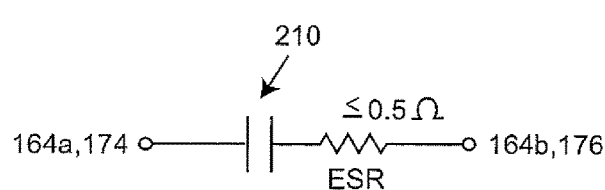
FIG. 53 is the electrical schematic representation of FIGS. 51 and 52.

FIG. 53 is the electrical schematic of FIGS. 51 and 52 showing that the ESR of MLCC chip capacitor 210 is less than 0.5 ohm.

Figure 54:
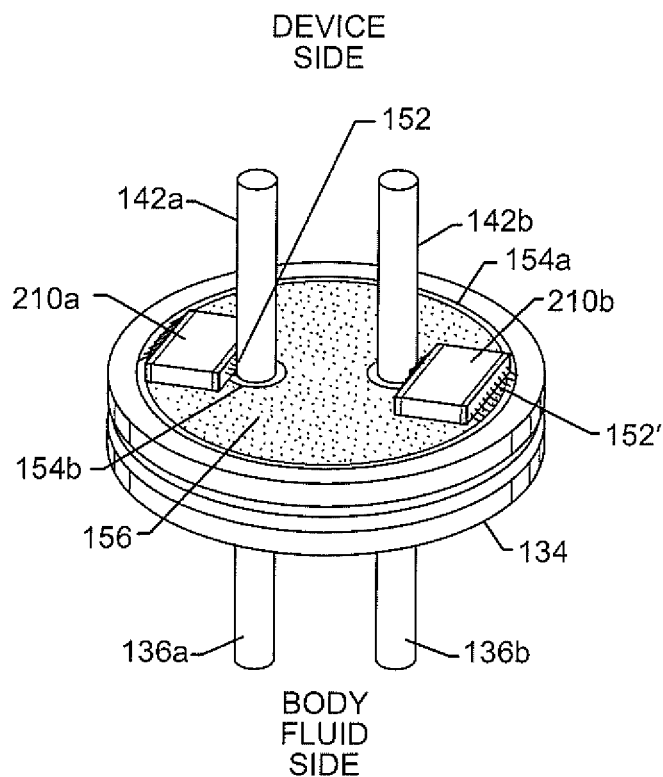
FIG. 54 is an isometric view of a bipolar hermetic seal having a ferrule and two leads passing through the conductive ferrule in insulative relationship.

FIG. 54 is a bipolar hermetic feedthrough having a metallic ferrule 134 and two terminal pins 142a and 142b passing through the insulator 156 in insulative relationship with the conductive ferrule 134. There are two MLCC chip capacitors 210a and 210b, as illustrated in FIGS. 51 and 52, connected respectively to terminal pins 142a and 142b. The MLCC chip capacitors are shown attached to a gold braze 154a, the gold braze hermetically sealing the insulator 156 to the ferrule 134 of the hermetic feedthrough so that an essentially oxide-free (oxide-resistant) and low resistance electrical connection is made. Such oxide-resistant electrical connections are more thoroughly disclosed in U.S. Pat. No. 6,765,779, the content of which is fully incorporated herein by this reference. MLCC chip capacitors attached to a gold braze of a hermetic feedthrough are also disclosed in U.S. Pat. No. 10,080,889, the content of which is fully incorporated herein by this reference.

Referring now back to FIG. 19 of the present application, it is contemplated that the MLCC chip capacitor 210 of FIGS. 51 and 52 can also be mounted to a substrate 147 as shown in FIG. 19. Additionally, the MLCC chip capacitor 210 can be mounted on a circuit board. Moreover, the substrate and/or the circuit board can be mounted to the hermetic feedthrough adjacent one of the ferrule 134, the insulator 156, or both the ferrule and the insulator in accordance with the definition of adjacent previously disclosed. Furthermore, such circuit boards and substrates can be mounted immediately adjacent the hermetic feedthrough, distant from the hermetic feedthrough or even at a remote location of the hermetic feedthrough. As defined herein, the remote location is still inside of the AIMD housing, but located remotely from the hermetic terminal, including the feedthrough ferrule and/or insulator.

Figure 55:
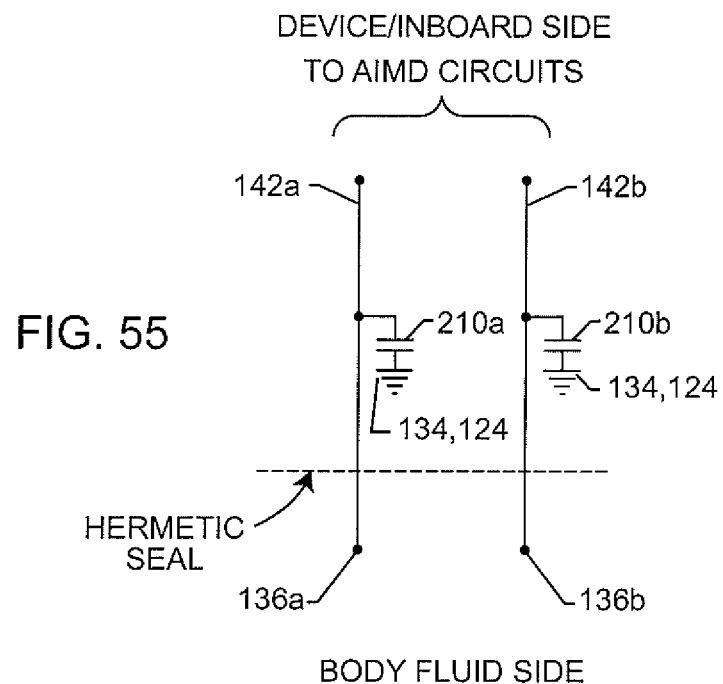
FIG. 55 is the electrical schematic representation of FIG. 54.

FIG. 55 is a schematic diagram of the bipolar filtered hermetic feedthrough of FIG. 54.

Figure 56:
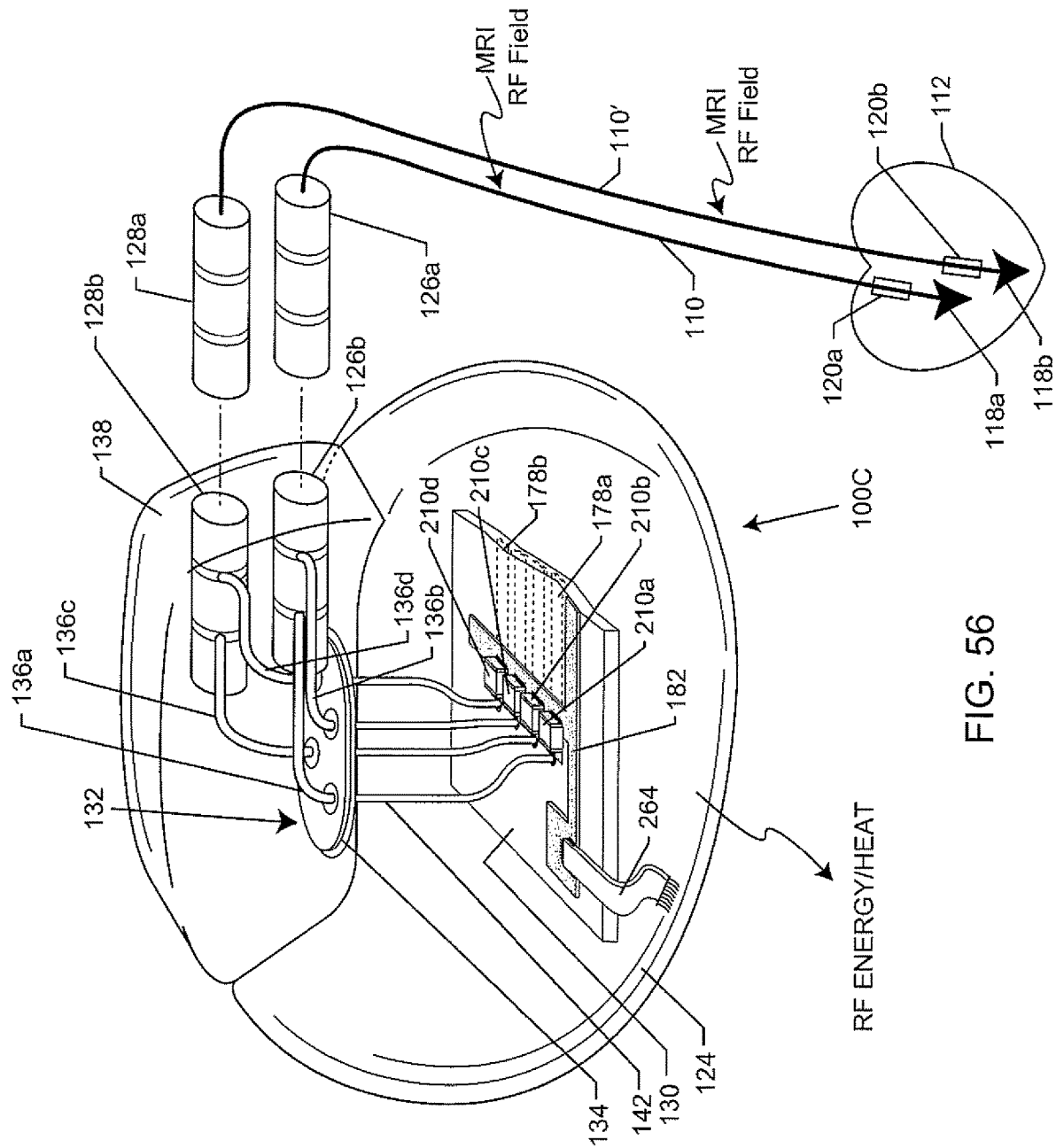
FIG. 56 is similar to FIG. 6 showing a breakaway cross-section of a typical AIMD with novel capacitors mounted to an internally disposed circuit board.

FIG. 56 is similar to FIGS. 6 and 39 illustrating a breakaway cross-section of a typical AIMD, such as a cardiac pacemaker, except that instead of a feedthrough capacitor (140 of FIG. 6 and 210' of FIG. 39) attached adjacent the ferrule 134 of the hermetic feedthrough, a circuit board having filter MLCC chip capacitors are attached to the hermetic feedthrough. As previously disclosed, prior art feedthrough capacitors such as the feedthrough filter capacitor 140 of FIG. 6, and which are used for primary EMI filtering of AIMDs, have always been built from dielectric materials having k>1,000 k. The feedthrough filter capacitor 210' of FIG. 39 has a dielectric material having k<1,000.

Referring to FIG. 56, illustrated is a circuit board 130 similar to the circuit board 130 previously illustrated in FIG. 39, however, in this case, each of the device side terminal pins 142 of the quad polar hermetic feedthrough 132 are attached to a respective MLCC chip capacitor 210a through 210d. The MLCC chip capacitors 201a through 210d are low ESR (low k MLCC chip capacitors having k<1,000) in accordance with the teachings of FIGS. 51 and 52. The leadwires 136a through 136d of the hermetic feedthrough 132 each connect on the device side terminal pin 142 to an active capacitor metallization 164 (not labelled) of their respective low k MLCC chip capacitor 210a through 210d. These extremely low ESR (low k) MLCC chip capacitors functionally draw a great deal of RF energy and/or heat from an implanted lead when in an MRI environment. It is important that this RF energy be efficiently dissipated to the AIMD housing 124, wherein the RF energy can be dissipated as RF energy and/or heat. As such, there is a low inductance ground circuit trace 182, which provides a ground connection to the ground capacitor metallization 166 (not labelled) of each MLCC chip capacitor 210a through 210d to each respective device side terminal pin 142 of leadwires 136a through 136d. This efficiently diverts RF energy from the leadwires 136a through 136d to the ground circuit trace 182. There is also an optional RF grounding strap 264 attached to ground circuit trace 182. The RF grounding strap 264 may be used to substantially reduce inductance making the filter circuit board 130 more efficient for diverting the RF energy to the AIMD housing 124 at high frequencies. The circuit trace may comprise may have increased width commensurate with the connection pad to which the RF grounding strap 264 is attached. The RF grounding strap may be substantially wide compared to its thickness. In an embodiment, the RF grounding strap may comprise a width >4 times its thickness.

Figure 56A:
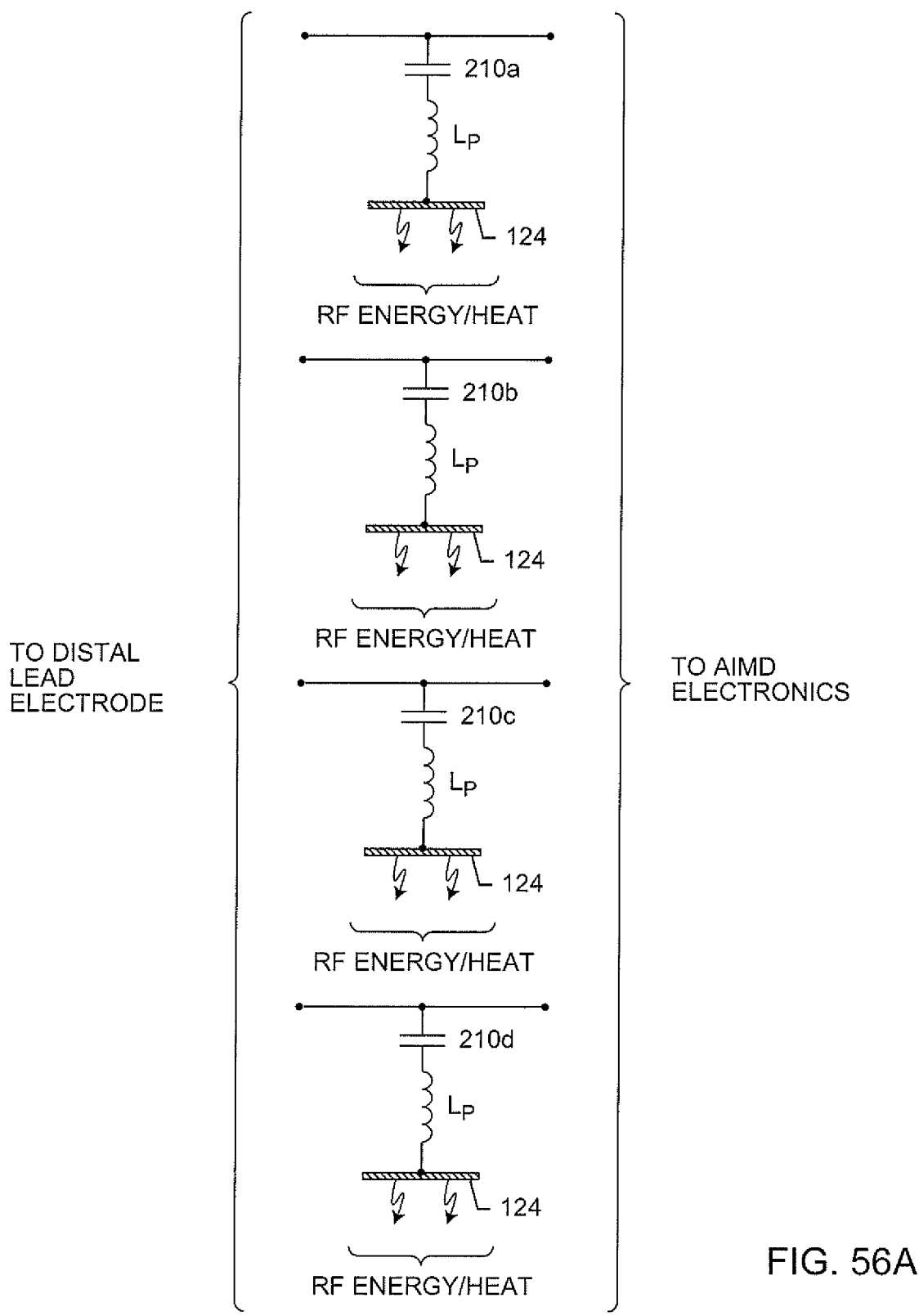
FIG. 56A is the electrical schematic of FIG. 56.

FIG. 56A is a schematic diagram of the primary work horse filter MLCC chip capacitors 210a through 210d illustrated in FIG. 56. Shown are each one of the work horse low ESR filter MLCC chip capacitors 210a through 210d in series with a parasitic inductance LP. This parasitic inductance $L_P$ comprises the inductance of the leadwire, from the length of the leadwire at the point of leadwire ingress, through the hermetic feedthrough, to the circuit board connection, to the MLCC chip capacitor (the four MLCC chip capacitors 210a through 210d are represented in the schematic diagram of FIG. 56A). The parasitic inductance $L_P$ also includes the inductance of the ground circuit trace 182 and the RF grounding strap 264. It is desirable to keep this parasitic inductance LP as low as possible. That is why the ground circuit traces 182 and the RF grounding strap 264 are relatively wide. It is also important to minimize the inductance of the device send terminal pin 142 between the hermetic feedthrough and the active end (non-ground end) of the primary filter MLCC chip capacitors 210a through 210d. This can be done by making the device end terminal pin 142 shorter, larger in diameter, flat, rectangular or a combination thereof.

Referring once again to FIG. 56, one can see that the leadwires 136 of hermetic feedthrough 132 are directed to via holes in the multi-layer circuit board 130. The via hole of the multi-layer circuit board 130 comprises a via hole metallization to which the active capacitor metallization 164 (on the left-hand side of the MLCC chip capacitors not labelled) of the filter MLCC chip capacitors 210a through 210d is attached. The active metallization 164 provides electrical connection to the active electrode plates of the MLCC chip capacitor. The device side terminal pins 142 pass through the via holes in the multi-layer circuit board 130 to the layers of said multi-layer circuit board, wherein the device side terminal pins 142 contact active circuit traces shown as dashed lines (hidden lines). Thus, the circuit from the body fluid side leadwires 136 through the primary filter MLCC chip capacitors 210a through 210d through the circuit traces of the multi-layer circuit board 130 to the ground circuit trace 182, wherein the ground circuit trace 182 connects to other via holes (not shown), is completed. The not via holes (not shown) connected to the ground circuit 182 are connected to other AIMD electronics, such as an ASIC electronics chip or other AIMD circuits.

Figure 57:
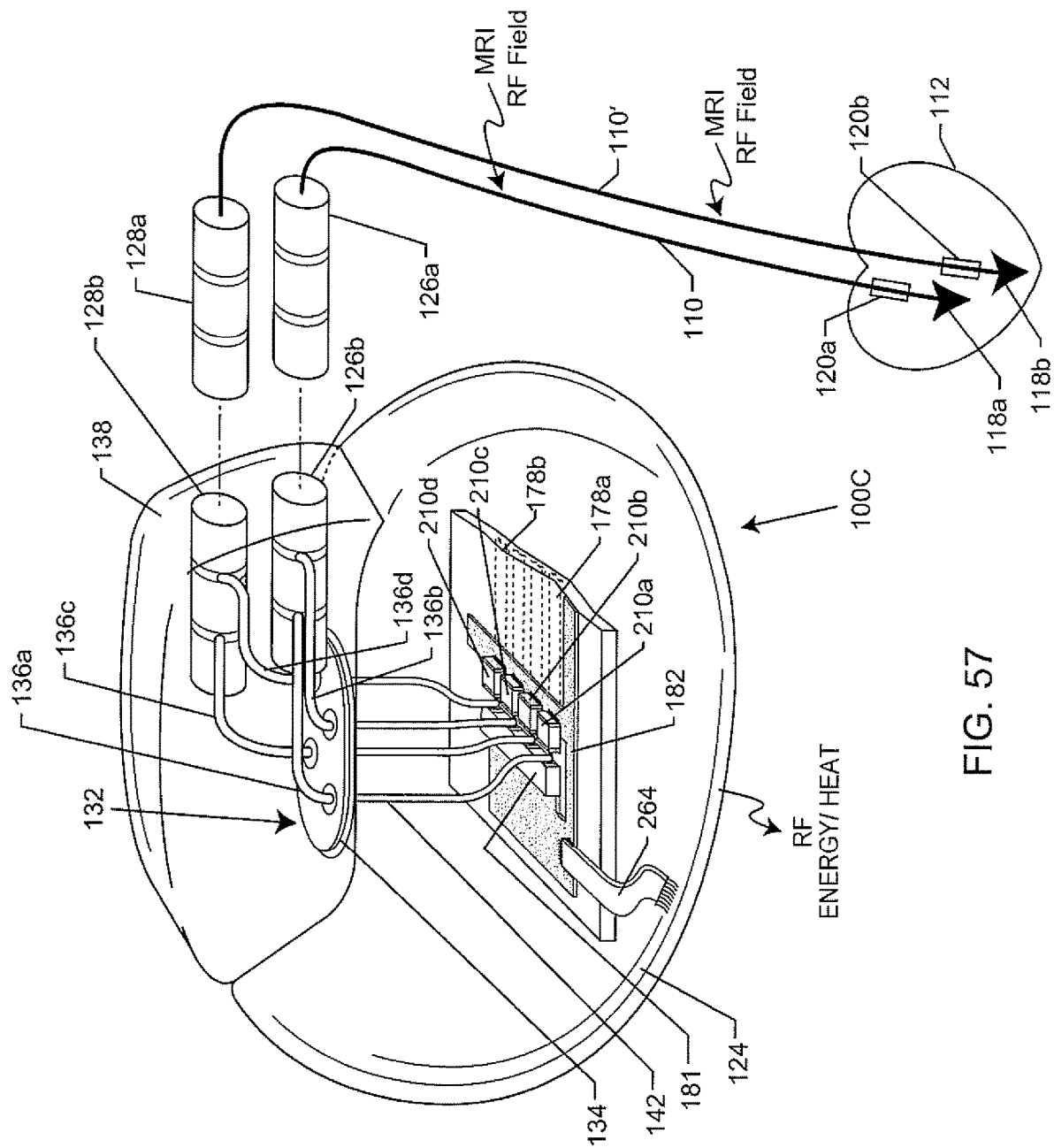
FIG. 57 is very similar to FIG. 56 except that a diode array has been added.

FIG. 57 is very similar to FIG. 56 except that an overvoltage diode protection array 181 has been added. It is very common in the input circuitry of AIMDs to provide an overvoltage protection diode array 181 mainly against the use of automatic external defibrillators (AEDs). AEDs can induce a very large high voltage pulse into implanted leads and the high voltage of such a pulse can be undesirably directed toward sensitive AIMD electronic circuits. Thus, the overvoltage protection diode array 181 provides high voltage overprotection for each one of the quad polar leads 136a through 136d to ground, which in FIG. 57 is the AIMD housing 124.

Figure 58:
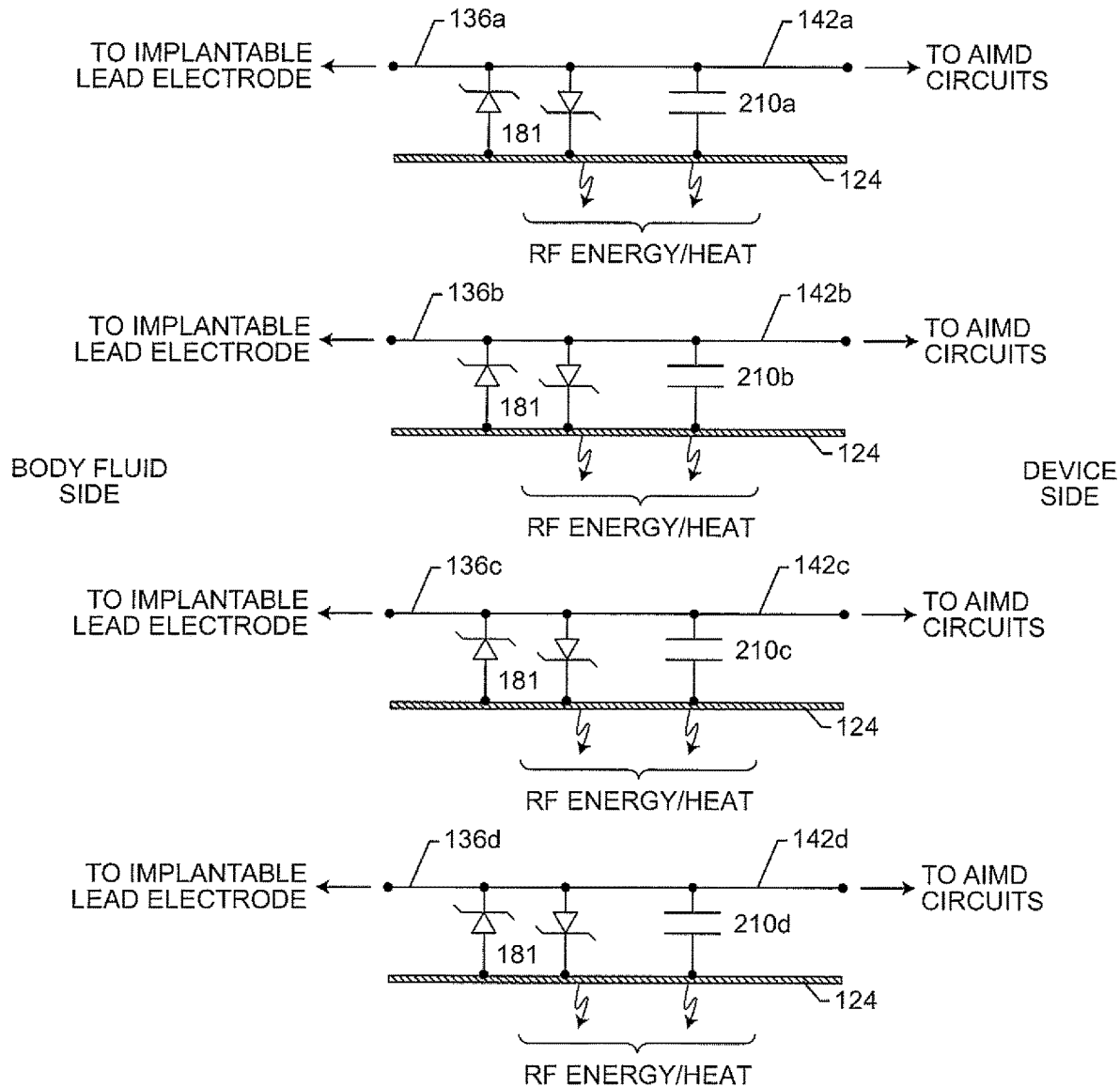
FIG. 58 is the electrical schematic representation of FIG. 57.

Overvoltage protection is better understood by referring to the schematic diagram of FIG. 58, which is representative of the AIMD system of FIG. 57. One can see that there is a continuous electrical circuit connection from the implantable lead electrode to the AIMD circuits. Leadwires 136a through 136d, the low ESR high RF-energy dissipating capacitors MLCC chip capacitors 210a through 210d of the present invention and a high voltage protection diode array 181 are continuously connected. Each MLCC chip capacitor 210a through 210d remains the work horse capacitor as the primary diverter of high frequency MRI RF energy/heat to the AIMD housing 124. It is noted that the embodiment of FIG. 57 illustrates the circuit ground path to the AIMD housing 124 comprising an RF grounding strap 264. The overvoltage diode protection array 181 of FIG. 58, now part of the circuit between the implantable lead electrode and the AIMD circuits, is positioned on the left-hand side of the MLCC chip capacitors 210a through 210d.

Figure 59:
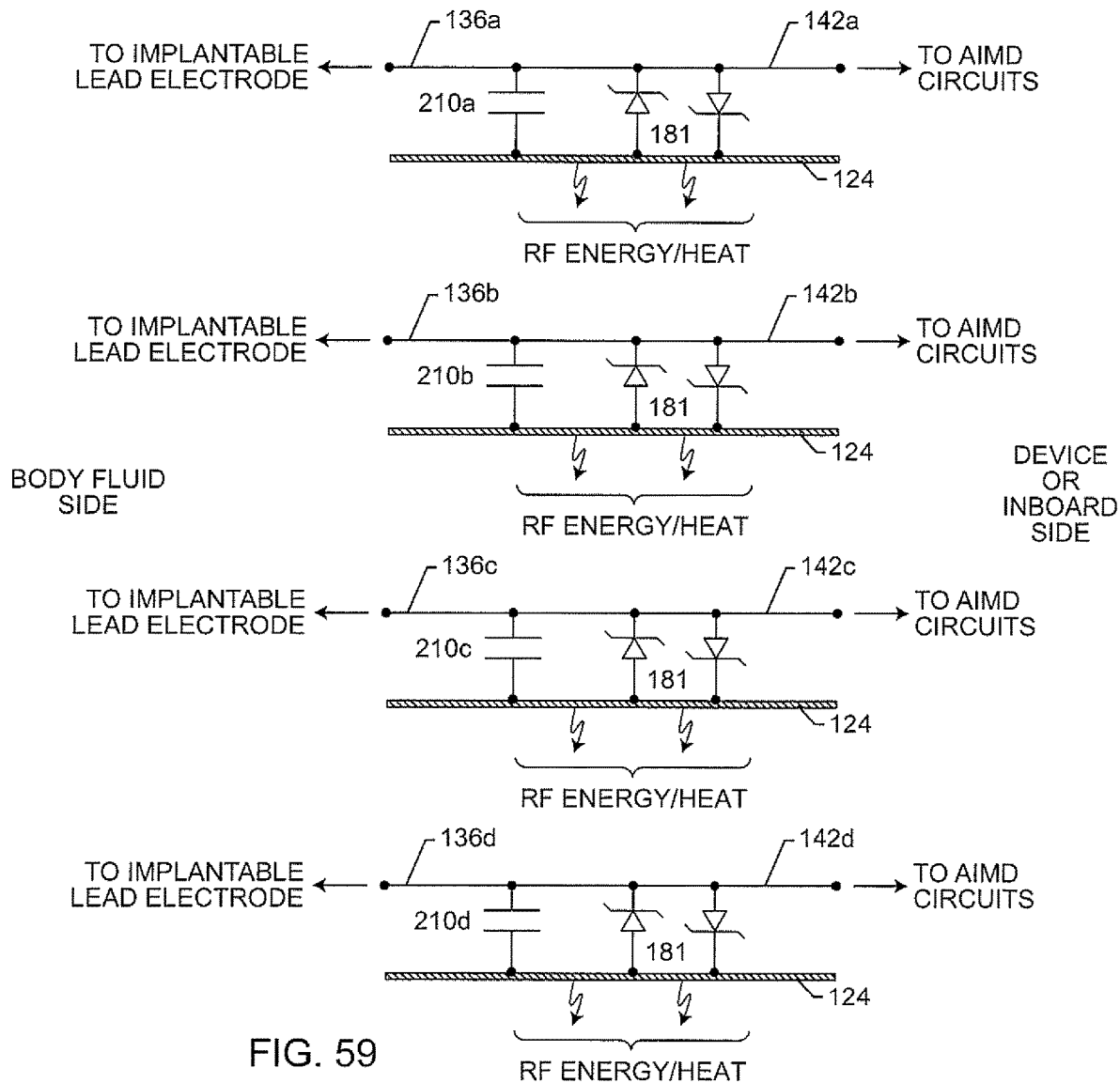
FIG. 59 is very similar to FIG. 58 except the high voltage protection diode array is shown on the other side of the low ESR capacitors.

FIG. 59 is very similar to FIG. 58 except that the high voltage protection diode array 181 is shown on the right-hand side of the low ESR capacitors MLCC chip capacitors 210a through 210d of the present invention. Since the high voltage protection diode array 181 is not in series, but is in parallel with the low ESR capacitors, it is understood by one of ordinary skill in the art that the low ESR MLCC chip capacitors 219a through 210d can be placed anywhere along the length of the leadwires 136a through 136d. Regardless of where the high voltage protection diode array 181 is positioned, it is understood that the low ESR capacitor of the present invention is always directly connected by way of continuous electrical circuit connections, such as the circuit connections to the circuit pads of the circuit traces illustrated in FIG. 57. Thus, a continuous electrical path between the AIMD circuits and the implantable lead electrode contactable to biological cells through the leadwires of the hermetic feedthrough therebetween is provided.

Referring once again to FIG. 58, one will notice that the diodes of the overvoltage protection diode array 181 are back-to-back so that said diodes can clamp and shunt a positive or a negative polarity pulse. For AEDs, it is common for shocking pulses to be biphasic, meaning that the shocking pulse switches polarity. Therefore, it is common practice to orient the diodes of the overvoltage protection diode array 181 back-to-back so that the diodes may shunt energy having both positive and negative polarities. It is noted that the diodes of the overvoltage protection diode array 181 must be positioned before or after the primary EMI low ESR capacitor before placing any other electronic components like electronic chips, ASIC chips, active filters or other sensitive electronics in this portion of the circuit path, as such electronic components are the very components that can be damaged by an overvoltage or can be interfered with by EMI. As a result, in general, such 'sensitive' AIMD electronic components are always positioned downstream (to the right) of the circuits of FIG. 58 or 59.

Figure 60:
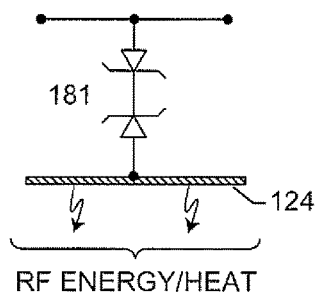
FIG. 60 is an electrical schematic of a back-to-back diode placed in series taken from lines 60-60 of FIG. 59.

FIG. 60 is an alternative diode connection for the circuit schematics of FIGS. 58 and 59. FIG. 60 illustrates that instead of two discrete separate diodes wired back-to-back, the diodes of an overvoltage protection diode array 181 can be alternatively placed back-to-back in series. Sometimes such back-to-back series diode arrays are called Transorbs©. Ii is understood that, in general, the diodes of the overvoltage protection diode array 181 can be selected from the group consisting of a transient voltage suppressor, a varister, an avalanche diode or a Zener diode.

Figure 61:
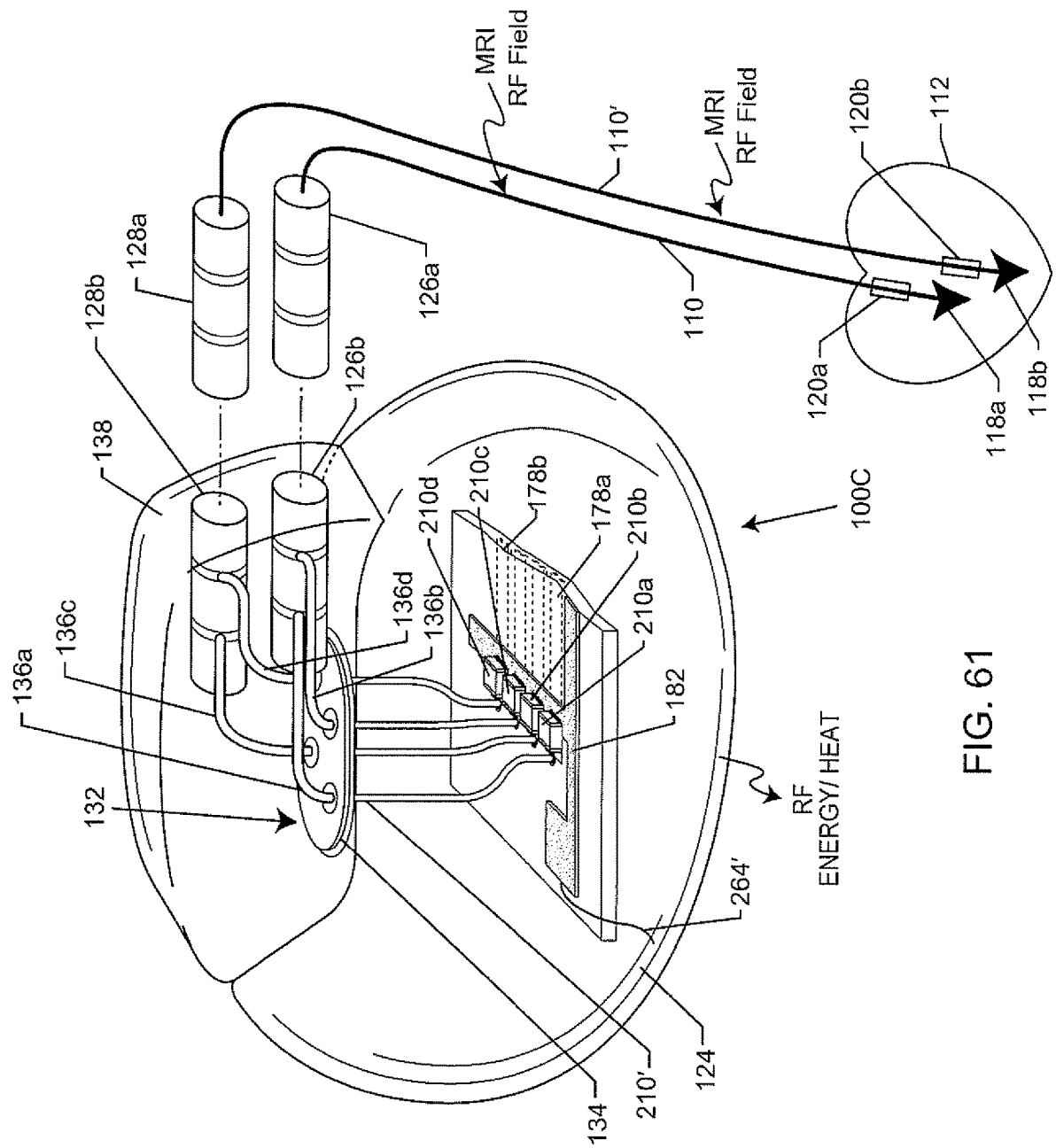
FIG. 61 is very similar to FIG. 56 except that the RF grounding strap has been replaced with a simple leadwire connection.

FIG. 61 is very similar to FIG. 56 except that the RF grounding strap 264 has been replaced with a simple RF grounding leadwire 264'. An RF grounding leadwire 264' works okay at relatively low RF frequencies. For example, for a 1.5 Tesla scanner, the RF-pulse frequency is 64 MHz. As scanners have evolved to higher and higher frequencies, the inductance of such a small wire can become problematic. For example, there are many modern scanners in the market operating at 3 Tesla, which means that the RF frequency is 128 MHz. The inductive reactance is equal to 2×π×frequency×inductance. So, if the inductance is small and the frequency is large, one can get a great deal of inductive reactance which makes the diversion of high frequency energy through the primary low ESR chip capacitors 210 less efficient. Another way of saying this is that you really don't want anything in the ground path that impedes diverting the high frequency RF energy to the AIMD housing 124. One way around this (not shown) is to use multiple RF grounding leadwires 264', thereby creating additional circuit paths to ground and reducing the inductance.

Figure 62:
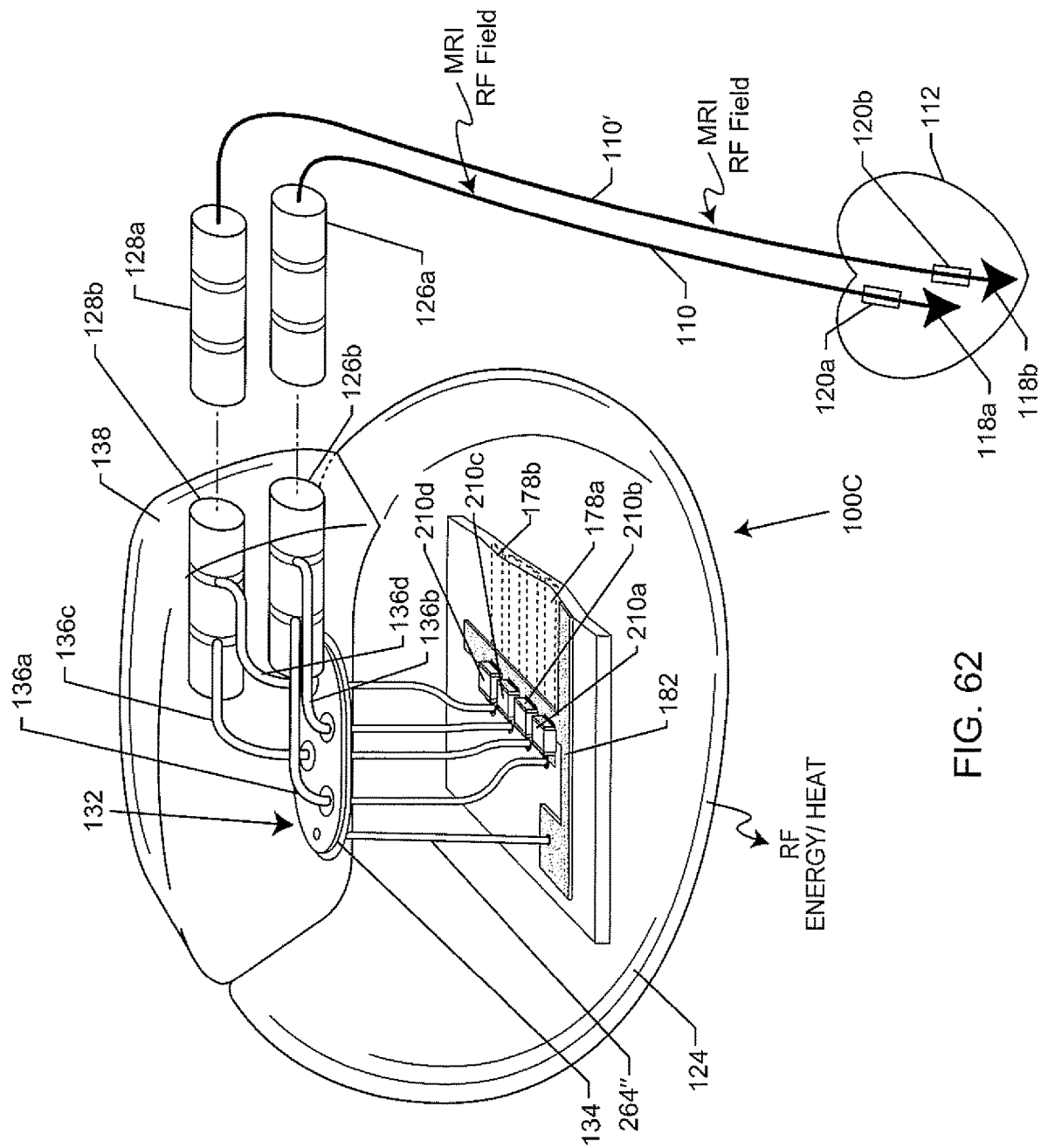
FIG. 62 is very similar to FIG. 61 now with the grounding leadwire routed directly to the ferrule of the hermetic terminal subassembly.

FIG. 62 is very similar to FIG. 61 except in this case, a grounding leadwire 264" is routed directly from the ferrule 134 of the hermetic feedthrough 132 to the ground circuit trace 182 of the AIMD circuit board 130 (not labelled).

Figure 63:
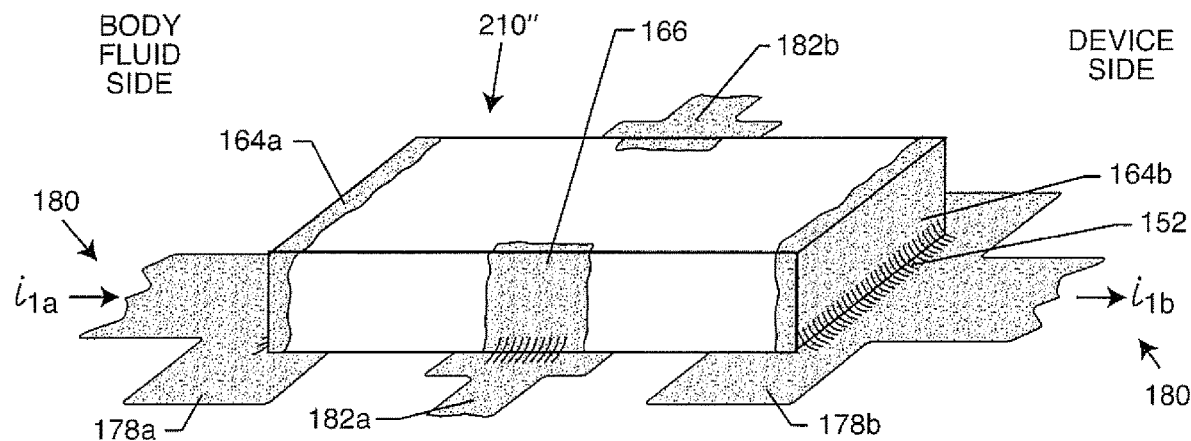
FIG. 63 is very similar to prior art FIG. 17 that illustrated a flat-through type of feedthrough capacitor.
Figure 64:
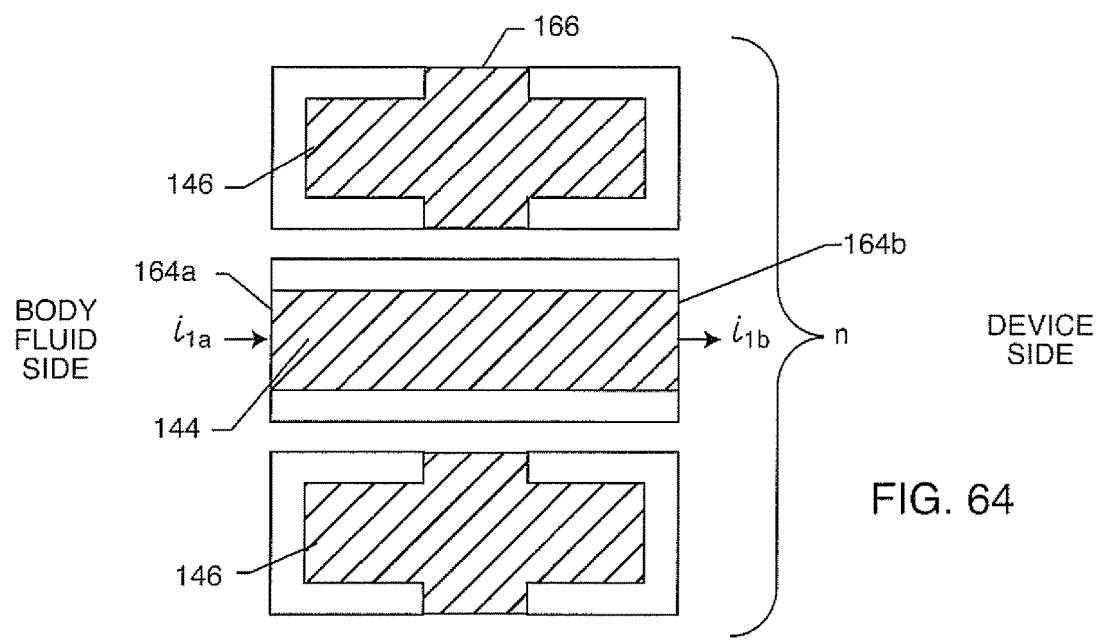
FIG. 64 is very similar to prior art FIG. 18 that illustrated the electrode plates of the flat-through type of feedthrough capacitor.

FIG. 63 and FIG. 64 are very similar to the prior art flat-through type feedthrough capacitor of FIGS. 17 and 18. These flat-through type capacitors are unique in that the circuit current must pass through the flat-through capacitor's own active electrode plates instead of through a feedthrough leadwire 136 extending through a metallized via electrically connecting the active electrode plates 144 as shown in the feedthrough filter capacitors 140 of FIGS. 7-10. Regarding FIGS. 63 and 64, the circuit current $i_1$ of the flat-through capacitor 210" is shown entering the active electrode plates 144 as $i_{1a}$ and exiting said active electrode plates as $i_{1b}$.

Figure 64A:
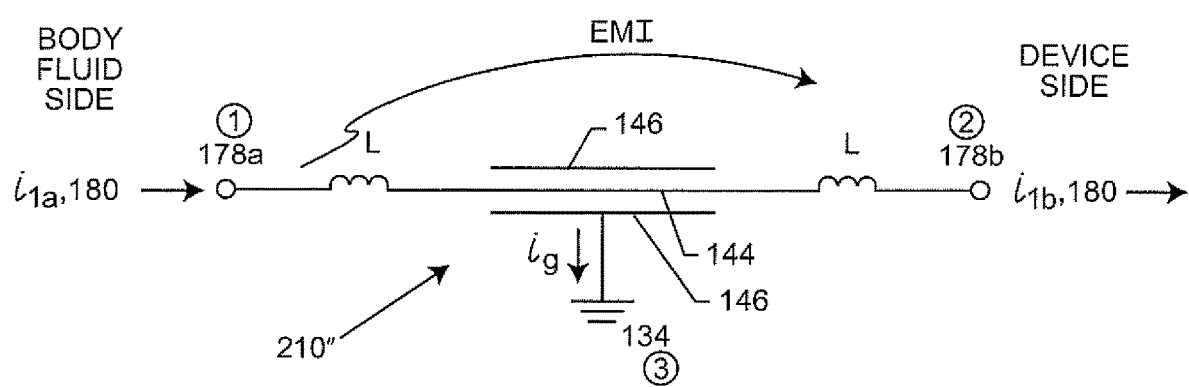
FIG. 64A is the electrical schematic for FIGS. 63 and 64.

FIG. 64A is the circuit diagram of the flat-through capacitor 210" of FIGS. 63 and 64. Illustrated is that the flat-through capacitor 210" is a three-terminal filter capacitor. However, instead of having a leadwire 136 going through the center of the three-terminal capacitor as illustrated in the schematic diagram of the feedthrough filter capacitor 140 of FIG. 11, one actually has the active electrode plates 144 going through the center of the three-terminal flat-through capacitor 210". The circuit current (not shown) of FIG. 11 passes to the active electrodes plates 144 of a three-terminal feedthrough filter capacitor by way of the leadwire 136, while the circuit current 180 of the flat-through capacitor 210" of FIG. 64A passes through the active electrode plate 144 itself. In accordance with the present invention, the capacitor dielectric of the flat-through capacitor 210" has a k greater than 0 but less than 1,000, k<1,000, and an ESR generally less than 0.5 ohm at an MRI RF-pulse frequency including an MRI RF-pulse frequency of 64 MHz (1.5 T) and 128 MHz (3 T).

Referring once again to FIG. 63, one can see that the flat-through capacitor 210" is installed on an AIMD circuit board 130 (not shown) a little differently. Installation of the flat-through capacitor 210" of FIG. 63 require circuit traces 178a and 178b. Circuit traces 178a and 178b are made on a circuit board substrate such that the end metallizations of the flat-through capacitor 210" can properly be attached, in other words, the circuit traces 178a and 178b of the circuit board are positioned to accommodate a flat-through capacitor attachment. Such circuit traces are separated by an insulating area, that is, there is a break in the circuit trace, such that, when the flat-through capacitor 210" is attached to the circuit traces 178a and 178b, a circuit current $i_1$ can pass all the way through the active electrode plates 144 from the left-hand side of the flat-through capacitor, labelled ha, through the active electrode plates 144, to the right side of the flat-through capacitor, labelled ill). As shown, $i_1$ is going from the left-hand side to the right-hand side, but it is understood that $i_1$ can also pass through the active electrode plates in the opposite direction, namely from the right-hand side to the left-hand side of the flat-through capacitor 210" depending on the AIMD therapeutic algorithms.

Referring once again to FIG. 63, one can see that there is a ground connection 182a and 182b. This ground connection is routed to the AIMD housing 124.

Referring once again to FIG. 64A, the schematic diagram of the flat-through filter of FIGS. 63 and 64 shows that the circuit current $i_1$ passes through the flat-through capacitor at an input terminal 178a (terminal 1) and then exits the active capacitor electrode plates 144 at an output terminal 178b (terminal 2). It is appreciated that the flat-through capacitor being a three-terminal device is symmetrical, meaning that the attachment of the flat-through capacitor 210" to the circuit can be reversed and still operates in the same fashion. Referring again to FIG. 63, it is noted that the left-hand side of the flat-through capacitor 210" has been arbitrarily labelled as the body fluid side and the right-hand side as the device side. As previously disclosed, electromagnetic interference (EMI) can be coupled or radiated to body fluid device side leads and electrodes and can undesirably appear as an RF current ha at the input terminal 178a (terminal 1) of the flat-through capacitor 210"; it is noted that $i_1$ also comprises low frequency therapeutic pacing pulses or biologic signals in addition to any EMI RF current. Such EMI passes through the active electrode plates 144 of the flat-through capacitor 210" and is continuously decoupled through capacitive filter action to the ground electrode plates 146 (terminal 3). When the current $i_{1b}$ exits at the device side terminal 178b (terminal 2), the EMI has been greatly attenuated (filtered) such that said EMI can no longer dangerously interfere with AIMD circuitry. As shown, the attenuated current $i_g$ is diverted (filtered) to ground, which as shown is the ferrule 134 of the hermetic feedthrough 132 (not shown). This three-terminal filter behavior is very similar to feedthrough filter capacitors, which are also three-terminal devices. The difference is that, for a feedthrough capacitor, circuit currents pass through a leadwire, such as leadwire 142 illustrated in the prior art feedthrough filter capacitors of FIGS. 7 to 10, while the circuit currents for flat-through capacitors flow through its own active electrode plates 144. Therefore, it is important that the active electrode plates 144 be robust and low in DC resistance, Typically, this means that a relatively large number of active electrode plates 144 appears in parallel and interleaves between ground electrode plates 146. By having additional electrodes in parallel, one reduces the overall resistance to the flow of current, otherwise known as DC resistivity.

In accordance with the present invention, the embodiments, which comprise a first filter capacitor, meaning the first capacitor from the point of implanted leadwire ingress that EMI encounters, has a k greater than zero and less than one thousand, k<1,000. This is distinct and in marked contrast to prior art filter devices, which generally have dielectric constants of k greater than 1,200, or 2,500, or even higher. By reducing the dielectric constant of the filter capacitor, an increase in the number of active electrode plates 144 and ground plates 146 is required in order to achieve an equivalent capacitance value and amount of filtering comparable to that of prior art high k, k>1,200 filter capacitors. This makes the low k flat-through capacitors 210", as illustrated in FIGS. 63 and 64, highly suitable for use in AIMDs, as the higher number of active electrode plates 144 of such low k, k<1,000, flat-through capacitors 210" reduce the DC resistance of said low k flat-through filter capacitors. It is noted that it is also important that the impedance of the active electrode plates 144 of the low k flat-through capacitors also be low. However, if the low k flat-through capacitors have inductance L as shown in FIG. 64A, the inductance L shown aides in the EMI filtering because this inductance L is along the $i_1$ circuit path. It is noted that at high frequencies, such as EMI RF frequencies, the inductive reactance is given by the equation $XL=2\pi FL$. This means that at high frequencies, the amount of inductance reactance becomes very high thereby further impeding EMI from undesirably entering from the body fluid side to the device side of an AIMD.

Referring once again to FIG. 64A, shown is that EMI can radiate across a flat-through capacitor. The potential for radiating EMI across a flat-through capacitor occurs at exceptionally high frequencies. At such exceptionally high frequencies, EMI is not attenuated by the flat-through capacitor. Because such high frequency coupling only occurs at very short-wave lengths, generally at microwave frequencies, and because the human body both reflects and absorbs microwave energy, the amount of EMI picked up by implanted leads is substantially degraded and essentially inconsequential. Accordingly, flat-through capacitors make an attractive alternative to MLCC chip capacitors as primary filter capacitors, which can be extremely helpful for AIMDs having particularly small geometries. In summary, EMI can effectively be diverted by the low k flat-through capacitor of the present application to an AIMD system ground (attenuated current $i_g$), the system ground being the ferrule 134 (terminal 3) of the hermetic feedthrough, which is at the same electrical potential as the overall electromagnetic shield (housing) of the AIMD.

Figure 64B:
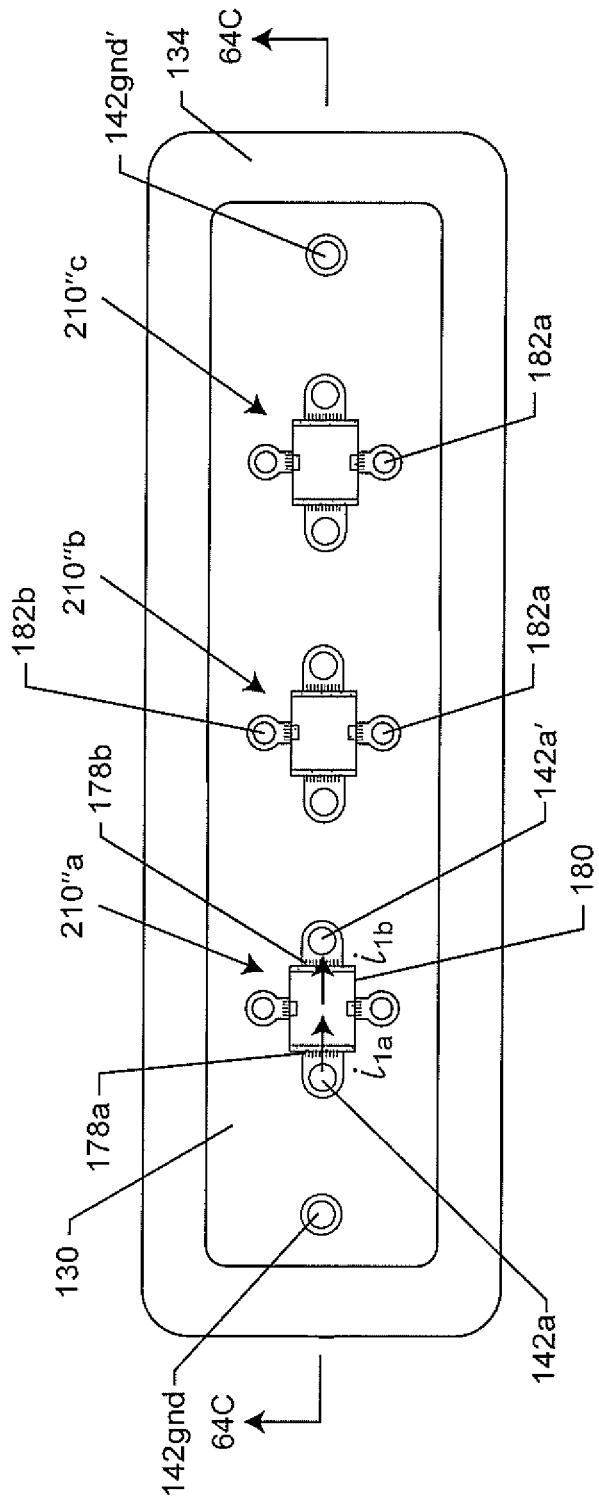
FIG. 64B is a top view of an embodiment of the flat-through capacitor of FIG. 63 now mounted upon a circuit board.

FIG. 64B is a top view of a tri-polar filter circuit board 130 having three flat-through capacitors 210"a, 210"b and 210"c or, alternatively, three MLCC chip capacitors 210 (not shown). FIG. 64B illustrates on the left-hand side of each flat-through capacitor 210", a circuit current $i_{1a}$ that enters at the input 178a (terminal 1) of the flat-through capacitor 210". The leadwire positioned at 178a is cut off on the device side but is routed to implanted leadwires and the lead electrodes (not shown) on the body fluid side. On the right-hand side of the flat-through capacitors 210", the output current ilb exits at output 178b (terminal 2), which is also connected to a leadwire inside the AIMD. The leadwire positioned at 178b projects upwardly out of the hermetic feedthrough. The leadwire layout and configuration is best understood by reviewing the cross-sectional view of FIG. 64C.

Referring once again to FIG. 64B, circuit current ha enters the flat-through capacitor 210" on the left-hand side and freely passes through the flat-through capacitor exiting as circuit current $i_{1b}$ because circuit current $i_{1a}$-$i_{1b}$ comprises either biologic signals or therapeutic pacing pulses, which are low frequency circuit currents. However, at high frequencies, such as EMI RF frequencies, circuit current ha on the left-hand side 178a (terminal 1) is of a relatively high amplitude, therefore, as circuit current lib exits on the right-hand side 178b (terminal 2) of the flat-through capacitor 210", the EMI, which appears as an RF current, is substantially attenuated because the flat-through capacitor 210" acts as a filter capacitor at high frequencies such as the EMI RF frequencies.

Figure 64C:
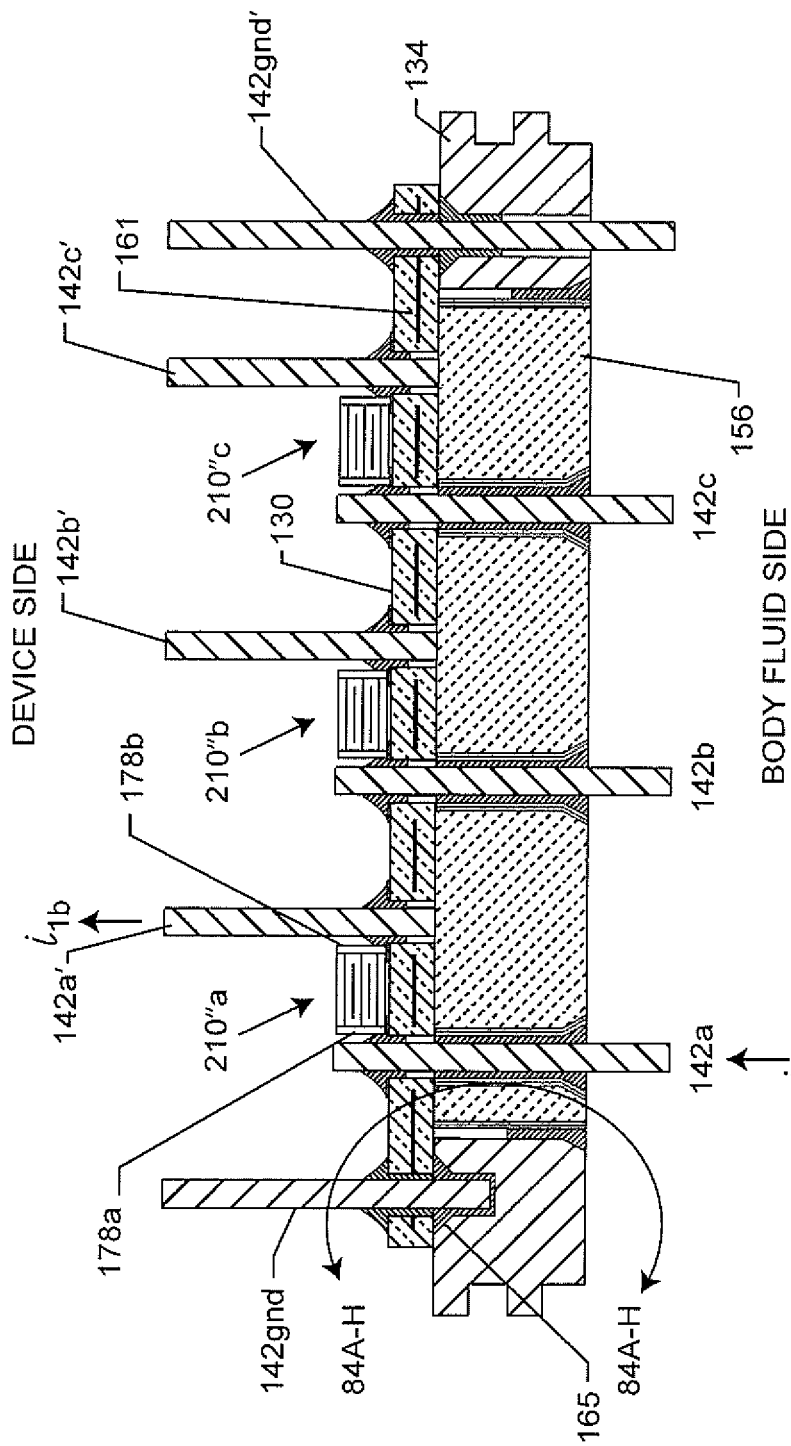
FIG. 64C is a cross-sectional view taken along lines 64C-64C from the structure of FIG. 64B.

Referring now to FIG. 64C, one can see that on the body fluid side of the hermetic feedthrough, the circuit current $i_{1a}$ flows toward the device side of the hermetic feedthrough through a terminal pin 142a to the input 178a (terminal 1) of the flat-through capacitor 210"a. The circuit current ha then flows through the flat-through capacitor 210"a and exits at the output 178b (terminal 2) of said flat-through capacitor as circuit current $i_{1b}$. Circuit current $i_{1b}$ then flows toward the device side of the hermetic feedthrough through terminal pin 142a'. Circuit current $i_{1b}$ is then routed to the AIMD electronic circuits. The AIMD electronic circuits typically reside in or on an AIMD electronic circuit board (not shown). Any undesirable RF currents, such as an EMI RF current, are diverted (filtered) by the flat-through capacitor 210" as attenuated current $i_g$ to the AIMD system ground, such as ferrule 134, which is attached to the AIMD housing 124 (not shown). Referring once again to FIG. 64C, one will appreciate that circuit current $i_1$ can desirably contain therapeutic pacing pulses, which are being routed from the AIMD to implanted leads and distal electrodes or circuit current $i_1$ can include biological sensing frequencies, such as cardiac signals, which are being sensed by the internal circuitry of the AIMD. In other words, circuit current $i_1$ can flow in either direction. In addition, circuit current $i_1$ can undesirably contain very high EMI RF currents, which can be dangerous, even life-threatening, to a patient as previously disclosed.

FIG. 64C further shows a method of grounding a filter circuit board, wherein the filter circuit board has at least one internal (or alternatively external) ground plate 161. The ground plate 161 of the filter circuit board is connected to an AIMD system ground, which in FIG. 64C is the ferrule 134 (terminal 3) of a hermetic feedthrough 132 (not labelled). In this exemplary embodiment, illustrated on the left-hand side is a ground pin 142gnd, which is gold brazed 165 (or alternatively laser welded 157, not shown) into the ferrule 134 of the hermetic feedthrough. The terminal pin 142gnd is shown attached in a blind via of the ferrule 134. An alternative embodiment is shown on the right-hand size, wherein the terminal pin 142gnd' extends through a via in the ferrule 134 to a body fluid side and a device side. The terminal pin 142gnd, 142gnd' of FIG. 6C comprises an oxide-resistant material (or may alternatively comprise an oxide-resistant outer layer, such as an oxide-resistant coating, plating, or cladding) such that a very low impedance electrical connection can be made both to the terminal pin and to various via hole connections to the at least one filter circuit board ground plate 161. Filter circuit board ground plate 161 is shown connected to six (or can alternatively be connected to "n" number) flat-through capacitor grounds (exemplary grounds 182a, 182b are shown in FIG. 64B). Referring to FIG. 64B, one will appreciate that the grounds 182a, 182b can be circuit board via holes or include circuit traces. What is important is that both the grounds 182a and 182b are conductively coupled through the circuit board via holes to the at least one ground plate 161. This creates a multipoint grounding system, which makes flat-through capacitors very effective three-terminal filters for use in AIMDs, including filter circuit boards connected to a hermetic feedthrough of an AIMD that effectively filters EMI.

Figure 64D:
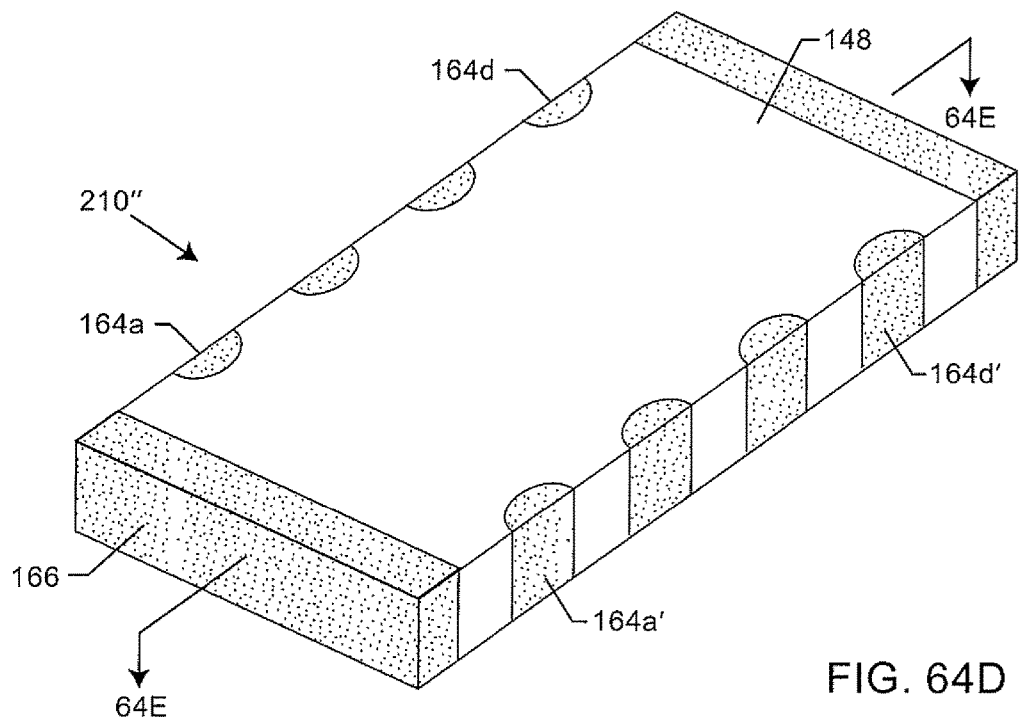
FIG. 64D is an isometric view of a quad polar flat-through filter capacitor.

FIG. 64D is an isometric view of a quad polar flat-through capacitor 210". The quad polar flat-through capacitor 210" is similar to the unipolar flat-through capacitor of FIG. 63, except in this case there are four active electrode plates 144 (see FIG. 64E). As previously disclosed, circuit currents $i_1$ ($i_{1a}$-$i_{1b}$) pass through the active electrode plates of the quad polar flat-through capacitor of FIG. 64D. The quad polar flat-through capacitor of FIG. 64D also comprises a common ground plate 146 (also illustrated in FIG. 64E). Referring once again to FIG. 64D, each of the active electrode plates 144 has an active termination comprising active capacitor metallizations 164a, 164a' through 164d,164d'. The ground electrode plate 146 has an edge termination comprising ground capacitor metallization 166 suitable for electrical attachment to an AIMD system ground, for example, the ferrule 134 of the hermetic feedthrough, which is attached to the housing 124 of the AIMD, the ferrule and the AIMD housing having the same electrical potential as the system ground potential.

Referring once again to FIG. 63, one can see that there are ground connection circuit traces 182a and 182b. These ground circuit traces are routed to the AIMD housing 124.

Figure 64E:
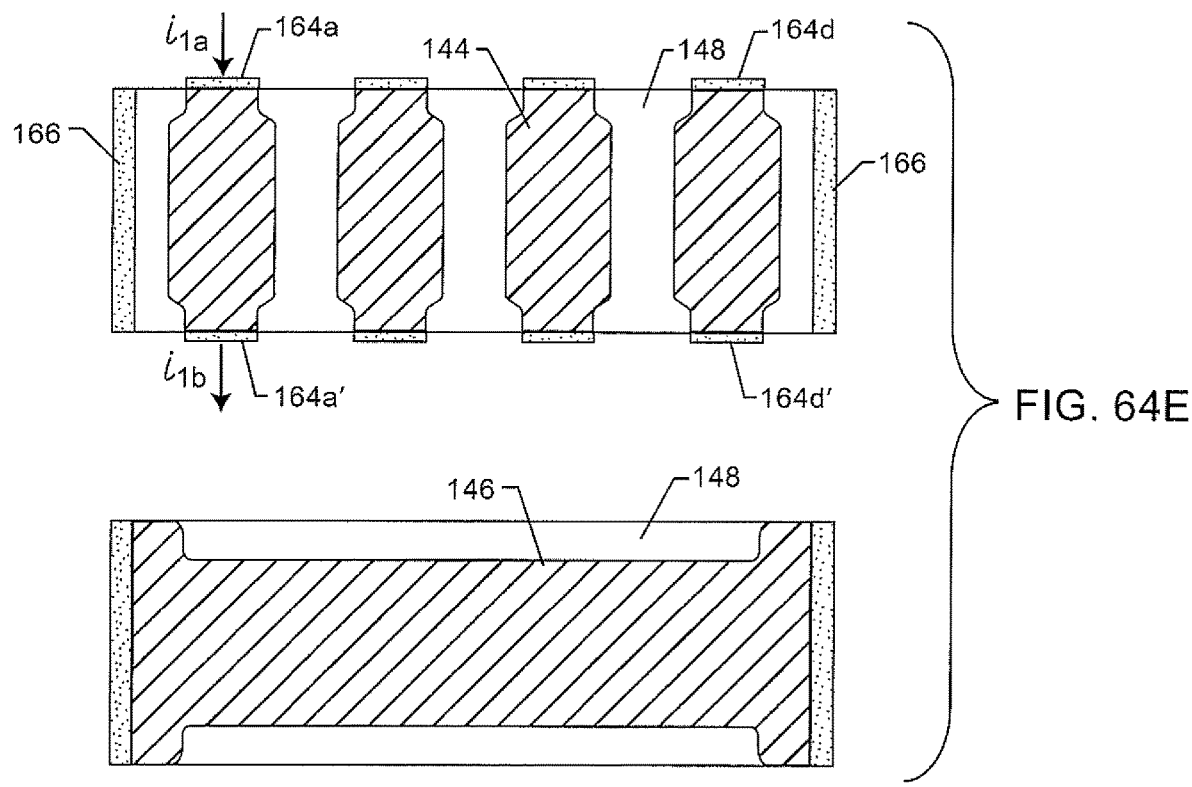
FIG. 64E is a sectional view taken along lines 64E-64E from the structure of FIG. 64D.
Figure 64F:
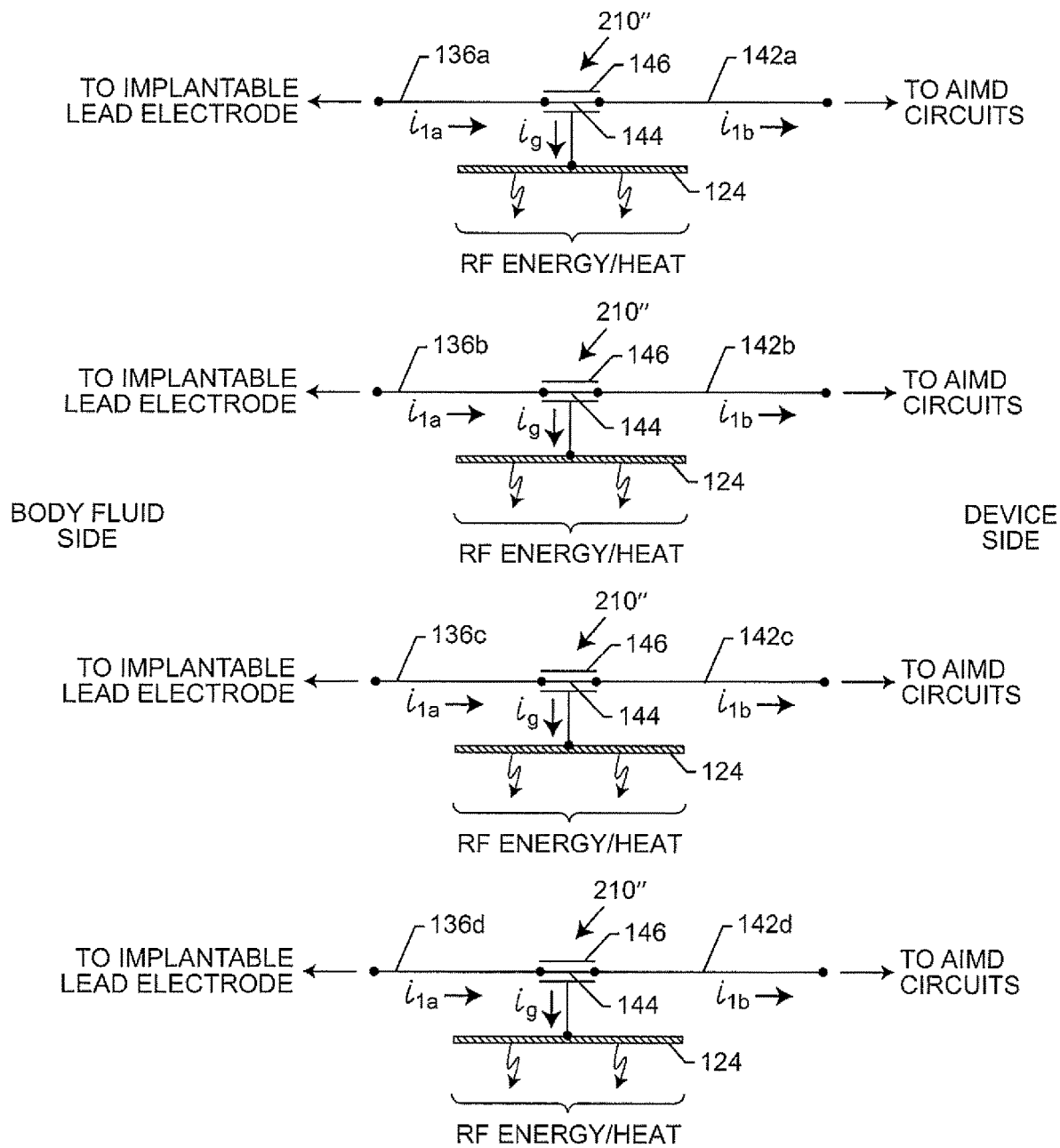
FIG. 64F is the electrical schematic for FIGS. 64D and 64E.

FIG. 64F is a schematic electrical diagram of the quad polar flat-through capacitor 210" of FIGS. 64D and 64E. The body fluid side is depicted on the left-hand side showing that circuit currents $i_{1a}$ entry, which then exits as current $i_{1b}$ on the right-hand side, which is the device side, to the AIMD circuits. When the circuit current $i_{1a}$ is an undesirable EMI RF current, $i_{1b}$, is greatly attenuated (filtered). The filtering action of the flat-through filter capacitor 210" diverts any high-frequency EMI signals as an attenuated current $i_g$ to the AIMD system ground 124. The attenuated current $i_g$ is a diverter current or a filtered current, wherein any undesirable or even dangerous EMI signals are diverted or filtered to ground where such EMI signals are dissipated by the AIMD housing 124 as RF energy or heat.

Figure 65A:
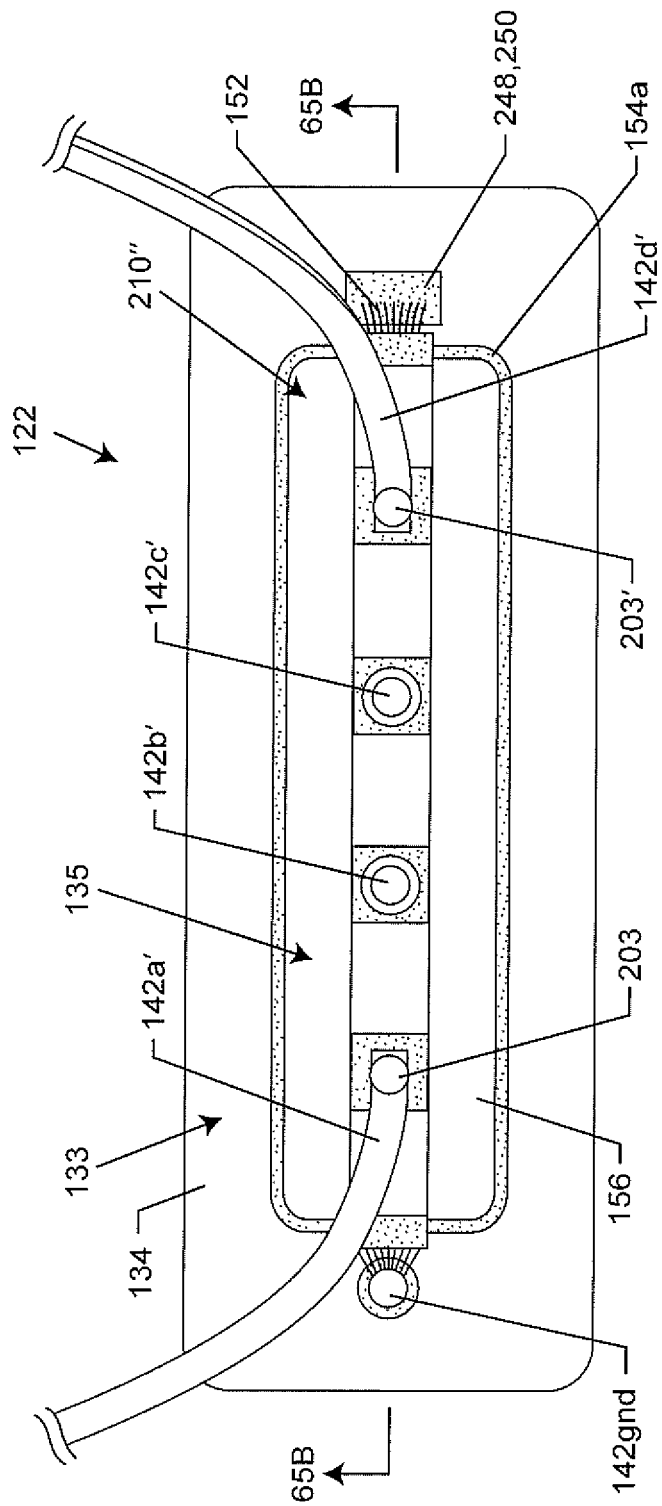
FIG. 65A is a top view of an embodiment of the quad polar flat-through filter capacitor of FIG. 64D now mounted above a ferrule and insulator in a tombstone mounting position.

FIG. 65A is a top view (looking down on the device side of the ferrule 134) of the quad polar flat-through capacitor 210" of FIG. 64D edge-mounted in a tombstone position. The edge ground capacitor metallizations 166 (not labelled) are shown electrically connected to a terminal pin 142gnd on the left-hand side and to an oxide-resistant area 248, 250 on the right-hand side. These oxide-resistant ground connections is further described in FIG. 65B. It is understood that the oxide-resistant area 248, 250 may comprise a pocket-pad, a pocket, a pad, a metal addition or an ECA stripe. The ECA stripe is taught in U.S. provisional 62/979,600, the content of which is fully incorporated herein by this reference. The oxide-resistant area 248, 250 may comprise a material selected from the group consisting of platinum, gold, tungsten, iridium, palladium, niobium, tantalum, ruthenium, rhodium, silver, osmium, and alloys or combinations thereof. The oxide-resistant material of the ground terminal pins 182gnd may further be selected from the group consisting of platinum-based materials including platinum-rhodium, platinum-iridium, platinum-palladium, or platinum-gold and naturally occurring alloys such as platiniridium (platinum-iridium), iridiosmium and osmiridium (iridium-osmium). Furthermore, the electrical connection material 152 can attach directly to the gold braze 154a of the hermetic feedthrough thereby providing an oxide resistance electrical attachment.

The tombstone mounting position refers to a filter capacitor orientation in which the ground electrode plates and the active electrode plates of the filter capacitor are positioned perpendicular to the surfaces of the ferrule and the insulator of the hermetic feedthrough. Typically, the ground and active electrode plates of a filter capacitor are aligned parallel with the body fluid side and device side surfaces of the ferrule and the insulator of the hermetic feedthrough (see FIGS. 7, 8, 9, 10, 13, 34, 54, 64B, 64C, 70A, 70B, 71B, 71C, 72B, 72C, 73, 74A, 74B, 74C, 75, 76, 77, 78, 79, 80, 82, 84, 85 of the present application). In contrast, the tombstone mounting position positions the ground electrode plates and the active electrode plates perpendicular to the body fluid side and device side surfaces of the ferrule and the insulator (see FIGS. 65A, 65B, 65E, 65F, 65I, 65J, 65K, 65L, 65M, 65O, 65Q, 65R, 65S, 65T, 70C and 70D of the present application). Referring specifically to FIG. 65A, illustrated is a device side surface 133 of the ferrule 134 and a device side surface 135 of the insulator 156. The ground electrode plates 146 and the active electrode plates 144 of the flat-through capacitor 210" are positioned perpendicular in relation to ferrule and insulator surfaces 133 and 135.

Further regarding FIG. 65A, electrical connections from the hermetic feedthrough to the AIMD circuit board and/or the AIMD circuitry can be made by one of a round wire such as 142a of FIG. 65A', a nail-head leadwire such as 142b' and 142c', a flat ribbon such as 142d' or combinations thereof. These are only exemplary connection options, as there are various other ways of connecting to an AIMD circuit board and/or AIMD circuitry (not shown), including directly abutting the circuit board to terminations and making a direct electrical connection. Also, a connection to flexible circuit boards or at least a portion of a flexible circuit board can be done. Any of the electrical connections previously disclosed in U.S. Pat. No. 8,195,295 can also be incorporated into the embodiments of the present application. Accordingly, the content of U.S. Pat. No. 8,195,295 is fully incorporated herein by this reference.

Figure 65B:
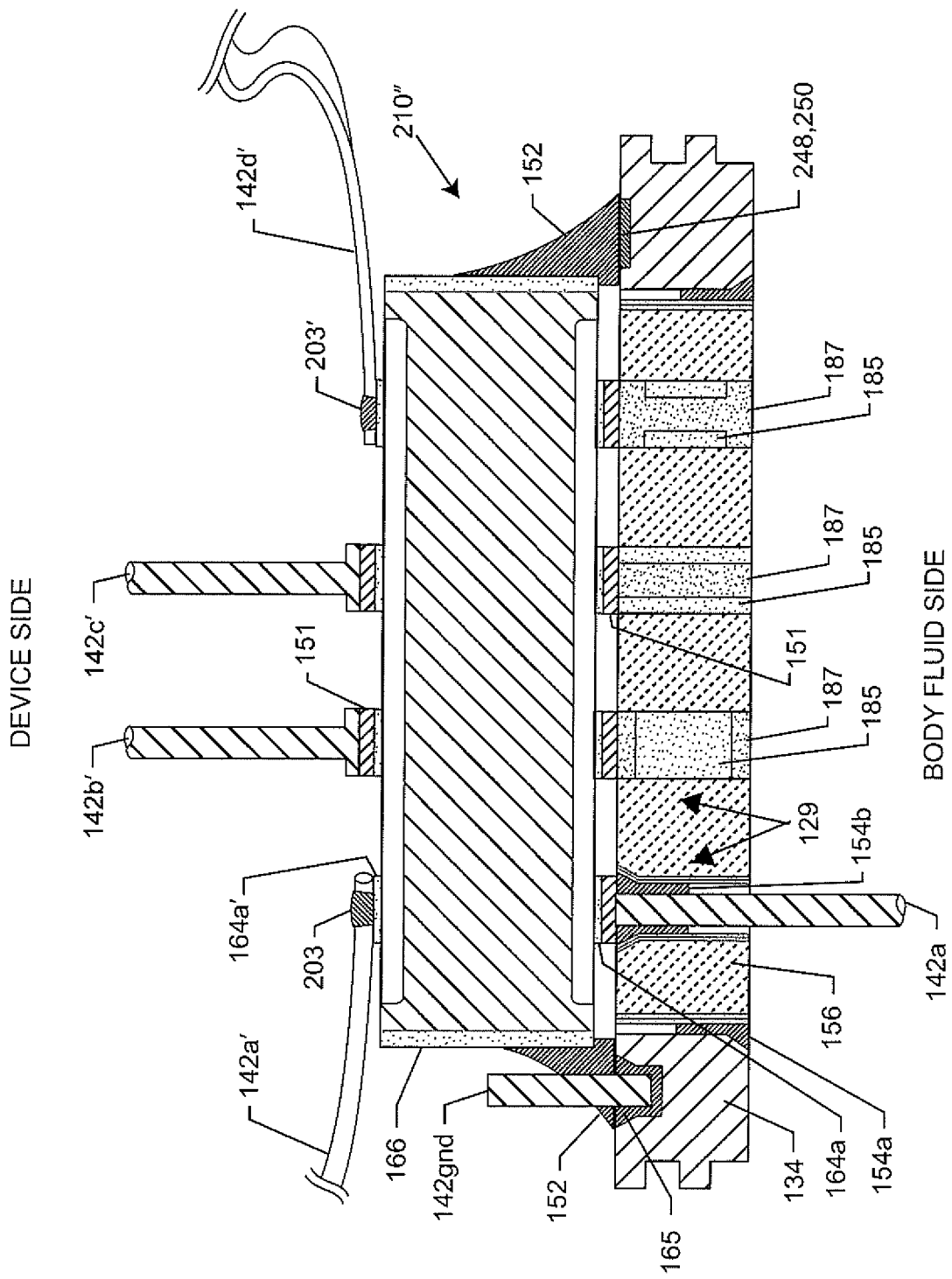
FIG. 65B is a cross-sectional view taken along lines 65B-65B from the structure of FIG. 65A.

FIG. 65B is a cross-sectional view taken from section 65B-65B of FIG. 65A. The insulator 156 of the hermetic feedthrough comprises various feedthrough conductive paths 129. For example, an embodiment on the far left-hand side of the hermetic feedthrough illustrates a conductive path comprising a nail-head leadwire 142a, which can alternatively be just a plain leadwire. Another embodiment to the right of far left-hand side embodiment comprises a co-sintered past-filled via comprising a ceramic reinforced composite (CRMC) 185 and platinum caps 187. Next, to the right of the embodiment just disclosed is another a co-sintered past-filled via embodiment comprising a platinum core 187 surrounded by a CRMC outer layer 185. It is appreciated that, alternatively, the entire co-sintered via can comprise just an essentially pure co-sintered platinum paste-filled via without any CRMC. On the far right-hand side is another co-sintered past-filled via embodiment comprising a dumbbell shape formed by the combination of the platinum 187 and the CRMC 185 materials. The embodiments of the feedthrough conductive paths 129 of the hermetic feedthrough of FIG. 65B are exemplary only and may comprise variations thereof. For example, the feedthrough conductive pathway 129 may be selected from the group consisting of a terminal pin, a pin, a leadwire, a lead wire, a two-part pin, a lead conductor, a sintered paste-filled via, a co-sintered via, a co-sintered paste-filled via, a co-sintered via with one or more metallic inserts, or combinations thereof. The feedthrough conductive pathway 129 may comprise the same embodiment for all feedthrough conductive pathways of the hermetic feedthrough, or alternatively may comprise at least one different feedthrough conductive pathway of the total feedthrough conductive pathways of the hermetic feedthrough.

Referring again to FIG. 65B, two methods of grounding the flat-through capacitor is shown. On the right-hand side, the electrical connection material 152 is shown attached to an oxide-resistant area 248, 250. The oxide-resistant area may comprise a pocket, a pad (for example, a gold pocket or a gold pad), a metal addition or an ECA strip. Gold pockets and gold pads are more thoroughly described in U.S. Pat. No. 10,350,421, the content of which is fully incorporated herein by this reference. On the left-hand side, the ground capacitor termination 166 of the flat-through capacitor is shown connected to an oxide-resistant terminal pin 142gnd. The oxide-resistant terminal pin 142gnd is attached to the ferrule 134 either by a gold braze 165 or a laser weld 157 (not shown), as previously disclosed. It is understood by those skilled in the art that the electrical connection on the right-hand side can alternately comprise an electrical connection material 152 connected to an ECA stripe or to the gold braze 154a of the hermetic feedthrough for an essentially oxide-free electrical attachment.

FIG. 64C further shows a method of grounding a filter circuit board, wherein the filter circuit board has at least one internal (or alternatively external) ground plate 161. The ground plate 161 of the filter circuit board is connected to an AIMD system ground, which in FIG. 64C is the ferrule 134 (terminal 3) of a hermetic feedthrough 132 (not labelled). In this exemplary embodiment, illustrated on the left-hand side is a ground pin 142gnd, which is gold brazed 165 (or alternatively laser welded 157, not shown) into the ferrule 134 of the hermetic feedthrough. The terminal pin 142gnd is shown attached in a blind via of the ferrule 134. An alternative embodiment is shown on the right-hand size, wherein the terminal pin 142gnd' extends through a via in the ferrule 134 to a body fluid side and a device side. The terminal pin 142gnd, 142gnd' of FIG. 6C comprises an oxide-resistant material (or may alternatively comprise an oxide-resistant outer layer, such as an oxide-resistant coating, plating, or cladding) such that a very low impedance electrical connection can be made both to the terminal pin and to various via hole connections to the at least one filter circuit board ground plate 161. Filter circuit board ground plate 161 is shown connected to six (or can alternatively be connected to "n" number) flat-through capacitor grounds (exemplary ground circuit traces 182a, 182b are shown in FIG. 64B). Referring to FIG. 64B, one will appreciate that the ground circuit traces 182a, 182b can be circuit board via holes or include circuit traces. What is important is that both the ground circuit traces 182a and 182b are conductively coupled through the circuit board via holes to the at least one ground plate 161. This creates a multipoint grounding system, which makes flat-through capacitors very effective three-terminal filters for use in AIMDs, including filter circuit boards connected to a hermetic feedthrough of an AIMD that effectively filters EMI.

Figure 65C:
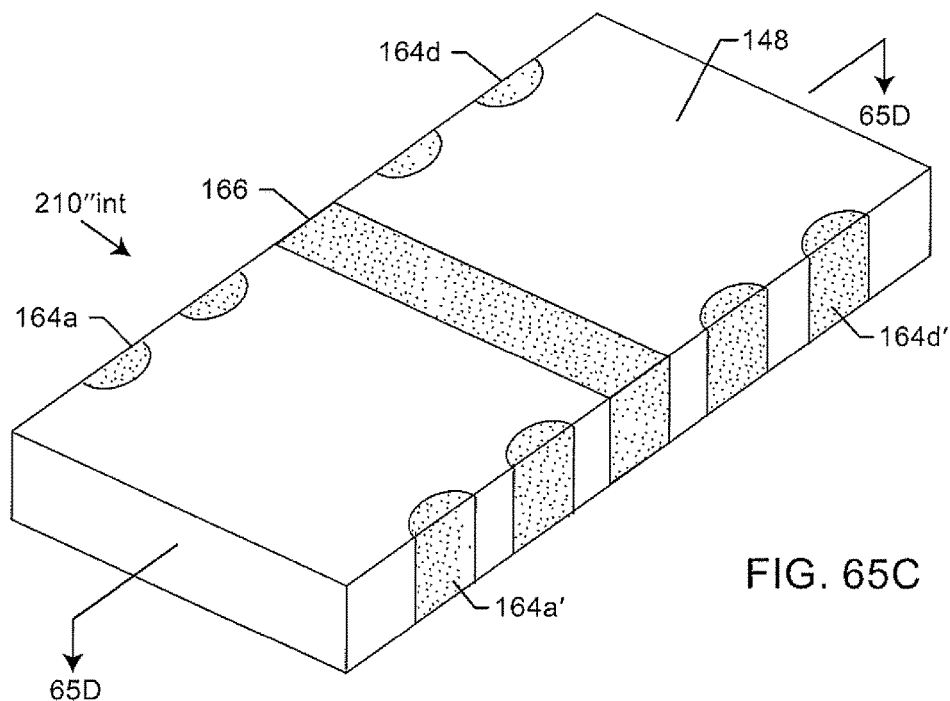
FIG. 65C is an isometric view of an internally grounded quad polar flat-through capacitor.

FIG. 65C is another type of quad polar flat-through capacitor 210"int which is an internally grounded flat-through capacitor. Internally grounded capacitors are more thoroughly described in U.S. Pat. No. 5,905,627, the content of which is fully incorporated herein by this reference. Referring to the internally grounded flat-through capacitor of FIG. 65C, the ground electrode plates 146 do not extend to the edges of the flat-through capacitor 210", but instead connect, as shown in FIG. 65D, to either two ground capacitor metallization areas 166 (not shown) or to a continuous ground capacitor metallization stripe 166 as shown in FIG. 65C.

Figure 65D:
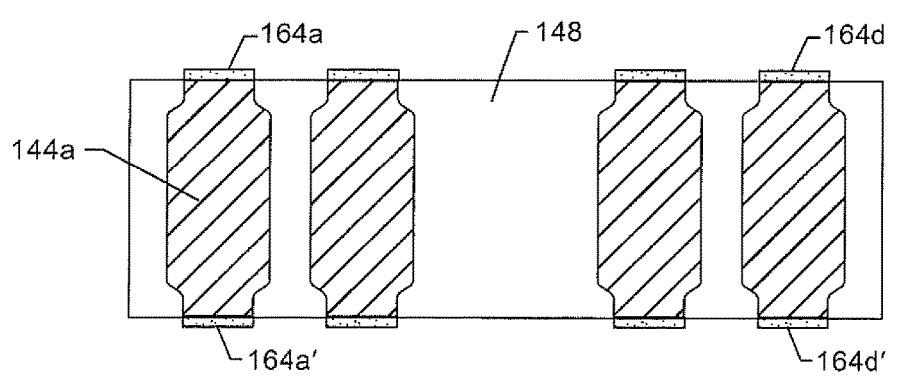
FIG. 65D is a sectional view taken along lines 65D-65D from the structure of FIG. 65C.
Figure 65D:
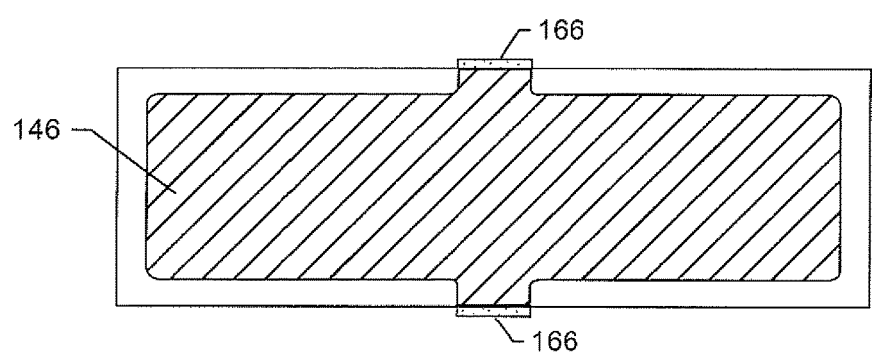

FIG. 65D is a sectional view taken from section 65D-65D of FIG. 65C illustrating the active electrode plates 144a through 144d and the ground electrode plates 146 of the flat-through capacitor of FIG. 65C.

FIG. 65E shows the top view of a device side internally grounded flat-through capacitor 210"int FIGS. 65C and 65D edge-mounted in a tombstone position. As illustrated, the flat-through capacitor 210"int at least partially shields the open windows of the insulator 156. The term "open windows" refers to an area that is not shielded such that dangerous EMI fields can enter and radiate through. The internally grounded flat-through capacitor 210" mounted to a hermetic feedthrough as shown in FIG. 65E works similarly to the door of a microwave comprising a metal plate perforated with holes. As microwave ovens, for convenience, have a glass window so one can watch the food being cooked, the holes of the metal plate encased by the glass window comprises a calculated hole diameter such that the perforated metal plate becomes a wave guide having wave beyond cutoffs so that dangerous microwave energy used to cook the food cannot get through the holes of the metal plate. Just as the perforated metal plate of the microwave door effectively shields at least a portion of the microwaves from escaping from the oven to the outside where one is watching the food cook, so too does the internally grounded flat-through capacitor 210"int and its associated ground electrode plates effectively shield at least a portion of the open windows of the insulator 156 of the hermetic feedthrough from letting undesirable EMI into the device side (inside) of the housing of an AIMD. As such, it is therefore not necessary that the open windows of the insulator 156 be completely shielded, as evidenced by everyday microwave ovens. Accordingly, the design of FIG. 65E carefully accounts for the width of the insulators 156 and the width of the flat-through capacitor 210"int, such that, any EMI that can undesirably couple, cannot pass through. In other words, the internally grounded flat-through capacitor provides sufficient shielding of the hermetic feedthrough such that the open window portions act as effective wave guides having beyond cutoffs to prevent dangerous EMI entry into the device side of an AIMD.

Figure 65F:
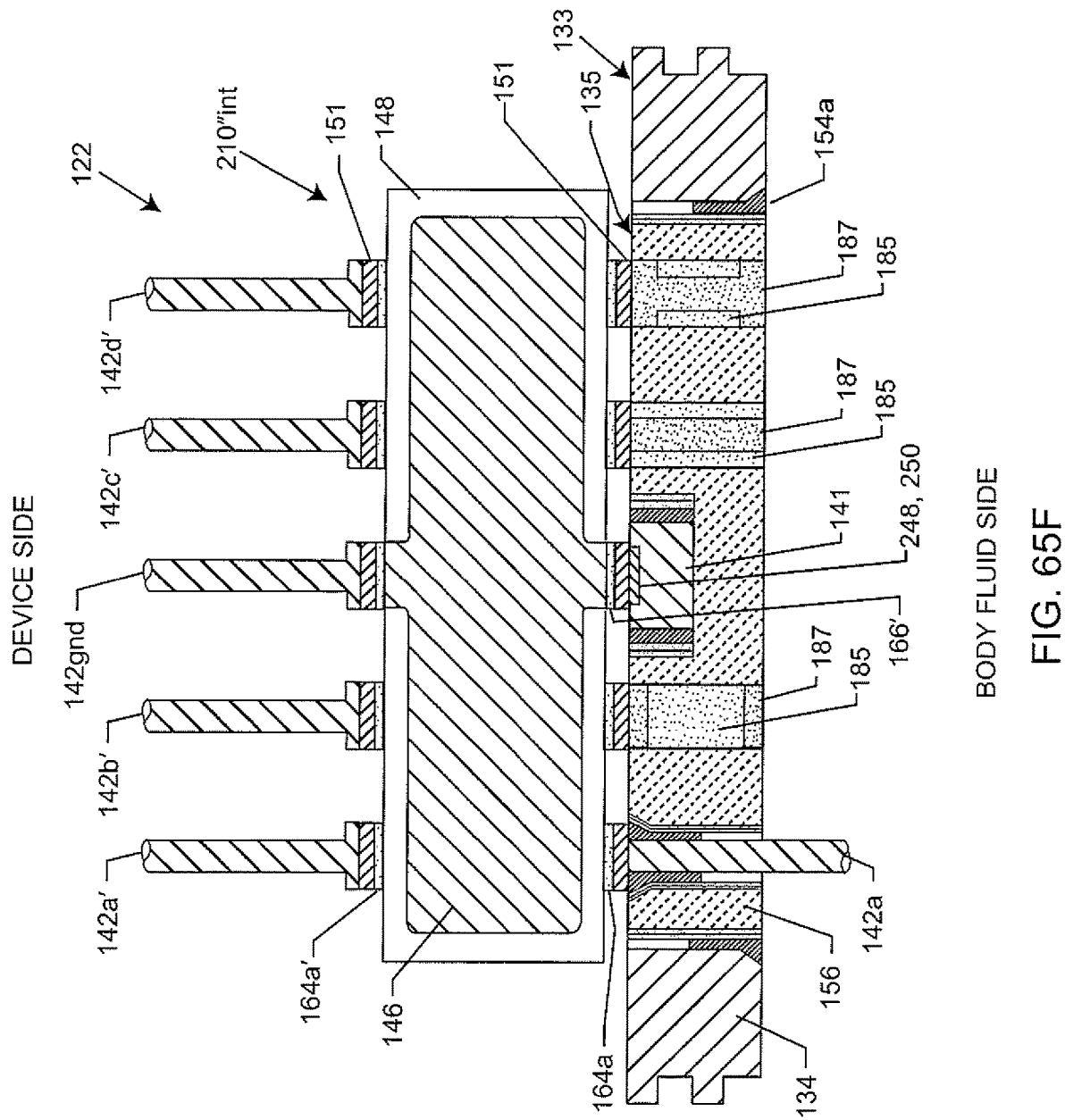
FIG. 65F is a cross-sectional view taken along lines 65F-65F from the structure of FIG. 65E.

FIG. 65F is a cross-sectional view taken from section 65F-65F of FIG. 65E. One can see that the flat-through capacitor 210"int is no longer connected directly to the ferrule 134 as shown in FIG. 65B. Instead, at the center, the capacitor ground electrode plates 146 are connected to the ground capacitor metallization 166'. There is an electrical connection material 151 that connects between the ground capacitor metallization 166' and a peninsula 139 or bridge 141 of the ferrule 134. Peninsulas and bridges are more thoroughly disclosed in U.S. Pat. No. 6,765,780, the content of which is fully incorporated herein by this reference. On the device side, nail-head leadwires 142a' through 142d' are shown. It is appreciated that the previously described round wires, flat ribbons, or other types of connections can alternatively be used.

Figure 65G:
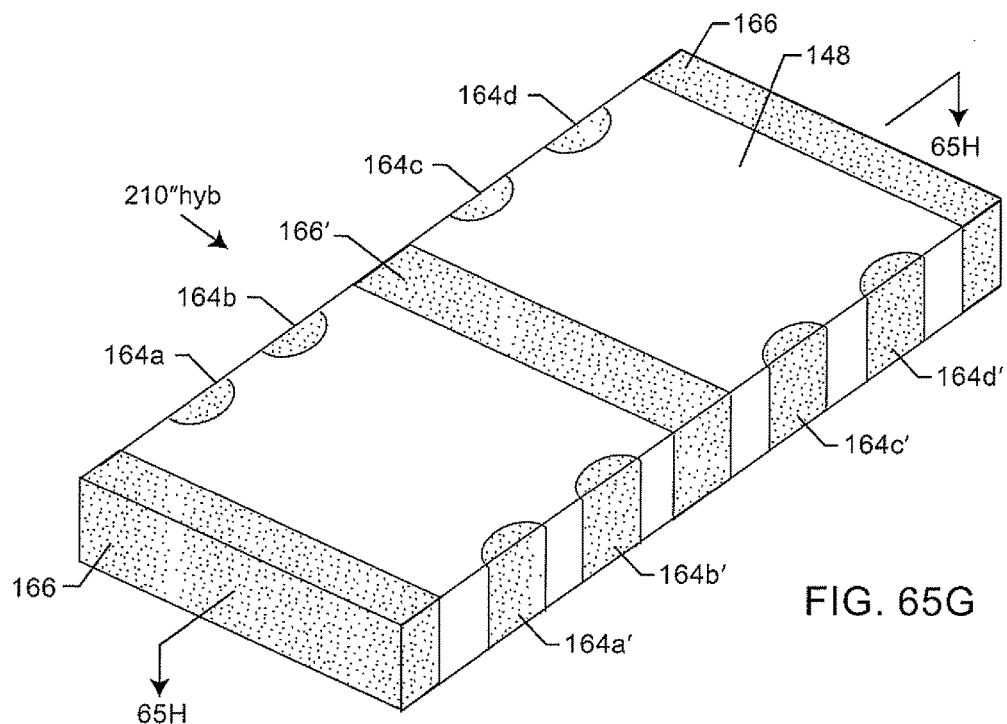
FIG. 65G is an isometric view of a hybrid quad polar flat-through capacitor.

FIG. 65G illustrates a hybrid flat-through capacitor 210"hyb. This hybrid design comprises edge ground capacitor metallizations 166 and a center ground capacitor metallization 166' as shown.

Figure 65H:
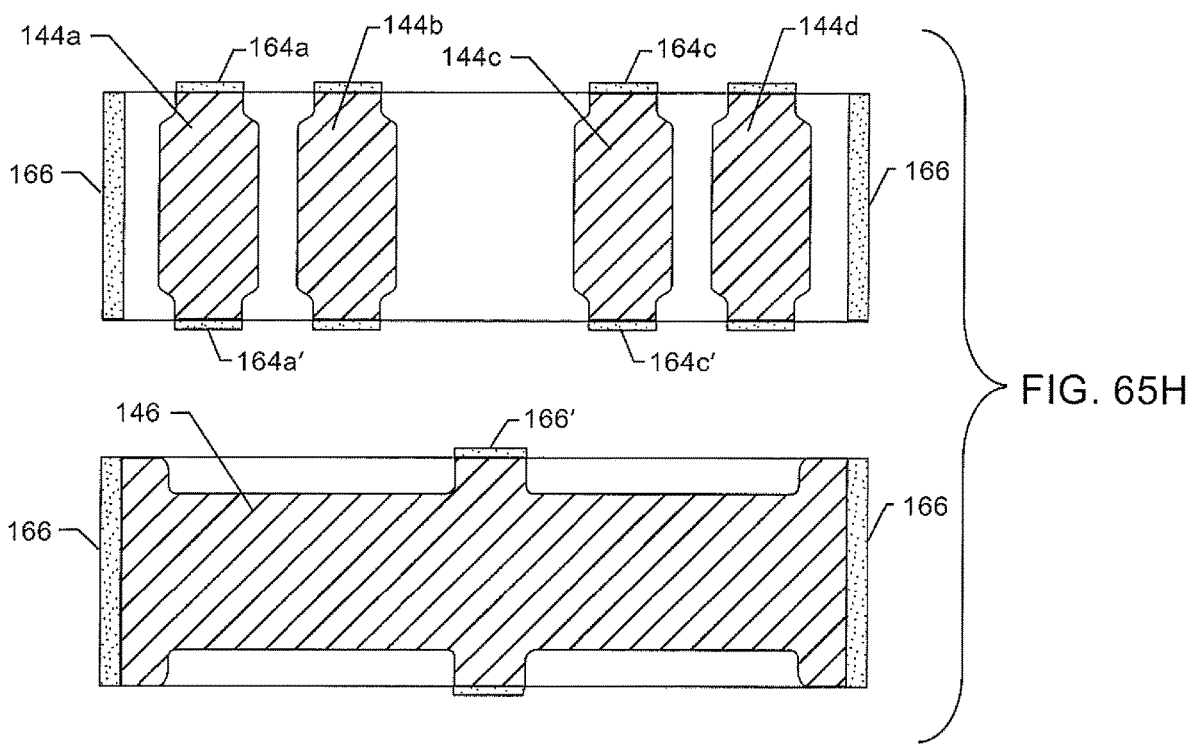
FIG. 65H is a sectional view taken along lines 65H-65H from the structure of FIG. 65G.
Figure 65:
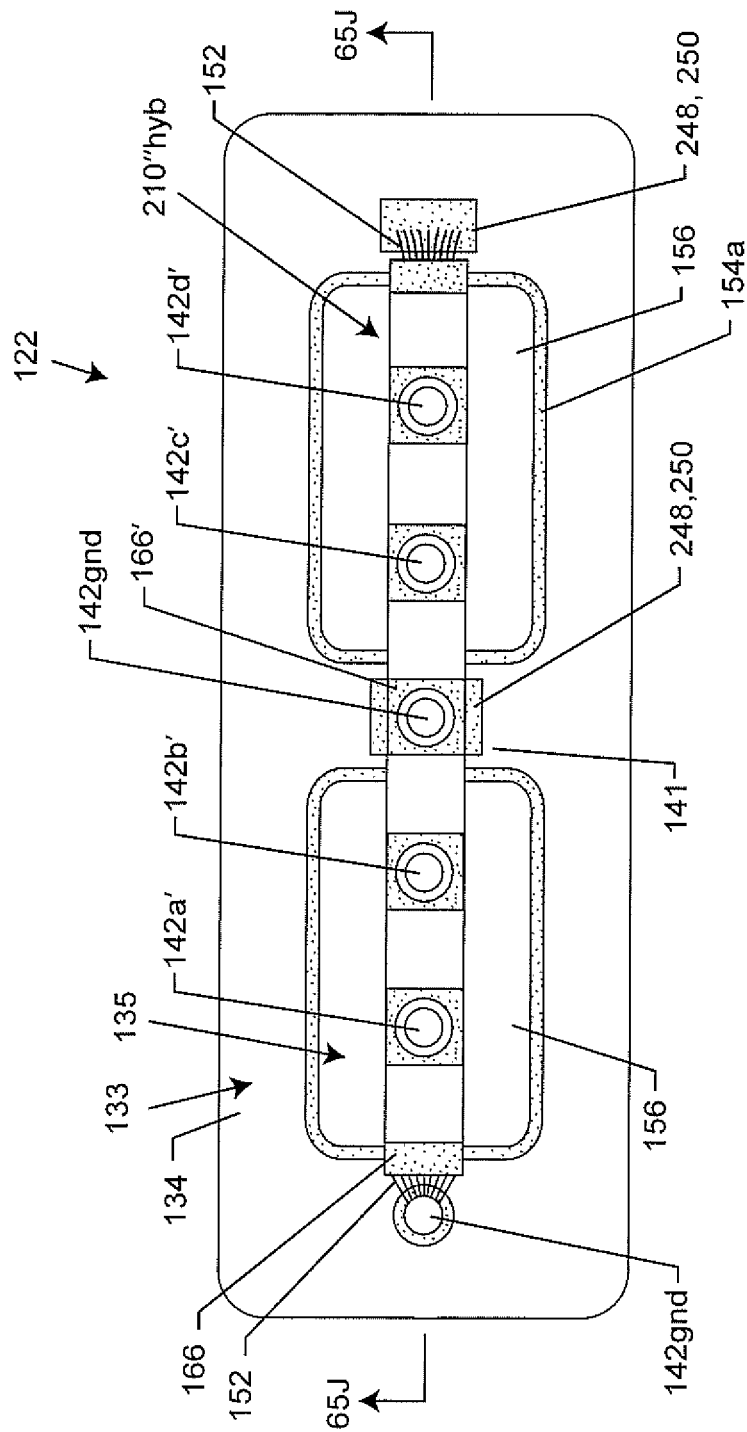
FIG. 65E is a top of view of an embodiment of the internally grounded quad polar flat-through capacitor of FIG. 65C now mounted above a ferrule and insulator in a tombstone mounting position.
FIG. 65I is a top view of an embodiment of the hybrid quad polar flat-through capacitor of FIG. 65G now mounted above a ferrule and insulator in a tombstone mounting position.
FIG. 65J is a cross-sectional view taken along lines 65J-65J from the structure of FIG. 65I.
FIG. 65K is a top view of an embodiment of the hybrid quad polar flat-through capacitor of FIG. 65G now mounted above a ferrule and insulator in a tombstone mounting position.
FIG. 65L is a side view taken along lines 65L-65L from the structure of FIG. 65K.
FIG. 65M is a side view taken along lines 65M-65M from the structure of FIG. 65K.
FIG. 65N is a top view of another embodiment of a ferrule and insulator structure.
FIG. 65O is an isometric view of a novel flat-through capacitor of the present invention.
FIG. 65P is a view similar to that of FIG. 65O now with the dielectric and outside metallizations removed.
FIG. 65Q is a top view of an embodiment of a flat-through capacitor of FIG. 65O now mounted above a ferrule and insulator in a tombstone mounting position.
FIG. 65R is a cross-sectional view taken along lines 65R-65R from the structure of FIG. 65Q.
FIG. 65S is a cross-sectional view taken along lines 65S-65S from the structure of FIG. 65Q.
FIG. 65T is a cross-sectional view taken along lines 65T-65T from the structure of FIG. 65Q.

FIG. 65H is a sectional view taken from section 65H-65H of FIG. 65G illustrating the active electrode plates 144a through 144d and the ground electrode plates 146 of the flat-through capacitor of FIG. 65G. Referring now to FIG. 65H, the quad polar active electrode plates 144a through 144d each respectively connect to an active capacitor metallization 164a through 164d of the flat-through capacitor 210"hyb, as indicated. The flat-through capacitor 210"hyb also comprises ground capacitor metallizations, the ground capacitor metallizations comprising an edge ground capacitor metallization 166 on the left-hand side and the right-hand side of the flat-through capacitor and a ground capacitor metallization 166' positioned in the center of the flat-through capacitor. The ground electrode plates 146 are electrically connected externally to the edge ground capacitor metallizations 166 on the left-hand and right-hand sides of the flat-through capacitor and internally to the center ground capacitor metallization 166' thereby forming the hybrid filter flat-through capacitor 210"hyb. It is noted that there can be a multiplicity of internal ground capacitor metallizations 166', which can be particularly important for longer flat-through capacitors, as increasing the number of internal ground metallizations in a substantially longer flat-through capacitor acts to keep the inductance of the longer flat-through capacitor low.

FIG. 65I illustrates a hybrid filter flat-through capacitor 210"hyb edge-mounted in a tombstone position to a device side of a hermetic feedthrough 132 (not labelled). One can see that there are nail head terminal pins 142a' through 142d' that are connectable to AIMD electronics, such as an AIMD active electronic circuit board (not shown). The hybrid filter flat-through capacitor 210"hyb is shown grounded at the right-hand side to an oxide-resistant area 248, 250 using electrical connection material 152. It is understood that the oxide-resistant area 248, 250 may comprise a pocket, a pad (for example, a gold pocket or a gold pad), a metal addition or an ECA stripe. An electrical connection can also alternatively comprise a direct connection to at least a portion of gold braze 154a. At the left-hand side, shown is a ground electrical connection electrically connecting an end ground capacitor metallization 166 to a ground terminal pin 142gnd using electrical connection material 152. The ground terminal pin 142gnd at the left-hand side is shown gold brazed or welded to the ferrule 134 of the hermetic feedthrough 132. At the center of the hybrid filter flat-through capacitor 210"hyb, an internal ground connection to an oxide-resistant area 248, 250 is also shown. The ferrule 134 of the hermetic feedthrough of FIG. 65I comprises either a peninsula 139 or a bridge 141, the peninsula or the bridge being integrally formed as a continuous part of the ferrule 134. As defined herein, a peninsula 139 partially extends inwardly into a ferrule opening 131 and a bridge 141 extends completely across a ferrule opening 131 (not labelled). A device side ground terminal pin 142gnd extends through a capacitor conductive passageway (a capacitor via hole) of the capacitor dielectric body 148 (not labeled). The ground terminal pin 142gnd is conductively and mechanically connectable to one of the peninsula 131 and the bridge 141 of the ferrule 134 of the hermetic feedthrough. As previously disclosed, the hybrid filter flat-through capacitor 210"hyb may comprise either a single internal ground connection or alternatively multiple internal ground connections. It is desirable that the hybrid filter flat-through capacitor 210"hyb have a multiplicity of ground plates, the multiplicity of ground plates being oriented in a tombstone position such that the hybrid filter flat-through capacitor 210"hyb at least partially shields radiated EMI from penetrating directly through any open windows of the insulator 156 of the hermetic feedthrough. It is appreciated that the insulator 156 can be a single insulator or comprise two or more separate insulators, such as shown in FIG. 65I. Again, it is important that the design qualification of a filtered feedthrough 122, such as illustrated in FIG. 65I, include wave guide calculations and suitable filter performance testing, including insertion loss at high frequency to assure EMI is effectively attenuated. It is also extremely important that, for all new EMI filter capacitor designs, filter capacitor insertion loss and attenuation be measured at various frequencies. Ideally, these measurements should be swept measurements using a network or spectrum analyzer. A critical capacitor EMI filter performance metric is its insertion loss, which is measured in decibels (dB). Measurements of capacitance, ESR, insulation resistance and dielectric withstanding voltage are other valuable capacitor measurements, however, these measurements do not directly measure the RF performance of a filter capacitor. As such, it is critical that the insertion loss characteristics of every new EMI filter capacitor design be thoroughly evaluated at least as a part of the initial qualification of the product and the insertion loss specified to ensure EMI attenuation is effectively achieved, thereby preventing undesirable and potentially AIMD therapy delivery malfunctions from occurring.

Figure 65J:
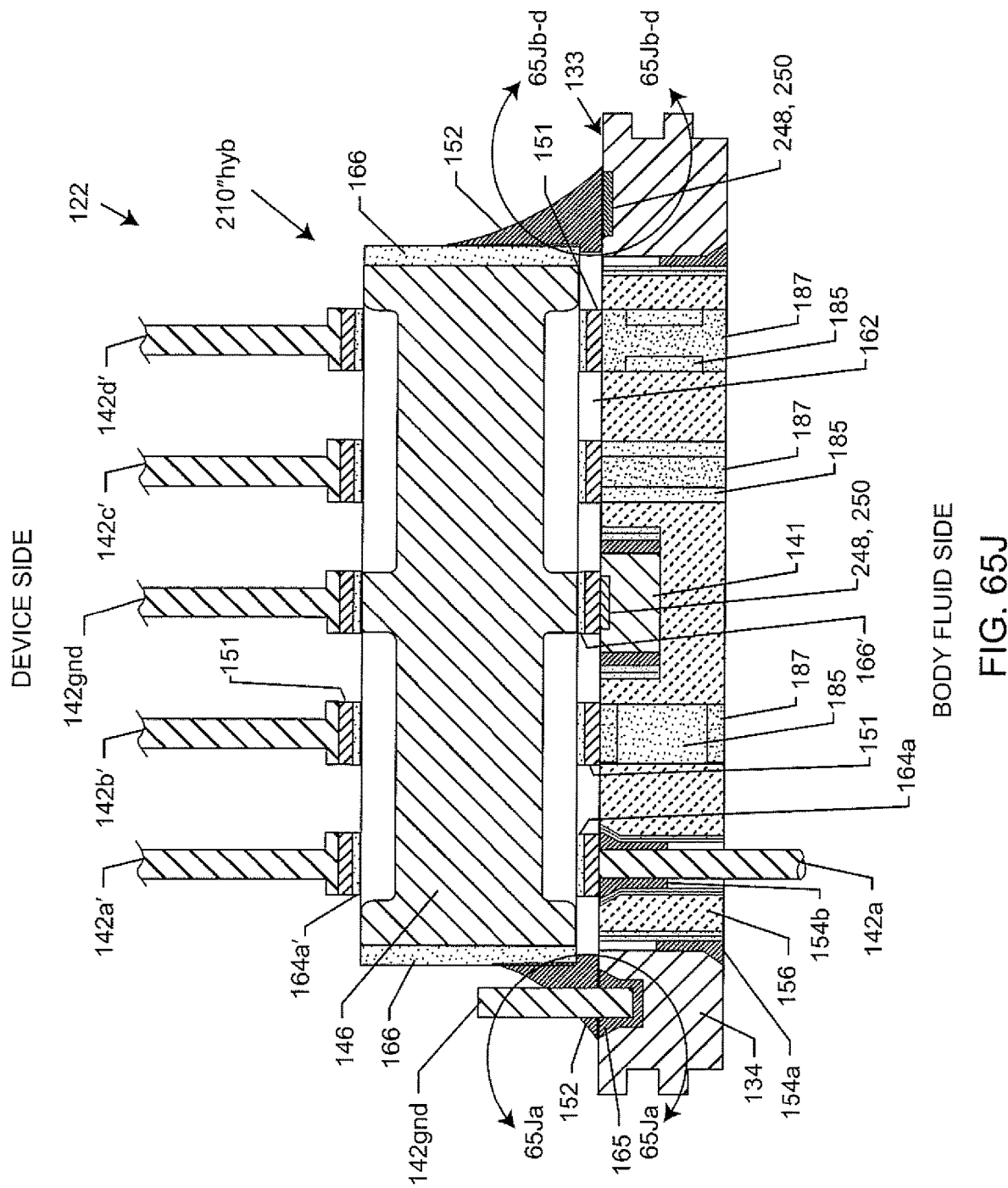
Figure 65J:
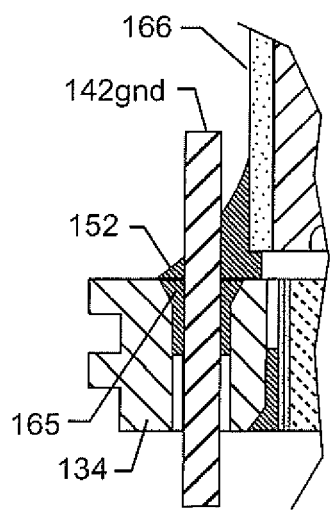
Figure 65J:
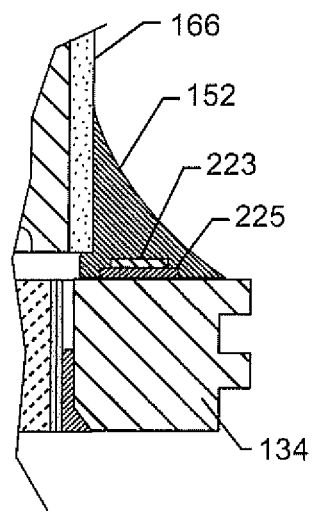
Figure 65J:
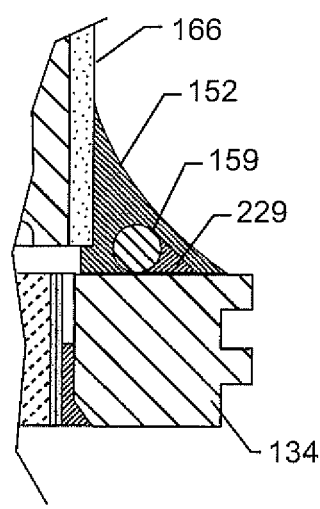
Figure 65J:
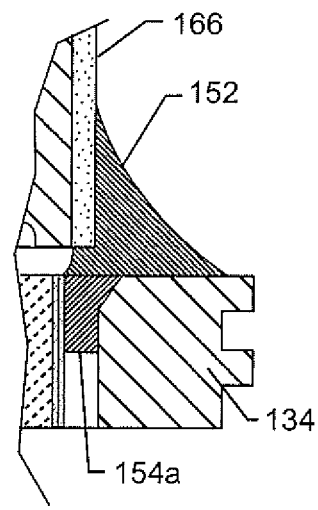

FIG. 65J is a cross-sectional view taken from section 65J-65J of FIG. 65I showing a filtered feedthrough 122 comprising the hybrid filter internally grounded flat-through capacitor 210"hyb attached to a hermetic feedthrough 132 (not labelled). Illustrated is quad polar hybrid filter flat-through capacitor 210"hyb comprising an internal ground connection at its center 166' and edge ground connections at its two end ground capacitor metallizations 166. Such a hybrid filter ground connection is important if the flat-through capacitor gets very long, as it is not desirable that the active electrode plates be located distant from the system ground. The hybrid ground connection of the present application is also known as a multipoint grounding system, which guarantees highly effective EMI filter performance at high frequencies. Another way of looking at this is that multipoint grounding does not allow too much inductance to build up across the critical ground electrode plates 146.

As previously described, the edge ground capacitor metallizations 166 of the hybrid filter flat-through capacitor 210"hyb can be connectable to an oxide-resistance area 248, 250, such as a pocket, a pad, a conductive stripe, or even a hermetic braze of the hermetic feedthrough, which is shown on the right-hand side of FIG. 65J. The oxide-resistant area of FOG. 65J is attached to the ferrule 134 of the hermetic feedthrough of the filtered feedthrough 122. The oxide-resistant area 248, 250 may comprise a gold pocket, a gold pad, a noble metal addition, for example, a metal addition comprising platinum, gold, palladium, or alloys thereof, an ECA stripe attached to a noble metal area of a ferrule, such as a noble metal laminated foil, a metallization, a vapor deposited film, a plating, or a coating, or combinations thereof. An electrical connection material 152 is used to make such electrical connections to the oxide-resistance area 248, 250. It is understood by those skilled in the art that an oxide-resistant attachment can also be made to the gold braze 154a of the hermetic feedthrough.

On the left-hand side of the hybrid filter flat-through capacitor 210"hyb of FIG. 64J is an oxide resistant ground terminal pin 142gnd. The oxide-resistant ground terminal pin 142gnd may be attached to the ferrule 134 of the hermetic feedthrough 132 (not labelled) by either a gold braze or a laser weld; however, other joining methods can be used to attach the oxide-resistant ground terminal pin 142gnd, including micro-welding, micro-TIG welding, ultrasonic welding, resistance welding, friction welding, butt welding, arc welding, gas welding, projection welding, flash welding, upset welding, solid state welding, diffusion welding, induction welding, percussion welding, electron beam welding, multi-stage brazing, or reactive brazing. While the oxide-resistant ground terminal pin 142gnd on the left-hand side of FIG. 64J is shown attached in a blind via of the ferrule 134, alternatively, the oxide-resistant ground terminal pin 142gnd can pass all the way through a via hole of the ferrule 134 of the hermetic feedthrough as previously disclosed in FIG. 64C. It will also be understood by those skilled in the art that an insulator washer 162 typically resides between the hybrid filter flat-through capacitor 210"hyb and the insulator 156 of the hermetic feedthrough. It will also be understood that the insulator washer 162 will also similarly reside in all of the filtered feedthroughs 122 of the present application having filter capacitors attached to the insulator 156 of the hermetic feedthrough. It is noted that, for simplicity, the insulator washer of the figures of the present application is not cross-hatched.

FIG. 65Ja is generally taken from section 65Ja-65Ja of FIG. 65J illustrating an embodiment comprising a ground terminal pin 142gnd passing all the way through the ferrule 134 of a hermetic feedthrough. The ground terminal pin 142gnd can be electrically and hermetically attached to the ferrule 134 by a gold braze 165 or a laser weld 157 or any of the joining methods previously disclosed.

FIG. 65Jb is generally taken from section 65Jb-65Jb of FIG. 65J illustrating an embodiment of an oxide-resistant area 248, 250 having a metallization layer 225 overlaid by an electrically conductive adhesive (for example an ECA stripe or an ECS dot) 223. ECA stripes over metallization layers are more thoroughly described in U.S. provisional 62/979,600, the content of which is fully incorporated herein by this reference. In the embodiment of FIG. 65Jb, the electrical connection material 152 contacts at least a portion of the ECA stripe 223. The electrical connection material 152 is also shown contacting a portion of the ferrule 134, however, the connection to the ferrule is not required as the ferrule 134, if made of an easily oxidizable material, such as titanium, can heavily oxidize as previously disclosed.

Further regarding titanium, it is generally understood that: 1) titanium has a great chemical affinity for combining with oxygen; and 2) titanium does not have a great affinity for combining with any other chemicals. It is generally understood that, in open air, freshly machined or cleaned titanium quickly forms a layer of oxides. This formation of oxides creates a natural passivity that inhibits reactions with other chemicals, such as salt or oxidizing acid solutions. The result is that titanium has superior corrosion resistance. However, titanium oxide layers can be present on a titanium ferrule at the time an electrical connection material is applied. Even if titanium oxide layers are removed prior to applying electrical connection material, the titanium can re-oxidize later on. For example, during laser welding of the ferrule 134 to the AIMD housing 124, substantial localized heat may be generated, which can accelerate titanium oxide layer formation. The industry generally believes that titanium oxide layers will not form on titanium components internal the AIMD housing once hermetically sealed, mostly because AIMDs can be assembled in or back-filled with an inert gas, such as helium, nitrogen or argon. The industry typically does so with the intent of inhibiting oxidation of sensitive metals like titanium. This belief is erroneous. Materials of construction used in the manufacture of AIMDs, such as polymers, plastics, adhesives, elastomers and the like, and even the printed circuit boards (PCBs) themselves inside the AIMD housing, generally have some level of gases trapped within their structures, for example, moisture, oxygen, other oxygen-containing gases, or even undetected residues comprising same, that eventually outgas during the operating life of the AIMD. Furthermore, processes that can involve increased temperature like welding, curing or heat treatment processes, or even actions having temperature shifts, such as are possible during shipping, can accelerate such outgassing. Hence, even if an AIMD is manufactured in an inert gas environment, or backfilled with an inert gas, such 'heating' of certain materials of construction can release oxygen, oxygen-containing gases or water vapor into an otherwise hermetically sealed environment causing the formation of oxide layers on easily oxidizable materials like titanium. The formation of such an oxide layer increases the RF ground impedance, which seriously degrades EMI filter performance. Moreover, even when titanium is heated during welding, titanium oxides form even faster, and as the temperature reaches titanium's melting point (1,668° C., 3034° F.), the oxides typically dissolve into solution and can contaminate the weld pool, which can cause an impure and/or a weak weld. This is why special care is generally taken to minimize exposure of titanium components to oxygen during welding, such as employing a shield gas, for example, argon or helium, or welding in a full vacuum (as is the case with electron beam welding). Regardless, welding, even laser welding as typically used by AIMD manufacturers, can cause heating along the weld seam of the AIMD, which may also involve heating of the device side ferrule surface as well. Hence, it is conceivable that when exposed to such heating by laser welding, the titanium ferrule 134, and in particular the device side ferrule surface, can undesirably re-oxidize. The inventors studied the effect of titanium oxides on feedthrough filters, measuring ESR/insertion loss (IL) pre- and post-laser welding. The inventors observed that post-laser welding, the ESR measurements of some feedthrough filters of a very large lot increased from the pre-laser welding measurement by orders of magnitude. To this day, when attachment is made directly to titanium or other oxidizable metal without the presence of an oxide-resistant intermediary between the titanium and the electrical attachment material, the inventors have found that, while most parts in a production lot remain within ESR/IL specification post-laser welding, there consistently are some parts in this same lot that fail ESR/IL horribly. Thus, since failing ESR measurements remain unpredictable even under protective laser welding protocols, attaching to an ECA stripe without an oxide-resistant intermediary is a highly undesirable practice. Accordingly, the generally accepted belief that a titanium oxide layer will not form on titanium components internal an AIMD housing once hermetically sealed simply because AIMDs can be assembled in or back-filled with an inert gas is flawed and inaccurate. Thus, electrically connecting to an easily oxidizable material such as titanium, more particularly, the deposition of an ECA stripe, without an intermediary oxide-resistant area 248, 250 is highly undesirable, as such electrical connections have proven to be a highly unreliable due to re-oxidation and related increasing resistance. For more detail referring to the effects of oxide layer formation on EMI filtering, refer to the paper entitled, "Dissipation Factor Testing is Inadequate for Medical Implant EMI Filters and Other High Frequency MLC Capacitor Applications", ISSN: 0887-7491, presented at CARTS 2003: 23rd Capacitor and Resistor Technology Symposium, Mar. 31-Apr. 3, 2003, the content of which is fully incorporated herein by this reference.

FIG. 65Jc is taken from section 65Jc-65Jc of FIG. 65J. In this embodiment, a metal addition 159 is shown welded 229 to the ferrule 134. There are various methods of attaching metal additions to the ferrule, which are more thoroughly disclosed in U.S. Pat. No. 9,931,514, the content of which is fully incorporated herein by this reference. The electrical connection material 152 must contact at least a portion of the metal addition 227 as shown to form a reliable oxide-resistant electrical connection.

FIG. 65Jd is very similar to FIGS. 65Ja through 65Jc, except that in this embodiment, the electrical connection material 152 at least partially contacts a gold braze 154a. Electrical connection to the gold braze of a hermetic feedthrough is disclosed in U.S. Pat. No. 6,765,779, the content of which is fully incorporated herein by this reference.

Referring once again to FIGS. 65J, 65Ja through FIG. 65Jd, it is appreciated that any of the filter capacitors of the present application can be grounded in a like manner.

Figure 65K:
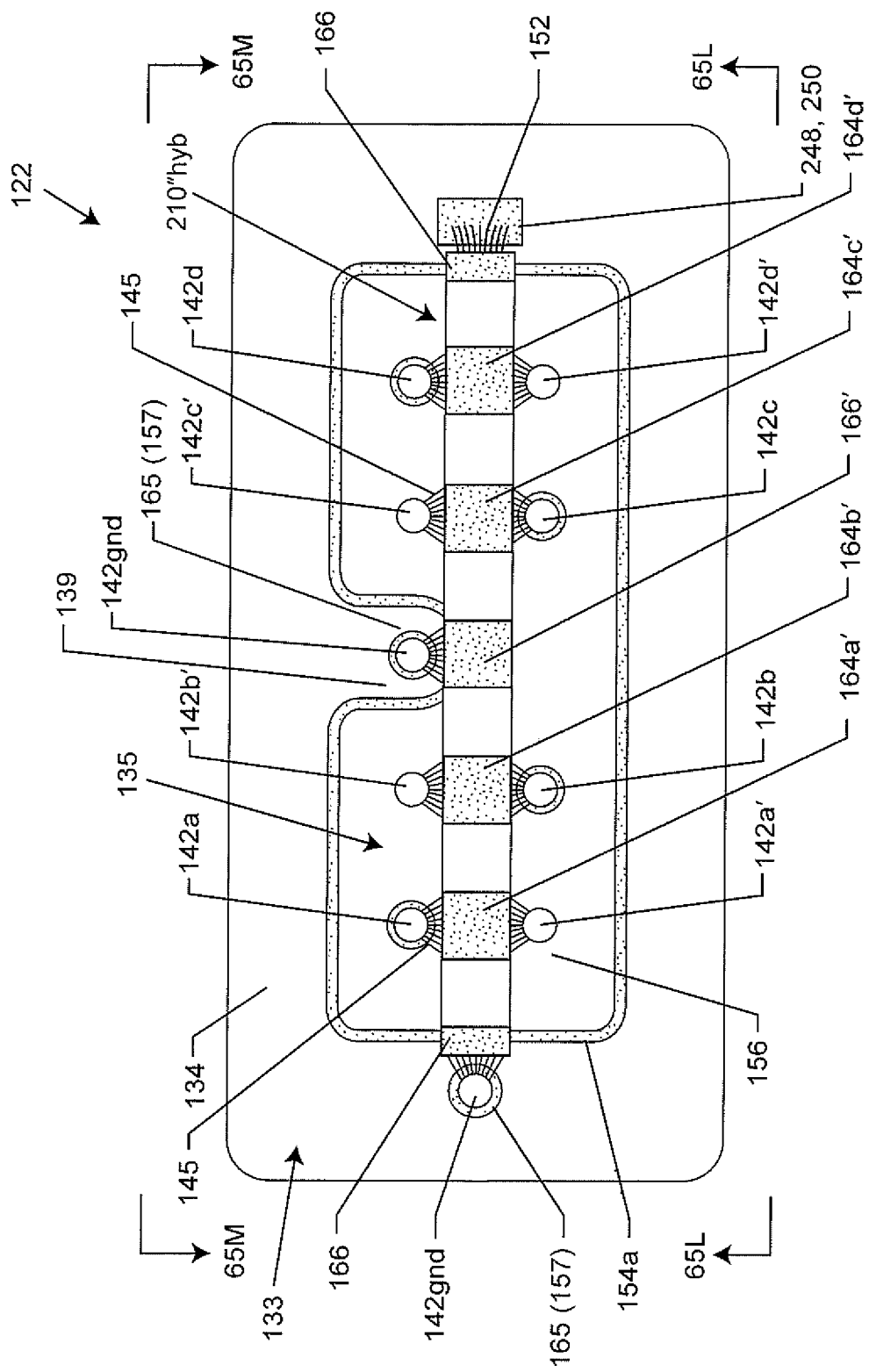

FIG. 65K is very similar to FIG. 65I illustrating a top view of an embodiment of a hybrid filter flat-through capacitor 210"hyb mounted in a tombstone position, except that instead of the bridge 141 of the ferrule 134 of the hermetic feedthrough, a peninsula 139 is shown. As previously disclosed, the hybrid filter flat-through capacitor 210"hyb at least partially effectively blocks direct penetration of EMI through the insulator 156 of the hermetic feedthrough. Additionally, the insulator 156 of FIG. 65I not a single insulator as is the insulator 156 of FIG. 56K. The insulator 156 of FIG. 65K is modified to accommodate the peninsula 139. The hybrid filter flat-through capacitor 210"hyb is a three-terminal capacitor, as are hybrid feedthrough filter capacitors. Hybrid feedthrough filter capacitors are disclosed in U.S. Pat. No. 6,765,780, the content of which is fully incorporated herein by this reference. As previously disclosed, the ferrule 134 of the hermetic feedthrough of the filtered feedthrough 122 can comprise "n" number of peninsulas 139 so that a multipoint grounding system can be created. Referring to FIG. 65K, similar to the hybrid feedthrough filter capacitor of the '780 patent, grounding of the hybrid filter flat-through capacitor 210"hyb comprises electrical connections of at least one edge ground capacitor metallization 166 and at least one internal ground capacitor metallization 166' (or internal ground connection). Shortening the bridge, as taught by the '780 patent, is a simple variation of just shortening up the bridge to make said bridge a peninsula. An advantage of shortening up the bridge to make a peninsula is that the hermetic feedthrough requires only one insulator 156, which can be gold brazed 154a in a single operation to the ferrule 134 of the hermetic feedthrough.

Figure 65L:
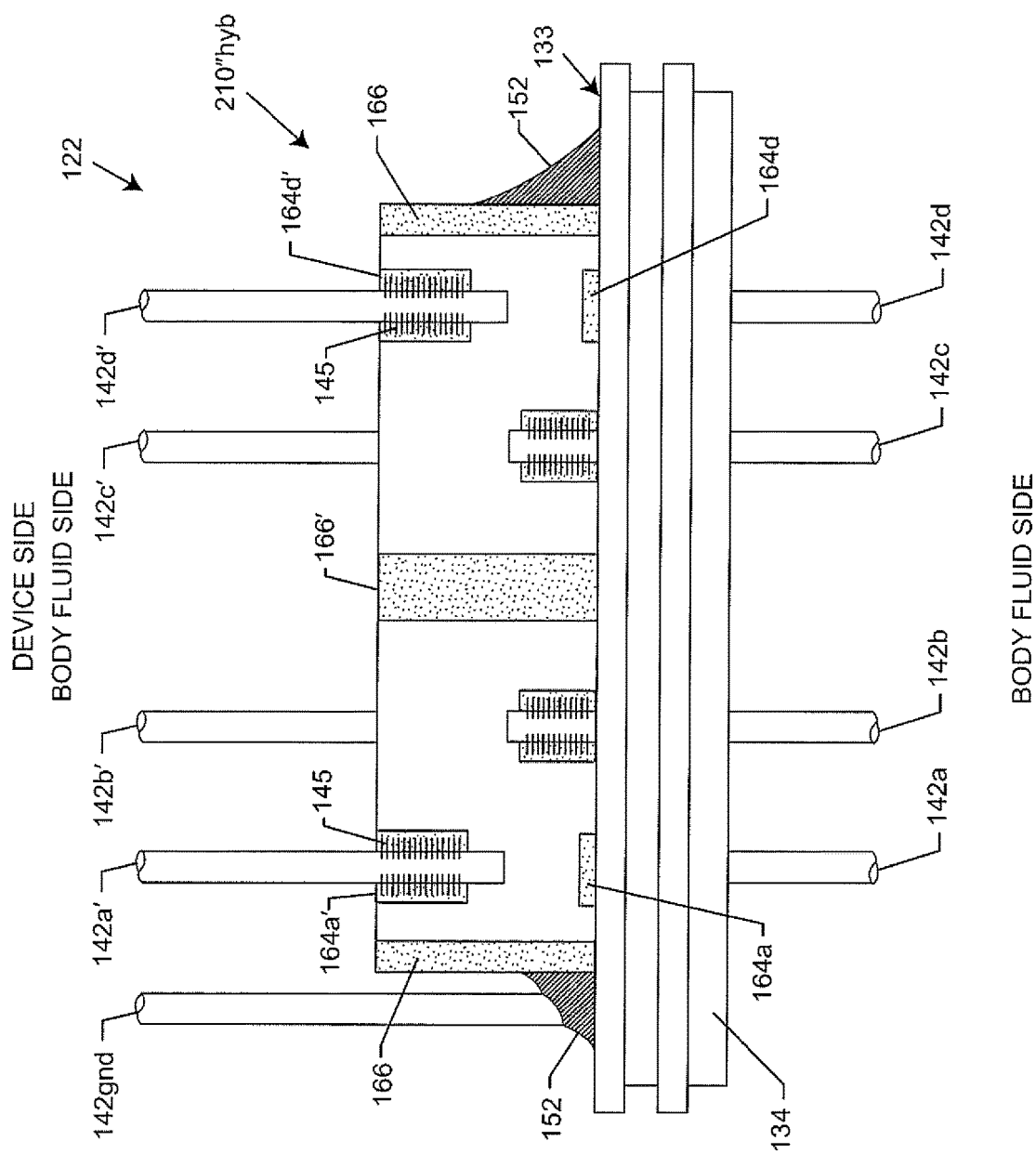
Figure 65M:
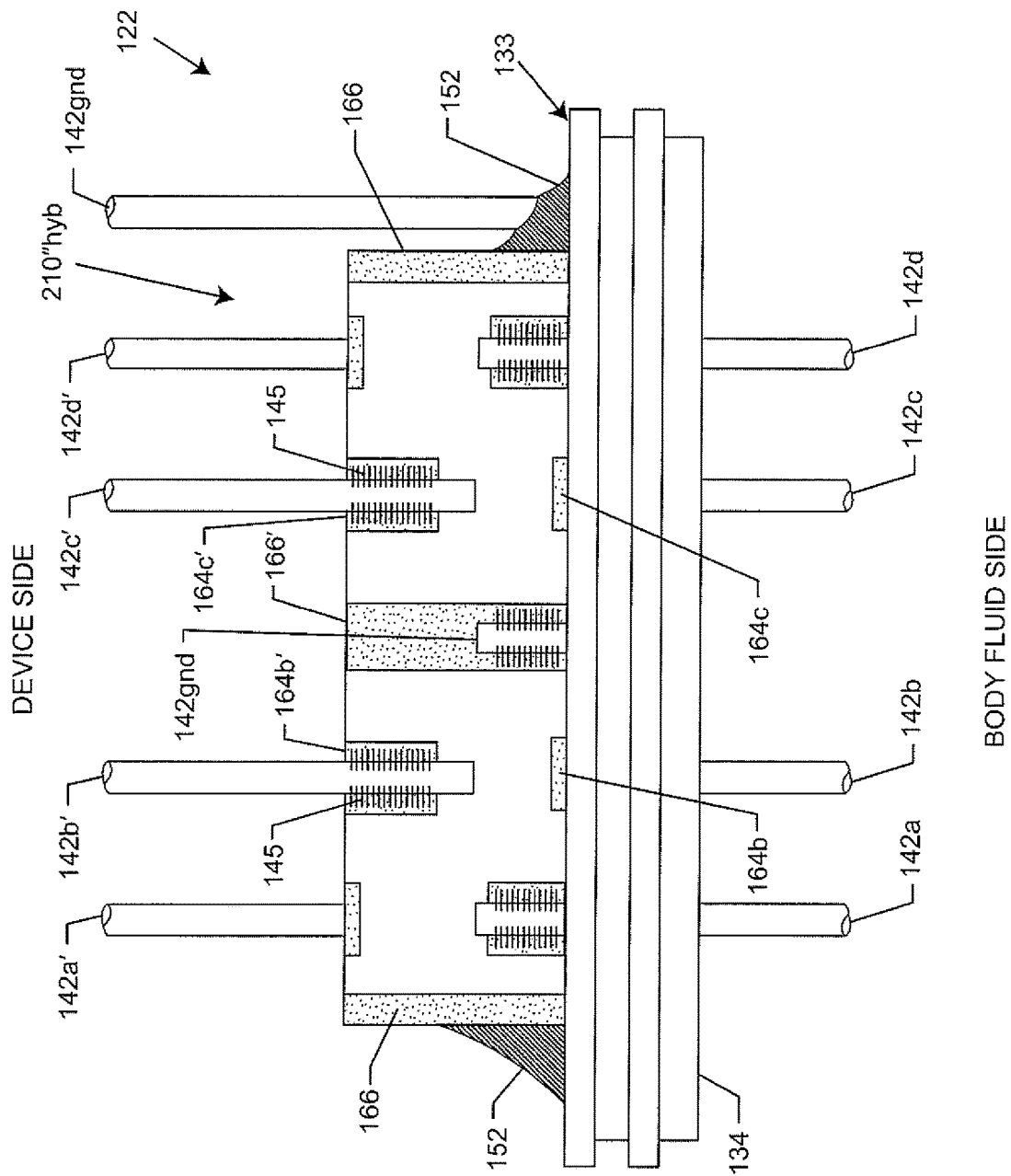

Referring once again to FIG. 65K, electrically connecting the active capacitor metallization 164a through 164d and 164'a through 164'd to the respective terminal pins 142a through 142d and 142'a through 142'd is best illustrated in FIG. 65L and FIG. 65M. FIG. 65L is a side view 65L-65L of FIG. 65K illustrating the active capacitor metallizations 164a through 164d and 164'a through 164'd connected with respective terminal pins 142a through 142d and 142'a through 142'd using an electrical connection material 145. The active capacitor metallizations of the hybrid filter flat-through capacitor 210"hyb partially extend along the surface of the side of the filter capacitor as shown, in order to secure the terminal pins to the filter capacitor in a mechanically and electrically robust manner. In other words, attachment of the terminal pins to the extended active capacitor metallization increases the bonding area of the electrical connections providing secure attachment that sustains mechanical shock and vibration. Referring once again to FIG. 65L, it is appreciated that the active capacitor metallizations 164a through 164d and 164'a through 164'd must wrap over the edge of the thickness of the hybrid filter flat-through capacitor 210"hyb, which is shown at the top and the bottom of the tombstone mounted capacitor so that electrical connection of the active electrode plates of said hybrid filter capacitor are made. Also illustrated in FIG. 65L are edge ground capacitor metallizations 166 and at least one internal ground capacitor metallization 166' (shown in the center of the hybrid filter capacitor). The internal ground capacitor metallization 166' must also wrap over the edge of the thickness of the hybrid filter flat-through capacitor 210"hyb at the top and the bottom of the tombstone mounted capacitor for proper connection to the hybrid filter capacitor's ground electrode plates 146. An electrical connection material 152 connects the hybrid filter capacitor edge ground capacitor metallization 166 on the right-hand side to the ferrule surface 133 and to an oxide-resistant ground terminal pin 142gnd on the left-hand side. Electrical connection to the ferrule surface 133 on the right-hand side can be made using any one of the oxide-resistant area 148, 150 embodiments of FIGS. 65J, 65Ja through 65Jd. Electrical connection can alternatively be made by a direct connection to a gold braze 154a.

FIG. 65M is the opposite (reverse) side view taken from section 65M-65M of FIG. 65K. In this view, one can see the centered internal ground terminal pin 142gnd. The ground terminal pin 12gnd is conductively and mechanically connected to at least one of a peninsula 139 or a bridge 141 of the ferrule 134 of the hermetic feedthrough. The centered internal ground terminal pin 142gnd is either gold brazed or welded to the peninsula 139 or to the bridge 141 of a ferrule structure 134. Importantly, the ground terminal pin 142gnd provides a very low resistance and low impedance electrical connection to the hybrid flat-through capacitor grounding system 210"hyb so that high frequency RF energy can be diverted to the ferrule and then, in turn, to the AIMD housing (not shown). It is appreciated that all the ferrule structures described herein are configured to be laser welded into an opening of the housing of an AIMD.

Figure 65N:
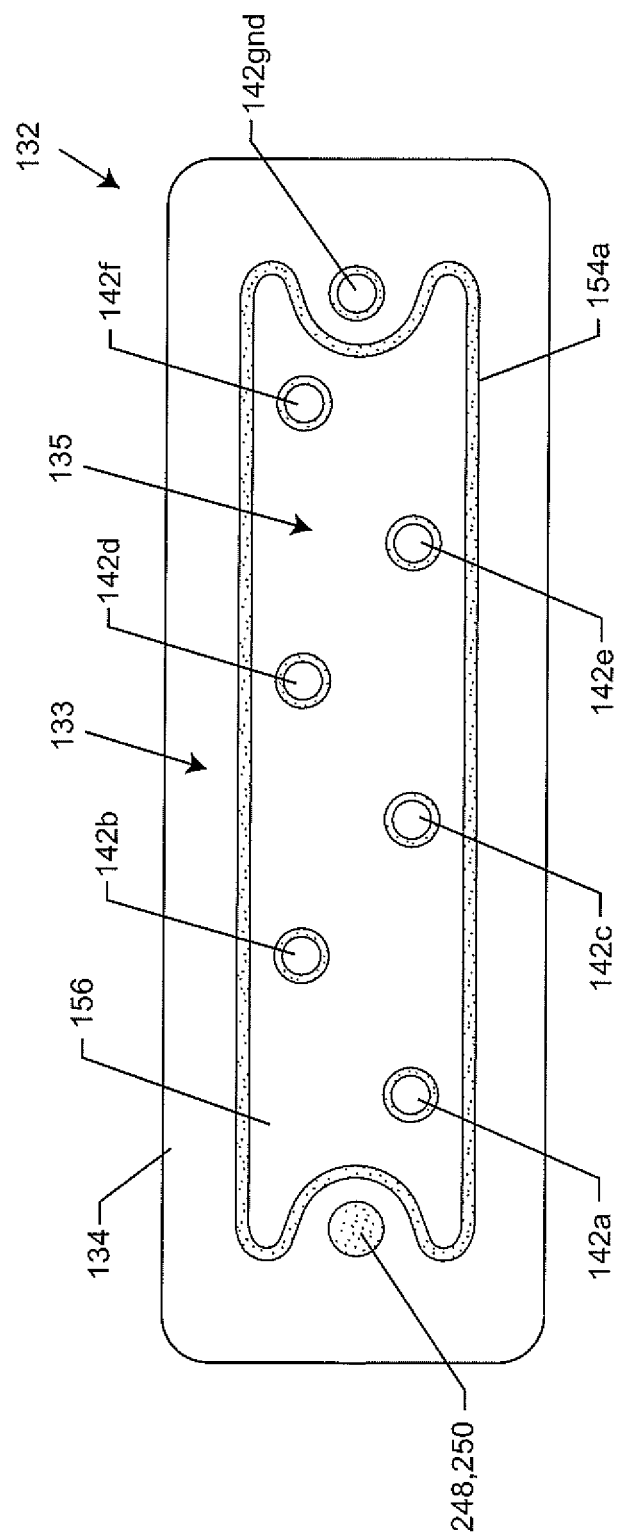

FIG. 65N is a top view of an embodiment of a hermetic feedthrough 132. Shown are six active terminal pins 142a through 142f, which alternatively may be co-sintered paste-filled vias. As illustrated, the active terminal pins 142a through 142f pass through the insulator 156 of the hermetic feedthrough 132 in non-conductive relationship with the ferrule 134. On the left-hand side of FIG. 65N, an oxide-resistant area 248 is shown, which in FIG. 65N may be a circular gold pocket-pad. It is understood that the gold pocket-pad may be any shape, including a circle, a rectangle, a square, an oval, a custom designed shape, or any shape commensurate with the needs of an application. Alternatively, the gold pocket-pad can instead be an ECA stripe as previously disclosed. An ECA stripe overlays an oxide-resistant metallized area as disclosed in U.S. provisional 62/979,600. On the right-hand side of FIG. 65N, shown is a ground terminal pin 142gnd. The ground terminal pin 142gnd is either gold brazed 165 or welded 229 directly to the ferrule 134 and comprises an oxide-resistant material such as previously disclosed. Both the right-hand and left-hand sides of the insulator 156 are curved, but can alternatively be a rectangular shape, which simply means that the ground locations are moved further out. In other words, the shape of the insulator can take on any shape that is required for an application. Referring once again to FIG. 65N, illustrated is what is known as a dual inline staggered pin feedthrough terminal pin layout.

Figure 65O:
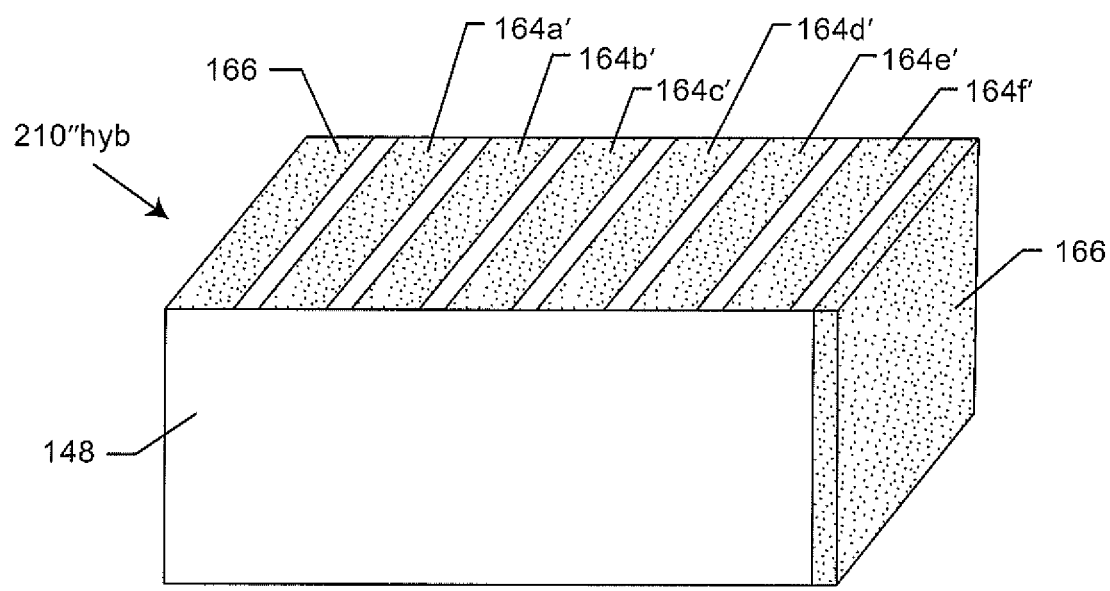

FIG. 65O is an isometric view of a dual inline hybrid filter flat-through capacitor 210"hyb. One can see on the far left-hand side of the hybrid filter flat-through capacitor 210"hyb that there is a first ground capacitor metallization 166 on the very top of the dielectric body 148 of said filter capacitor, while on the right-hand side of the hybrid filter flat-through capacitor 210"hyb there is a second ground capacitor metallization 166 at the very end of the dielectric body 148 of said filter capacitor. Visible are also six active capacitor metallizations 164a' through 164f on the top surface of the dielectric body 148 of the hybrid filter flat-through capacitor 210"hyb. There are also six corresponding active capacitor metallizations 164a through 164f on the bottom side of the dielectric body 148 of the hybrid filter flat-through capacitor 210"hyb that are not visible.

Figure 65P:
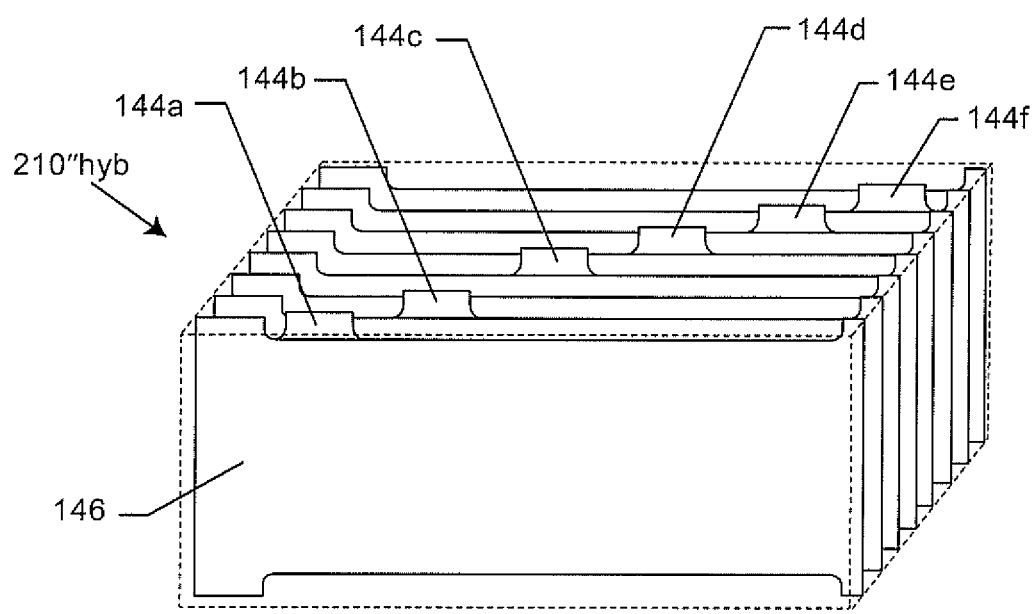

FIG. 65P is an isometric view of the hybrid filter flat-through capacitor 210"hyb of FIG. 65O illustrating the active electrode plates 144a through 144f and the ground plates 146 residing within the dielectric body 148 of said filter capacitor. In the embodiment shown, each active electrode plate 144a through 144f is sandwiched between a pair of ground electrode plates 146. Each active electrode plate 144a through 144f is electrically connected to its respective active capacitor metallization 164a' through 164f'. Each ground electrode plate 146 is electrically connected to the left-hand side and the right-hand side ground capacitor metallizations 166. It is noted that, while the first ground capacitor metallization 166 on the left-hand side is disposed on the top of the hybrid filter flat-through capacitor 210"hyb and the second ground capacitor metallization 166 on the right-hand is disposed on the end of said filter capacitor, the ground capacitor metallizations 166 can be positioned reversely, meaning the left-hand side can be an end ground capacitor metallization and the right-hand side can be a top ground capacitor metallization. Likewise, both ground capacitor metallizations can be top ground capacitor metallizations or, alternatively, both can be end ground capacitor metallizations. It is also understood that although just one active electrode plate is shown for connection to a feedthrough leadwire, in practice, multiple "n" number of active electrode plates and ground electrode plates can be electrically connected to each feedthrough leadwire.

Figure 65Q:
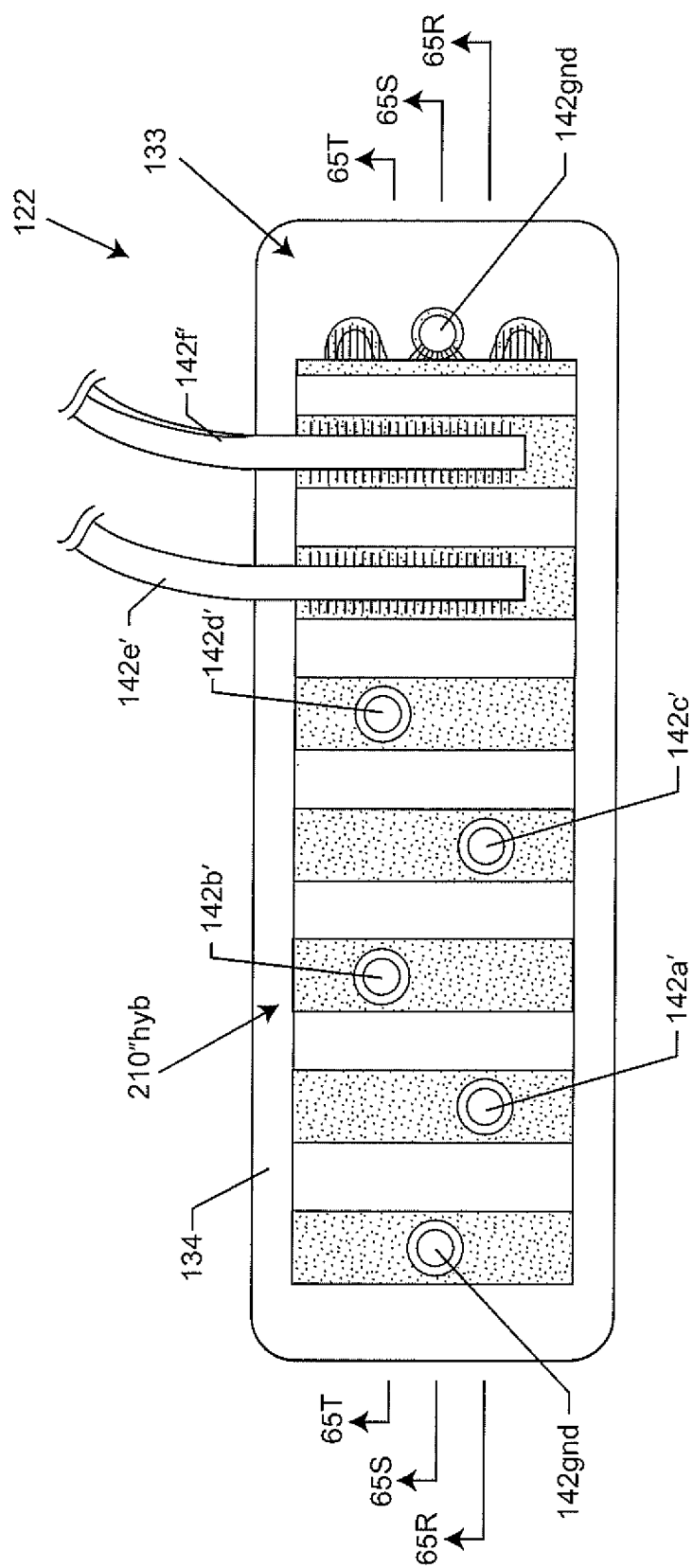

FIG. 65Q is a top view of the dual inline hybrid filter flat-through capacitor 210"hyb of FIGS. 65O and 65P mounted on a hermetic feedthrough 132 (not labelled). The capacitor shown has a ground connection at the left-hand side and the right-hand side of the ferrule 134 of the hermetic feedthrough. The ground connections are better understood in the cross-section of FIG. 65R. As can be seen in FIG. 65Q, there are six active capacitor metallizations 164a' through 164f' (not labelled), hence the hybrid filter flat-through capacitor 210"hyb is a hex-polar three-terminal hybrid filter capacitor. Also shown in this top view are the active terminal pins 142a' through 142f. Terminal pins 142a' through 142d' are nail head terminal pins, the nail head being suitable for attachment to the active capacitor metallizations 164a' through 164d' (not labelled) of the hybrid filter flat-through capacitor 210"hyb using an electrical connection material 151. Terminal pins 142e' and 142f' are lying sideways on their respective active capacitor metallizations 164e' and 164f' (not labelled) and are attached to said metallizations using an electrical connection material 145. It is appreciated that these terminal pins can be round wires, flat ribbon, wire bonding cables, leadwires, lead wires, pins, lead conductors or similar as previously disclosed. Alternatively, the electrical connection to the active capacitor metallizations can even be made to an AIMD active electronic circuit board butted up directly to and mating with said active capacitor metallizations without the need for a lead-wire interconnection. The dual inline hybrid filter flat-through capacitor 210"hyb of FIG. 65Q is wide and completely covers the entire surface of the insulator 156 of the hermetic feedthrough. As such, waveguide calculations are unnecessary because the ground electrode plates of the hybrid filter flat-through capacitor 210"hyb completely shield any open windows mitigating any threat of direct penetration by electromagnetic interference radiation through the insulator 156.

Figure 65R:
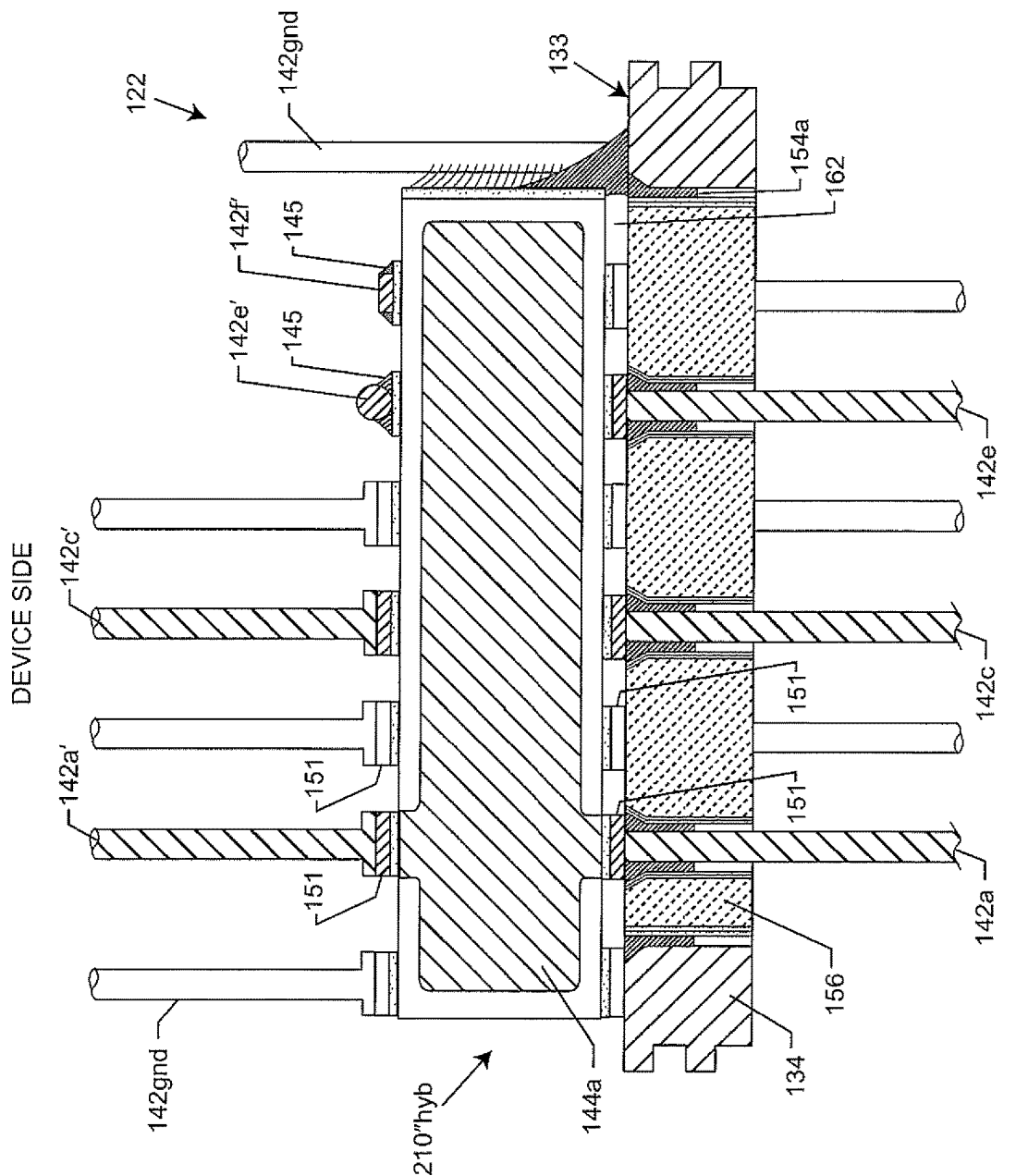

FIG. 65R is a cross-sectional view taken from 65R-65R of FIG. 65Q. Shown is the active electrode plate 144a associated with the terminal pin 142a'. It is appreciated that in practice multiple active electrode plates ("n" number of active electrode plates 144) are interleaved with ground electrode plates 146 sandwich style.

Figure 65S:
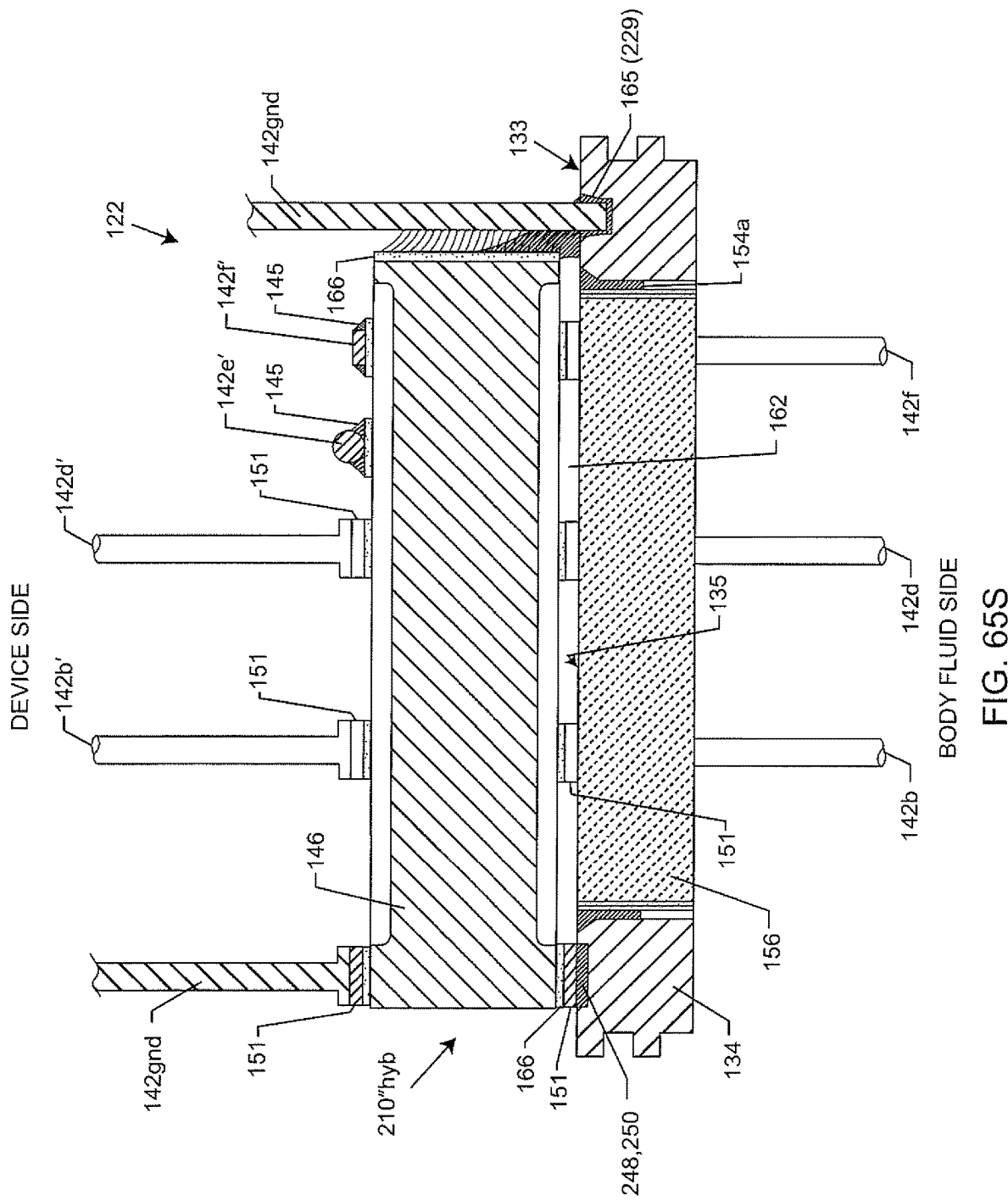

FIG. 65S is taken from 65S-65S of FIG. 65Q. Shown is one of the multiplicity of interleaved ground electrode plates 146. A variety of grounding methods for the ground electrode plate 146 and associated ground capacitor metallizations 166 are shown. On the left-hand side, an oxide-resistant area 248, 250 (such as a gold pocket or a gold pad) is used to provide electrical connection to the ferrule 134 of the hermetic feedthrough. On the right-hand side, a ground terminal pin 142gnd that is either gold brazed 165 or welded 229 to the ferrule 134 is used to provide electrical connection to the ferrule 134 of the hermetic feedthrough. Alternatively, an electrical connection material may be used on the right-hand and the left-hand sides to contact a gold braze 154a to achieve the oxide-resistant electrical connection. Referring once again to FIG. 65S, one can see that active terminal pins 142b' and 142d' comprise nail-head structures, which can be attached by BGA 151 or similar mounting methods to the active capacitor metallizations 164 (not labelled). Active terminal pins 142e' are longitudinally aligned in parallel with the surface of the active capacitor metallizations using electrical connection material 145 as shown. Such parallel alignment is desirable for a higher surface area attachment, which is generally more resistant to shock and vibration loads. Terminal pin 142e' illustrates a round wire and terminal pin 142f' illustrates a flat ribbon, both of which can be attached to the active capacitor metallization by an electrical attachment material 145 as shown or, alternately, by other industry methods such as wire bonding or ultrasonic bonding.

FIG. 65T is taken from 65T-65T of FIG. 65Q. Illustrated is an active electrode plate 144b that is associated with terminal pin 142b'. It is understood that all of the figures illustrating filtered feedthrough 122 typically comprise an insulation washer 162 disposed between the flat-through capacitor 210"hyb and the device sides of the insulator 156 and the ferrule 134 as illustrated in the exemplary embodiments of FIG. 65T. The insulating washer 162 provides a mechanical attachment to at least one of the ferrule 134 and the insulator 156, while, at the same time, said insulating washer insulates the terminal pins one from the other; for example, the insulating washer 162 insulates between two active terminal pins and also insulates between an active terminal pin and a ground connection, such as between an active terminal pin and a ground terminal pin. The insulation washer 162 is important because it prevents high voltage flashover, such as is possible in an implantable defibrillator application, and also inhibits undesirable migration of materials, which can lead to reduced insulation resistance between adjacent circuits (channels) or any of the active circuits and ground. It is noted that, for simplicity, the insulator washer 162 of the figures of the present application is not cross-hatched.

Figure 66:
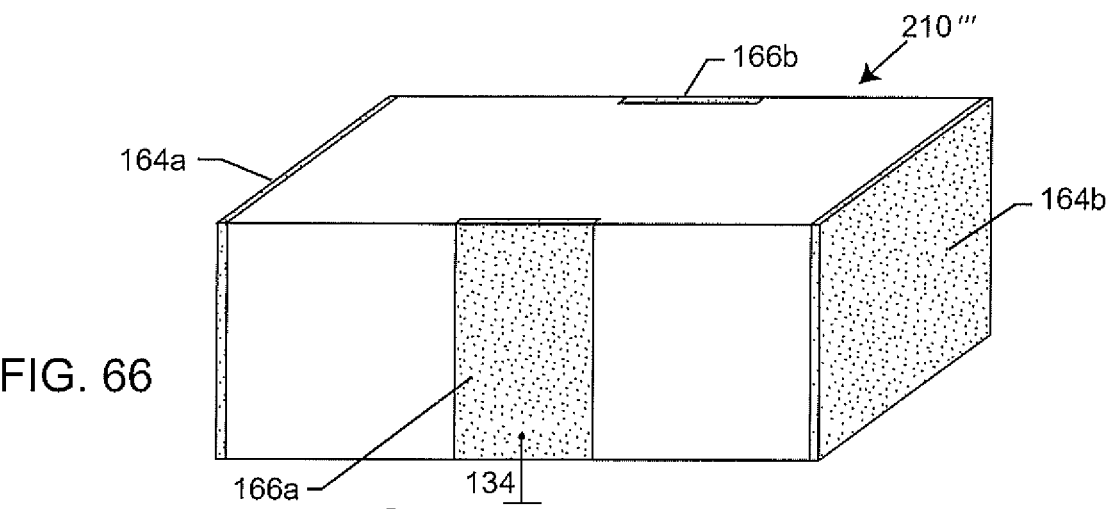
FIG. 66 is an isometric view of a bipolar X2Y attenuator.
Figure 67:
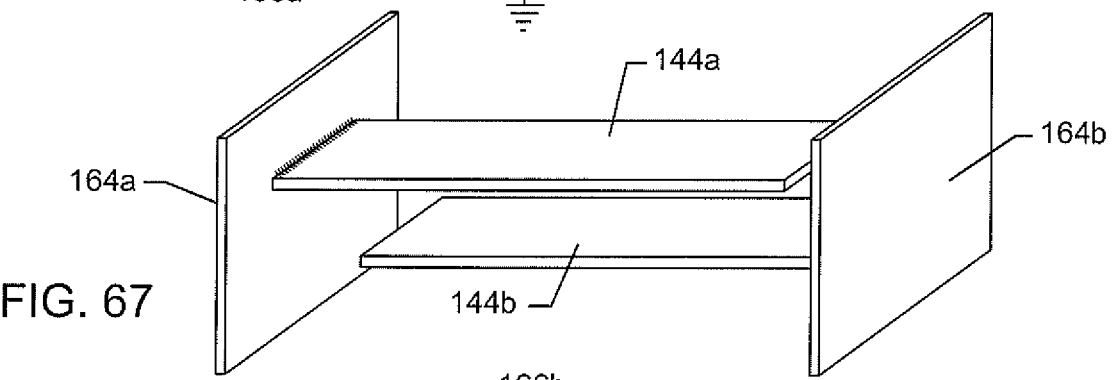
FIG. 67 shows the internal active electrode plates of FIG. 66 now with the dielectric removed.
Figure 68:
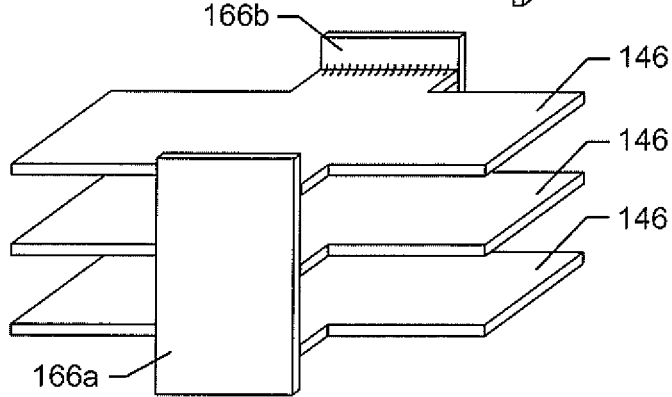
FIG. 68 shows the internal ground electrode plates of FIG. 66 now with the dielectric removed.
Figure 69:
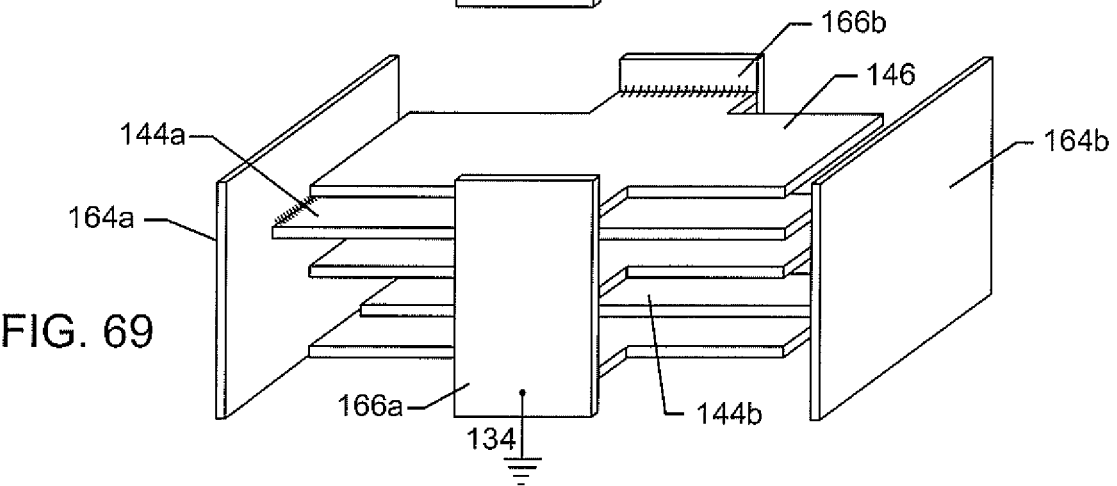
FIG. 69 shows how the active and ground electrode plates of FIG. 66 nest parallel to one another with the dielectric removed.

FIG. 66 illustrates a bipolar X2Y attenuator 210", bipolar meaning that the X2Y attenuator 210''' can filter two leadwires at the same time. This is better understood by examining the internal active electrode plates 144a and 144b of FIG. 67. The active electrode plates 144a are connected to the left-hand side active capacitor metallization 164a. The right-hand side active electrode plates 144b are connected to the right-hand side active capacitor metallization 164b. The active electrode plates are interleaved with the ground electrode plates 146 of FIG. 68. This interleaved configuration is illustrated in FIG. 69, showing that active electrode plates 164a and 164b are both interleaved with a plurality of ground electrode plates 146. It is appreciated that any number of active and ground electrode plates can be interleaved to create a desired line-to-line or a line-to-ground amount of capacitance or filtering. For example, if one wanted a great deal of line-to-line filtering, that is, filtering between active capacitor metallizations 164a and 164b, then one eliminates the interleaved ground electrode plate 146, which thus increases the effective capacitance area (ECA) between these two opposed active electrode plates. However, if one wanted mostly line-to-ground filtering, in other words, filtering from active capacitor metallization 164a to ground capacitor metallization 166 and active capacitor metallization 164b to ground capacitor metallization 166, then one interleaves ground electrode plates 146 as illustrated in FIG. 69.

Figure 69B:
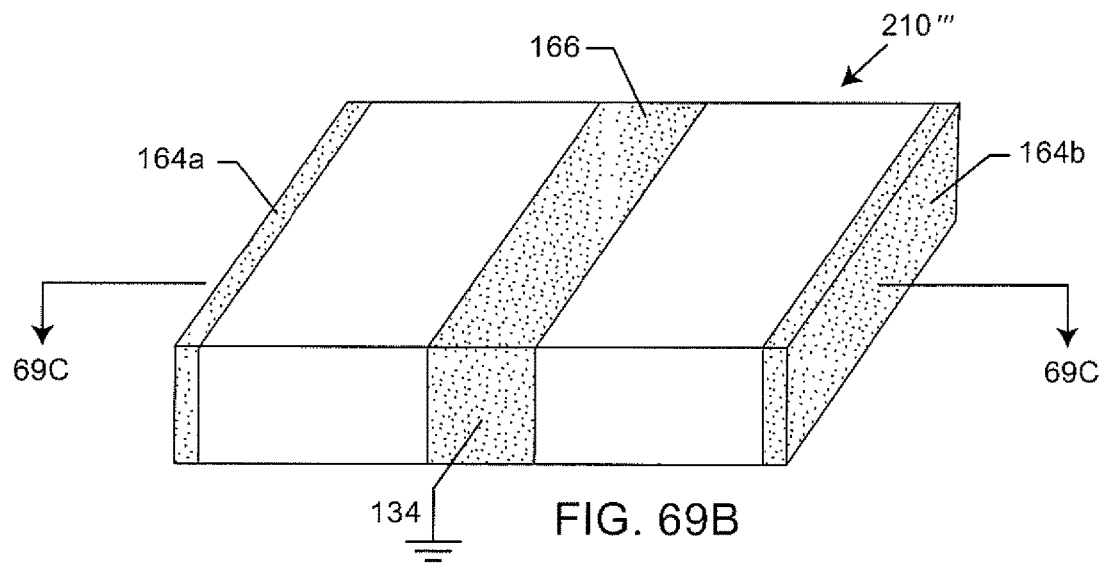
FIG. 69B is another view of a similar bipolar X2Y attenuator now having a grounding metallization stripe over the entire outside surface.

FIG. 69B is similar to FIG. 66 except that instead of the discontinuous discrete ground capacitor metallizations 166a and 166b of FIG. 66, a continuous ground capacitor metallization 166 is illustrated. The continuous ground capacitor metallization 166 of the X2Y attenuator 210''' is a metallization band disposed all the way around said X2Y attenuator. Either of the ground capacitor metallization embodiments of FIGS. 66 and 69B can be used for the X2Y attenuator 210''' as the ground electrode plates 146 shown in both FIGS. 66 and 69 are configured to selectively extend to the edge of each long side of the dielectric body of the X2Y attenuators. The selective extension of the ground electrode plates allows contact to be made to either ground capacitor metallization embodiment. The ground electrode plate edge extensions are illustrated in the discontinuous discrete ground capacitor metallizations 166a and 166b of FIGS. 68 and 69 and in the continuous ground capacitor metallization 166 of FIG. 69C. In summary, the selective extensions of the ground electrode plates 146 at the edge of the long sides of the dielectric body of the X2Y attenuator contacts the ground capacitor rnetallization(s) of said X2Y attenuator regardless of whether said ground capacitor metallization comprises a continuous ground capacitor metallization band as illustrated in FIG. 69 or discontinuous discrete ground capacitor metallization bands as illustrated in FIG. 66.

Figure 69C:
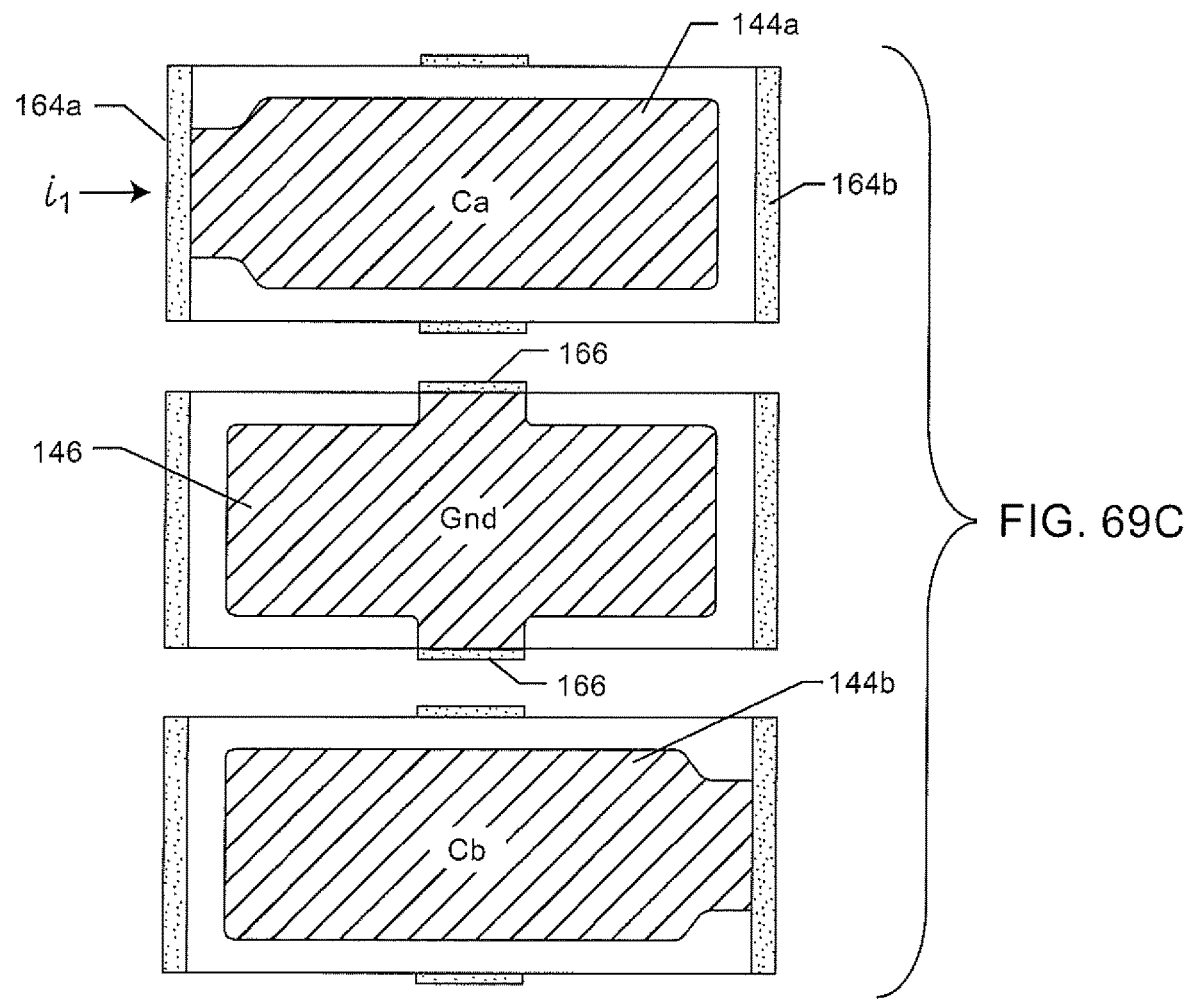
FIG. 69C is a sectional view taken along lines 69C-69C from the structure of FIG. 69B.

FIG. 69C is a sectional view illustrating the active electrode plates 144a, 144b and the ground electrode plate 146 that interleave the X2Y attenuator of FIG. 69B. The X2Y attenuator 210''' looks similar in physical appearance to the flat-through capacitors 210" previously disclosed, however, the X2Y attenuators of FIGS. 66 and 69B are unique bipolar devices that can filter two leadwires of the hermetic feedthrough at the same time. Simultaneous filtering of two feedthrough leadwires is possible because the active electrode plates Ca and Cb of the X2Y attenuators FIGS. 66 and 69B are designed such that the X2Y attenuator essentially comprises two different capacitors, one capacitor comprising the active electrode plates Ca electrically connected to an active capacitor metallization 164a and a second capacitor comprising the active electrode plates Cb electrically connected to an active capacitor metallization 164b. Each active electrode plate 164a, 164b is sandwiched by ground electrode plates 146, and are connected to their respective active capacitor metallizations 164a and 164b, thereby are electrically connectable to two leadwires of a hermetic feedthrough for EMI filtering of said leadwires. As such, one leadwire of the hermetic feedthrough is electrically connectable to the active electrode metallization 164a and a second leadwire of the hermetic feedthrough is electrically connectable to the active electrode metallization 164b.

Figure 69D:
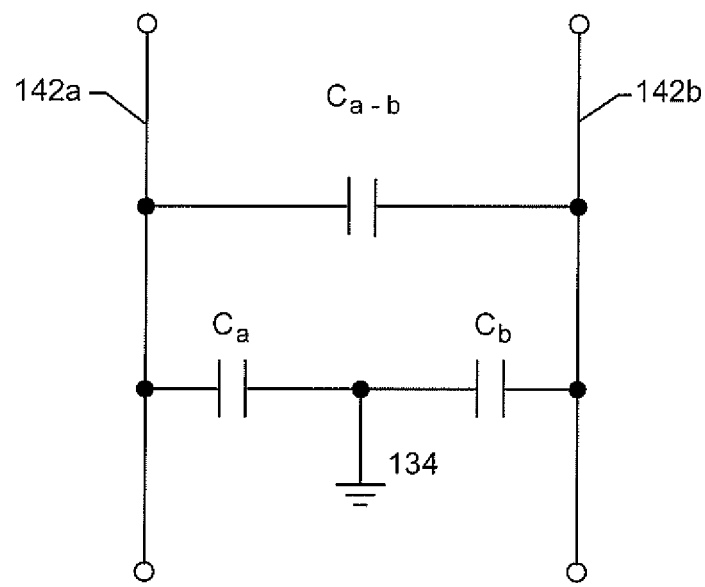
FIG. 69D is the electrical schematic of the X2Y attenuator of FIGS. 66-69C.

FIG. 69D is the schematic diagram of the X2Y attenuator 210''' of FIGS. 66 and 69B. Shown is a line-to-line capacitance Ca-b between lines 142a and 142b. Also shown are line-to-ground capacitances Ca and Cb grounded to the ferrule 134, which are both system grounds. As previously described, by adjusting the size of the active and ground electrode plates or by selectively limiting the number of ground electrode plates, the line-to-line capacitance Ca-b versus the amount of line-to-ground capacitances Ca and Cb can be adjusted.

It is understood that X2Y attenuators come in various sizes and shapes and are not always bipolar devices. X2Y attenuators may have a number of geometries and a number of additional POLES. The X2Y attenuators of the present application are mounted to an EMI filter circuit board for use in an AND for the purpose of illustration; however, can also alternately be used is various other electronic circuitry as well. The X2Y attenuators 210''' of FIGS. 66 and 69B are both bipolar X2Y attenuators.

Figure 70A:
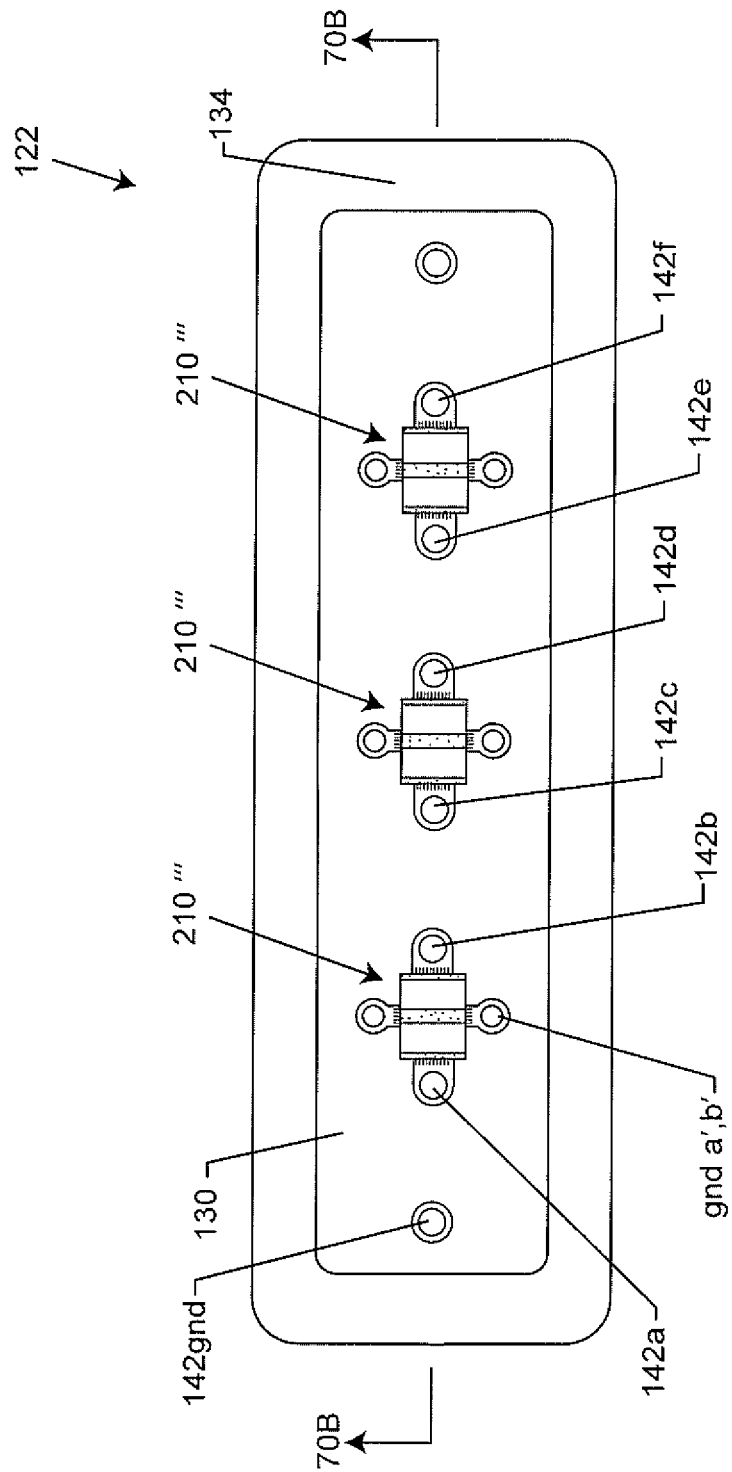
FIG. 70A is a top view of another embodiment of the X2Y attenuator in FIGS. 66-69D now disposed on a circuit board disposed over an insulator and ferrule.

FIG. 70A illustrates a filter circuit board 130 mounted at, near or adjacent the device side of an AIMD hermetic feedthrough 132 (not labelled). The circuit board 130 of FIG. 70A is mounted to the device side of the ferrule 134 as shown. The filter circuit board 130 of the present application can be a printed circuit board, an FR4 board, a multi-layer board, an alumina board, a flexible circuit board, or any other type of circuit board known in the art. As previously disclosed for flat-through capacitors 210", the circuit board 130 of FIG. 70A has one or more ground plates 161, which can be internal ground plates, external ground plates, or a combination of internal and external ground plates. The ground plates are very important in providing low impedance RF decoupling for each of the X2Y attenuators 210". A primary difference between X2Y attenuators 210''' and the flat-through capacitors 210" previously disclosed is that the circuit current of an AIMD does not pass through the active electrode plates of the flat-through capacitor. The only currents passing through the active electrode plates of the flat-through capacitor are the decoupled EMI currents.

Figure 70B:
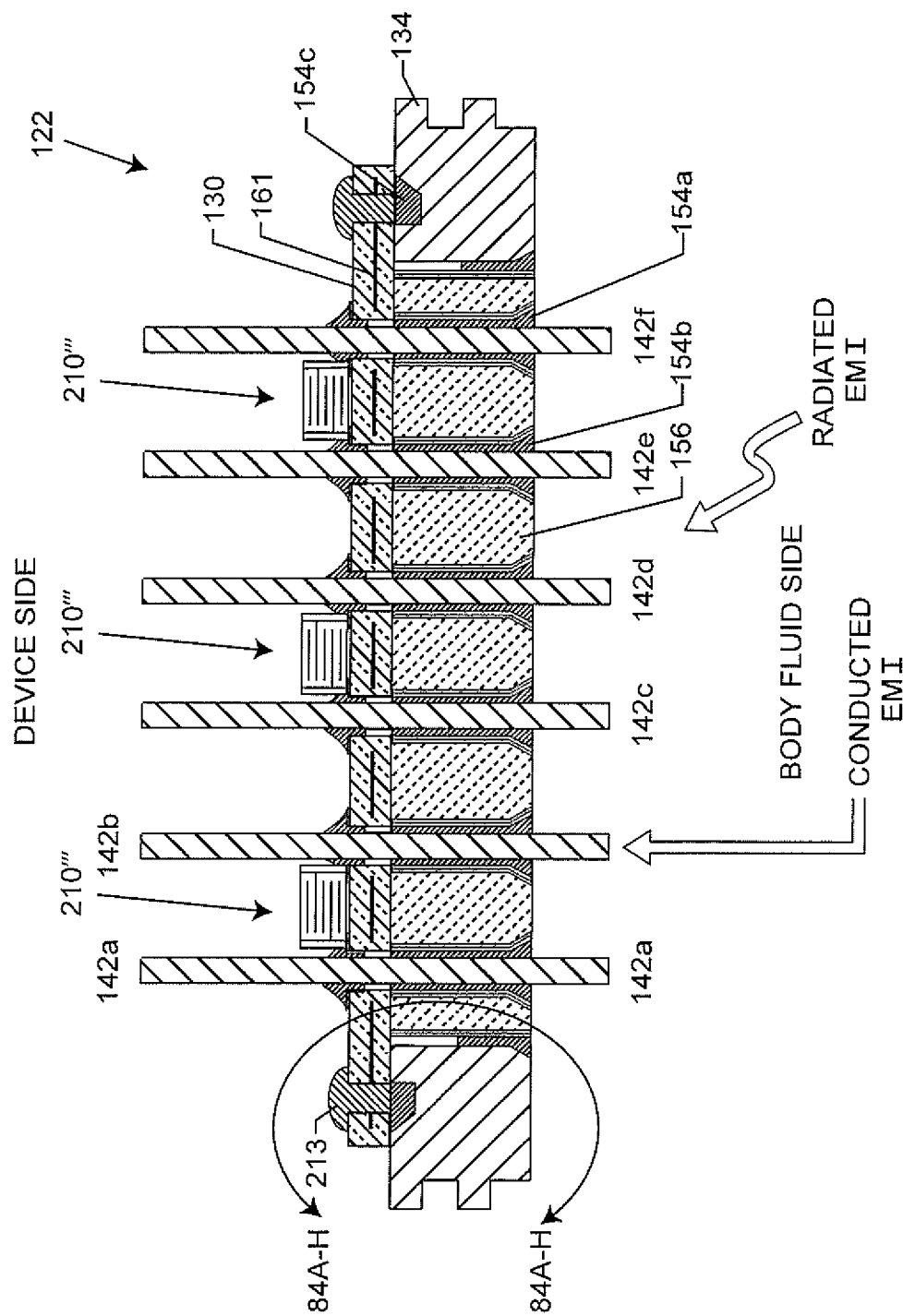
FIG. 70B is a cross-sectional view taken along lines 70B-70B from the structure of FIG. 70A.

FIG. 70B is taken from section 70B-70B of FIG. 70A, illustrating a cross-sectional view of the circuit board 130, including the at least one circuit board ground electrode plate 161, which, in this case, is also a shield electrode plate. Ground plates are very important for shielding or covering up at least the bulk of the insulator of a hermetic feedthrough. Emitters in close proximity to a patient having an implanted AIMD, such as cellular telephones, produce strong radiated EMI, which can pass directly through the insulator of a hermetic feedthrough to undesirably couple to sensitive AIMD electronic circuits. Filter circuit boards comprising ground electrode shield plates prevent that direct radiation of EMI energy. In the exemplary embodiment of FIGS. 70A and 70B, the ground electrode plate 161 illustrated, which is also the shield electrode plate, both reflects and absorbs incident radiated energy. In order for the ground electrode plate 161 to effectively reflect and absorb radiated EMI, the ground electrode plate must be connected to the system ground in a very low impedance manner, meaning that both the inductance and the resistance of the electrical connection must be very low. It is appreciated that a multiplicity of ground electrode shield plates 161 can be used in the circuit board 130, including external ground electrode shield plates. Ideally, external ground electrode shield plates are disposed between the surface of the circuit board facing the hermetic feedthrough and the top of the insulator 156 of the hermetic feedthrough, as such a location most effectively reflects and absorbs radiated EMI impinging from the body fluid side of the AIMD.

Referring once again to FIG. 70B, illustrated is a radiated EMI impinging the hermetic feedthrough from the body fluid side of the AIMD. The body fluid side, as illustrated in FIG. 70B, shows both conducted and radiated EMI. Radiated EMI is impinging directly against the insulator 156 of the filtered feedthrough 122 attached to the AIMD housing 124 (not shown). Importantly, the at least one circuit board ground plate 161, which is also a shield electrode plates, reflects and absorbs this radiated EMI. There is also conducted EMI advancing from the body fluid side as illustrated. The conducted EMI is picked up by the implanted leadwires (not shown) and conducted by antenna action along the leadwire of the hermetic feedthrough, which is thereby routed to the device side inside of the AIMD housing. Importantly, the X2Y attenuators 210''' divert the EMI energy from each pair of leadwires to which the X2Y attenuator is connected, for example, to terminal pins 142*a* and 142*b* connected to their X2y attenuator respective active capacitor metallizations 164*a* and 164*b*, to the common ground of the AIMD, which is the ferrule 134 and the AIMD housing 124 (not shown). In this way, the two different filter capacitors of the X2Y attenuators desirably act as high frequency diverters.

Referring once again to FIG. 70B, illustrated are circuit board rivets 213. Rivets 213 are well known in the art for connecting a ground via hole of the circuit board to the at least one ground plate 161, which in this case is also a shield electrode plate. The rivet 213 can directly contact an oxide-resistant area 248, 250 (not shown) or a gold braze 154*c* as shown. Alternatively, an electrically conductive material 155 (not shown) may provide electrical connection between said rivet 213 and the oxide-resistant area 248, 250, such as a gold pocket or gold pad, or the gold braze 154*c*. Oxide-resistant areas including gold pockets, gold pads or equivalent oxide-resistant materials are more thoroughly described in U.S. Pat. No. 10,350,421, the content of which is fully incorporated herein by this reference. Alternative methods of grounding all types of filter circuit boards will be disclosed later. In all filter circuit board cases, however, it is very important that an oxide-resistant ground connection be made to the ferrule 134 of the hermetic feedthrough of the AIMD.

Ground electrode plates, shield electrode plates, oxide-resistant grounding methods and filter circuit boards are more thoroughly described in U.S. Pat. No. 8,195,295, the content of which is fully incorporated herein by this reference.

Referring back to the flat-through capacitors 210'' and the X2Y attenuators 210'' taught herein, it is noted that these capacitors are of a low k dielectric (k<1,000), the dielectric constant being greater than 0 and less than 1,000. These low k capacitors are the first filter capacitors on the device side inside the AIMD housing, which divert undesirable and/or unwanted EMI to the ferrule and/or the AIMD housing.

Figure 70C:
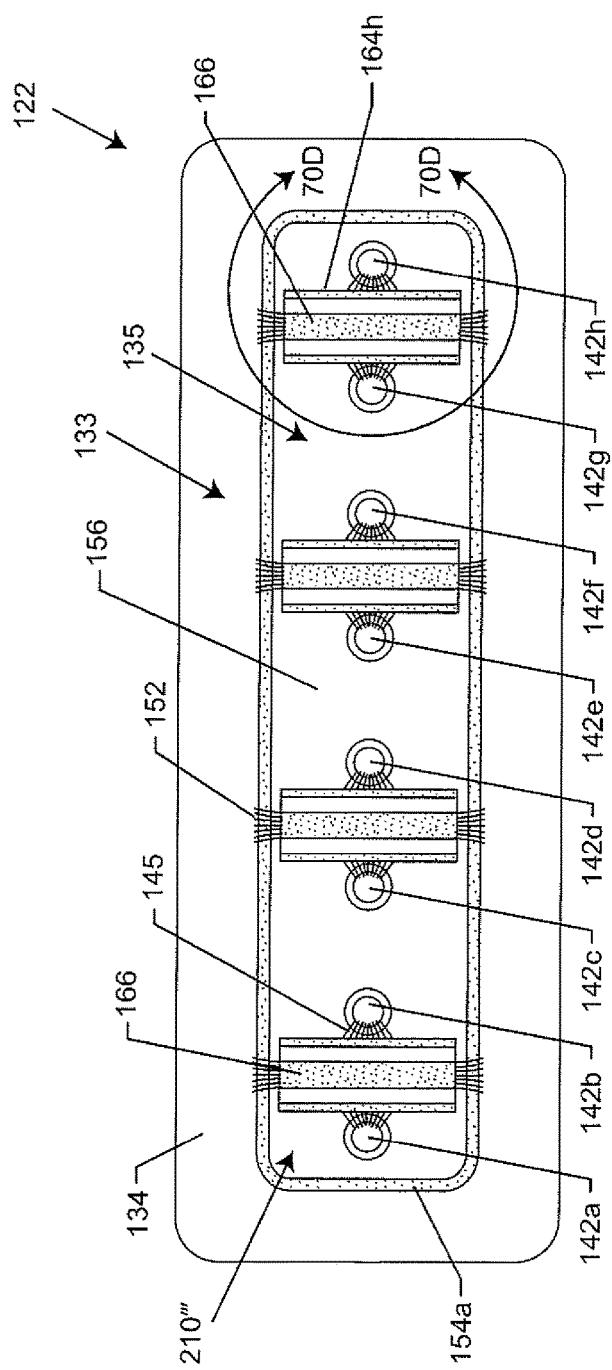
FIG. 70C is a top view of another embodiment of an X2Y attenuator disposed in a tombstone mounting position over an insulator and a ferrule.

FIG. 70C illustrates X2Y attenuators 210''' in a tombstone mounting position, consistent with the embodiments taught herein for the flat-through filter capacitor 210''. For example, the X2Y attenuator 210''' of FIG. 70A can have the active and ground electrode plates disposed perpendicular to the ferrule and insulator device side surfaces of the hermetic feedthrough. The embodiment of FIG. 70C illustrates eight terminal pins 142*a* through 142*h* electrically connected respectively to the active capacitor metallizations 164 of the X2Y attenuators 210''' using an electrical connection material 145. Additionally, the circuit board 130 of FIG. 70C is configured to expose the gold braze 154*a* between the insulator 156 and the ferrule 134 of the hermetic feedthrough. The ground capacitor metallizations 166 of the X2Y attenuators 210'' are directly connected to the gold braze 154*a* of the hermetic feedthrough using an electrically conductive material 152.

Figure 70D:
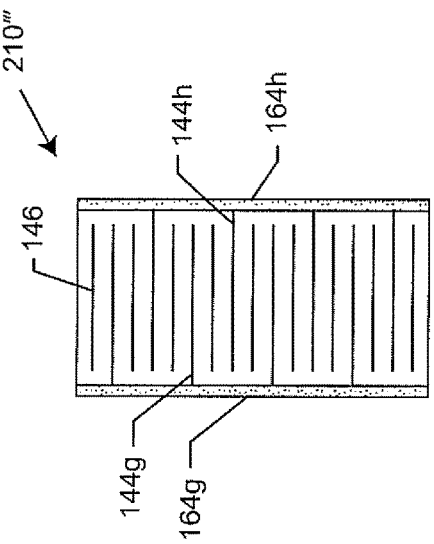
FIG. 70D is an enlarged view taken along lines 70D-70D from FIG. 70C showing just one of the X2Y attenuators where the active and ground electrode plates are now visible.

FIG. 70D is an enlarged cross-sectional view taken from section 70D-70D of FIG. 70C. Illustrated are the active electrode plates 144*g* connected to the left-hand side active capacitor metallization 164, the active electrode plates 144*h* connected to the right-hand side active capacitor metallization 164*h*, and the ground electrode plates 146 interleaved with the active electrode plates, which are representative of the electrode plate arrangement of the X2Y attenuators 210''' of FIG. 70C. Additionally, FIG. 70D helps visualizing how the active and ground electrode plates of the X2Y attenuator 210''' are disposed in relation to the ferrule 134 and the insulator 156 of a hermetic feedthrough when the X2Y attenuators are attached in a tombstone mounting position.

It is understood that the X2Y attenuator 210''' can be grounded to the ferrule 134 utilizing any of the methods previously taught herein, including but not limited to, oxide-resistant areas 248, 250, such as gold pockets, gold pads, or other oxide-resistant pockets and pads, peninsulas 139, bridges 141, grounding terminal pins 142gnd, ECA stripes 223, 225 and metal additions 159, 229. Furthermore, the width of the X2Y attenuator 210''' may be increased to accommodate a staggered leadwire hermetic feedthrough design. Wider X2Y attenuators 210''' for staggered leadwire hermetic feedthrough designs may be disposed at an angle to take advantage of the increased distance that exists between the staggered leadwires. It is understood that the X2Y attenuators 210''' can be disposed in the tombstone position on top of circuit board 130, and the circuit board 130 attached to the hermetic feedthrough as illustrated in FIGS. 70A and 70B.

Figure 71A:
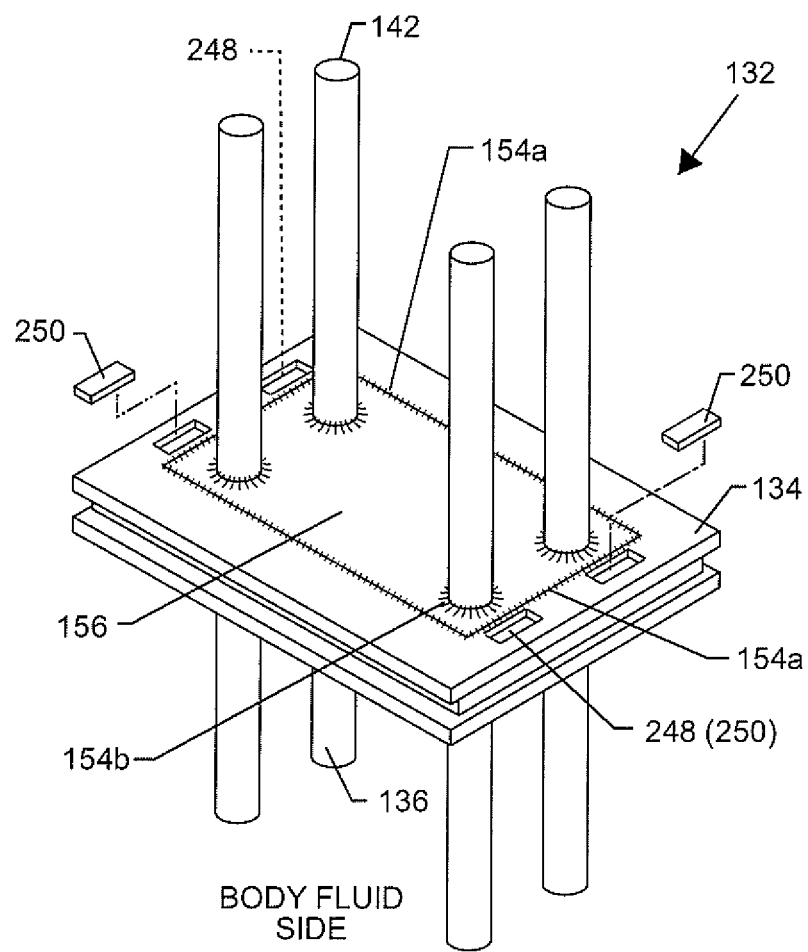
FIG. 71A illustrates an isometric view of a gold pocket-pad electrically connected to the ferrule for use with the present invention.

FIG. 71A is taken from FIG. 25 of U.S. provisional 62/646,552 (the '552 provisional), the content of which is fully incorporated herein by this reference. FIG. 71A illustrates a hermetic feedthrough wherein the ferrule 134 of said hermetic feedthrough comprises oxide-resistant areas 248, 250, which are shown as gold pocket-pads.

Figure 71B:
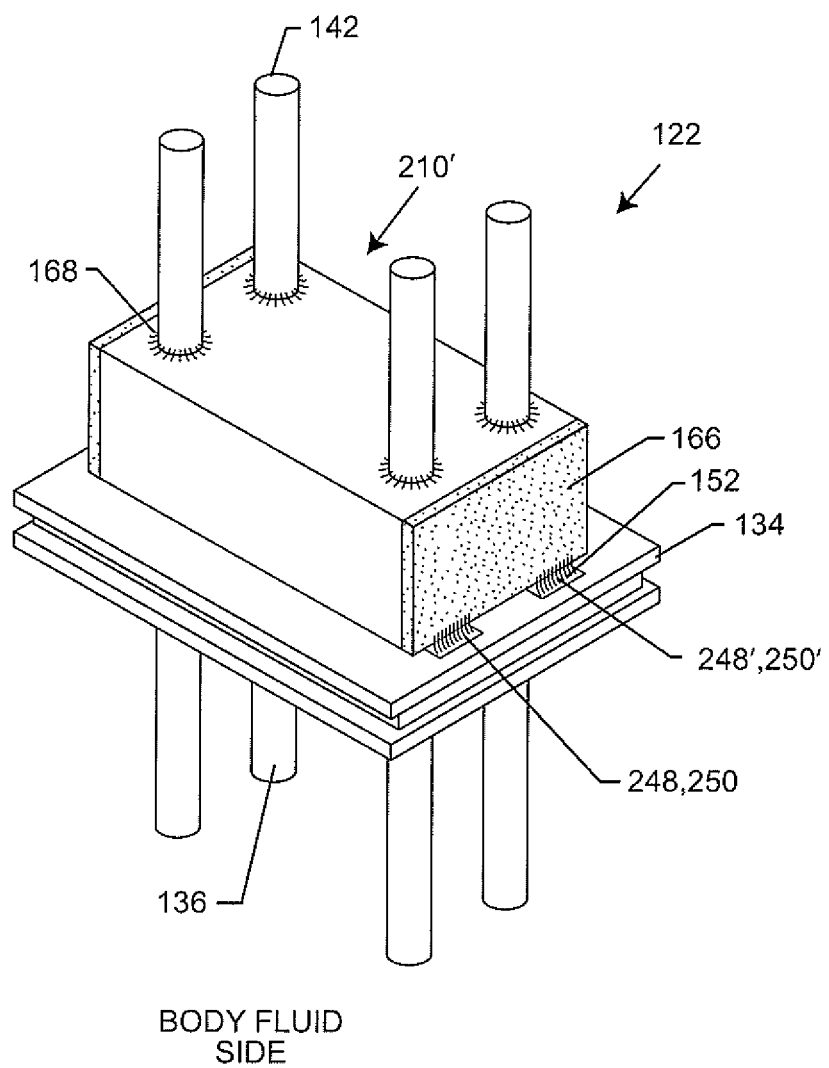
FIG. 71B illustrates the structure of FIG. 71A now with a capacitor of the present invention installed.

FIG. 71B is taken from FIG. 27 of the '552 provisional showing a quad polar rectangular feedthrough filter capacitor 210' wherein the ground electrode metallization 166 is electrically connected to the oxide-resistant areas 248, 250 (gold pocket-pads) using an electrically conductive material 152.

Figure 71C:
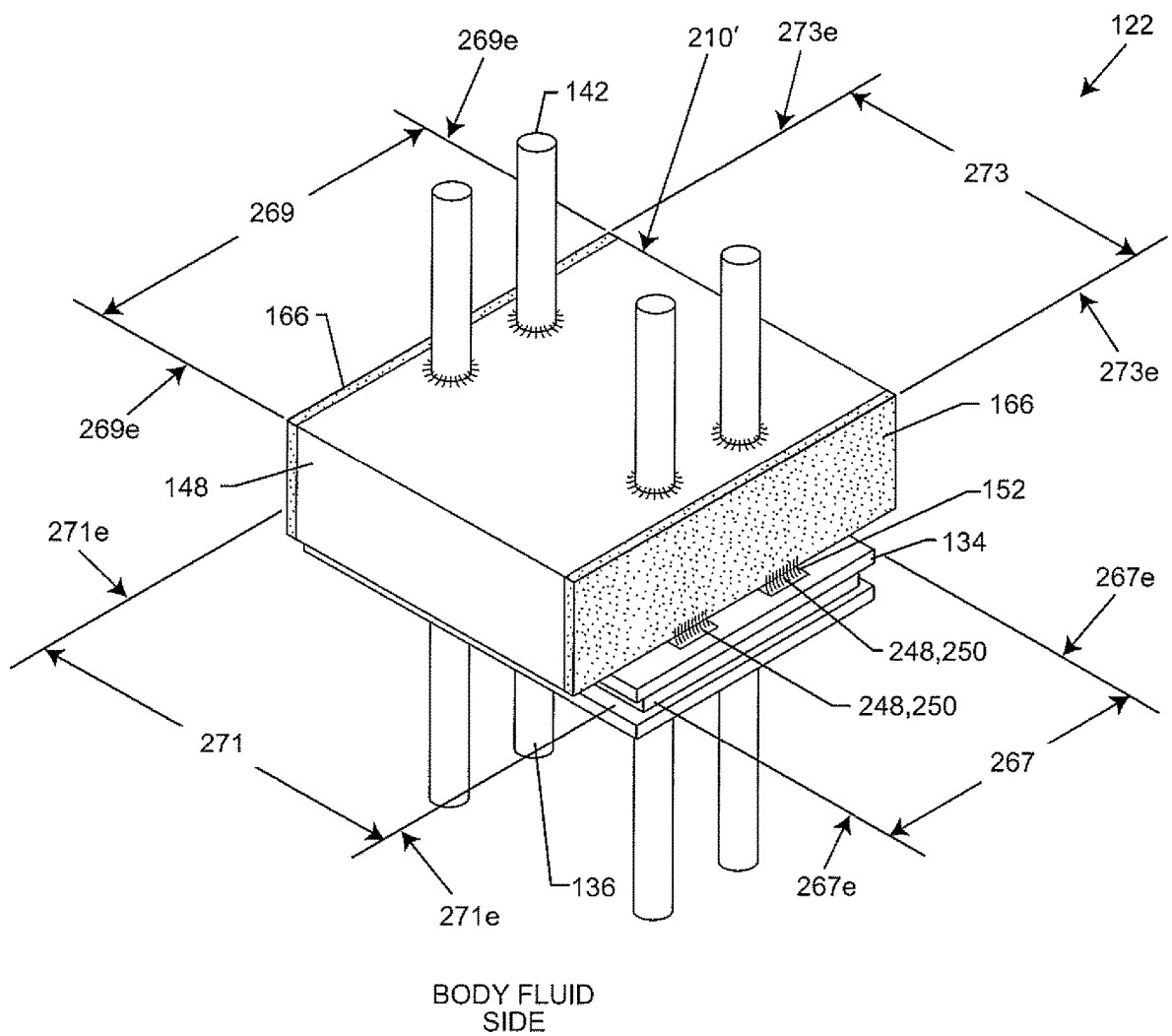
FIG. 71C is a view similar to FIG. 71B now illustrating how the capacitor can be oversized such at least one of its ends can extend past the edge of the ferrule.

FIG. 71C is taken from FIG. 31 of the '552 provisional illustrating a feedthrough filter capacitor 210' attached to a hermetic feedthrough 132, wherein a filter capacitor width 269 of the feedthrough filter capacitor 210' is greater than a ferrule width 267 of a ferrule 134 of the hermetic feedthrough 132. This embodiment is particularly enabling to the present invention as a k<1,000 or mid k filter capacitor (the dielectric material comprising a dielectric constant greater than 0 but less than 1,000) is less volumetrically efficient than the prior art 1,200 k to 2,600 k dielectric filter capacitors, hence is typically bigger than said prior art capacitors. In most AIMDs, such as cardiac pacemakers, ICDs, neurostimulators and the like, there is very little height available for the feedthrough filter capacitor 210'; however, it is generally possible to increase the filter capacitor width 269 of the feedthrough filter capacitor 210' if higher capacitance values are needed. Accordingly, a k<1,000 filter capacitor, such as the feedthrough filter capacitor 210' of FIG. 71C, which comprises a dielectric constant greater than 0 but less than 1,000 and a filter capacitor width 269 greater than the ferrule width 267 of the ferrule 134 of a hermetic feedthrough 132, is an enabling distinctive feature of the present invention. Furthermore, oxide-resistant areas 248, 250, in accordance with the '552 provisional, provide a unique embodiment for attaching k<1,000 filter capacitors.

Referring once again to FIG. 71C, it is appreciated that, if higher capacitance is needed, feedthrough filter capacitors 210' may alternatively comprise a filter capacitor length 273 greater than a length of a ferrule opening 131 (not shown) of a hermetic feedthrough 132. Given the importance of oxide-resistant attachment as previously explained, that is, so that low inductance and low resistance connections of the ground capacitor metallization 166 of the feedthrough filter capacitor 210' to the ferrule 134 of the hermetic feedthrough 132 can be made, and considering that a k<1,000 filter capacitor is typically larger in size than prior art filter capacitors in order to match prior art capacitance requirements, oxide-resistant area attachment alternatives provide additional filtered feedthrough design options for meeting application filter requirements. For example, instead of a feedthrough filter capacitor 210' comprising a short length 273 such that the ground electrode metallization 166 can be attached to the gold braze 154a that hermetically seals the insulator 156 and the ferrule 134 of the hermetic feedthrough 132, a feedthrough filter capacitor 210' can comprise a length 273 greater than a length of a ferrule opening such that the ground electrode metallization 166 can be attached to oxide-resistant areas 248, 250 disposed on or within the ferrule 134 of the hermetic feedthrough 132. Attachment of the ground electrode metallization 166 is made using an electrically conductive material 152. Referring once again to FIG. 71C, it is understood that the feedthrough filter capacitor 210' may comprise one of a width 269 greater than the width of the ferrule 134 of the hermetic feedthrough 132 (wherein the feedthrough filter capacitor overhangs at least one edge or a flange of the ferrule), a length 273 greater than the length of a ferrule opening 131 (not shown) of the hermetic feedthrough 132, or both a width greater than the width of the ferrule and a length longer than the length of the ferrule opening of the hermetic feedthrough, wherein the ground electrode capacitor metallization 166 of the feedthrough filter capacitor 210' is attached to at least a portion of an oxide-resistant area 248, 250 using an electrically conductive material 152. In summary, increasing the width 269 and/or the length 273 of the filter capacitor significantly increases its volumetric efficiency.

Referring once again to FIG. 71C, one can see that the filter capacitor width 269 is defined by 269e-269e. Likewise, the filter capacitor length 273 is defined by 273e-273e. Similarly, the ferrule width 267 is defined by 267e-267e and the ferrule length 271 is defined by 271e-271e.

Figure 72A:
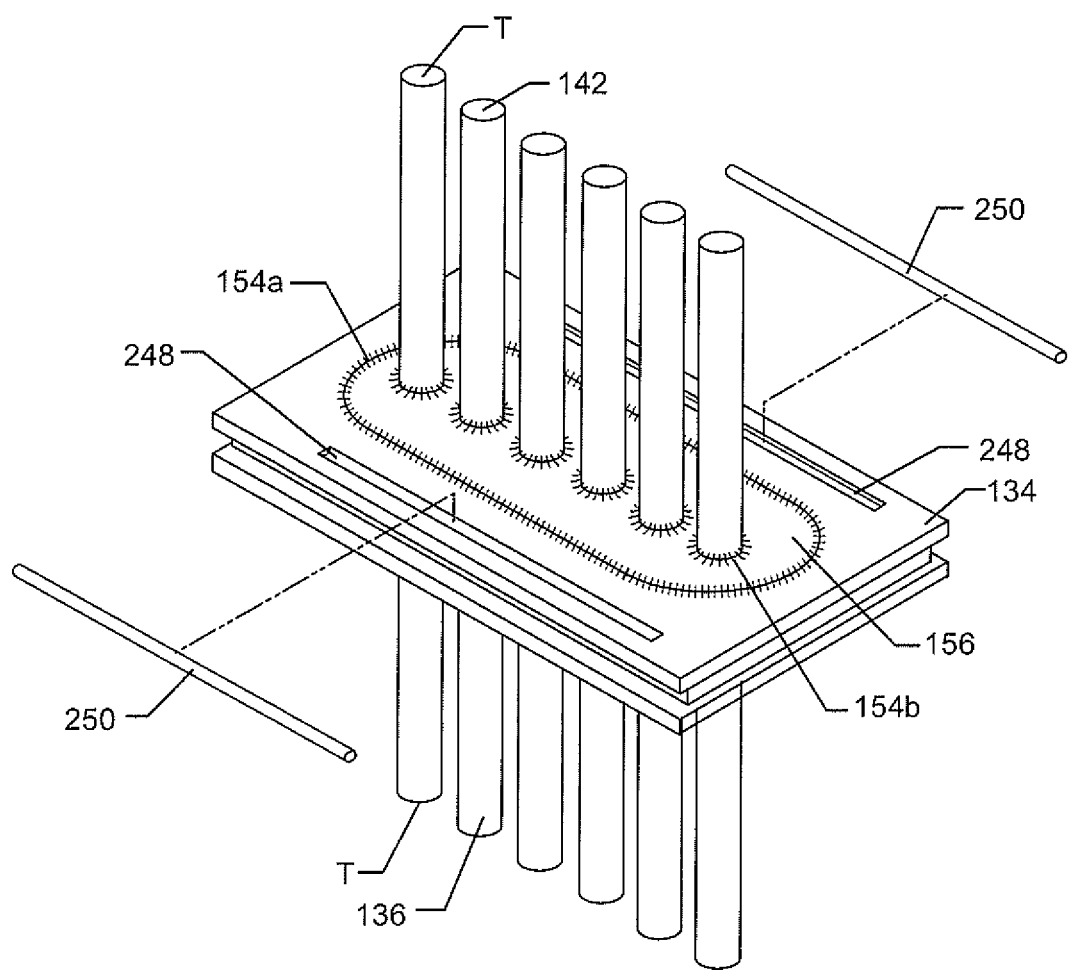
FIG. 72A is a view similar to FIG. 71A now illustrating a novel gold pocket-pad extending the long side of the ferrule thereby facilitating attachment of a larger capacitor.

FIG. 72A is similar to FIG. 71A except that the gold pocket-pads 248 are now illustrated along the length of the ferrule 134. In this embodiment, the gold pocket-pads 248 are elongated and shaped to receive a length of an oxide-resistant wire 250 as shown. The oxide-resistant wire 250 may be selected from the group consisting of platinum, gold, tungsten, iridium, palladium, niobium, tantalum, ruthenium, rhodium, silver, osmium, and alloys or combinations thereof. The oxide-resistant material of the ground terminal pins 182gnd may further be selected from the group consisting of platinum-based materials including platinum-rhodium, platinum-iridium, platinum-palladium, or platinum-gold and naturally occurring alloys such as platiniridium (platinum-iridium), iridiosmium and osmiridium (iridium-osmium). The embodiment of FIG. 72A, may be designed for attachment of the oxide-resistant wire during a brazing operation such that the oxide-resistant wire is attached at the same time the feedthrough is hermetically sealed. For example, during a single brazing operation, a first gold braze 154a forms a hermetic seal between the insulator 156 and the ferrule 134, such as a titanium ferrule; a second gold braze 154b forms a hermetic seal between each of the terminal pins/leadwires T and 142 and the insulator 156; and a gold braze wire 250 disposed in the pocket-pads 248 melts and reflows within the pocket-pads 248. Instead of a gold braze wire 250, a third gold braze (not shown) disposed within the pocket-pad 248 may alternatively be used to attach an oxide-resistant wire 250 to the ferrule 134. The use of pocket-pads 248 allows wider and/or longer feedthrough filter capacitors to be attached to a hermetic feedthrough, wherein a ground path can be attached to an oxide-resistant material, and wherein the oxide-resistant material consists of a gold braze material 250 in the form of a gold braze wire or as a gold braze preform to attach an oxide-resistant wire.

It contemplated that a ribbon, a woven wire, a braided mesh, a braided wire, a cable, pressed nano-particles, laminated nano-particles, pressed particles, coils and the like can be used instead of the wire 250. In addition to gold or pure gold (99.99%), a gold alloy braze material may alternately be used. A preferred gold alloy braze is one which contains more than 50% gold by weight. Non-limiting examples include: 82Au-18In, 88Au-12Ge, the various Johnson Matthey Pallabraze and Orobraze alloys, and the gold alloys of U.S. Pat. No. 4,938,922, the content of which is fully incorporated herein by this reference. Other acceptable metals that form a metallurgical bond to the underlying titanium ferrule, include platinum, palladium or any alloys thereof, including alloys of gold. What is important is that the resulting pocket-pad is oxide-resistant, forms a metallurgical bond with the underlying base metal of the ferrule (which is typically of titanium), and readily accepts an electrical connection. An electrical connection material, such as a solder, a thermal-setting conductive adhesive or a braze may be used to form the electrical connection.

Referring once again to FIG. 72A, one can see that there are five active terminal pins 142,136 and one telemetry pin marked T. It is appreciated that the telemetry pin T can optionally be hermetically sealed to a separate insulator instead of in a single insulator 156 as shown. Additionally, any of the terminal pins 142,136 can be hermetically sealed into two or more separate insulators 156. Each of the terminal pins 142,136 and the telemetry pin T can be hermetically sealed in individual insulators. It is appreciated that the embodiment of FIG. 72A is not meant to be limiting as any number of active and/or telemetry pins can be hermetically sealed to an insulator of a hermetic feedthrough. Additionally, it is not necessary that the terminal pins be in-line as shown in FIG. 27 but can be hermetically in the insulator in any position required by an application. For example, the terminal pins of a feedthrough can alternatively be hermetically sealed in one of a staggered terminal pin configuration, a dual in-line terminal pin configuration, diagonally spaced in pairs, or a custom terminal pin configuration.

Referring once again to FIG. 72A, the elongated pocket-pads 248 are generally very shallow and may be separately machined after the ferrule is made, or may alternatively be formed during the machining, stamping or metal injection molding of the ferrule 134. One convenient way to manufacture the elongated pocket-pads 248 is with a ball-shaped cutting tool of an end mill that only partially penetrates the surface of the ferrule. The pocket-pads 248 are generally very narrow, for example, 1 mil to 4 mils, allowing a small diameter oxide-resistant wire 250, for example, less than 1 mil to 2 mils, to be used. As previously disclosed, oxides of titanium are generally only angstroms thick. Therefore, even a 1 mil coating of an oxide-resistant material is sufficient to prevent titanium oxidation thereby providing an oxide-resistant attachment surface.

Referring now back to FIG. 71A, it is understood that the gold pocket-pads 248 of FIG. 71A can be elongated similar to the elongated pocket-pads of FIG. 72A such that a thin gold wire can be used, thereby providing a single elongated oxide-resistant attachment surface along the width at both ends of the ferrule 134. Referring again to FIG. 71A, it is also understood that the gold pocket-pads 248 can be made at the corners of the ferrule 134 to facilitate suitable electrical connection should it be needed. Regardless of the oxide-resistant pocket-pad location or configuration, the pocket-pad 248 design should be made so that an oxide-resistant electrical connection can be made to the ground capacitor metallization 166 of the filter capacitor, whether that ground capacitor metallization 166 resides on the short side, the long side, or both the short and the long sides of said filter capacitor.

Figure 72B:
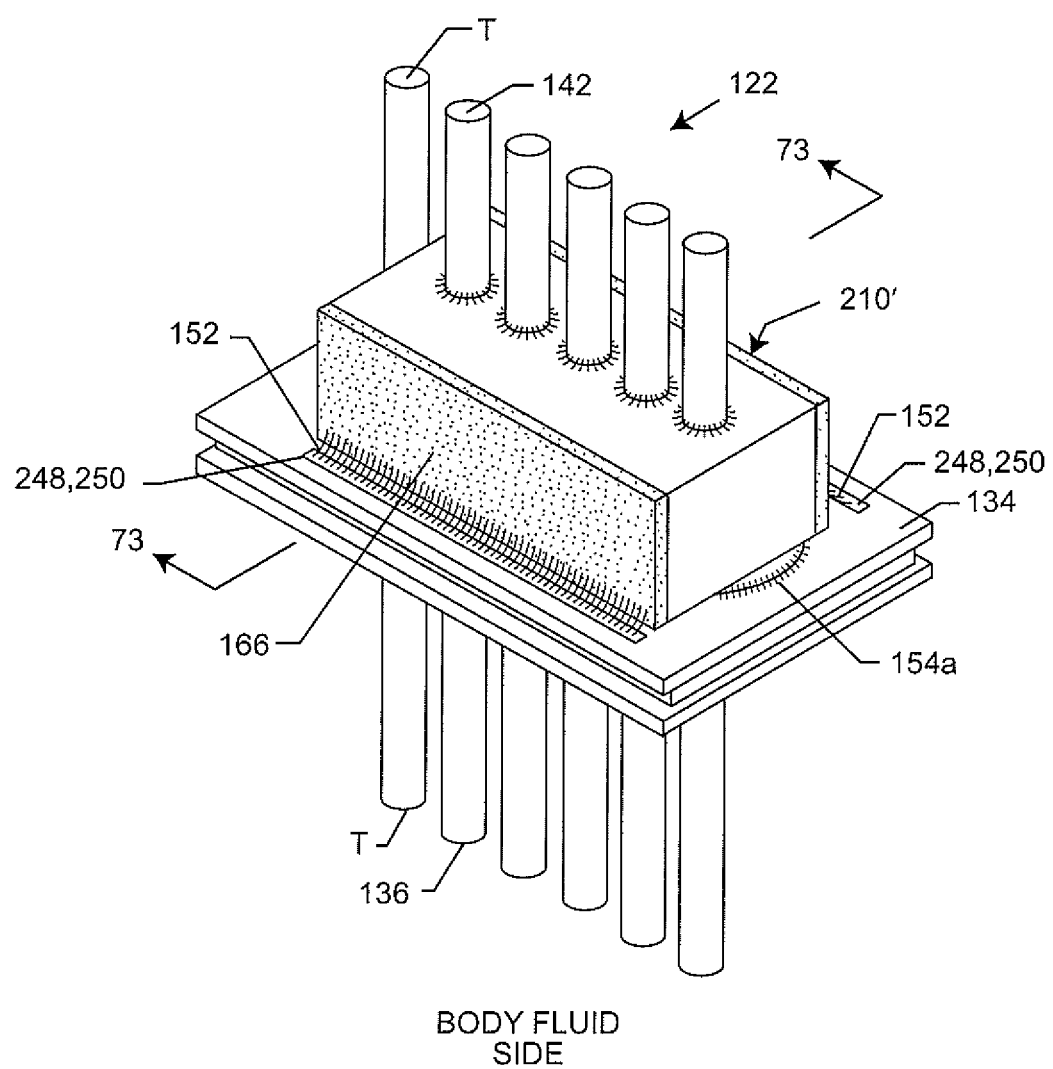
FIG. 72B is a view similar to FIG. 72A now illustrating the capacitor attached.

FIG. 72B illustrates a filter capacitor 210' mounted atop the hermetic feedthrough of FIG. 72A forming a filtered feedthrough 122. Importantly, the telemetry pin T of the hermetic feedthrough is not included in the filter capacitor 210' because the telemetry signal is a high frequency signal that is filtered by the filter capacitor 210'. In general, high frequency filtering by a feedthrough filter capacitor 210' cannot be applied to telemetry pins, as the telemetry signal, being a high frequency signal, is attenuated rendering the telemetry pin ineffective. All of the active terminal pins 142, however, passing through and electrically connected to the filter capacitor 210' are appropriately filtered. Importantly, the ground capacitor metallization (termination) 166, which contacts the filter capacitor's ground electrode plates 146, are electrically attached using an electrically conductive material 152 such as a solder or a thermal-setting conductive adhesive. It is noted that the electrically conductive material 152 of FIG. 72B is shown electrically connecting across the full length of the oxide-resistant pocket-pad 248, 250, however, the electrically conductive material 152 may alternatively at least partially contact the gold braze or wire 250 associated with pocket-pad 248.

Referring once again to FIG. 72B, it is not necessary that the oxide-resistant pocket-pad 248, 250 extend the whole length of a feedthrough filter capacitor. It can extend, for example, for three quarters of the length and be centered and will work just fine from an electrical high-frequency impedance point of view. The oxide-resistant pocket-pad 248, 250 can also be discontinuous, for example, two or three short oxide-resistant pocket-pad segments distributed along the length on each side of the ferrule 134 are sufficient in the event that the cost of the oxide-resistant material, such as a gold, is a concern. Since the oxide-resistant pocket-pad 248 of the present application is like a swimming pool-type structure, small amounts of gold such as very thin ribbons or foils, or even small diameter wires, can be used. This swimming-pool structure approach is totally unlike anything in the prior art, as gold, for example, a gold braze, is always free to flow and used in large quantities to be effective. Accordingly, the filter capacitor of FIG. 72B provides excellent attenuation at all frequencies up to 3 GHz, or even 10 GHz and beyond, thereby, attenuating undesirable interferences from, for example, cellular telephones, microwave ovens and the like.

The attachment to an oxide-resistant metallurgically bonded surface 248, 250, such as a gold braze or a gold pocket-pad, is very important to properly ground the feedthrough filter capacitor 210'. In the prior art, the inventors know of one attempt to eliminate an attachment to gold and instead clean the titanium surface of the titanium ferrule 134 so that a stripe of a thermal-setting electrically conductive adhesive can be painted on the surface of the titanium (the painted thermal-setting electrically conductive adhesive stripe is typically known as an ECA stripe). The problem with an ECA stripe painted directly on the surface of a cleaned titanium is that a titanium metal easily re-oxidizes. In fact, a surface titanium oxide film forms almost instantly when a fresh titanium metal surface is exposed to air and/or moisture. Even a damaged titanium oxide film can generally re-heal itself instantaneously if even at least traces (that is, a few parts per million) of oxygen or water are present in an environment. Researchers have proven that within a millisecond of exposure to air, a 10 nm oxide layer will be formed on a cut surface of exposed essentially pure titanium metal, which will grow to about 100 nm thick within a minute. Hence, a first problem of an ECA stripe directly applied to a cleaned titanium surface results from the ECA stripe typically being cured at a high-temperature, between 200° C. and 300° C., in air. Thus, during curing in air, a titanium oxide re-forms on the surface of a cleaned titanium between the ECA stripe and the bulk titanium of the ferrule. A second problem of an ECA stripe is due to an oxygen release from the ECA during curing in addition to the air environment thereof. It is known that elevated temperature exposure of an ECA, such as an epoxy or a polymer, allows release or outgassing of oxygen and/or oxygen-containing constituents or residues that may be present within the ECA material. Hence, this added exposure to released oxygen or oxygen-containing constituents from the ECA stripe further causes a thickening of the oxide layer resultant from curing the ECA stripe in air. A third problem regarding ECA stripes is that the filtered feedthrough 122 of FIG. 72B is designed to be laser welded into an opening of an active implantable medical device housing, for example, an opening in the housing of a cardiac pacemaker. Laser welding imparts a very high temperature rise to occur in the area of the ECA stripe connecting the feedthrough filter capacitor 210' to the titanium ferrule of a hermetic feedthrough 132 (not labelled). Heating of an epoxy or a polymer during laser welding is sufficient to raise the temperature at, near or adjacent the laser weld such that a further release of oxygen or oxygen-containing constituents or residues, including any moisture ($H_2O$) associated with said epoxy or polymer, further contributes to oxidizing the titanium metal between the ECA stripe and the surface of the ferrule 134. As such, titanium oxides can be removed mechanically or chemically from a titanium ferrule by either abrasive grit blasting, such as by alumina blasting, mechanical grinding, sanding processes, hydrofluoric acid cleaning, or combinations thereof; however, the titanium oxides typically re-form due to titanium being a highly reactive material that has an extremely high affinity for oxygen. While a titanium oxide layer on the highly reactive titanium metal surface imparts good corrosion behavior and high biocompatibility, the titanium oxide layer can and does negatively impact AIMD EMI filter performance, the negative impact being particularly observable at higher frequency applications. When titanium oxides develop between an ECA stripe and the cleaned titanium surface of the ferrule of a hermetic feedthrough, the equivalent series resistance (ESR)/insertion loss (IL) of the EMI filter can dangerously increase due to the very presence of the titanium oxides such that EMI filtering is compromised. Such ESR/IL increases are particularly observable at frequencies above 10 MHz. Of particular significance, is that such ESR/IL increases (in other words, EMI capacitor ohmic losses) are often masked at low frequencies by an EMI filter's dielectric losses. Such masking is particularly egregious to present day pacemakers and implantable cardioverter-defibrillators, which are considered/labelled MRI conditionally approved, as in an MRI environment, EMI filters divert substantial, potentially dangerous, RF current generated in implanted therapy delivery leads of an AIMD during MRI to the AIMD housing for dissipation. Hence, reliance solely on ECA stripe direct attachment to an oxidizable metal surface, such as a titanium surface, is considered to be dangerous and of poor practice by the inventors. It is also important to note that titanium oxides can also compromise performance in switching applications, coupling applications, and bypass applications in addition to EMI filtering applications.

In summary, the oxide-resistant pocket-pads 248, 248', 250, 250' of the present invention prevent re-oxidation of a cleaned titanium surface, as such oxide-resistant pocket-pads provide a metallurgical bond to the base metal of the ferrule that affords a reliable, long-term, stable, and low impedance electrical connection to the ground capacitor metallization 166 of the feedthrough filter capacitor 210'. A reliable, long-term, stable, and low impedance electrical connection to the ground capacitor metallization 166 of the feedthrough filter capacitor 210' to the hermetic feedthrough 132 is particularly important for modern pacemakers and defibrillators, which are now generally labelled MRI conditionally approved. As previously disclosed, in an MRI environment, the feedthrough capacitor 210' diverts a very large amount of RF current that is picked up by the implanted leads during an MRI scan to the housing of the AIMD. Accordingly, a great deal of RF current passes directly through the ground capacitor metallization 166, through the electrical attachment material 152, to the oxide-resistant gold pocket-pad 248, 250, and, in turn, to the ferrule 134 for dissipation by the AIMD housing to which the ferrule is laser welded. Thus, the conductive housing of the AIMD acts as an overall energy dissipating surface for this diverted MRI energy, and, as previously stated, relying solely on a thermal-setting conductive adhesive attachment to an oxidizable surface like titanium, is considered to poor practice and dangerous.

Figure 72C:
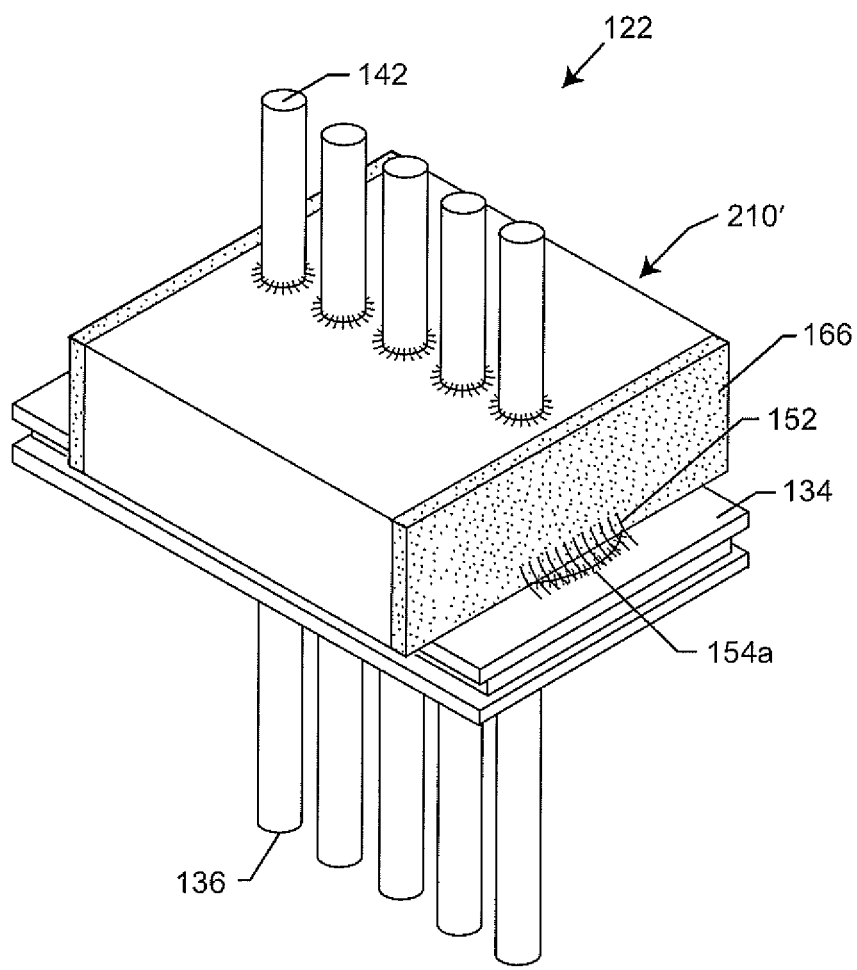
FIG. 72C is a view similar to FIG. 72B now illustrating the capacitor metallization being grounded to the gold braze of the insulator.

FIG. 72C is similar to FIG. 72B except that the ground capacitor metallization (termination) 166 is along two short ends of the filter capacitor 210' and electrical attachment is made to a gold braze 154a of the heretic feedthrough 132 (not labelled). The electrical attachment to a gold braze is disclosed in U.S. Pat. No. 6,765,779, the content of which is fully incorporated herein by this reference. In accordance with the present invention, the feedthrough filter capacitor 210' extends beyond the edges of the width of (in other words, overhangs) the ferrule as shown, thereby increasing the capacitors effective capacitance area or ECA. This is particularly important for enabling filter capacitors that have a dielectric constant less than 1,000 k or even less than 500 k as larger electrode plates can be made. Alternatively, the feedthrough filter capacitor 210' may only extend to the edges of the width of the ferrule. Another alternative embodiment is that one side of the feedthrough filter capacitor 210' may extend to an edge of the width of the ferrule while the opposite side of the feedthrough filter capacitor 210' overhangs the edge of the width of the ferrule.

Figure 73:
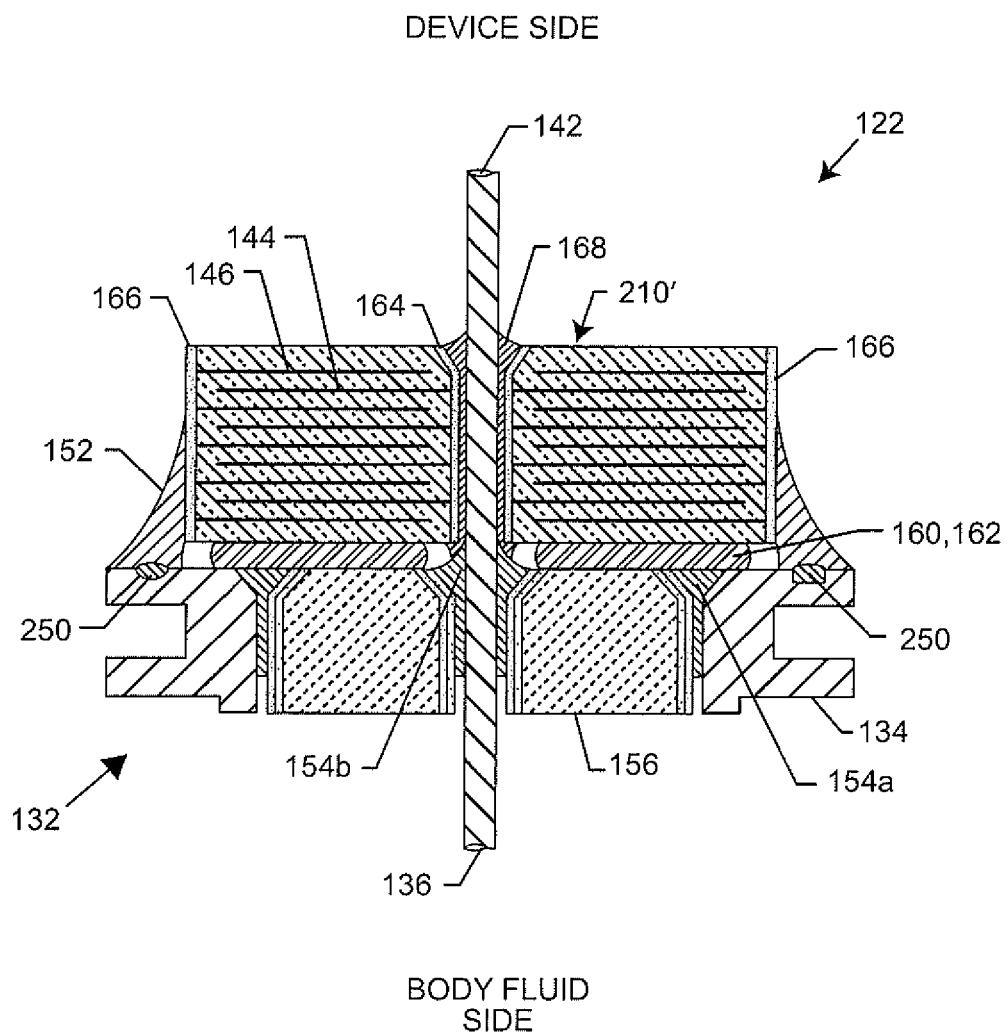

FIG. 73 is a cross-section taken generally from section 73-73 of FIG. 72B illustrating a feedthrough filter capacitor 210', including its internal electrode plates. The ground electrode plates are labelled 146 and the active electrode plates are labelled 144. Importantly, the capacitor's ground electrode plates 146 are attached to a ground capacitor metallization (termination) 166 using an electrically conductive material 152, which at least partially connects to an oxide-resistant pocket-pad 248 (not labelled) such as gold braze or a gold pocket-pad 250.

Referring once again to FIG. 73, it is noted that a dramatic improvement in volumetric efficiency of the filter capacitor 210' is achieved because the filter capacitor is much wider in size, therefore, the overlap of the interleaved electrode plates 144 and 146 is also much greater. The larger sized electrode plates due to the increased filter capacitor width thereby increases the capacitor's "effective capacitance area" (ECA). Increased ECA, s previously disclosed, is particularly enabling for a filter capacitor having dielectric constant k less than 1,000 or 500. By increasing the ECA of low k filter capacitors, one can achieve the required capacitance value needed to effectively filter EMI without sacrificing EMI filter reliability. In this embodiment, because the filter capacitor 210' is wider, the ground capacitor metallizations 166 are electrically connected to the oxide-resistant pocket-pads 250, which can be gold or gold braze pocket-pads. The oxide-resistant pocket-pads 250 enable attachment of a wider filter capacitor 250' to the hermetic feedthrough 132 such that both an increased ECA and an oxide-resistant electrical attachment to the ferrule 134 is achieved. Looking closely at the left-hand side of the ferrule 134 of the hermetic feedthrough 132, one can see that the oxide-resistant pocket-pad 250 is rounded and on the right-hand side of the ferrule 134 of the hermetic feedthrough 132, the oxide-resistant pocket-pad 250 has square corners. As previously disclosed, the oxide-resistant pocket-pads 250 can be made by machining, stamping or metal injection molding the ferrule 134. For example, if machining is used, the rounded shape can easily be machined with a ball mill end. Additionally, either a rounded, a rectangular or a square shaped oxide-resistant pocket-pad 250 can alternatively be achieved by stamping and metal injection molding. Also, as previously disclosed, the feedthrough filter capacitor 210' may only extend to the edges of the width of the ferrule, or one side of the feedthrough filter capacitor 210' may extend to an edge of the width of the ferrule while the opposite side of the feedthrough filter capacitor 210' may overhang the edge of the width of the ferrule. In an embodiment, the filter capacitor 210' is electrically connected to both an oxide-resistant pocket-pad 250 of the ferrule 134 of the filtered feedthrough 132 and at least a portion of the gold braze 154*a* hermetically sealing the insulator 156 and the ferrule 134 of the hermetic feedthrough 132.

Referring once again to FIG. 73, one can see that the terminal pin 142,136 is continuous from the device side (142) to the body fluid side (136). The terminal pin 142,136 is gold brazed 154*b* to the insulator 156 such that a hermetic seal is formed. The insulator comprises via hole metallizations (not labelled) that are sputtered on the insulator 156 as shown. It is understood that one or more sputter layers are applied to the insulator via holes to facilitate wetting of a braze material. In some embodiments, a first sputter layer is applied to the insulator via hole, which is an adhesion layer, and a second layer is applied over the adhesion layer, which is a wetting layer. In some embodiments, a single layer which has both adhesion and wetting properties is applied to an insulator via hole. Importantly, electrically conductive material 168 flows down through the passageway of the feedthrough capacitor (also known as a feedthrough capacitor via hole) and contacts the active capacitor metallization 164 of the capacitor via hole and the gold braze 154*b* of the hermetic feedthrough 132. Accordingly, an oxide-resistant electrical connection is made between the active capacitor metallization 164 and the gold braze 154*b* of the hermetic feedthrough 132 using an electrically conductive material 168. An oxide-resistant electrical connection is very important if the terminal pin 142. 136 comprises an oxidizable material, for example, niobium, tantalum, titanium or molybdenum. The oxide-resistant electrical connection is also particularly important if the terminal pins comprise alloys, such as platinum-iridium or palladium-iridium alloys, as even a small percentage of iridium can cause oxidation on the surface of the terminal pin. During the brazing process, the gold braze 154*b* burns through a terminal pin oxide layer thereby forming a low resistance, low impedance metallurgical bond to the base metal of said terminal pin. Attaching the active capacitor metallization of a capacitor via hole to the gold braze of a terminal pin of a hermetic feedthrough is more thoroughly disclosed in U.S. Pat. No. 6,888,715, the content of which is fully incorporated herein by this reference.

FIGS. 74A, 74B and 74C are taken from FIGS. 32A, 32B and 32C of U.S. Provisional application, Ser. No. 62/646, 552 (the '552 provisional). These figures illustrate an internally grounded feedthrough filter capacitor 210'*i* that has no diameter or perimeter metallization at all. In other words, the electrode ground plates of the filter capacitor 210'*i* are grounded through a ground terminal pin 142gnd. Referring to FIG. 74C, it is appreciated that, since there is no need for any external ground capacitor metallization for electrical connection between the feedthrough capacitor and the ferrule, the need for the gold pocket-pads of the ferrule is also completely eliminated. However, importantly, it is also appreciated that, for a low k filter capacitor k<1,000, to substantially increase the ECA of the filter capacitor, said filter capacitor of FIG. 74C can be designed to significantly overhang the ferrule in either the width, the length or both the width and length dimensions. Accordingly, internally grounded feedthrough filter capacitors in combination with low k dielectric filter capacitors k<1,000 can be designed to fit very tight geometries characteristic inside the hermetically sealed housing of modern AIMDs.

Figure 75:
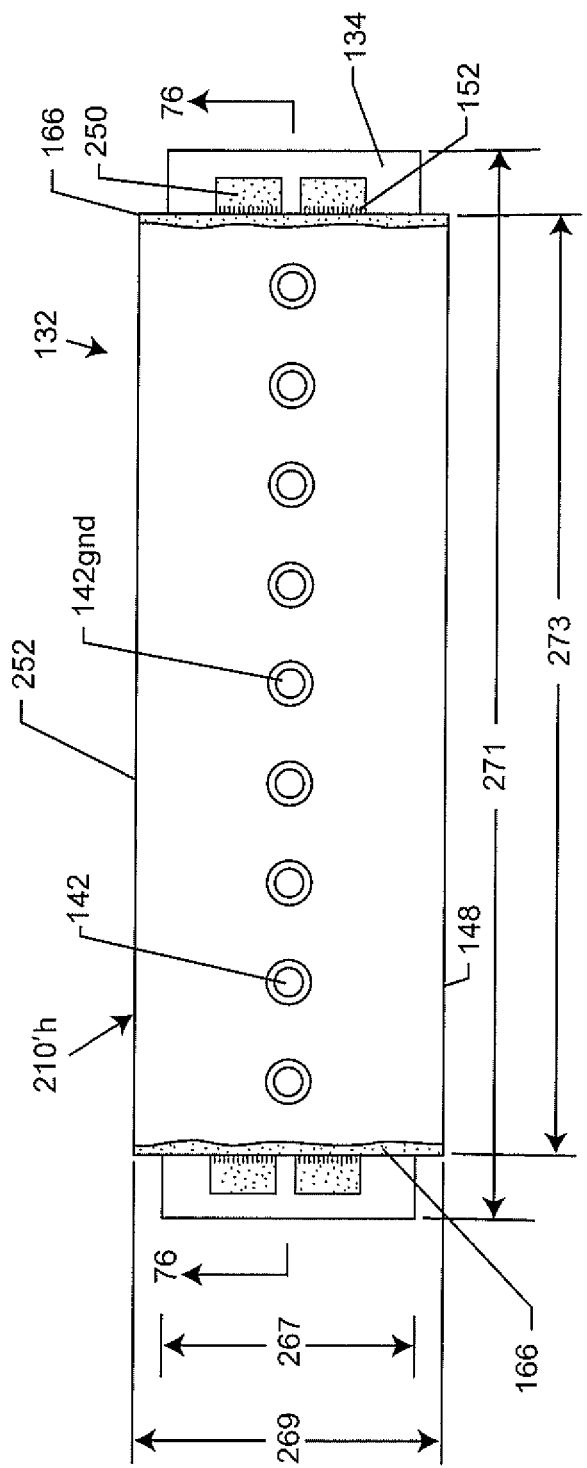

FIG. 75 is taken from FIG. 37 of the '552 provisional. In this embodiment, illustrated is a long rectangular feedthrough filter capacitor 210'*h*, which comprises and internal ground terminal pin 142gnd and external end ground capacitor metallizations 166. This embodiment is a hybrid filter capacitor, as the filter capacitor 210'*h* comprises both internal and external grounding technologies. Hybrid filter capacitors are best understood by referring to the cross-sectional view shown in FIG. 76 taken from FIG. 38 of the '552 provisional.

Referring back to FIG. 75, it is understood that other shapes can be used for this filter capacitor embodiment such as previously disclosed, meaning that the filter capacitor of FIG. 75 can be flush with the edge of the ferrule of the hermetic feedthrough, or alternatively overhang one or more edges of the ferrule of the hermetic feedthrough. For example, the rectangular-shaped capacitor can have rounded corners. Alternatively, the capacitor can even be round, oblong (racetrack) or any other geometric shape possible, where a portion of the capacitor is either flush with or overhangs the edges of the ferrule to greatly increase the ECA of the filter capacitor. It is understood that oxide-resistant attachments can also similarly be made.

Figure 76:
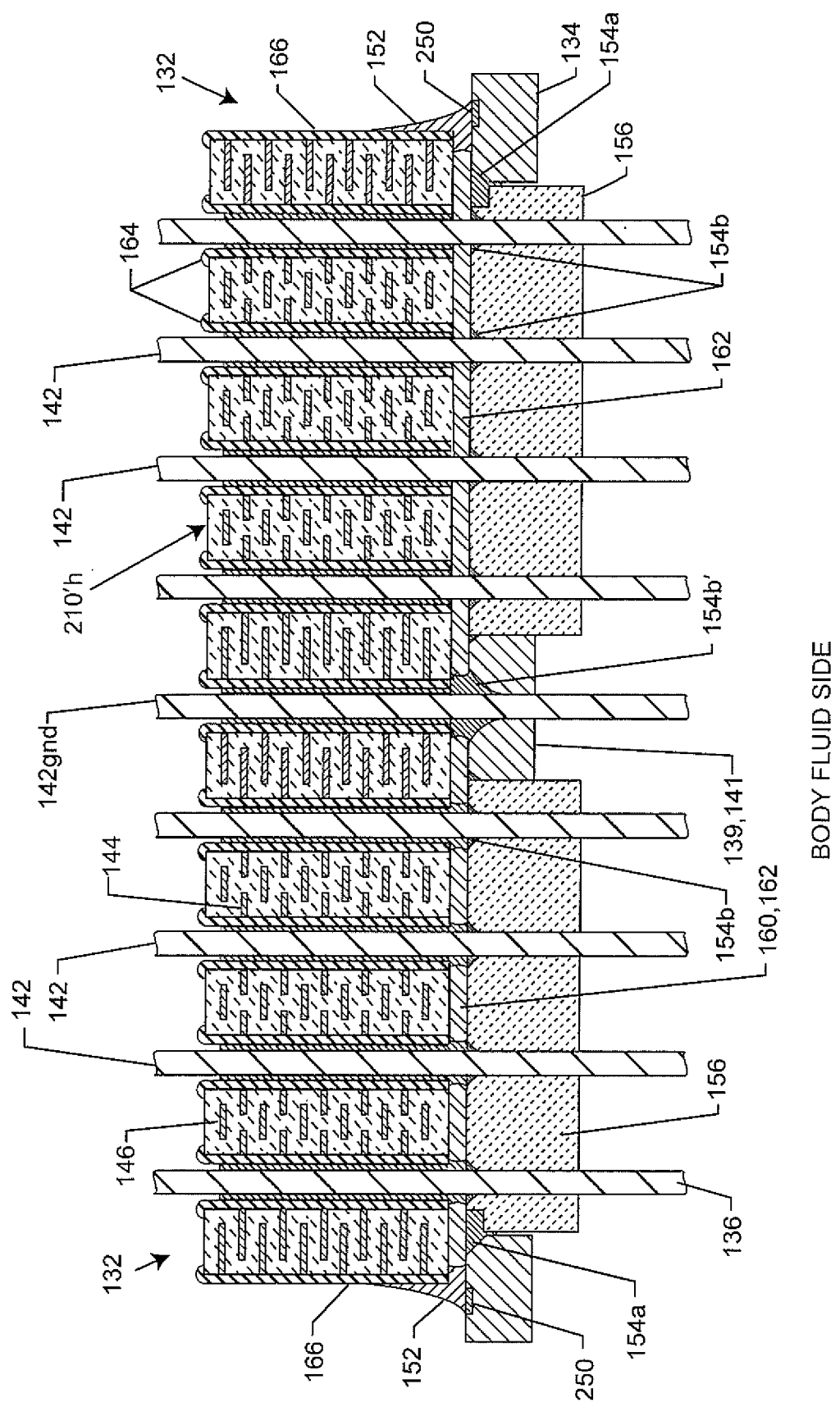

FIG. 76 is taken from cross-section 76-76 of FIG. 75 showing the internal construction of the hybrid feedthrough filter capacitor 210'*h*. Illustrated in more detail are the ground electrode plates 146 and active electrode plates 144 of the hybrid filter capacitor. In the center of the hybrid filter capacitor, one can see a ground terminal pin 142gnd, which is gold brazed 154*b'* to either a peninsula 139 or a bridge 141 embodied by the ferrule 134. Importantly, ground terminal pin 142gnd is attached in a very low resistance and low impedance manner so that the hybrid filter capacitor can divert high frequency RF energy through the ground terminal pin 182gnd to the ferrule 134 and then, in turn, to the AIMD housing (not shown). It is appreciated that all the ferrule embodiments disclosed herein are configured to be laser welded into an opening of the housing of an AIMD; however, it is understood that the ferrule may be co-formed with the housing of the AIMD, or a ferrule may be entirely omitted, with the insulator of the hermetic feedthrough being directly hermetically sealed to the AIMD housing itself.

Referring once again to FIG. 76, one can see that the ground electrode plates 146 are electrically connected to the internal ground terminal pin 142gnd and to the external metallizations 166 on opposite ends of the rectangular hybrid filter capacitor as shown. These ground capacitor metallizations 166 are electrically connected to the novel oxide-resistant pocket-pads 250 using an electrically conductive material 152. Hence, the term "hybrid" internally grounded filter capacitor 210'*h*, as the ground electrode plates are grounded both to the ground terminal pin 142gnd and to the external ground capacitor metallizations 166. Hybrid filter capacitor electrical connections are particularly enabling when the filter capacitor becomes long, and the active terminal pins are a substantial distance (a long way or distant) from the ground terminal pin 142gnd, as the inductance and the resistance can build up across the ground electrode plates such that the insertion loss or filter performance of the terminal pins furthest away from the ground terminal pins 142gnd is degraded. Referring once again to FIG. 76, it is also appreciated that additional ground terminal pins 142gnd can be added as necessary for optimal filter performance. In accordance with the present invention, one can see that the filter capacitor of FIG. 76 has a high number of internal electrode plates, which is essential to drive down its equivalent series resistance (ESR).

Figure 77:
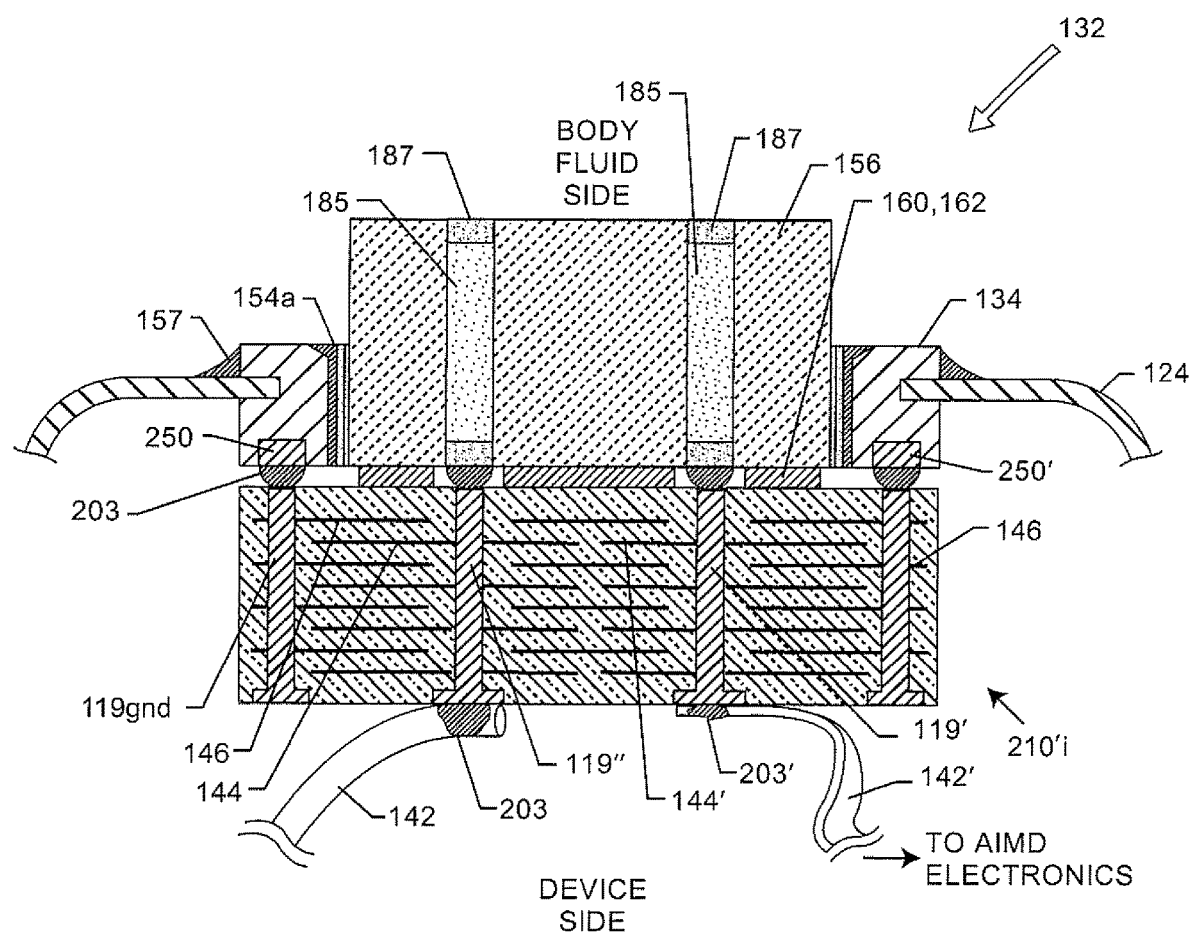

FIG. 77 is taken from FIG. 41 of the '552 provisional, which illustrates that instead of ground terminal pins, the insulator has co-sintered paste-filled vias. In this embodiment, the co-sintered paste-filled vias comprise a ceramic reinforced metal composite (CRMC) 185 having essentially pure platinum end caps 187. Referring back to FIG. 77, it is appreciated that the co-sintered paste-filled via can alternatively be entirely replaced by a substantially pure platinum (Pt), as described in U.S. Pat. Nos. 8,653,384 and 9,492,659, the contents of which are fully incorporated herein by these references. The CRMC 185 may also comprise a CERMET. Additionally, the co-sintered paste-filled vias of the present application may further comprise any of the CRMC/Pt paste-filled via embodiments disclosed in the '552 provisional. Novel oxide-resistant pocket-pads 250 and 250' are provided for grounding the internally grounded feedthrough filter capacitor 210'i of FIG. 77. In this embodiment, the feedthrough filter capacitor also has solid-filled vias 119', 119", 199gnd, and an electrical connection material 203, which can be a BGA, microdots or solder bumps. The electrical connection material further comprises one of a solder, a thermal-setting conductive adhesive, a thermal-setting conductive epoxy or combinations thereof. As such, the feedthrough filter capacitor 210'i can be electrically connected to both the grounding oxide-resistant pocket-pads 250, for example a gold pocket-pad, and also to the active co-sintered paste-filled vias in one operation. Referring once again to FIG. 77, it is appreciated that because of the presence of the oxide-resistant pocket-pads, the filter capacitor can be made substantially wider than the width of the ferrule, thereby keeping the height of the filter capacitor relatively low while increasing the volumetric efficiency of the filter capacitor for use in an AIMD. Referring again to FIG. 77, because the internally grounded feedthrough capacitor does not have any external capacitor metallization and therefore no external electrical connection material for attaching to the ferrule, the filter capacitor is mechanically free to float during laser welding of the hermetic feedthrough 132 into an opening of the AIMD housing 124. The laser weld is labelled 157. Since the laser welding can cause a great deal of heat and thermal stress, it is advantageous for the internally grounded feedthrough filter capacitor 210'i to be free floating during such laser welding. Experiments by the inventors have shown that the absence of electrical connection material mitigated thermal coefficient of expansion mismatch of the filtered feedthrough, and in particular, of the filter capacitor 210'i itself, due to heat imparted during laser welding. Moreover, because there is no electrical connection material required, the feedthrough filter capacitor can not only extend to the edges of the length and the width of the ferrule, but also can overhang the edges of both the length and the width of the ferrule, thereby providing increased ECA.

Figure 78:
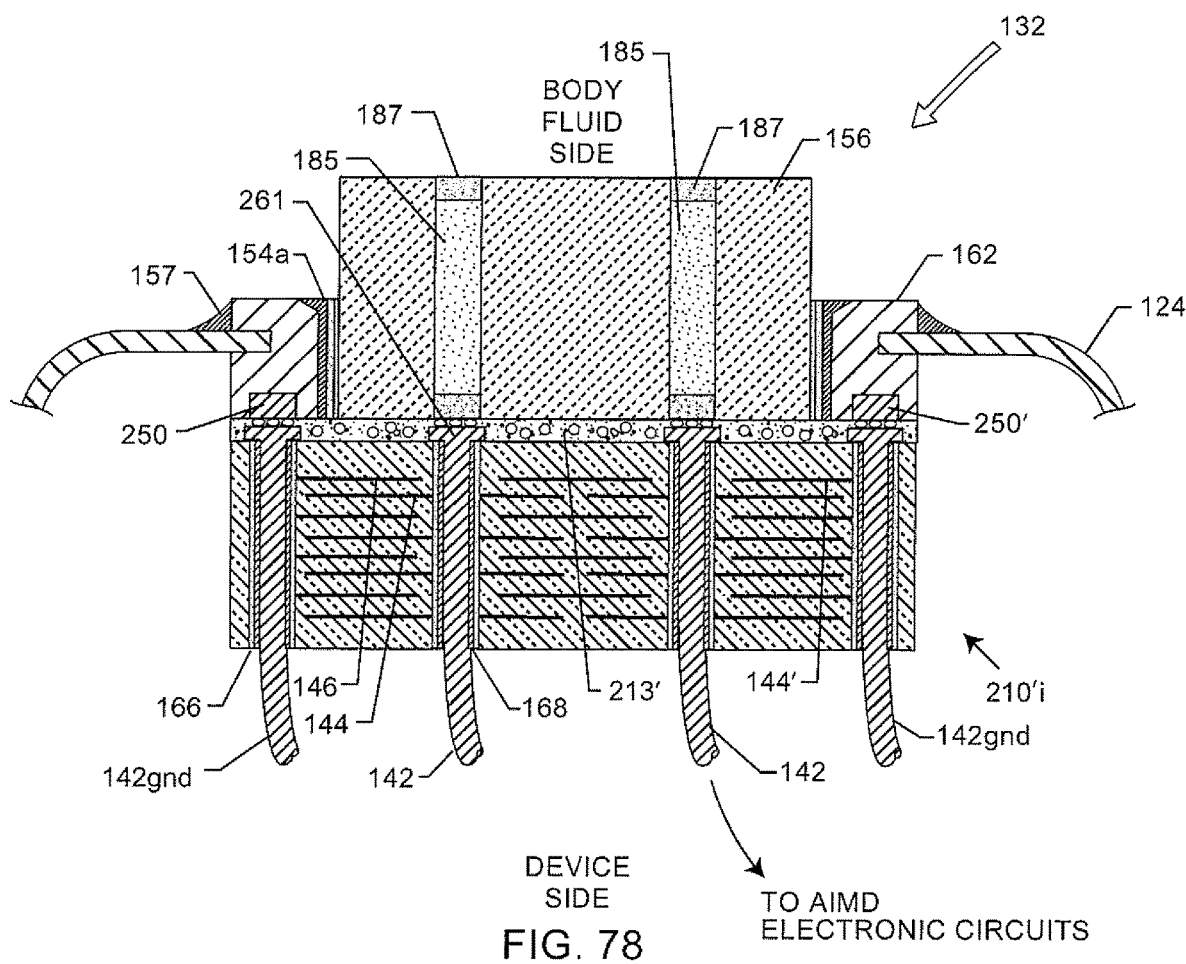

FIG. 78 is taken from FIG. 41B of the '552 provisional. FIG. 78 is similar to FIG. 77, except that all of the electrical connections are by way of an anisotropic conductive film (ACF). The novel nail-head 261 of the leadwires shown are pre-assembled to the feedthrough filter capacitor and stand proud of said feedthrough filter capacitor, thereby, providing a mating surface in which the conductive particles within the ACF can be compressed to form an electrical connection between the nail-heads of the leadwires and the platinum cap of the co-sintered past-filled vias as shown. Referring again to FIG. 78, it is appreciated that, while the feedthrough filter capacitor in this embodiment is shown having the same width as the width of the ferrule, the filter capacitor can alternatively overhang the width of the ferrule. Again, this is particularly important for filter capacitors having low k dielectric constants k<1,000.

Figure 79:
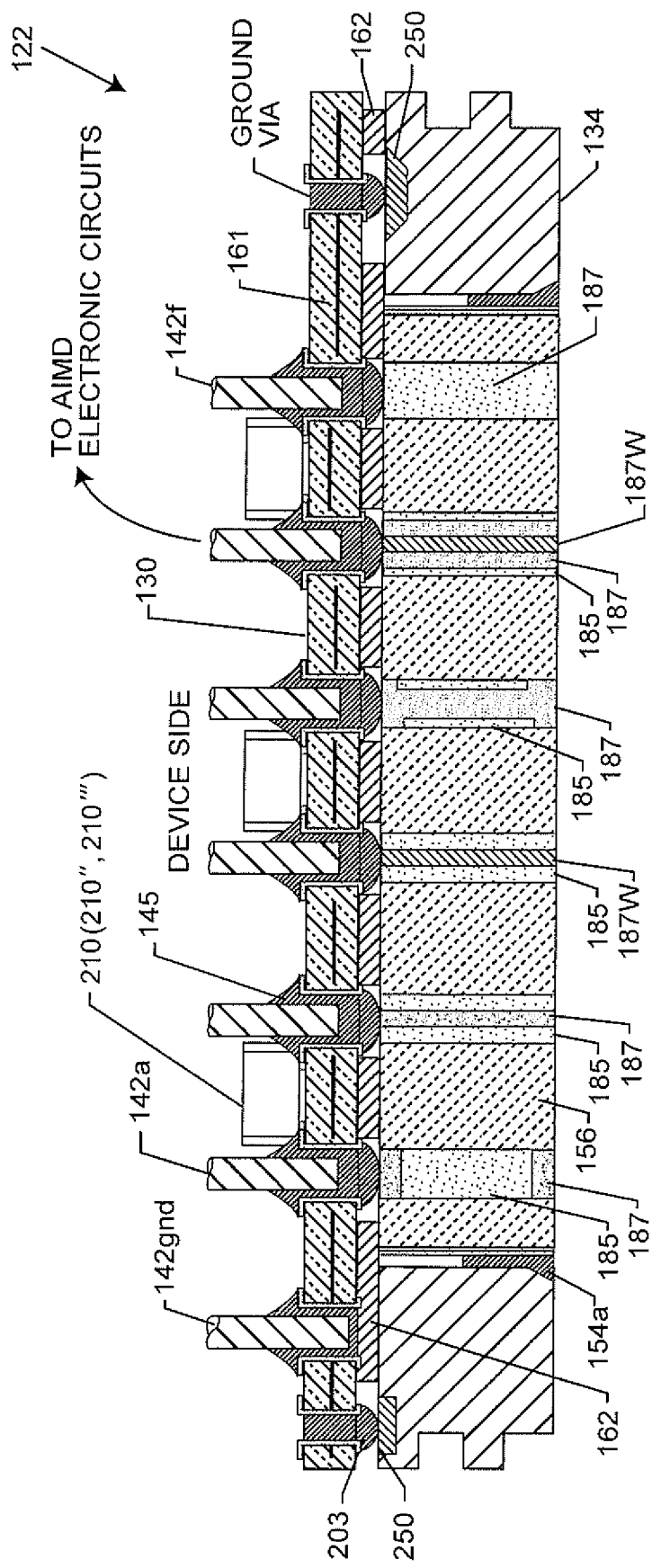

FIG. 79 is taken from FIG. 48 of the '552 provisional illustrating a filter circuit board 130 disposed on one of the ferrule 134, the insulator 156, or both the ferrule and the insulator of the hermetic feedthrough 132. The filter circuit board 130 may alternatively be disposed adjacent on one of the ferrule 134, the insulator 156, or both the ferrule and the insulator of the hermetic feedthrough 132. Illustrated are various exemplary embodiments of co-sinter paste-filled via conductive pathways extending to the device and the body fluid sides of the insulator 156 of the hermetic feedthrough 132 (not labelled). It is understood that the co-sintered paste-filled via conductive pathways may have numerous combinations of CRMC, CERMETS, pure platinum, solid wires, terminal pins, leadwires, two-part pins, metal inserts and the like to form various conductive pathway configurations. One is referred to the '552 provisional for additional detail regarding co-sinter paste-filled via conductive pathways. Importantly, the filter circuit board 130 and its associated leadwires 142 are each electrically connected to a corresponding conductive pathway of the insulator as illustrated. In this exemplary embodiment, the filter circuit board 130 has at least one internal ground electrode plate 161. A low impedance and low resistance electrical connection is made from the internal ground electrode plate 161 of the filter circuit board 130 through the circuit board ground vias through an electrical connection material 203 to oxide-resistant pocket-pads 250 to the ferrule 134 as illustrated. It is appreciated that 2, 3 or "n" number of ground electrode plates 161 can be disposed on the surface of the filter circuit board 130 or embedded within the body of the filter circuit board 130 or both disposed on the surface of the circuit board and embedded within the body of the circuit board. In an embodiment, there are at least two internal ground electrode plates and at least one external ground electrode plate, the at least one external ground electrode plate being disposed between the filter circuit board and the device side of the insulator and/or the ferrule of the hermetic feedthrough.

Also illustrated in FIG. 79 are filter capacitors electrically connected to the active terminal pins (there are 6 shown in this example embodiment) and to the ground via holes of the filter circuit board 130. The filter circuit board illustrated has one filter circuit board ground electrode plate 161. It is noted that the filter circuit board 130 of the present application comprises at least one filter circuit board ground electrode plate. The at least one filter circuit board ground electrode plate may be either an external ground electrode plate (meaning that the ground electrode plate is disposed on the filter circuit board) or an internal ground electrode plate (meaning that the ground electrode plate is embedded within the body of the circuit board). Each filter capacitor of the filter circuit board is configured to divert high frequency energy from the active terminal pins 142a through 14f to the ferrule 134 of the hermetic feedthrough 132 (not labelled) to the AIMD housing (not shown), the ferrule and housing being the AIMD ground. The filter capacitors of the present application are selected from the group consisting of an MLCC chip capacitor 210, an X2Y attenuator 210″, a flat-through capacitor 210‴, or combinations thereof.

Referring back to FIG. 79, it is understood by those skilled in the art that a wire 187W of a conductive pathway of the hermetic feedthrough can be extended beyond the thickness of the insulator 156 of the hermetic feedthrough to the body fluid side, to the device side, or both to the body fluid and device sides of said hermetic feedthrough for attachment to either internal circuits of the AIMD or to the connectors or other electronic components of the header block. Furthermore, the CRMC 185 or the CRMC 185 and the Pt 187 materials of the co-sintered paste-filled vias illustrated may be replaced entirely by only an essentially pure platinum co-sintered paste-filled via as disclosed by the incorporated U.S. Pat. Nos. 8,653,384 and 9,492,659. The far-right co-sintered paste-filled via is exemplary of an essentially pure platinum 187 co-sintered conductive pathway of a hermetic feedthrough.

FIG. 80 is taken from FIG. 129 of U.S. Pat. No. 10,272,253, referred to hereinafter as the 253 patent, the content of which is fully incorporated herein by this reference. FIG. 80 illustrates a general top view of an exemplary embodiment of the filter circuit board 130 of FIG. 79. In this exemplary embodiment, the MLCC chip capacitors 210 are electrically connected to the active terminal pins 142a through 142f and to the ground via holes 163a through 163f using circuit traces disposed on the filter circuit board 130.

Figure 81:
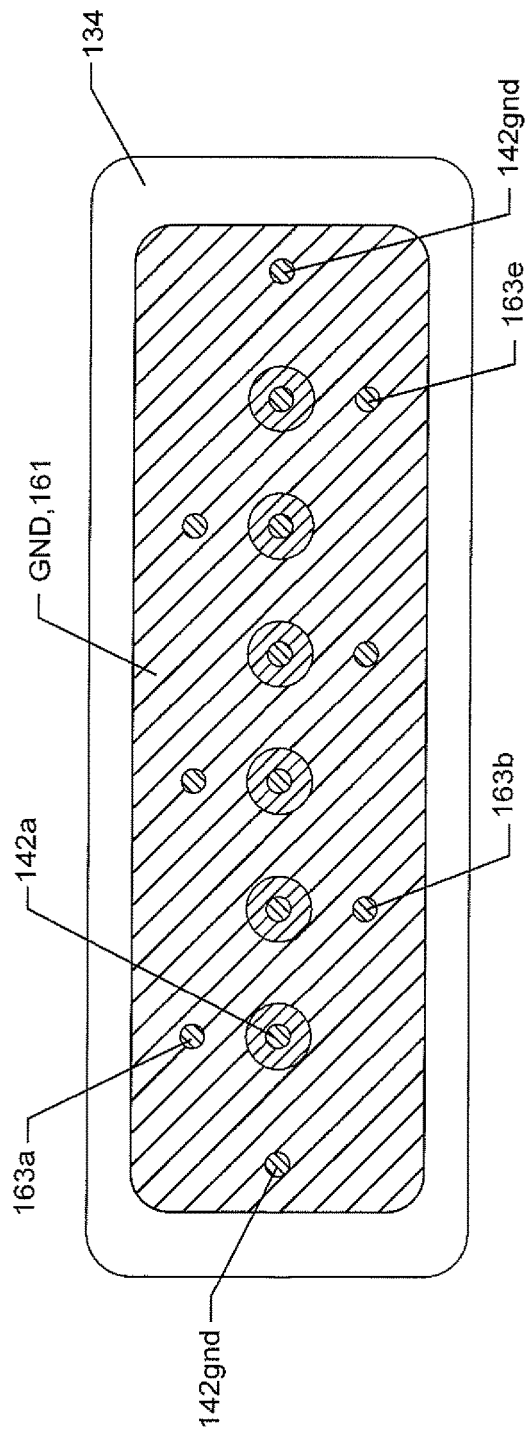

FIG. 81, which is taken from FIG. 130 of the '253 patent, is a sectional view of 81-81 of FIG. 80. Illustrated is a ground electrode plate 161 electrically connected to each of the ground via holes of the filter circuit board 130 (not labelled). Accordingly, each one of the MLCC chip capacitors 210 of filter circuit board of FIG. 80 is physically disposed very close to their corresponding ground via hole 163a through 163f and is electrically connected in a low resistance and low impedance manner through the ground via holes 163a through 163f of the filter circuit board to the co-sintered paste-filled via active conductive pathways of the hermetic feedthrough forming the filtered feedthrough 122 as shown. Referring back to FIG. 80, the circuit traces of the filter circuit board have active circuit traces 205 and ground circuit traces 207. It is contemplated that the MLCC chip capacitor can be positioned on the filter circuit board such that the length of the active circuit trace 205 can be shortened while the ground circuit trace 207 can be lengthened. It is also contemplated that by simply moving or realigning the MLCC chip capacitor, the ground circuit trace 207 can be completely eliminated. By moving or realigning the MLCC chip capacitor, the ground termination 166 of each MLCC chip capacitor 210 can butt up and directly be attached to their corresponding ground via hole 163a through 163f making the ground electrical connection. It is also contemplated that by rotating and lengthening the MLCC chip capacitor, the active circuit trace 205 can also be eliminated. By rotating and lengthening the MLCC chip capacitor 210, the active termination 164 of the MLCC chip capacitor can butt up and directly be attached to their corresponding active terminal pins 142a through 142f making the active electrical connection. As such, re-positioning and/or changing the size of the MLCC chip capacitor and/or adjusting the length of or eliminating either the active circuit trace 205 or the ground circuit trace 207 or both the active circuit trace 205 and the ground circuit trace 207 allows circuit board design flexibility, which can be important, for example, when size limitations or enhanced filter performance are required.

Figure 82:
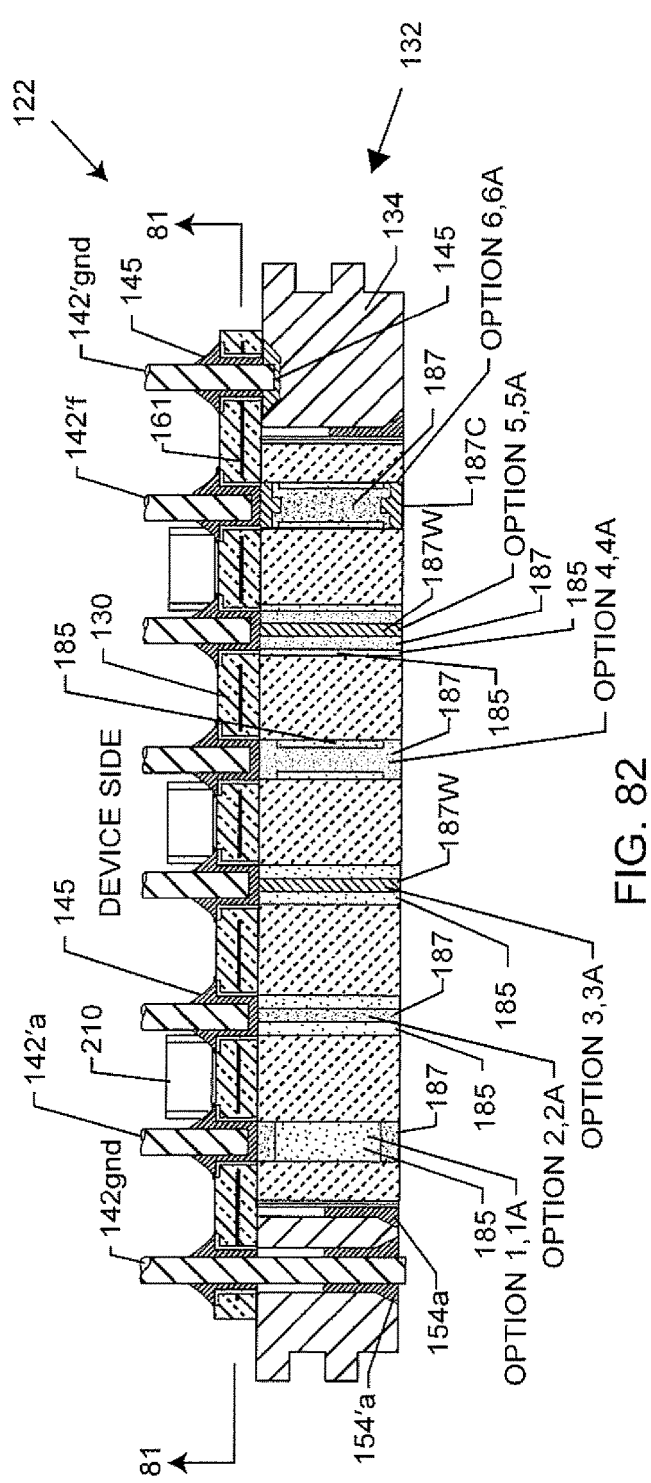

FIG. 82, which is taken from FIG. 131 of the '253 patent, is a sectional view of 82-82 of FIG. 80. Illustrated is a filtered feedthrough 122 having ground terminal pins attached to the ferrule 134 of a hermetic feedthrough (not labelled). On the left-hand side of FIG. 82, a ground terminal pin 142gnd is brazed into a via hole that extends through the thickness of the ferrule 134. On the right-hand side of FIG. 82, a ground terminal pin 142′gnd is attached within a counterbore of the ferrule 134. It is contemplated that more than two or "n" number of ground terminal pins may be brazed into a ferrule 134 of a hermetic feedthrough 132. Further, it is contemplated the hermetic feedthrough may have ground terminal pin embodiments that are the same or different pending the requirement of the application. The embodiments of FIG. 82 are not limiting. It is contemplated that the ground terminal pins may alternatively be attached to a peninsula or a bridge of a ferrule, to pocket-pads residing on or in a ferrule, or combinations thereof, so that a ground electrical connection can be made to the filter circuit board of a filtered feedthrough. While FIG. 82 shows ground terminal pins attached to the ferrule, it is understood that the ground terminal pins may be replaced with filled ground vias. Additionally, a filtered feedthrough may comprise a ferrule having any number and or combination of ground terminal pins and ground filled vias for grounding.

FIG. 83 taken from FIG. 132 of the '253 patent is a sectional view of 83-83 of FIG. 80 illustrating the ground electrical connections 163b, 163d and 163f to respective MLCC chip capacitors 210.

FIG. 84 is similar to FIG. 159 of the '253 patent except that FIG. 84 has an active terminal pin passing all the way through the conductive pathway of the insulator 156 of the hermetic feedthrough. It is noted that the active terminal pin is labelled 142 on the device side and 136 on the body fluid side. The terminal pin is shown gold brazed 154b to sputtered metalized surfaces of the alumina insulator 156, thereby hermetically sealing the terminal pin 142,136 and the insulator 156. Referring once again to FIG. 84, one can see that there is a gold meniscus 154b' that forms at the terminal pin 142 during the high temperature gold brazing operation. The gold meniscus 154b' provides an electrical connection 145 between the filter capacitor 210 active capacitor metallization 164 and the gold braze meniscus 154b' as shown. The gold braze electrical connection 145 enabled by the gold braze meniscus 154b' is important because attaching to an oxide-resistant material, such as the gold braze meniscus 154b', makes a low resistant and low impedance electrical connection between the capacitor active termination 164 and the feedthrough pin 142. Moreover, such oxide-resistant electrical connections enable the use of highly oxidizable terminal pins 142,136, for example, niobium, tantalum, molybdenum or the like.

FIG. 78 is taken from FIG. 41B of the '552 provisional. FIG. 78 is similar to FIG. 77, except that all of the electrical connections are by way of an anisotropic conductive film (ACF) 213′. The novel nail-head 261 of the leadwires shown are pre-assembled to the feedthrough filter capacitor and stand proud of said feedthrough filter capacitor, thereby, providing a mating surface in which the conductive particles within the ACF can be compressed to form an electrical connection between the nail-heads of the leadwires and the platinum cap of the co-sintered past-filled vias as shown. Referring again to FIG. 78, it is appreciated that, while the feedthrough filter capacitor in this embodiment is shown having the same width as the width of the ferrule, the filter capacitor can alternatively overhang the width of the ferrule.

Again, this is particularly important for filter capacitors having low k dielectric constants k<1,000.

FIG. 85 is taken from FIG. 23 of U.S. Pat. No. 10,272,252, hereinafter referred to as '252 patent, the content of which is fully incorporated herein by this reference. It is contemplated that the present invention applies to any of the embodiments disclosed in the '252 patent. Referring to FIG. 85, illustrated is a novel two-part pin residing within a conductive pathway of a filtered feedthrough 122 (not labelled). Because the conductive pathway of the hermetic feedthrough comprises a two-part pin, the body fluid side of the hermetic feedthrough can comprise a first terminal pin 136 that is low cost but biocompatible, such as niobium, tantalum, titanium, molybdenum or the like. The second pin 117 of the two-part pin can then be an oxide-resistant terminal pin, for example, platinum, palladium or alloys thereof, so that a low resistance and low impedance electrical connection can be made when the filter capacitor is attached to the hermetic feedthrough, thereby forming a filtered feedthrough. As illustrated in FIG. 85, a gold braze 154b co-joins and co-brazes the body fluid side terminal pin 136 to the device side terminal pin 117. In an embodiment (shown on the right side of FIG. 85), the two-part pin may be joined, for example by welding 424, before co-brazing. The device side terminal pin 117 is shown as a short pin to which a third pin is provided within the capacitor conductive pathway of a feedthrough filter capacitor 210'. The third pin is attached to the two-part of the hermetic feedthrough using an electrically conductive material 168 as illustrated. In this embodiment, therefore, the third pin can be low cost pin 142 or leadwire, such as copper, aluminum, copper-beryllium, tin-copper, that can then be routed to the device electronic circuits (such as the device circuit board not shown). Alternatively, the device side terminal pin 117 of the hermetic feedthrough may optionally extend all the way through the conductive pathway of the feedthrough filter capacitor 210' for attachment to the AIMD electronics, thereby eliminating the third pin. The feedthrough filter capacitor 210' of FIG. 85 is a conventional filter capacitor having an external or perimeter ground capacitor metallization. Shown is a ground electrical connection between the external or perimeter ground capacitor metallization of the filter capacitor 210' and the gold braze 154a hermetically sealing the ferrule 134 to the insulator 156 of the hermetic feedthrough using an electrically conductive material 152. The electrically conductive material 152 contacts at least a portion of the gold braze 154a. As previously disclosed, electrical connection may alternatively be to a gold pocket-pad. It is appreciated that the feedthrough filter capacitor 210' can alternatively be an internally grounded filter capacitor 210'i, thereby eliminating the need for an external ground electrical connection.

FIG. 85 also shows an insulator metallization 177, 179 at least partially disposed on the perimeter surface of the insulator 156. A first gold braze 154a hermetically seals the ferrule 134 to the insulator metallization. The insulator metallization may comprise an adhesion layer 177 and a wetting layer 179, wherein the adhesion layer is disposed on the insulator and the wetting layer is disposed on the adhesion layer; however, the insulator metallization may comprise one layer having both adhesion and wetting properties. The insulator metallization may further comprise a titanium adhesion layer and a molybdenum and/or a niobium wetting layer.

FIG. 86 is a flow chart taken from FIG. 165 of U.S. Pat. No. 10,249,415, the content of which is fully incorporated herein by this reference. A pressing (also known as a second lamination step or second pressing step) is shown between the "Fill with Pt paste" and "Singulate" method steps. The inventors have discovered that this second pressing step is very important as the second pressing step forces the conductive via filled pastes into every opening, nook and cranny along their interfaces, facilitating co-sintering. This second pressing step is also important as the intimacy provided between the ceramic insulator and the conductive paste permits diffusion and bonding of the ceramic and the conductive paste along their interface, which is disclosed in more detail below.

Referring once again to FIG. 86, during the "Fill with CRMC" step, at least some small air cavities or vacancies are created. The "Dry" step prepares the insulator paste-filled vias for drilling so that a platinum paste can be added, which may create yet more air pockets or voids. The addition of a second pressing step, wherein an entire green bar or insulator body is pressed under very high pressure, by either mechanical or isostatic pressing, forcing compaction and flow of the CRMC 185 and/or the platinum 187 pastes to fill and close such voids, thereby forming a more solid void-free or air pocket-free green bar or insulator. The laminated green bar of insulator body can then be singulated and fired.

FIG. 87 is a cross-sectional perspective of a laminate embodiment that illustrates stacked laminated sheets prior to the second "Pressing" step in accordance with the left-hand side of the flow chart FIG. 86. The dashed lamination lines 216 indicate the layers of stacked sheets. It is understood that the insulator may comprise a single solid green body (see the right-hand side of the flow chart of FIG. 86), thus the dashed lamination lines 216 of FIG. 87 would not be present.

FIG. 87 is idealized, in that, it shows an alumina substrate 156 that has a drilled via hole that is completely filled with a paste comprising CRMC 185, is then dried, drilled and re-filled again with a paste comprising pure platinum or substantially pure platinum 187. At very high magnification levels, one would see air bubble, voids or open pockets along the interface between the CRMC 185 and the alumina 156 and between the platinum 187 and the CRMC 185 pastes.

FIG. 88 shows what happens to FIG. 87 after the addition of the novel second "Pressing" step (second lamination step). The laminated bar is pressed a second time under high pressure to fill and close the bubbles, voids and pockets, in preparation for singulation and firing. The effect of this is to force integration of the materials such that an integrated mixing zone is made. As shown, there are actually two mixing zones. The first mixing zone 222 is between the green alumina insulator 156 and the CRMC 185 paste. A second mixing zone 226 is between the CRMC 185 and the substantially pure platinum 187 pastes. By driving these materials and intermixing them prior to sintering, an intimacy between the alumina and the CRMC and between the CRMC and the pure platinum is achieved, facilitating diffusion and bonding at the interfaces of these materials thereby providing a more robust hermetic seal.

It is understood to those skilled in the art that the novel second pressing step has wide applicability to a number of other teachings. In particular, this process comprising the novel second pressing step is applicable to U.S. Pat. Nos. 8,653,384; 8,938,309; 9,233,253; 9,352,150; 9,511,220; 9,889,306; 9,993,650 and 10,272,253, U.S. Patents, the contents of which are fully incorporated herein by these references. Referring now to U.S. Pat. No. 9,889,306 disclosing co-sintered vias having conductive inserts, it is appreciated that the novel second pressing step of FIG. 86 may alternatively be accomplished prior to counter-boring or adding a metal insert.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A filtered feedthrough for an active implantable medical device (AIMD), the filtered feedthrough comprising:
    a) a hermetic feedthrough, comprising:
        i) an electrically conductive ferrule comprising a ferrule opening;
        ii) an insulator residing in the ferrule opening where a first hermetic seal hermetically seals the insulator to the ferrule, wherein at least one insulator passageway extends through the insulator to an insulator body fluid side surface opposite an insulator device side surface, and wherein, when the ferrule hermetically sealed to the insulator is attached to an opening in an AIMD housing, the insulator body fluid side surface and the insulator device side surface reside outside and inside the AIMD, respectively; and
        iii) a platinum-containing active conductive pathway hermetically sealed to the insulator in the at least one insulator passageway and extending from an active pathway body fluid side to an active pathway device side, the active conductive pathway being in a non-conductive relationship with the ferrule and being characterized as having been a platinum-containing paste filled into the at least one insulator passageway and then co-sintered with the insulator when the insulator is in a green-state; and
    b) at least one flat-through filter capacitor disposed on or adjacent to the insulator device side surface of the hermetic feedthrough, the at least one flat-through filter capacitor comprising:
        i) a dielectric substrate supporting at least one active electrode plate interleaved between and in a capacitive relationship with at least two ground electrode plates, wherein the active electrode plate has active electrode plate first and second ends; and
        ii) a first active electrode metallization electrically connected to the at least one active electrode plate first end, a second active electrode metallization electrically connected to the active electrode plate second end, and a ground electrode metallization electrically connected to the at least two ground electrode plates; and
    c) a first active electrical connection electrically connecting the active conductive pathway device side to the first active electrode metallization electrically connected to the at least one active electrode plate first end;
    d) a second active electrical connection which is connectable from the second active electrode metallization electrically connected to the active electrode plate second end of the at least one flat-through filter capacitor to AIMD circuits housed inside an AIMD housing; and
    e) a ground electrical connection electrically connecting the ground electrode metallization to the ferrule.

2. The filtered feedthrough of claim 1, wherein the first hermetic seal comprises a first gold braze.

3. The filtered feedthrough of claim 1, wherein the dielectric substrate has a dielectric constant k that is greater than 0 but less than 1000.

4. The filtered feedthrough of claim 1, wherein the at least one flat-through filter capacitor is located as the first filter capacitor electrically connected to the platinum-containing active conductive pathway at or adjacent to the insulator device side surface of the hermetic feedthrough.

5. The filtered feedthrough of claim 1, wherein the platinum-containing active conductive pathway of the hermetic feedthrough comprises a co-sintered ceramic reinforced metal composite material or a co-sintered substantially pure platinum material that is hermetically sealed to the insulator in the at least one insulator passageway.

6. The filtered feedthrough of claim 1, wherein the at least one flat-through filter capacitor is disposed on a circuit board, and wherein at least one circuit board ground plate is disposed on or inside the circuit board, wherein the ground electrical connection comprises a first ground electrical connection electrically connecting the ground electrode metallization of the at least one flat-through filter capacitor to the at least one circuit board ground plate and a second ground electrical connection electrically connecting the at least one circuit board ground plate to the ferrule.

7. The filtered feedthrough of claim 1, wherein the at least one flat-through filter capacitor is disposed at least partially over the insulator in a tombstone mounted position with the at least one active electrode plate and the at least two ground electrode plates disposed in a perpendicular orientation with respect to the insulator device side surface of the hermetic feedthrough.

8. The filtered feedthrough of claim 2, wherein the ground electrical connection electrically connects the ground electrode metallization of the at least one flat-through filter capacitor to the first gold braze hermetically sealing the insulator to the ferrule.

9. The filtered feedthrough of claim 6, wherein the ground electrical connection electrically connecting the at least one circuit board ground plate to the ferrule comprises an oxide-resistant material, the oxide-resistant material being selected from the group of:
    a) the first hermetic seal hermetically sealing the insulator to the ferrule;
    b) at least one oxide-resistant ground pin that is connected to the ferrule by a third second gold braze or a laser weld;
    c) an oxide-resistant area supported by the ferrule, the oxide-resistant area being selected from the group of a gold pocket-pad, a gold pad, an oxide-resistant metal addition, a thermal-setting electrically conductive adhesive (ECA) stripe, and combinations thereof;
    d) a ferrule peninsula; and
    e) a ferrule-bridge.

10. The filtered feedthrough of claim 9, wherein the oxide-resistant material is selected from the group of platinum, gold, tungsten, iridium, palladium, niobium, tantalum, ruthenium, rhodium, silver, osmium, and alloys and combinations thereof.

11. The filtered feedthrough of claim 9, wherein the at least one oxide-resistant ground pin is of a material selected from the group of platinum-rhodium, platinum-iridium, platinum-palladium, platinum-gold and naturally occurring alloys such as platiniridium (platinum-iridium), iridiosmium and osmiridium (iridium-osmium).

12. The filtered feedthrough of claim 1, wherein an insulating washer is disposed between the at least one flat-through filter capacitor and the hermetic feedthrough.

13. A filtered feedthrough for an active implantable medical device (AIMD), the filtered feedthrough comprising:
   a) a hermetic feedthrough, comprising:
      i) an electrically conductive ferrule comprising a ferrule opening;
      ii) an insulator residing in the ferrule opening where a first gold braze hermetically seals the insulator to the ferrule, wherein at least one insulator passageway extends through the insulator to an insulator body fluid side surface opposite an insulator device side surface, and wherein, when the ferrule hermetically sealed to the insulator is attached to an opening in an AIMD housing, the insulator body fluid side surface and the insulator device side surface reside outside and inside the AIMD, respectively; and
      iii) a platinum-containing active conductive pathway hermetically sealed to the insulator in the at least one insulator passageway and extending from an active pathway body fluid side to an active pathway device side, the platinum-containing active conductive pathway being in a non-conductive relationship with the ferrule and being characterized as having been a platinum-containing paste filled into the at least one insulator passageway and then co-sintered with the insulator when the insulator is in a green-state; and
   b) at least one flat-through filter capacitor disposed on or adjacent to the insulator device side surface of the hermetic feedthrough, the at least one flat-through filter capacitor comprising:
      i) a dielectric substrate supporting at least one active electrode plate interleaved between and in a capacitive relationship with at least two ground electrode plates, wherein the active electrode plate has active electrode plate first and second ends; and
      ii) a first active electrode metallization electrically connected to the at least one active electrode plate first end, a second active electrode metallization electrically connected to the active electrode plate second end, and a ground electrode metallization electrically connected to the at least two ground electrode plates; and
   c) a circuit board comprising at least one ground electrode plate disposed on or inside the circuit board, wherein the at least one flat-through filter capacitor is disposed on the circuit board;
   d) a first active electrical connection electrically connecting the first platinum-containing active conductive pathway device side to the first active electrode metallization electrically connected to the active electrode plate first end;
   e) a second active electrical connection which is connectable from the second active electrode metallization electrically connected to the active electrode plate second end of the at least one flat-through filter capacitor to AIMD circuits housed inside an AIMD housing;
   f) a first ground electrical connection electrically connecting the ground electrode metallization of the at least one flat-through filter capacitor to the at least one circuit board ground plate; and
   g) a second ground electrical connection electrically connecting the at least one circuit board ground plate to the ferrule.

14. The filtered feedthrough of claim 13, wherein the platinum-containing active conductive pathway of the hermetic feedthrough comprises a pure platinum paste that is filled into the at least one insulator passageway and then characterized as having been co-sintered with the insulator when the insulator is in a green-state to thereby hermetically seal the pure platinum material conductive pathway to the insulator in the at least one insulator passageway.

15. The filtered feedthrough of claim 13, wherein the platinum-containing active conductive pathway of the hermetic feedthrough comprises a ceramic reinforced platinum composite paste that is filled into the at least one insulator passageway and then characterized as having been co-sintered with the insulator when the insulator is in a green-state to thereby hermetically seal the ceramic reinforced platinum composite material conductive pathway to the insulator in the at least one insulator passageway.

16. The filtered feedthrough of claim 13, wherein an insulating washer is disposed between the at least one flat-through filter capacitor and the hermetic feedthrough.

17. The filtered feedthrough of claim 13, wherein the dielectric substrate of the at least one flat-through filter capacitor has a dielectric constant k that is greater than 0 but less than 1000.

18. The filtered feedthrough of claim 13, wherein the at least one flat-through filter capacitor is located as the first filter capacitor electrically connected to the platinum-containing active conductive pathway at or adjacent to the insulator device side surface of the hermetic feedthrough.

19. The filtered feedthrough of claim 13, wherein the second ground electrical connection electrically connecting the at least one circuit board ground plate to the ferrule comprises an oxide-resistant material, the oxide-resistant material being selected from the group of:
   a) the first hermetic seal hermetically sealing the insulator to the ferrule;
   b) at least one oxide-resistant ground pin connected to the ferrule by a second gold braze or a laser weld;
   c) an oxide-resistant area supported by the ferrule, the oxide-resistant material being selected from the group of a gold pocket-pad, a gold pad, an oxide-resistant metal addition, a thermal-setting electrically conductive adhesive (ECA) stripe, and combinations thereof;
   d) a ferrule peninsula; and
   e) a ferrule-bridge.

20. The filtered feedthrough of claim 13, wherein the second ground electrical connection electrically connects the at least one circuit board ground plate to the first gold braze hermetically sealing the insulator to the ferrule.

21. A filtered feedthrough for an active implantable medical device (AIMD), the filtered feedthrough comprising:
   a) a hermetic feedthrough, comprising:
      i) an electrically conductive ferrule comprising a ferrule opening;
      ii) an insulator residing in the ferrule opening where a first hermetic seal hermetically seals the insulator to the ferrule, wherein at least one insulator passageway extends through the insulator to an insulator body fluid side surface opposite an insulator device side surface, and wherein, when the ferrule hermetically sealed to the insulator is attached to an opening in an AIMD housing, the insulator body fluid side surface and the insulator device side surface reside outside and inside the AIMD, respectively; and
      iii) a active conductive pathway comprising a pure platinum material or a ceramic reinforced platinum composite material hermetically sealed to the insulator in the at least one insulator passageway, the active conductive pathway extending from an active pathway body fluid side to an active pathway device side, wherein the active conductive pathway is characterized as having been a platinum-containing paste filled into the at least one insulator passageway and then co-sintered with the insulator when the insulator is in a green-state; and b) at least one flat-through filter capacitor comprising:
   i) a dielectric substrate supporting at least one active electrode plate interleaved between and in a capacitive relationship with at least two ground electrode plates, wherein the active electrode plate has active electrode plate first and second ends, and wherein the dielectric substrate has a dielectric constant k that is greater than 0 but less than 1,000,
   ii) a first active electrode metallization electrically connected to the at least one active electrode plate first end, a second active electrical connection electrically connected to the active electrode plate second end, and a ground electrode metallization electrically connected to the at least two ground electrode plates of the flat-through filter capacitor, and
   iii) wherein the at least one flat-through filter capacitor is disposed at least partially over the insulator in a tombstone mounted position with the at least one active electrode plate and the at least two ground electrode plates disposed in a perpendicular orientation with respect to the insulator device side surface of the hermetic feedthrough, and
   iv) wherein the at least one flat-through filter capacitor is located as the first filter capacitor electrically connected to the active conductive pathway at or adjacent to the insulator device side surface of the hermetic feedthrough;

c) a first active electrical connection electrically connecting the platinum-containing active conductive pathway device side of the hermetic feedthrough to the first active electrode metallization electrically connected to the active electrode plate first end;

d) a second active electrical connection which is connectable from the second active electrode metallization electrically connected to the active electrode plate second end of the at least one flat-through filter capacitor to AIMD circuits housed inside an AIMD housing; and e) a ground electrical connection electrically connecting the ground electrode metallization to the ferrule.

* * * * *

UNITED STATES PATENT AND TRADEMARK OFFICE
CERTIFICATE OF CORRECTION

PATENT NO. : 11,406,817 B2
APPLICATION NO. : 16/880392
DATED : August 9, 2022
INVENTOR(S) : Robert A. Stevenson et al.

It is certified that error appears in the above-identified patent and that said Letters Patent is hereby corrected as shown below:

In the Specification

Column 52, Line 43 delete "is" and insert --are--
Column 52, Line 44 before "182a" insert --circuit traces--
Column 52, Line 44 delete "This" and insert --These--
Column 52, Line 44 delete "connection is" and insert --circuit traces are--
Column 55, Line 16 delete "grounds" and insert --ground circuit traces--
Column 55, Line 17 delete "grounds" and insert --ground circuit traces--
Column 55, Line 19 delete "grounds" and insert --ground circuit traces--
Column 79, Line 45 after "(ACF)" insert --213'--

Signed and Sealed this
Third Day of January, 2023

Katherine Kelly Vidal
*Director of the United States Patent and Trademark Office*